(12) United States Patent
Barda-Saad

(10) Patent No.: US 12,150,940 B2
(45) Date of Patent: *Nov. 26, 2024

(54) WASp-PROTECTING SMALL MOLECULES, COMPOSITIONS, METHODS AND USES THEREOF IN THE TREATMENT OF INNATE AND ACQUIRED IMMUNE-RELATED DISORDERS OR CONDITIONS

(71) Applicant: BAR ILAN UNIVERSITY, Ramat Gan (IL)

(72) Inventor: Mira Barda-Saad, Ganney Tikva (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 126 days.

This patent is subject to a terminal disclaimer.

(21) Appl. No.: 17/385,381

(22) Filed: Jul. 26, 2021

(65) Prior Publication Data
US 2021/0361642 A1 Nov. 25, 2021

Related U.S. Application Data

(63) Continuation of application No. 16/336,383, filed as application No. PCT/IL2017/051075 on Sep. 25, 2017, now Pat. No. 11,123,339.

(30) Foreign Application Priority Data

Sep. 25, 2016 (IL) .......................... 248028

(51) Int. Cl.
| | | |
|---|---|---|
| *A61K 31/4709* | (2006.01) | |
| *A61K 31/197* | (2006.01) | |
| *A61K 31/381* | (2006.01) | |
| *A61K 31/4192* | (2006.01) | |
| *A61K 31/426* | (2006.01) | |
| *A61K 31/427* | (2006.01) | |
| *A61K 31/4545* | (2006.01) | |
| *A61K 31/4706* | (2006.01) | |
| *A61K 31/495* | (2006.01) | |
| *A61K 31/517* | (2006.01) | |
| *A61K 31/519* | (2006.01) | |
| *A61K 45/06* | (2006.01) | |
| *A61P 7/00* | (2006.01) | |

(52) U.S. Cl.
CPC ........ *A61K 31/4709* (2013.01); *A61K 31/197* (2013.01); *A61K 31/381* (2013.01); *A61K 31/4192* (2013.01); *A61K 31/426* (2013.01); *A61K 31/427* (2013.01); *A61K 31/4545* (2013.01); *A61K 31/4706* (2013.01); *A61K 31/495* (2013.01); *A61K 31/517* (2013.01); *A61K 31/519* (2013.01); *A61K 45/06* (2013.01); *A61P 7/00* (2018.01)

(58) Field of Classification Search
CPC .............. A61K 31/4709; A61K 31/197; A61K 31/381; A61K 31/4192; A61K 31/426; A61K 31/427; A61K 31/4545; A61K 31/4706; A61K 31/495; A61K 31/517; A61K 31/519; C12Q 1/00
See application file for complete search history.

(56) References Cited

FOREIGN PATENT DOCUMENTS

| | | | |
|---|---|---|---|
| WO | 2008/082537 A2 | 7/2008 | |
| WO | 2009/062118 A2 | 5/2009 | |
| WO | 2012/102937 A2 | 8/2012 | |
| WO | 2014/195857 A1 | 12/2014 | |
| WO | 2015/065716 A1 | 5/2015 | |
| WO | 2015/181394 A1 | 12/2015 | |

OTHER PUBLICATIONS

H. D. Ochs, A. J. Thrasher, The Wiskott-Aldrich syndrome. The Journal of Allergy and Clinical Immunology 117, 725-738; quiz 739 (2006).
M. H. Albert, et al Blood 115, 3231-3238 (2010).
J. M. Derry, et al.,Cell 79, following 922 (1994).
O. Matalon, et al., Immunological Reviews 256, 10-29 (2013).
N. Joseph, Biochimica et Biophysica Acta (BBA)—Biomembranes, 105:481-93 (2013).
Y. Jin, et al., Blood 104, 4010-4019 (2004).
M. I. Lutskiy, F et al., Journal of Immunology 175, 1329-1336 (2005).
D. Buchbinder, et al.,The Application of Clinical Genetics 7, 55-66 (2014).
Filipovich, Bone Marrow Transplantation 42 Suppl 1, S49-S52 (2008).
C. R. Shin, et al.,Bone Marrow Transplantation 47, 1428-1435 (2012).
J. Litzman, et al., Archives of Disease in Childhood 75, 436-439 (1996). L.
Khavrutskii, et al.,Journal of Visualized Experiments : JoVE 15, (2013) A.
Konno, et al., International Immunology 19, 185-192 (2007).
S. Fried, et al., Science Signaling 7, ra60 (2014).
B. Reicher, et al.,Molecular and Cellular Biology 32, 3153-3163 (2012).

(Continued)

*Primary Examiner* — Susanna Moore
(74) *Attorney, Agent, or Firm* — FISHERBROYLES, LLP; Roger L. Browdy

(57) ABSTRACT

The present invention provides specific small molecule compounds that modulate degradation and stability of Wiskott-Aldrich Syndrome protein (WASp), methods and uses thereof in innate and acquired immune-related disorders or conditions, specifically, in primary and secondary immune-deficiencies.

19 Claims, 20 Drawing Sheets

Specification includes a Sequence Listing.

(56) References Cited

OTHER PUBLICATIONS

M. Barda-Saad, et al.,Nature Immunology 6, 80-89 (2005).
M. I. Lutskiy, et al., British Journal of Haematology 139, 98-105 (2007).
A. Shcherbina, et al.,Blood 98, 2988-2991 (2001).
J. K. Burkhardt, et al.,Annual Review of Immunology 26, 233-259 (2008).
D. Varga-Szabo, et al., Journal of Thrombosis and Haemostasis 7, 1057-1066 (2009).
Aiuti, L. et al., Science 341, 1233151 (2013).
E. Noy, et al., International Journal of Molecular Sciences 13, 7629-7647 (2012).
S. Hacein-Bey Abina, et al.,JAMA 313, 1550-1563 (2015).
H. Albert, et al.,Science translational medicine 6, 227ra233 (2014).
F. C. Peterson, et al.,The Journal of biological chemistry 282, 8446-8453 (2007).
M. H. Pauker, et al., Molecular and cellular biology 31, 2653-2666 (2011).
H.M.Pauker, et al.,Science Signaling 5(221):rs3 (2012).
F. A. Ran, et al.,Nature protocols 8, 2281-2308 (2013).
S. B. Snapper, et al., Immunity 9, 81-91 (1998).
J. A. Doudna, et al., Science 346, 1258096 (2014).
Charrier, S., et al.,Gene therapy 14 (2007), 415-428.
Snapper, S.B., et al.,Journal of leukocyte biology 77 (2005), 993-998.
Zhang, H., et al., Immunity 25 (2006), 285-295.
Gunn, M.D., et al.,The Journal of experimental medicine 189 (1999), 451-460.
Altman, L.C., et al.,The Journal of clinical investigation 54 (1974), 486-493.
Linder, S. & Kopp, P. Journal of cell science 118 (2005), 2079-2082.
Linder, S., et al.,Proceedings of the National Academy of Sciences of the United States of America 96 (1999), 9648-9653.
Zhang, J., et al.,The Journal of experimental medicine 190 (1999), 1329-1342.
Matalon, O., et al.,Science signaling 9 (2016), ra54.
Lee, S.H., et al., J Immunol 183 (2009), 7931-7938.
Anfossi, N., et al.,Immunity 25 (2006), 331-342.
D. Schneidman-Duhovny, et al. Nucleic acids research 33, W363-367 (2005).
Stella (J. Pharmaceutical Sciences, 2010, 99(12), pp. 4755-4765).

Platelets

PBMCs

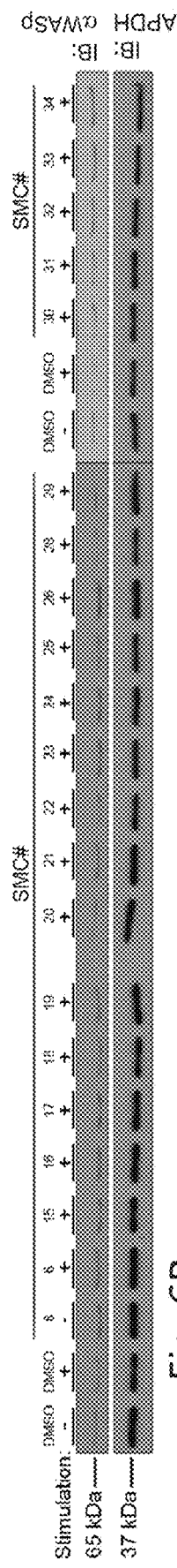
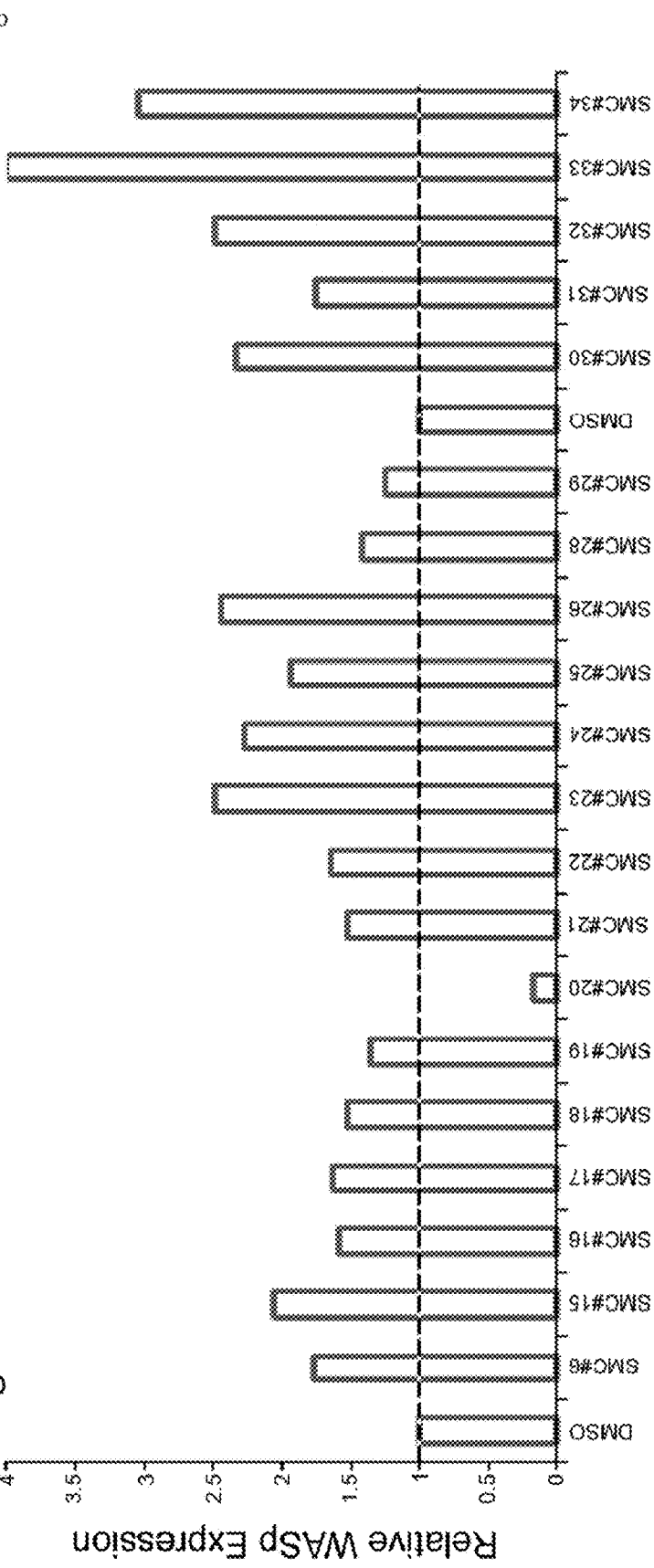
Fig. 6A
Fig. 6B

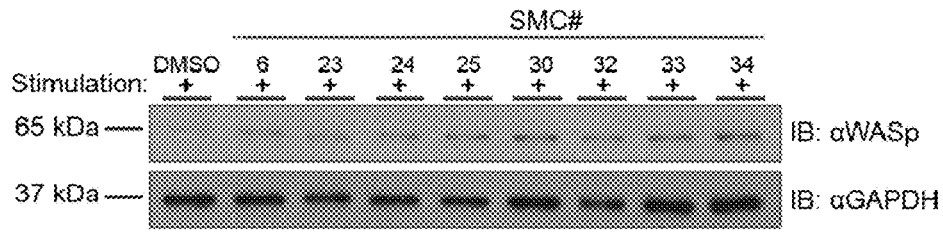
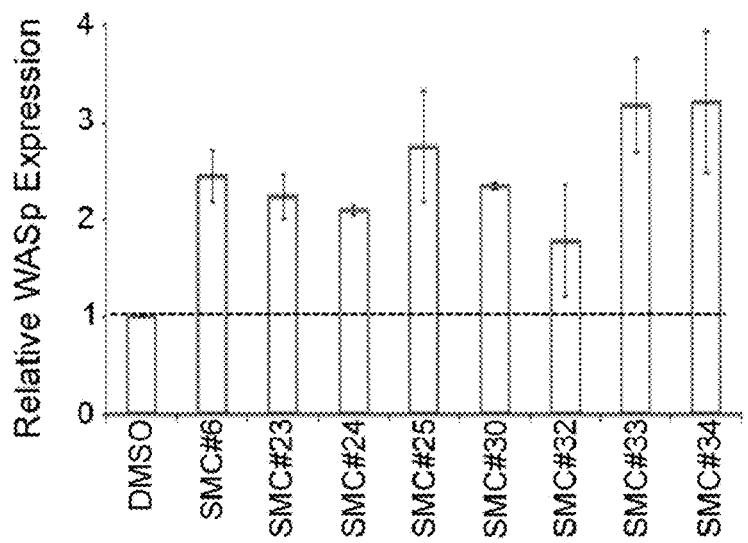
Fig. 6C
Fig. 6D
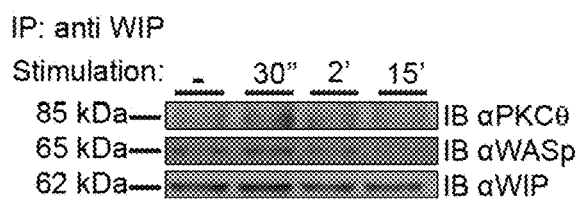
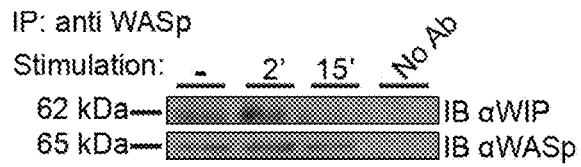
Fig. 7A
Fig. 7B

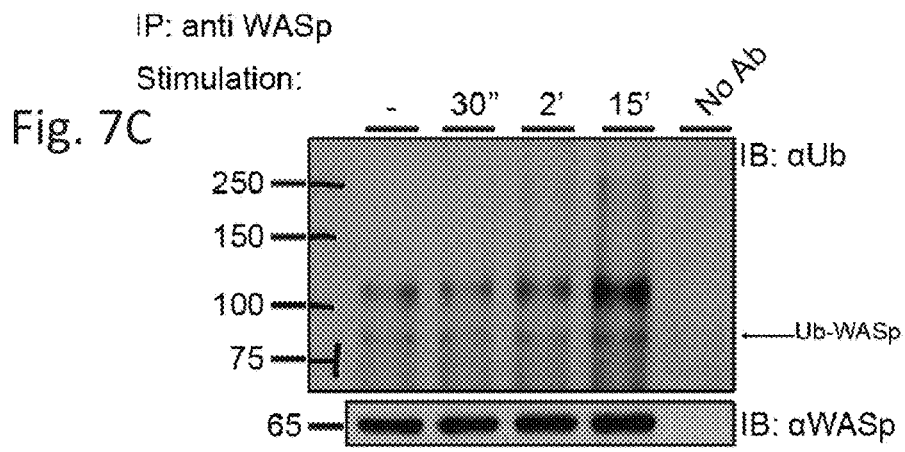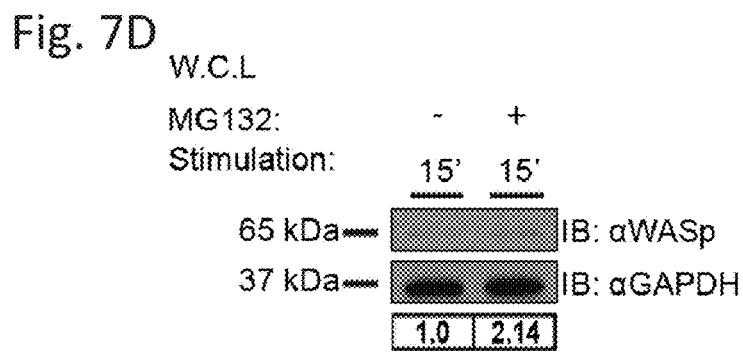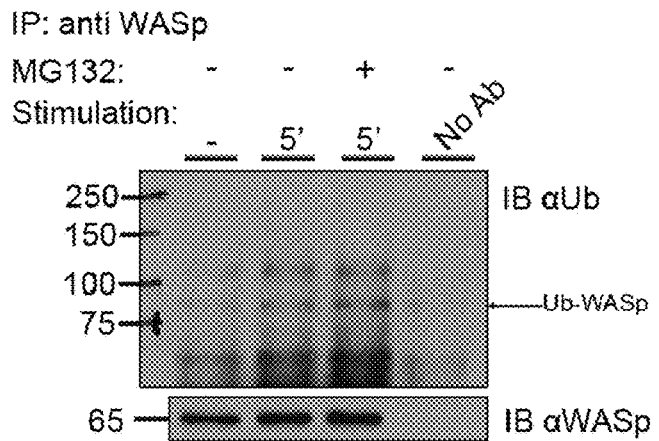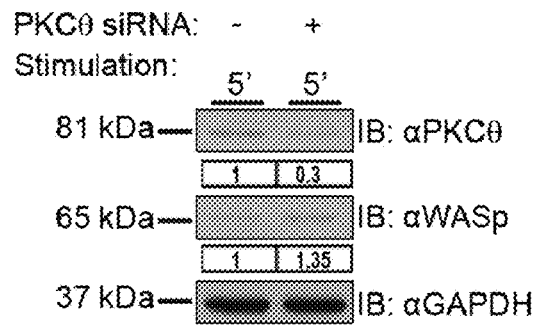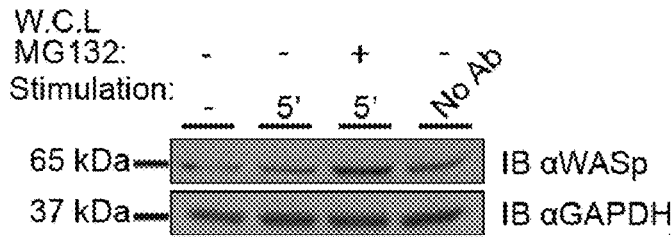

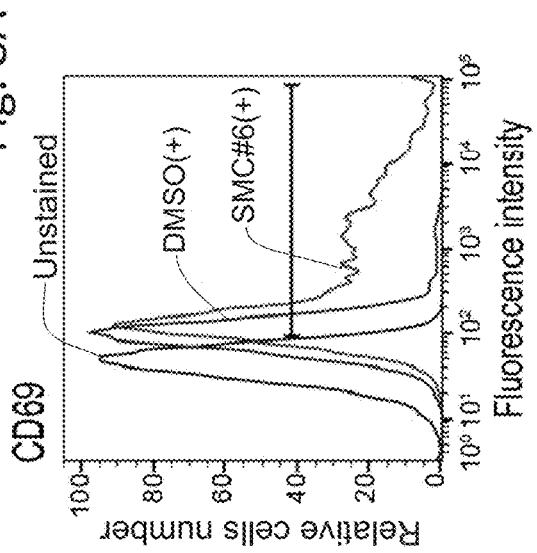
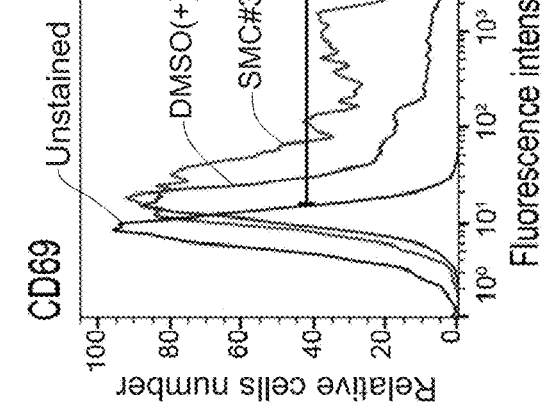
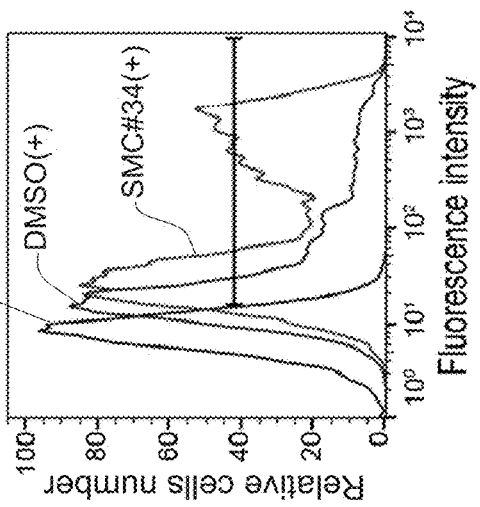
Fig. 8A
Fig. 8B
Fig. 8C
Fig. 8D

WASp-PROTECTING SMALL MOLECULES, COMPOSITIONS, METHODS AND USES THEREOF IN THE TREATMENT OF INNATE AND ACQUIRED IMMUNE-RELATED DISORDERS OR CONDITIONS

The Sequence Listing in ASCII text file format of 29,090 bytes in size, created on Jul. 2, 26, 2021, with the file name "2021-07-26SequenceListing_BARDA-SAAD2A_ST25," filed in the U.S. Patent and Trademark Office on even date herewith, is hereby incorporated herein by reference.

FIELD OF THE INVENTION

The present invention pertains to the field of molecular immunology and hematology. More specifically, the present invention provides specific small molecule compounds that modulate degradation of Wiskott-Aldrich Syndrome protein (WASp), methods and uses thereof in innate and acquired immune-related disorders or conditions.

BACKGROUND ART

References considered to be relevant as background to the presently disclosed subject matter are listed below:
H. D. Ochs, A. J. Thrasher, The Wiskott-Aldrich syndrome. *The Journal of Allergy and Clinical Immunology* 117, 725-738; quiz 739 (2006).
M. H. Albert, et al *Blood* 115, 3231-3238 (2010).
J. M. Derry, et al., *Cell* 79, following 922 (1994).
O. Matalon, et al., *Immunological Reviews* 256, 10-29 (2013).
N. Joseph, *Biochimica et Biophysica Acta (BBA)—Biomembranes*, 105:481-93 (2013).
Y. Jin, et al., *Blood* 104, 4010-4019 (2004).
M. I. Lutskiy, F et al., *Journal of Immunology* 175, 1329-1336 (2005).
D. Buchbinder, et al., *The Application of Clinical Genetics* 7, 55-66 (2014). Filipovich, *Bone Marrow Transplantation* 42 Suppl 1, S49-S52 (2008).
C. R. Shin, et al., *Bone Marrow Transplantation* 47, 1428-1435 (2012).
J. Litzman, et al., *Archives of Disease in Childhood* 75, 436-439 (1996). L. Khavrutskii, et al., *Journal of Visualized Experiments: JoVE* 15, (2013) A. Konno, et al., *International Immunology* 19, 185-192 (2007).
E. Noy, et al., *International Journal of Molecular Sciences* 13, 7629-7647 (2012).
S. Fried, et al., *Science Signaling* 7, ra60 (2014).
B. Reicher, et al., *Molecular and Cellular Biology* 32, 3153-3163 (2012)
M. Barda-Saad, et al., *Nature Immunology* 6, 80-89 (2005)
M. I. Lutskiy, et al., *British Journal of Haematology* 139, 98-105 (2007)
A. Shcherbina, et al., *Blood* 98, 2988-2991 (2001)
J. K. Burkhardt, et al., *Annual Review of Immunology* 26, 233-259 (2008).
D. Varga-Szabo, et al., *Journal of Thrombosis and Haemostasis* 7, 1057-1066 (2009).
Aiuti, L, et al., *Science* 341, 1233151 (2013).
S. Hacein-Bey Abina, et al., *JAMA* 313, 1550-1563 (2015).
H. Albert, et al., *Science translational medicine* 6, 227ra233 (2014).
F. C. Peterson, et al., *The Journal of biological chemistry* 282, 8446-8453 (2007).
M. H. Pauker, et al., *Molecular and cellular biology* 31, 2653-2666 (2011).
H. M. Pauker, et al., *Science Signaling* 5(221):rs3 (2012)
F. A. Ran, et al., *Nature protocols* 8, 2281-2308 (2013).
S. B. Snapper, et al., Immunity 9, 81-91 (1998).
J. A. Doudna, et al., Science 346, 1258096 (2014).
Charrier, S., et al., Gene therapy 14 (2007), 415-428.
Snapper, S. B., et al., Journal of leukocyte biology 77 (2005), 993-998.
Zhang, H., et al., Immunity 25 (2006), 285-295.
Gunn, M. D., et al., The Journal of experimental medicine 189 (1999), 451-460.
Altman, L. C., et al., The Journal of clinical investigation 54 (1974), 486-493.
Linder, S. & Kopp, P. Journal of cell science 118 (2005), 2079-2082.
Linder, S., et al., Proceedings of the National Academy of Sciences of the United States of America 96 (1999), 9648-9653.
Zhang, J., et al., The Journal of experimental medicine 190 (1999), 1329-1342.
Matalon, O., et al., Science signaling 9 (2016), ra54.
Lee, S. H., et al., J Immunol 183 (2009), 7931-7938.
Anfossi, N., et al., Immunity 25 (2006), 331-342.
D. Schneidman-Duhovny, et al. *Nucleic acids research* 33, W363-367 (2005).

Acknowledgement of the above references herein is not to be inferred as meaning that these are in any way relevant to the patentability of the presently disclosed subject matter.

BACKGROUND OF THE INVENTION

Wiskott-Aldrich syndrome (WAS) is a severe primary immunodeficiency whose symptoms include recurrent infections, severe bleedings caused by microthrombocytopenia; a decrease in the number and size of platelets, and an increased incidence of autoimmunity and lymphoma (Ochs et al, 2006). X-linked thrombocytopenia (XLT) is considered a "mild" version of WAS, and is characterized mainly by frequent bleeding events caused by the severe microthrombocytopenia of these patients (Albert et al 2010). The defective gene responsible for WAS or XLT, the WAS gene, is located on the short arm of the X chromosome (Xp11.22-p11.23.1) and encodes a 502-amino acid protein—the WAS protein (WASp) (Derry et al, 1994).

WASp, which is expressed in hematopoietic cells, is an adaptor protein that facilitates actin cytoskeletal rearrangements, which are essential for normal immune cell responses. WASp-dependent immune cell functions include actin polymerization, sustaining of the immunological synapse, endocytosis, calcium flux, NFAT gene transcription, cellular activation and proliferation (Matalon et al, 2013; Joseph et al, 2013). More than 300 mutations spanning the entire WAS gene have been identified. These mutations reduce WASp expression, which is strongly correlated with the severity of the disease. The severe phenotypes manifested in classical WAS usually occur where WASp is completely absent, while partial or residual WASp expression is associated mainly with the less severe phenotype of XLT (Jin et al, 2004; Lutskiy et al, 2005). WAS and XLT are diagnosed in about 1 to 10 patients per million male newborns worldwide. Without early intervention, most WAS patients die during the first decade of their life from opportunist infections, while XLT patients exhibit a normal life span but frequently suffer from life-threatening hemorrhages (Ochs et al, 2006; Buchbinder et al, 2014).

Intriguingly, WAS gene mutations are usually normally transcribed, and aberrant WASp expression is therefore the result of post-translational protein instability. Accordingly, the majority of WAS mutations alter WASp binding to WASp-interacting protein (WIP), a chaperone of WASp that protects WASp from proteolysis (Reicher et al, 2012; Lutskiy et al, 2005; Konno et al 2007; Noy et al, 2012). The molecular degradation mechanism of WASp was recently deciphered by the present inventors (Reicher et al, 2012; Fried et al, 2014). In resting cells WASp is auto inhibited and is tightly bound to WIP, which masks its degradation sites, lysine residues 76 and 81, located in a pocket at the N'-terminal WASp-homology-1 (WH1) domain of WASp. Following cellular activation a cascade of signaling events leads to the release of WASp from auto inhibition, its recruitment to the cell membrane and actin rearrangement at the leading edge. Later in the activation process, WASp is phosphorylated on tyrosine 291 and WIP is phosphorylated by PKCθ on serine 488. These phosphorylation events induce the recruitment of Cbl-family E3 ligases to WASp, and trigger a conformational change that releases WIP protection from the degradation pocket of WASp. Subsequently, WASp lysines 76 and 81 are ubiquitylated, marking it for proteasomal degradation. Thus, partial or complete WASp deficiency of WAS/XLT patients is the result of constant, unregulated, ubiquitylation and degradation of WASp that is not properly protected by WIP.

Unfortunately, currently there are no curative treatments for WAS/XLT, except for allogeneic hematopoietic stem cell transplantation (HSCT), which requires identification of a suitable donor and can result in significant complications (Filipovich et al, 2008; Shin et al, 2012). Moreover, due to high risk-benefit ratio, HSCT is usually not a recommended treatment for XLT patients. For these patients, elective splenectomy is usually the treatment of choice, as removal of the spleen has shown to increase platelet count. However, splenectomy is not curative and has potential risks, such as insufficient production of antibodies and infections (Albert et al 2010; Litzman et al, 1996). Therefore, a safe and effective treatment is needed, which addresses the needs of both WAS and XLT patients.

WO 2014/195857 that is a previous publication by the inventors, discloses liposomal compositions comprising WASp modulators that may be used either in reducing WASp levels in hematopoietic malignancies, or alternatively, enhance WASp levels in WAS, XLT and associated disorders.

As WASp is a key regulator essential for the activity and function of most immune cells, increasing WASp expression offers a method to potentially boost the performance of the immune response.

The need for a safe and efficient treatment for both WAS and XLT led the inventors to develop a new and different therapeutic approach, which unlike gene correction, is based on the molecular mechanism of the disease and focuses on defending native WASp from degradation rather than replacing it.

SUMMARY OF THE INVENTION

A first aspect of the invention relates to an effective amount of at least one small molecule compound (SMC) modulator or any vehicle, matrix, nano- or micro-particle comprising the same, for use in a method for modulating the degradation and stability of Wiskott-Aldrich Syndrome protein (WASp) in a cell. In more specific embodiments, the modulator of the invention may have the general formula (XI):

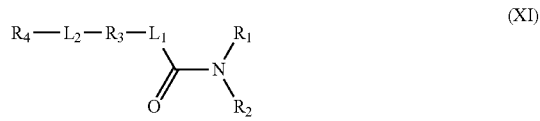

or a pharmaceutically acceptable salt, solvate, hydrate, stereoisomer or physiologically functional derivative thereof, wherein $R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl or $R_1$ and $R_2$ together with the nitrogen atom they are connected to form a five to seven membered saturated or unsaturated ring optionally include at least one of N, O and optionally substituted with at least one of straight $C_1$-$C_5$ alkyl, L1 and L2 are each independently from each other to be absent or selected to be absent or from —$CH_2$— ($CH_2$—C(O)—N)—($CH_2$)$_2$, —($CH_2$)—S—, —($CH_2$)—, —($CH_2$)—O—, —NH—($CH_2$)—, and each optionally substituted with $C_1$-$C_5$ alkyl, a ring system containing five to twelve atoms optionally substituted with $C_1$-$C_5$ alkyl;

$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl.

A further aspect of the invention relates to a method for modulating degradation and/or stability of WASp in a cell. More specifically, the method comprises the step of contacting the cell with an effective amount of at least one of the SMC modulators of WASp as described by the invention or a pharmaceutically acceptable salt, esters or hydrate thereof or any analogs or derivatives thereof, any combination thereof, or any vehicle, matrix, nano- or micro-particle, or composition comprising the same.

In yet a further aspect, the invention relates to a method for treating, preventing, inhibiting, reducing, eliminating, protecting or delaying the onset of a disorder associated (either hereditary or acquired) with dysfunction of WASp in a subject in need thereof. More specifically, the method may comprise administering to the subject a therapeutically effective amount of at least one of the SMC modulators of WASp as described by the invention or a pharmaceutically acceptable salt, esters or hydrate thereof or any analogs or derivatives thereof, any combinations thereof, or of any vehicle, matrix, nano- or micro-particle or composition comprising the same.

In yet another aspect thereof, the invention provides the use of an effective amount of at least one of the SMC modulators of WASp as described by the invention or a pharmaceutically acceptable salt, esters or hydrate thereof, any analogs or derivatives thereof or any combination thereof, or any vehicle, matrix, nano- or micro-particle comprising the same, in the preparation of a composition for treating, preventing, inhibiting, reducing, eliminating, protecting or delaying the onset of a hereditary or acquired disorders associated with dysfunction of WASp in a subject in need thereof.

The invention further provides SMC modulator of WASp degradation and/or stability. In more specific embodiments, the modulator of the invention may have the general formula (XI):

$$R_4-L_2-R_3-L_1 \underset{O}{\overset{R_1}{\underset{\|}{\diagdown}}}N\diagdown R_2$$
(XI)

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl
or
$R_1$ and $R_2$ together with the nitrogen atom they are connected to form a five to seven membered saturated or unsaturated ring optionally include at least one of N, O and optionally substituted with at least one of straight $C_1$-$C_5$ alkyl,
L1 and L2 are each independently from each other selected to be absent or from —$CH_2$—($CH_2$—C(O)—N)—($CH_2$)$_2$, —($CH_2$)—S—, —($CH_2$)—, —($CH_2$)—O—, —NH—($CH_2$)—, and each optionally substituted with $C_1$-$C_5$ alkyl, a ring system containing five to twelve atoms optionally substituted with $C_1$-$C_5$ alkyl;
$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl.

A further aspect of the invention relates to a pharmaceutical composition comprising a therapeutically effective amount of at least one of the SMC modulators of WASp as described by the invention or a pharmaceutically acceptable salt, esters or hydrate thereof or any analogs or derivative thereof, or any vehicle, matrix, nano- or micro-particle comprising the same, said composition optionally further comprises at least one pharmaceutically acceptable carrier/s, excipient/s, auxiliaries, and/or diluent/s.

Still further, the invention provides a kit comprising: a. at least one SMC modulator as disclosed by the invention; and at least one of: b. at least one chemotherapeutic agent; c. at least one biological therapy agent; and d. at least one agent that induces differentiation of hematopoietic progenitor cells.

These and other aspects of the invention will become apparent by the hand of the following drawings.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1B-1C. shows a ribbon and surface structures of WASp WH1 model. Lysine residues 76 and 81 are light gray and dark gray, respectively.

A schematic representation of the in silico prediction process. Rectangles denote data representative from a single protein-ligand interaction. Stacks of rectangles denote the data representative of all ligand models that were used. Oval shapes denote the major programs that were used in the process. The protein surface diagram denotes the modified NMR model of the N-WASp WH1 domain in PDB format. Using the FAST algorithm, 3D conformations of the various ligands were generated, and inputted to PatchDock with the modified NMR model. Features were extracted from the leading docking model and from the docking scores of all the models generated by PatchDock, and combined into a data vector. Finally, the predictor classified each ligand-protein docking using the data vector, giving each a score denoting whether it is predicted to be representative of a possible binding.

FIG. 3A-3G. MST analysis validates the binding of virtually-screened SMCs to WASp but not to its homologous, N-WASp and WAVE2

Diluted cell lysates of YFP-WASp/N-WASp/WAVE2-expressing HEK 293T cells were incubated with serially-diluted (100 μM-3 nM) SMCs. The mixed lysates and SMCs were then loaded into standard-treated Monolith™ capillaries and the fluorescence of the samples was measured by the Monolith NT.115 instrument at 60% MST power. Binding curves of WASp with SMC #6 (FIG. 3A), SMC #30 (FIG. 3B), SMC #33 (FIG. 3C), SMC #34 (FIG. 3D) and Y-27632 (FIG. 3E) or of N-WASp (FIG. 3F) or WAVE2 (FIG. 3G) with SMC #34 were generated by the NanoTemper Analysis 2.231 software. Normalized fluorescence (hot fluorescence/initial fluorescence) is plotted as a function of SMC concentration. Data shown are representative of at least three independent experiments.

Figure 4A:
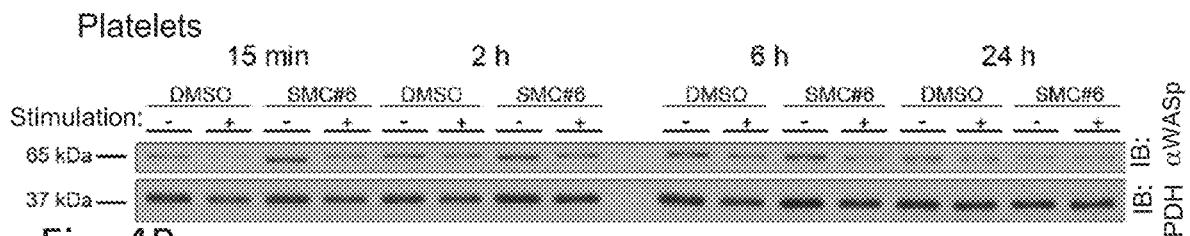
Figure 4B:
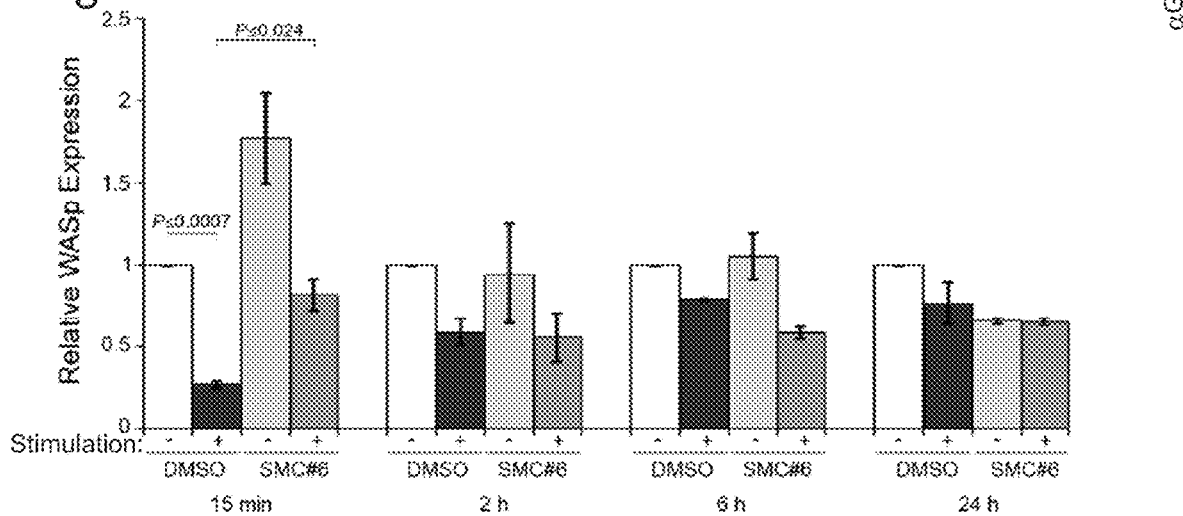

FIG. 4A-4D. SMC of the invention upregulates WASp expression in platelets and primary lymphocytes FIG. 4A-4B. Freshly-isolated platelets were incubated with SMC #6 or control at 37° C. for the indicated times. The platelets were either stimulated (+) with TRAP-6 (10 μM) or left unstimulated (−), followed by lysis. Lysates were analyzed for WASp expression by immunoblotting with anti-WASp and anti-GAPDH as loading control (FIG. 4A). Relative WASp expression was determined by densitometric analysis and is presented in a summarizing graph of FIG. 4B. Error bars represent the SE from the mean. P values are presented and were calculated by two-tailed Student's t-test. Data are representative of three independent experiments.

Figure 4C:
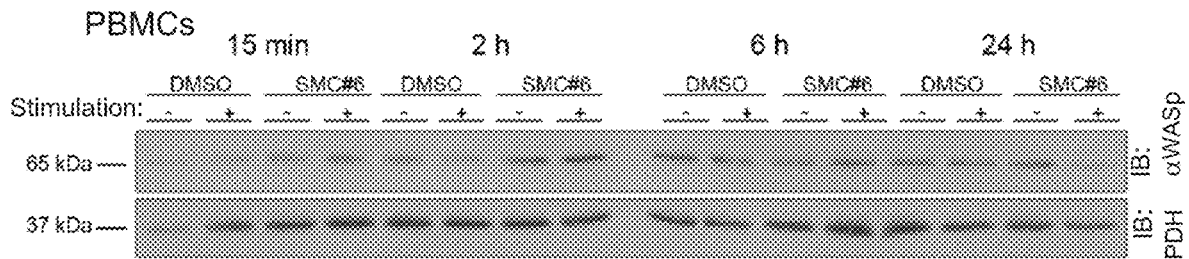
Figure 4D:
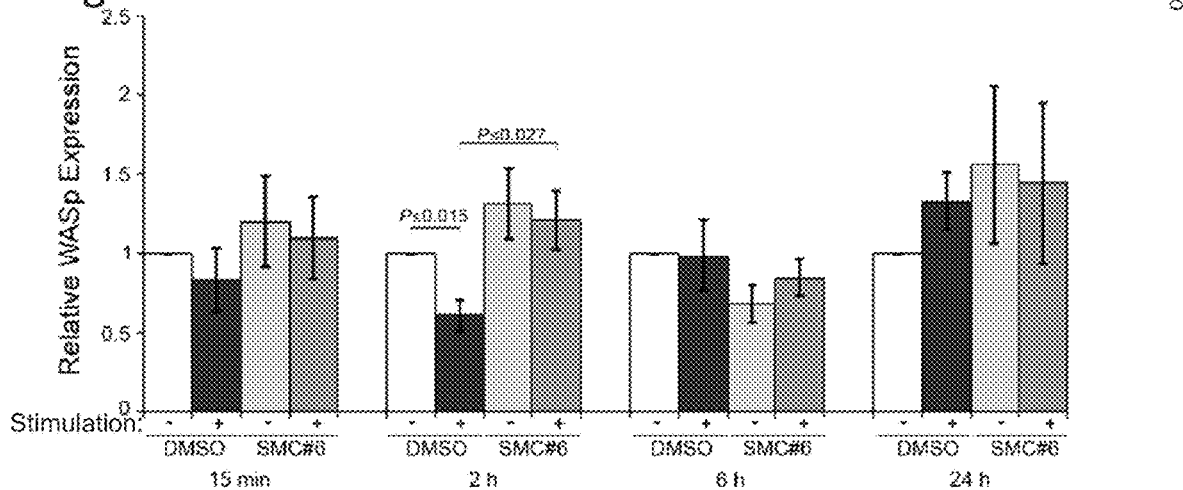

FIG. 4C-4D. Freshly-isolated PBMCs were incubated with SMC #6 or control at 37° C. for the indicated times. The PBMCs were either co-stimulated (+) with anti-CD3 and anti-CD28 or left unstimulated (−), followed by lysis. Lysates were analyzed for WASp expression by immunoblotting with anti-WASp and anti-GAPDH as loading control (FIG. 4C). Relative WASp expression was determined by densitometric analysis and is presented in a summarizing graph of FIG. 4D. Error bars represent the SE from the mean. P values were calculated versus DMSO-treated control cells by two-tailed Student's t-test, and is indicated therein. Data are representative of three independent experiments.

Figure 5A:
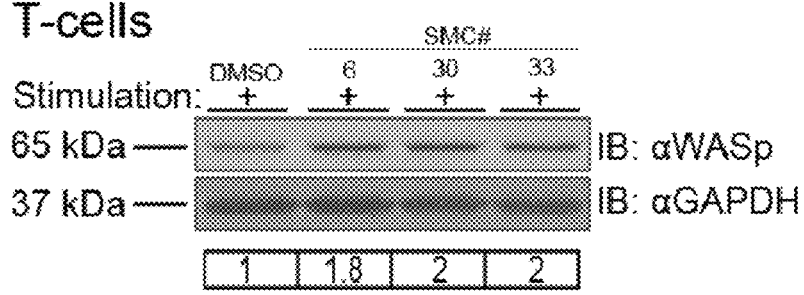
Figure 5B:
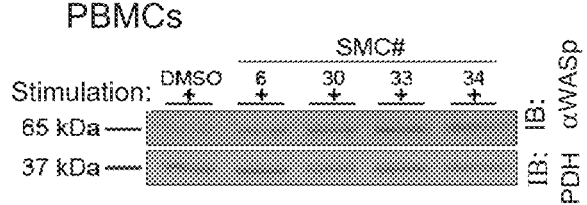
Figure 5C:
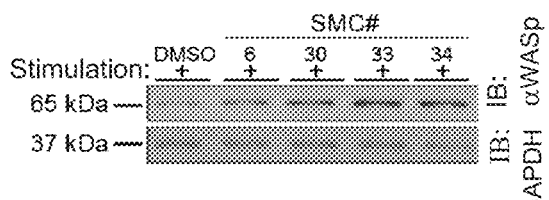
Figure 5D:
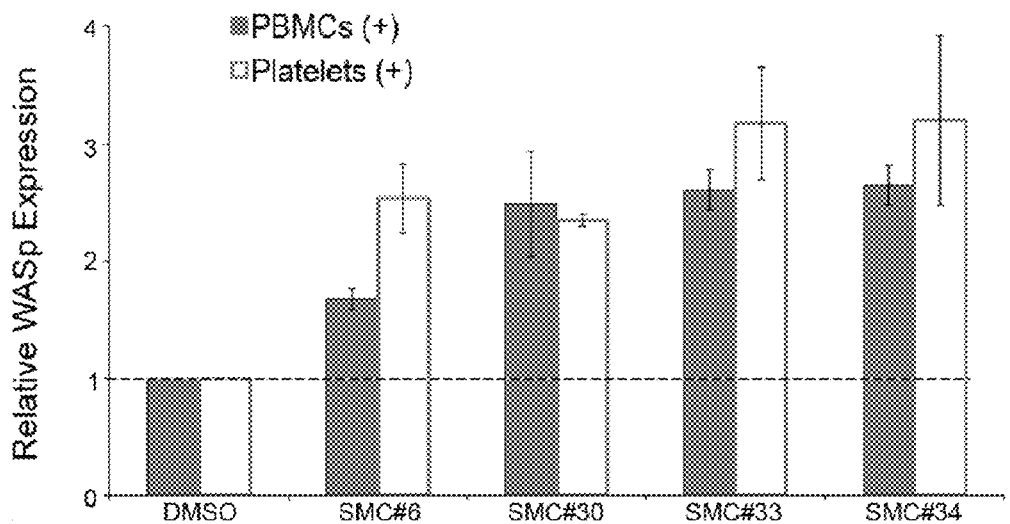

FIG. 5A-5D. WASp-binding SMCs upregulate WASp expression in T-cells, primary lymphocytes and platelets Jurkat T-cells (FIG. 5A) or Freshly-isolated PBMCs (FIG. 5B) were incubated for 15 min at 37° C. with either control or the indicated WASp-binding SMCs, followed by co-stimulation with anti-CD3 and anti-CD28 and lysis. Freshly-isolated platelets were incubated for 15 min at 37° C. with either control or the indicated WASp-binding SMCs, followed by stimulation with TRAP-6 (10 µM) and lysis (FIG. 5C). Lysates were analyzed for WASp expression by immunoblotting with anti-WASp and anti-GAPDH as loading control. Western blot is representative of three independent experiments. FIG. 5D shows a summary of WASp expression analysis in PBMCs and platelets. Relative WASp expression was determined by densitometric analysis. Error bars represent the SE from the mean. Data are representative of three independent experiments.

FIG. 6A-6D. WASp-binding SMCs upregulate WASp expression in platelets FIG. 6A-6B. show freshly-isolated platelets that were incubated for 15 min at 37° C. with either DMSO or the indicated WASp-binding SMCs, followed by stimulation (+) with TRAP-6 (10 µM) and lysis. Lysates were analyzed for WASp expression by immunoblotting with anti-WASp and anti-GAPDH as loading control (FIG. 6A). Summarizing graph is presented in FIG. 6B.

FIG. 6C-6D. show the western blot of freshly-isolated platelets incubated for 15 min at 37° C. with either DMSO or potent WASp-binding SMCs that were stimulated with TRAP-6 (10 µM), followed by lysis (FIG. 6C). Error bars represent the SE from the mean. Data are representative of three independent experiments. Summarizing graph is presented in FIG. 6D.

FIG. 7A-7G. Characterization of ubiquitylation-dependent degradation mechanism of WASp in platelets and megakaryocytes Freshly-isolated platelets were stimulated with 10 µM of TRAP-6 for the indicated time points, followed by lysis. WIP (FIG. 7A) or WASp (FIG. 7B) were immunoprecipitated from the lysates and analyzed by western blot for co-immunoprecipitation, using anti-WASp, anti-WIP or anti-PKCθ antibodies. WASp immunoprecipitates were immunoblotted for WASp ubiquitylation using anti-ubiquitin (Ub) antibody (FIG. 7C). Ubiquitylated WASp appears as a smear of bands above the MW of 65 kDa with a prominent band at ~81 kDa. FIG. 7D shows western blot analysis of WASp expression in activated platelets, with (+) or without (−) the addition of MG132 proteasome inhibitor. Blots are representative of three independent experiments. Meg-01 megakaryocyte cell line was activated in the presence (+) or absence (−) of MG132, followed by lysis (FIG. 7E). WASp ubiquitylation was determined by co-immunoprecipitation analysis as in FIG. 7C. FIG. 7F illustrates Meg-01 cells that were transfected with PKCθ-specific siRNA (+) or non-specific (NS) siRNA (−). 24 h later, the cells were stimulated and lysed. PKCθ and WASp protein expression levels were analyzed by western blot with anti-PKCθ and anti-WASp antibodies, and with anti-GAPDH as loading control. Relative protein expression was determined by densitometric analysis and is presented below the corresponding lanes. FIG. 7G. shows western blot analysis of WASp expression in whole cell lysates (W.C.L) of megakaryocyte, with (+) or without (−) the addition of MG132 proteasome inhibitor. Blots are representative of three independent experiments.

FIG. 8A-8D. WASp-binding SMCs up-regulate lymphocyte activation and proliferation Figures show $1 \times 10^6$ PBMC cells/ml stimulated with PMA and Ionomycin that were treated with DMSO or WASp-binding SMCs. After incubation, the cells were stained with PE-Cy5™-conjugated mouse anti-human CD69 and lymphocyte activation was measured by flow-cytometry as described in the Experimental procedures. Histograms of DMSO versus SMC #6 (FIG. 8A), SMC #30 (FIG. 8B), SMC #33 (FIG. 8C), and SMC #34 (FIG. 8D) are presented and represent three independent experiments.

Figure 9A:
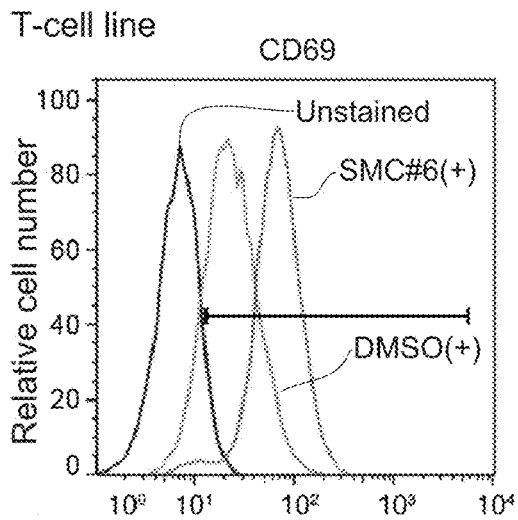
Figure 9B:
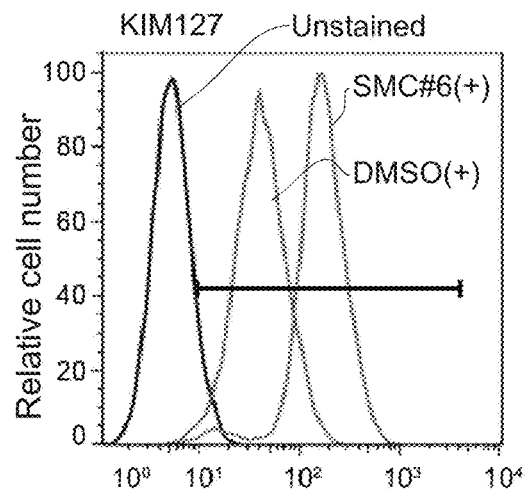

FIG. 9A-9E. WASp-binding SMCs upregulate lymphocyte activation and proliferation FIGS. 9A and 9B, show $1 \times 10^6$ Jurkat T cells/ml, stimulated with PMA and Ionomycin, were treated with WASp-binding SMC #6 or control. After incubation, the cells were stained with anti-activated LFA-1 antibody (KIM127), followed by staining with Alexa488-Fluor goat anti-mouse $IgG_1$ secondary antibody (FIG. 9B). Cells were co-stained with PE-Cy5™-conjugated mouse anti-human CD69 and lymphocyte activation was measured by flow-cytometry as described in the Experimental procedures (FIG. 9A). Histograms of negative control versus SMC #6 are presented.

Figure 9C:
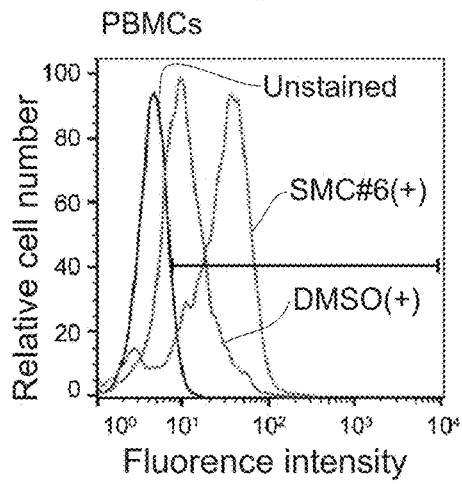

FIG. 9C. shows $1 \times 10^6$ PBMC cells/ml, stimulated with PMA and Ionomycin that were treated with WASp-binding SMC #6 or DMSO as negative control. After incubation, the cells were stained with anti-activated LFA-1 antibody (KIM127), followed by staining with Alexa488-Fluor goat anti-mouse $IgG_1$ secondary antibody, and lymphocyte activation was measured by flow-cytometry as described in the Experimental procedures. Histogram of negative control versus SMC #6 is presented.

Figure 9D:
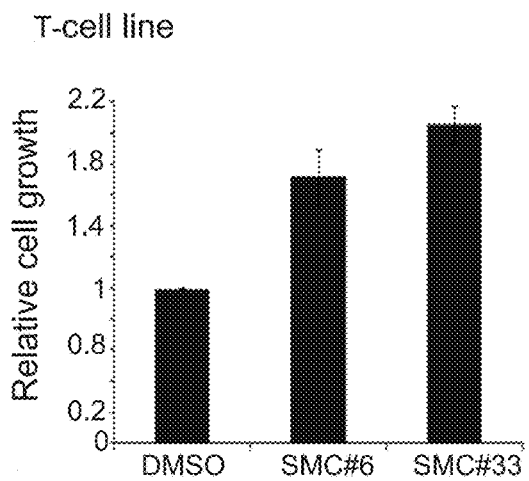

FIG. 9D. shows the mean relative proliferation of stimulated Jurkat T-cells, treated with the indicated WASp-binding SMCs or DMSO as negative control from three independent experiments. Error bars represent the SE from the mean.

Figure 9E:
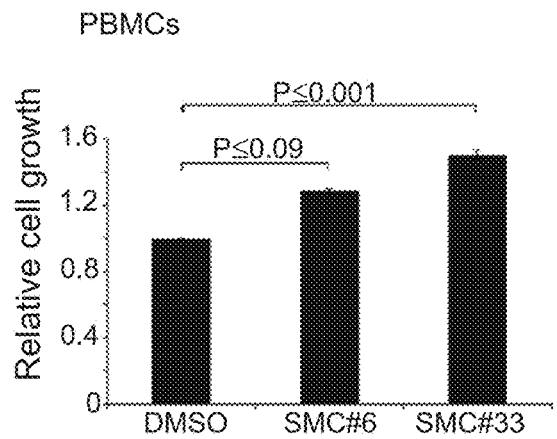

FIG. 9E. shows the mean relative proliferation of stimulated PBMCs, treated with the indicated WASp-binding SMCs or DMSO as negative control from three independent experiments. Error bars represent the SE from the mean.

Figure 10A:
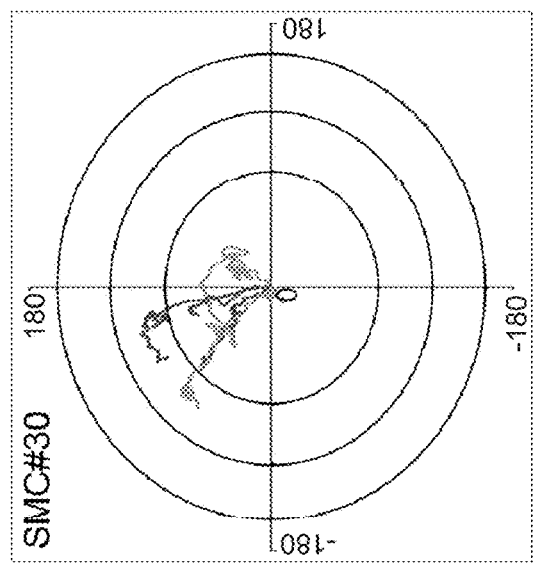
Figure 10A:
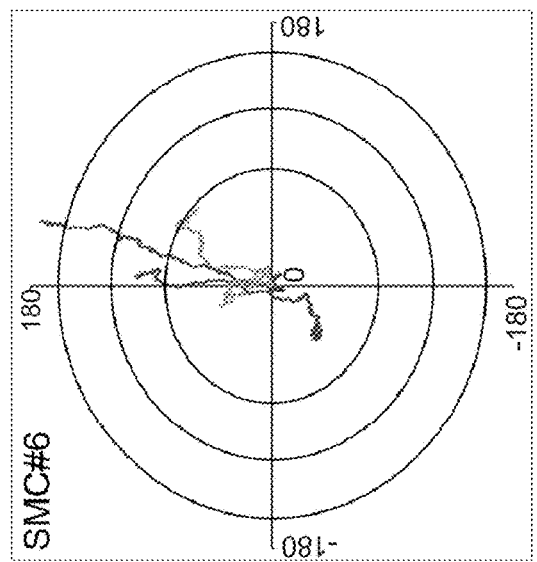
Figure 10A:
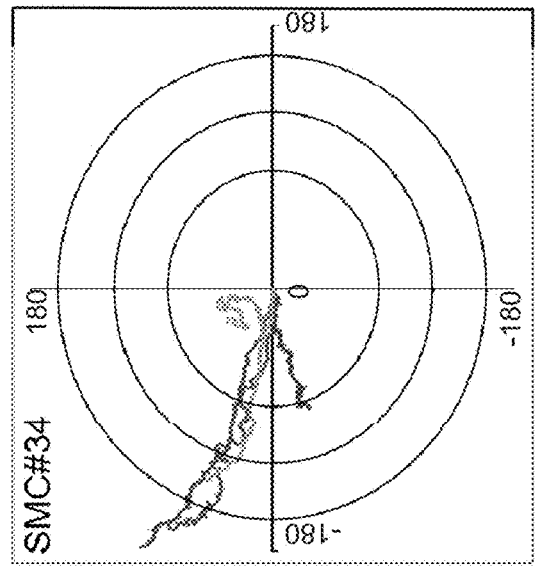
Figure 10A:
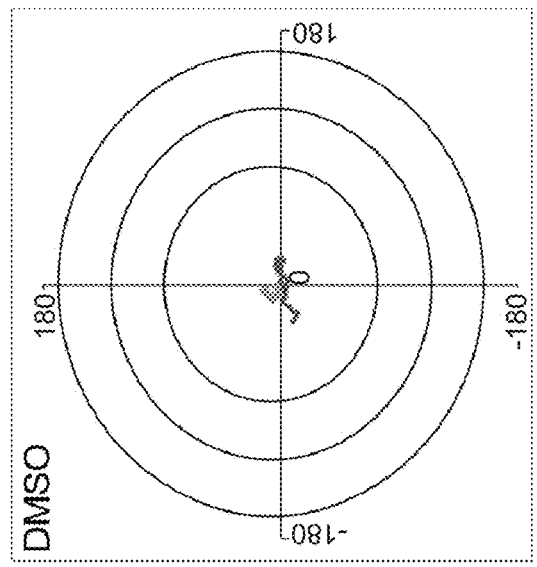
Figure 10A:
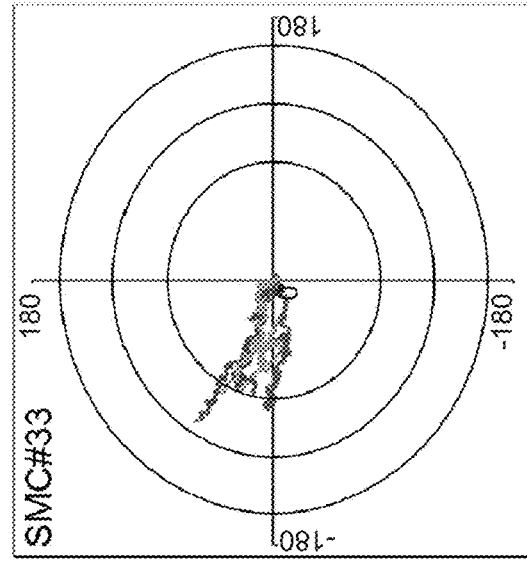
Figure 10B:
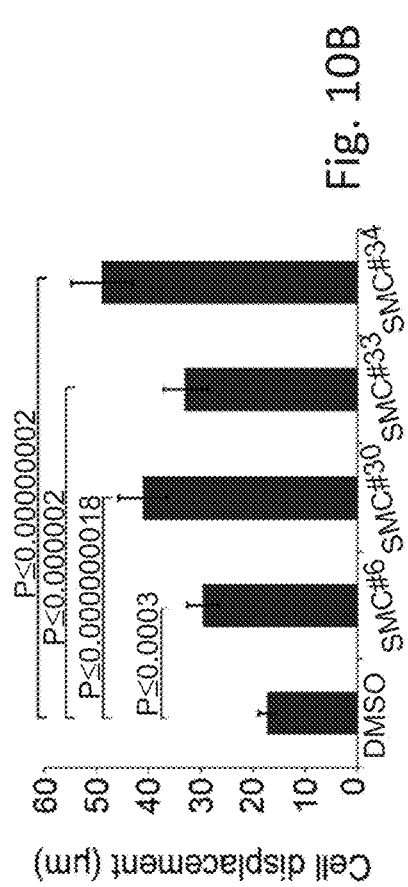
Figure 10C:
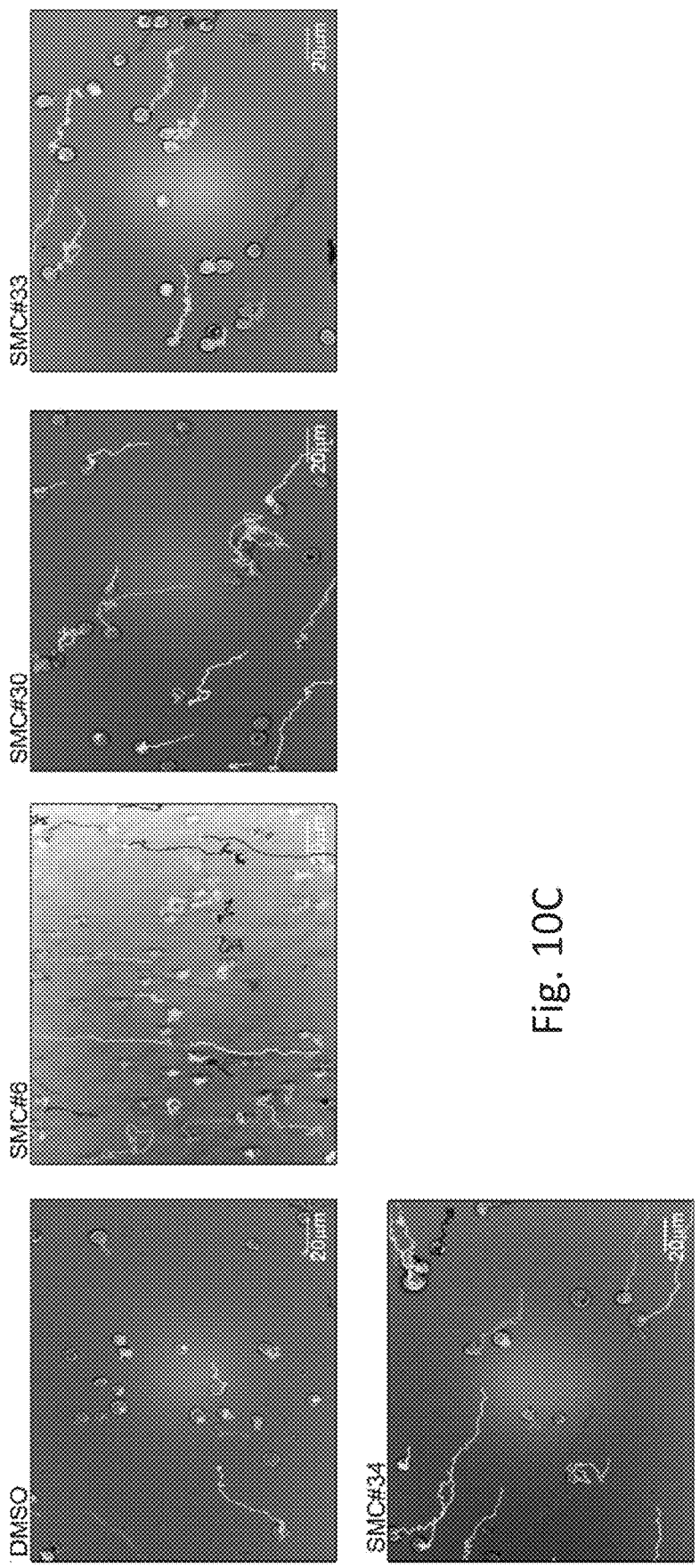

FIG. 10A-10C. WASp-binding SMCs enhance the migration of lymphocytes on ICAM-1

Jurkat T cells were pretreated with DMSO or the indicated WASp-binding SMCs, and cell migration on ICAM-1/SDF-1α-coated cover glasses was tracked over a 20-min period, as described in Experimental procedures. Each line in FIG. 10A represents one cell. The tracks of five representative cells from each treatment are presented.

FIG. 10B. shows mean cell displacement (DMSO: 17.25±1.58 n=337; SMC #6: 29.52±2.96 n=214; SMC #30: 41.07±4.69 n=55; SMC #33: 32.92±4.28 n=50; SMC #34: 48.91±6 n=60). Error bars represent the SE from the mean. P values versus DMSO-treated control cells are presented and were calculated by two-tailed Student's t-test.

FIG. 10C. illustrates the final frame of cells treated with DMSO or with the indicated WASp-binding SMCs.

Figure 11B:
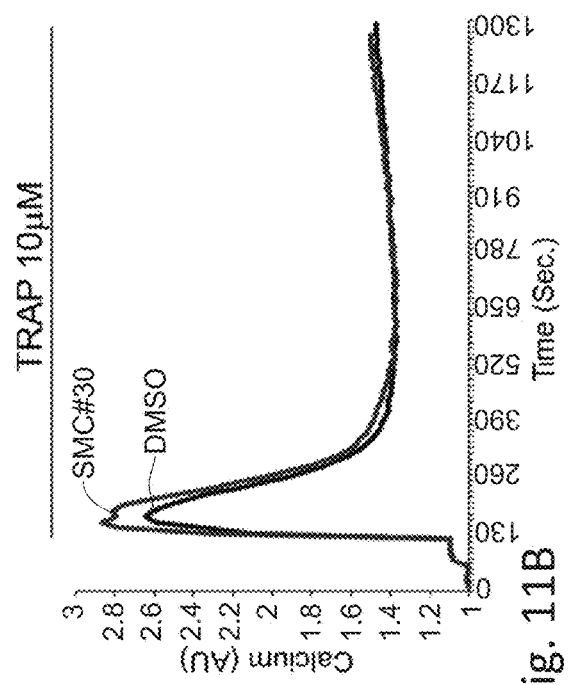
Figure 11D:
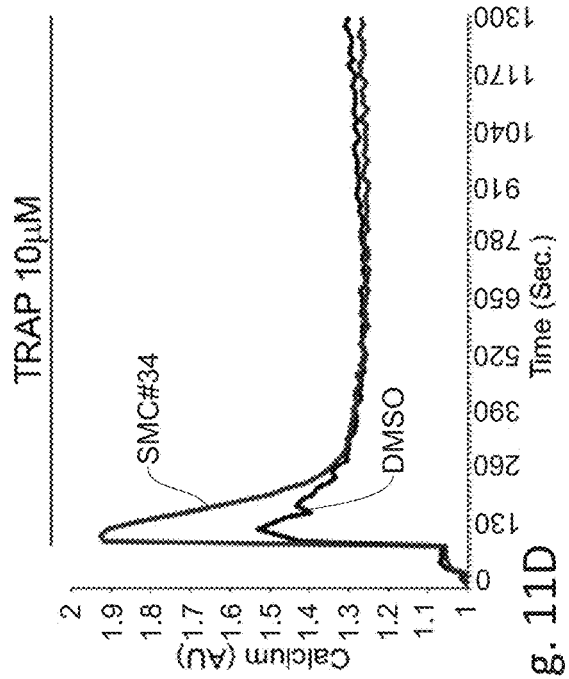
Figure 11A:
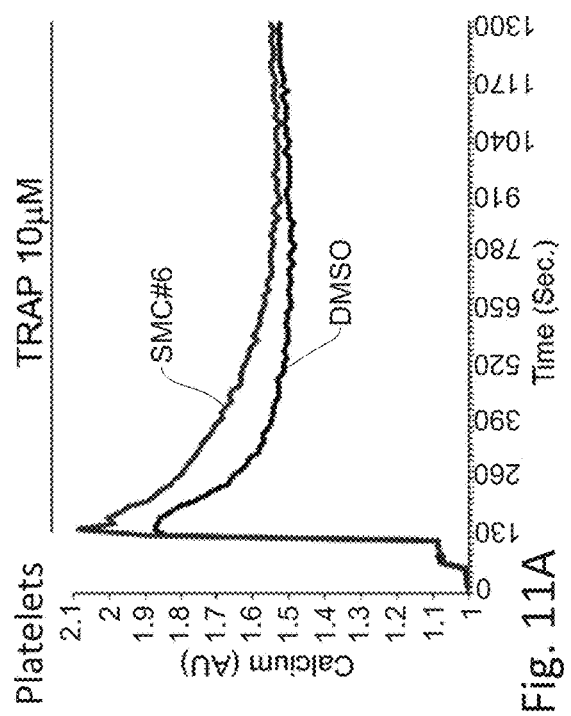
Figure 11C:
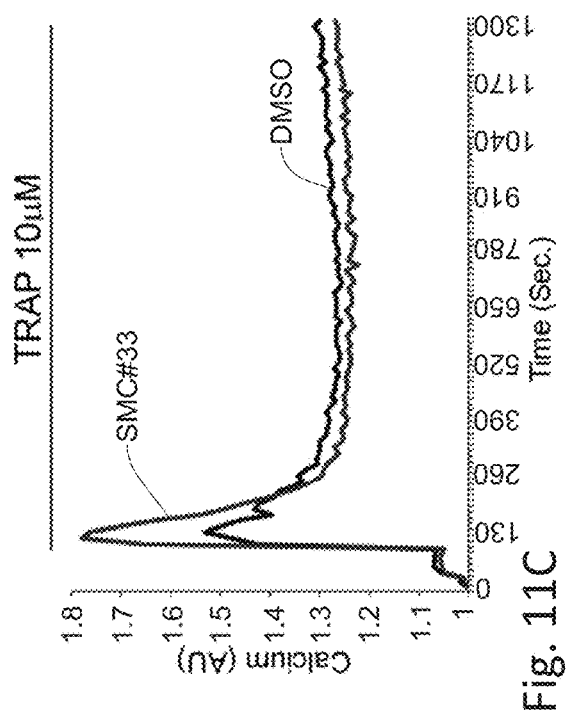

FIG. 11A-11D. WASp-binding SMCs increase intra-cellular calcium concentration in platelets Freshly-isolated human platelets were incubated with either control DMSO or the indicated WASp-binding SMCs, specifically, SMC #6 (FIG. 11A), SMC #30 (FIG. 11B), SMC #33 (FIG. 11C) and SMC #34 (FIG. 11D). Platelets were stimulated with TRAP-6 and calcium levels were measured by spectrofluorometer, as described in Experimental procedures. Data are representative of three independent experiments.

Figure 12A:
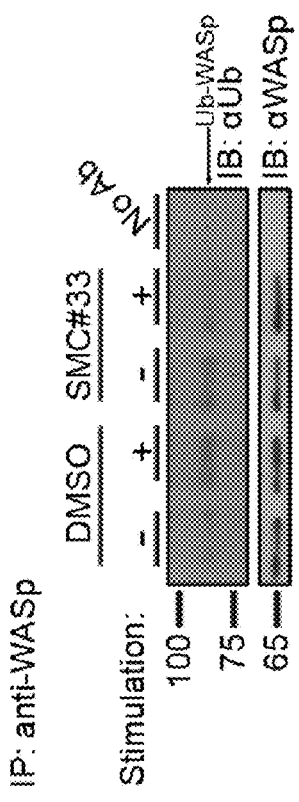
Figure 12B:
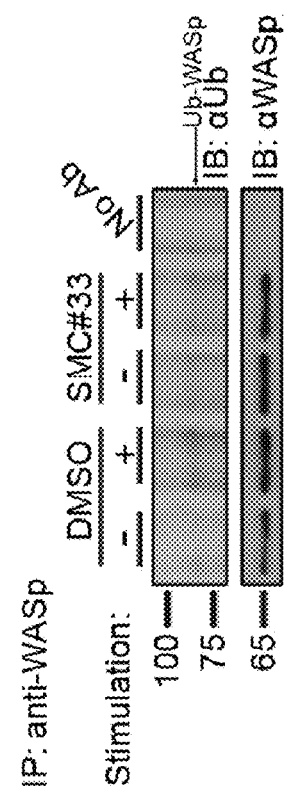

FIG. 12A-12D. WASp-binding SMCs decrease WASp ubiquitylation in platelets and primary lymphocytes FIGS. 12A and 12B. show freshly-isolated platelets that were either stimulated (+) with TRAP-6 (10 µM) or unstimulated (−) and pre-incubated at 37° C. for 15 min with either DMSO or the indicated WASp-binding SMCs (FIG. 12A—SMC #6; FIG. 12B—SMC #33), followed by lysis. Lysates were subjected to immunoprecipitation with anti-WASp antibody and were analyzed by western blotting with anti-ubiquitin (Ub) and with anti-WASp as precipitation control. Ubiquitylated WASp appears as a smear of bands above the molecular weight (MW) of 65 kDa with a prominent band at ~81 kDa. Blots are representative of three independent experiments.

Figure 12C:
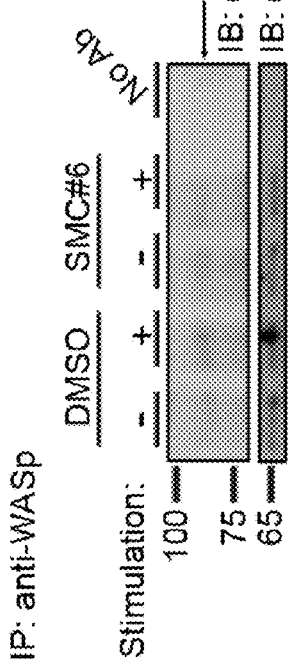
Figure 12D:
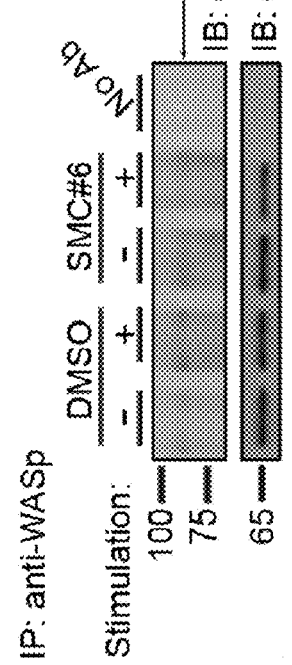

FIGS. 12C and 12D. show freshly-isolated PBMCs that were either co-stimulated (+) with anti-CD3 and anti-CD28 or unstimulated (−). The PBMCs were pre-incubated at 37° C. for 15 min with either DMSO or the indicated WASp-binding SMCs (FIG. 12C—SMC #6; FIG. 12D—SMC #33), followed by lysis. WASp ubiquitylation was determined by immunoprecipitation as in FIG. 12A-12B. Ubiquitylated WASp appears as a smear of bands above the MW of 65 kDa with a prominent band at ~81 kDa. Blots are representative of three independent experiments.

Figure 13A:
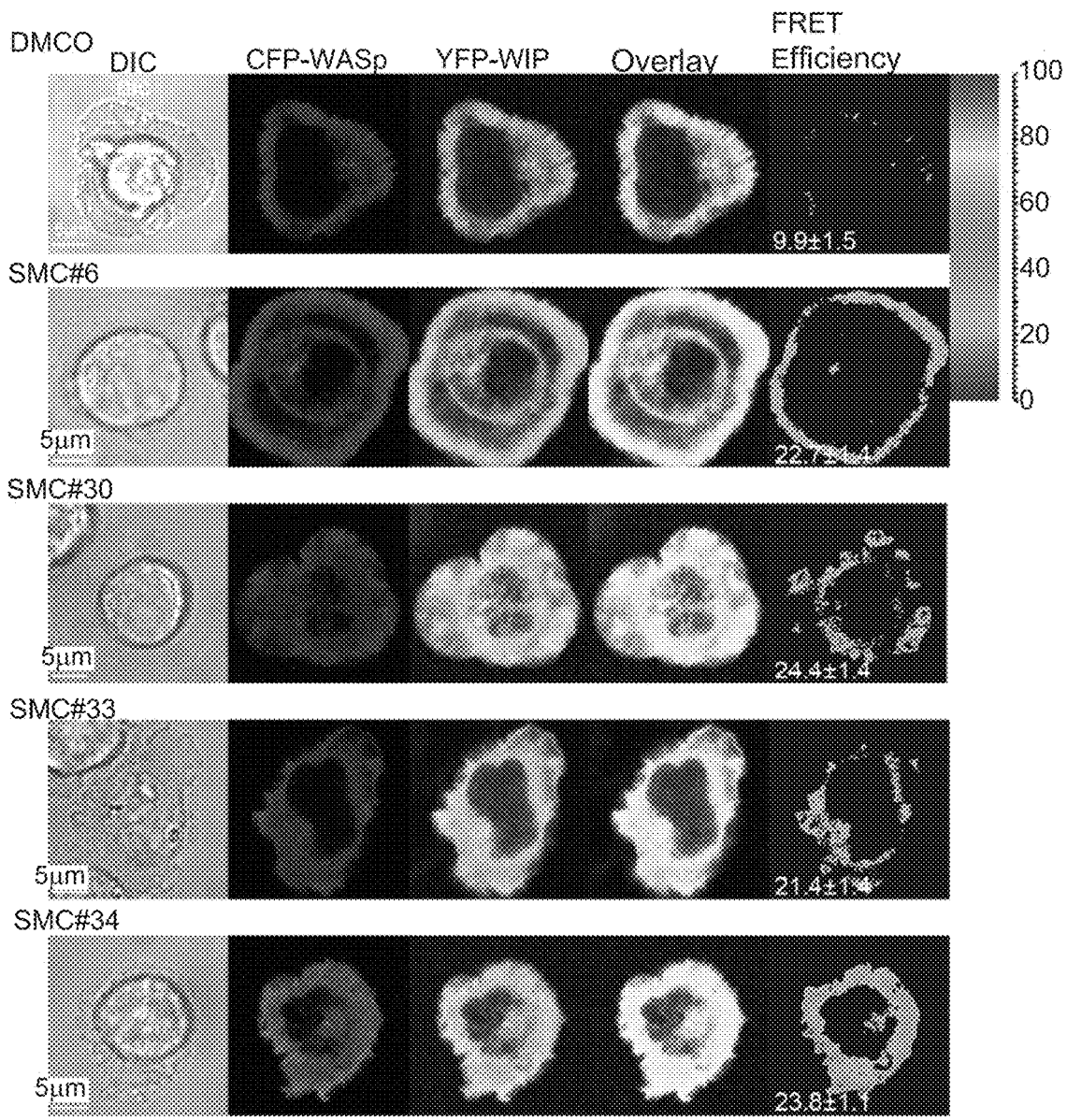
Figure 13B:
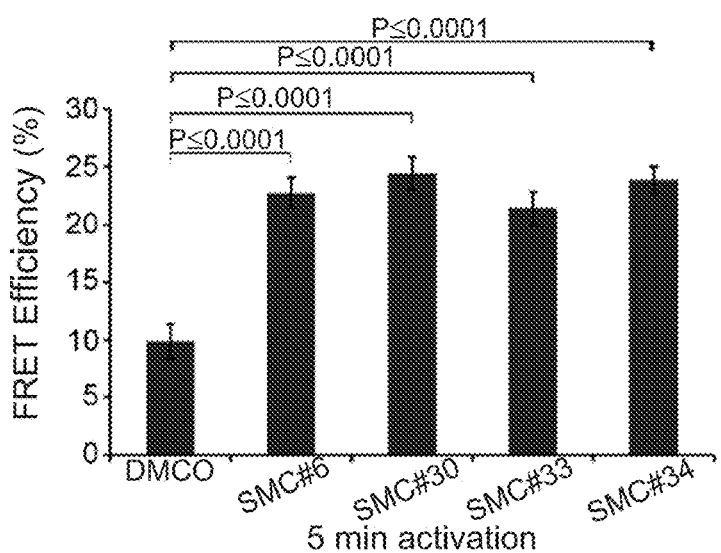

FIG. 13A-13B. FRET analysis of the WIP-WASp interaction in activated T-cells treated with WASp-binding SMC #6, SMC #30, SMC #33 or SMC #34

FIG. 13A: Jurkat T cells stably expressing CFP-WASp and YFP-WIP were treated with WASp-binding SMC #6, SMC #30, SMC #33, SMC #34 or control. The cells were then plated on stimulatory coverslips (coated with an anti-CD3 antibody), and fixed after 5 min. Cells were imaged by confocal microscope, and FRET efficiency was measured by the donor-sensitized acceptor emission technology (see Experimental procedures for details).

FIG. 13B: graph summarizing the percentage FRET efficiency in cells plated on the stimulatory coverslips, with the indicated treatment. Data are from four independent experiments. Error bars represent the SE from the mean. P values were calculated by two-tailed Student's t-test.

FIG. 14A-14E. WASp-binding SMCs restore WASp expression of common WAS/XLT WASp mutations FIG. 14A. presents a FACS analysis of Jurkat T-cells expressing YFP-WASp mutants.

Figure 14A:
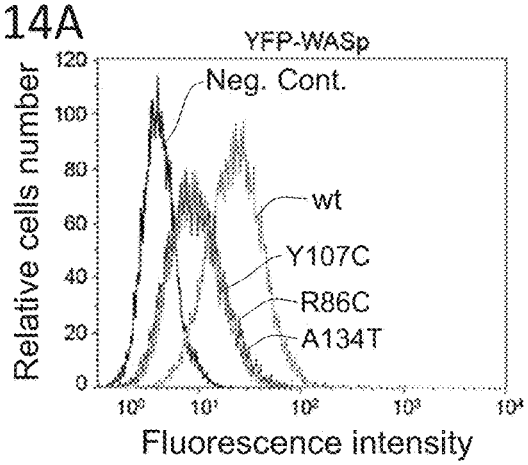
Figure 14B:
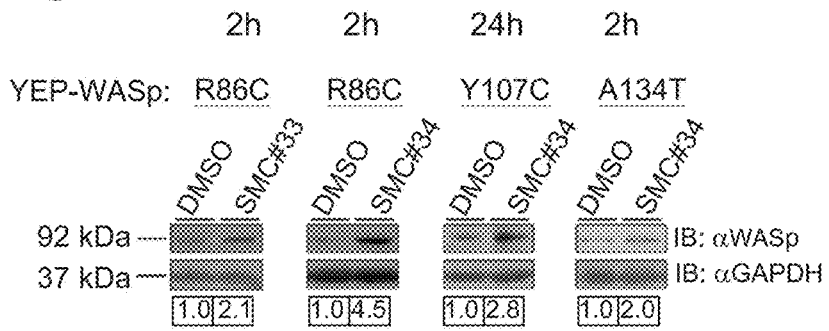

FIG. 14B. shows Jurkat T-cells stably expressing YFP-WASp mutants that were pretreated with either negative control or the indicated WASp-binding SMCs. The cells were then co-stimulated with anti-CD3 and anti-CD28, followed by lysis. Lysates were analyzed for WASp expression by immunoblotting with anti-WASp and anti-GAPDH as loading control. Relative protein expression was determined by densitometric analysis and is presented below the corresponding lanes. Western blots are representative of three independent experiments.

Figure 14C:
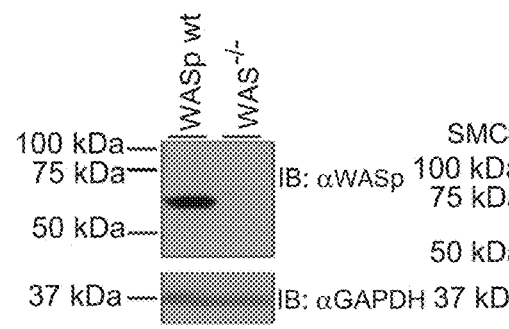

FIG. 14C. shows western blot analysis of Jurkat T-cell line which have no expression of endogenous WASp wt (WAS$^{-/-}$). Western blot is representative of three independent experiments.

Figure 14D:
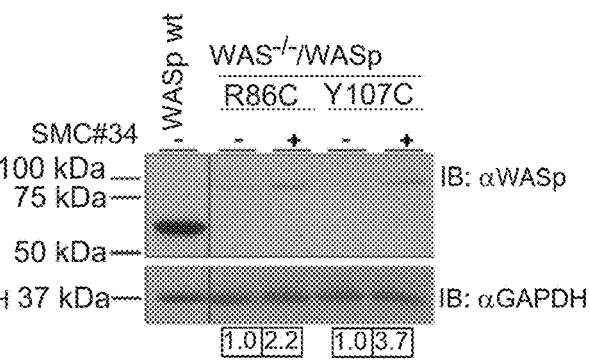

FIG. 14D. shows WASp knockout Jurkat T-cell lines that express only exogenous YFP-WASp harboring the common human WAS and XLT mutations, R86C (WAS$^{-/-}$/WASp R86C) or Y107C (WAS$^{-/-}$/WASp Y107C) that were pretreated with either negative control or SMC #34. The cells were then co-stimulated with anti-CD3 and anti-CD28 and analyzed by western blot as described in FIG. 14B. Endogenous WASp displays a band at 65 kDa and exogenous YFP-WASp displays a band at 92 kDa. Relative protein expression was determined by densitometric analysis and is presented below the corresponding lanes.

Figure 14E:
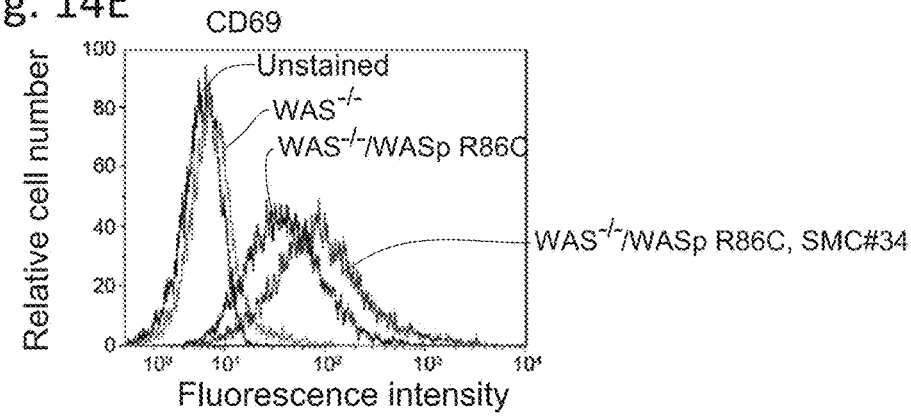

FIG. 14E. shows WASp-binding SMC up-regulates lymphocyte activation. $1 \times 10^6$ WASp knockout Jurkat T-cell line that expresses only exogenous YFP-WASp harboring the common human WAS and XLT mutation, R86C (WAS-/-/WASp R86C) was pretreated with either negative control or SMC #34. Cells that completely lack WASp expression (WAS$^{-/-}$) were also treated with the control. The cells were then stimulated with PMA and Ionomycin. After incubation, the cells were stained with PE-Cy5™-conjugated mouse anti-human CD69 and lymphocyte activation was measured by flow cytometry as described in Experimental procedures. Histogram of negative control versus SMC #34 is presented.

Figure 15A:
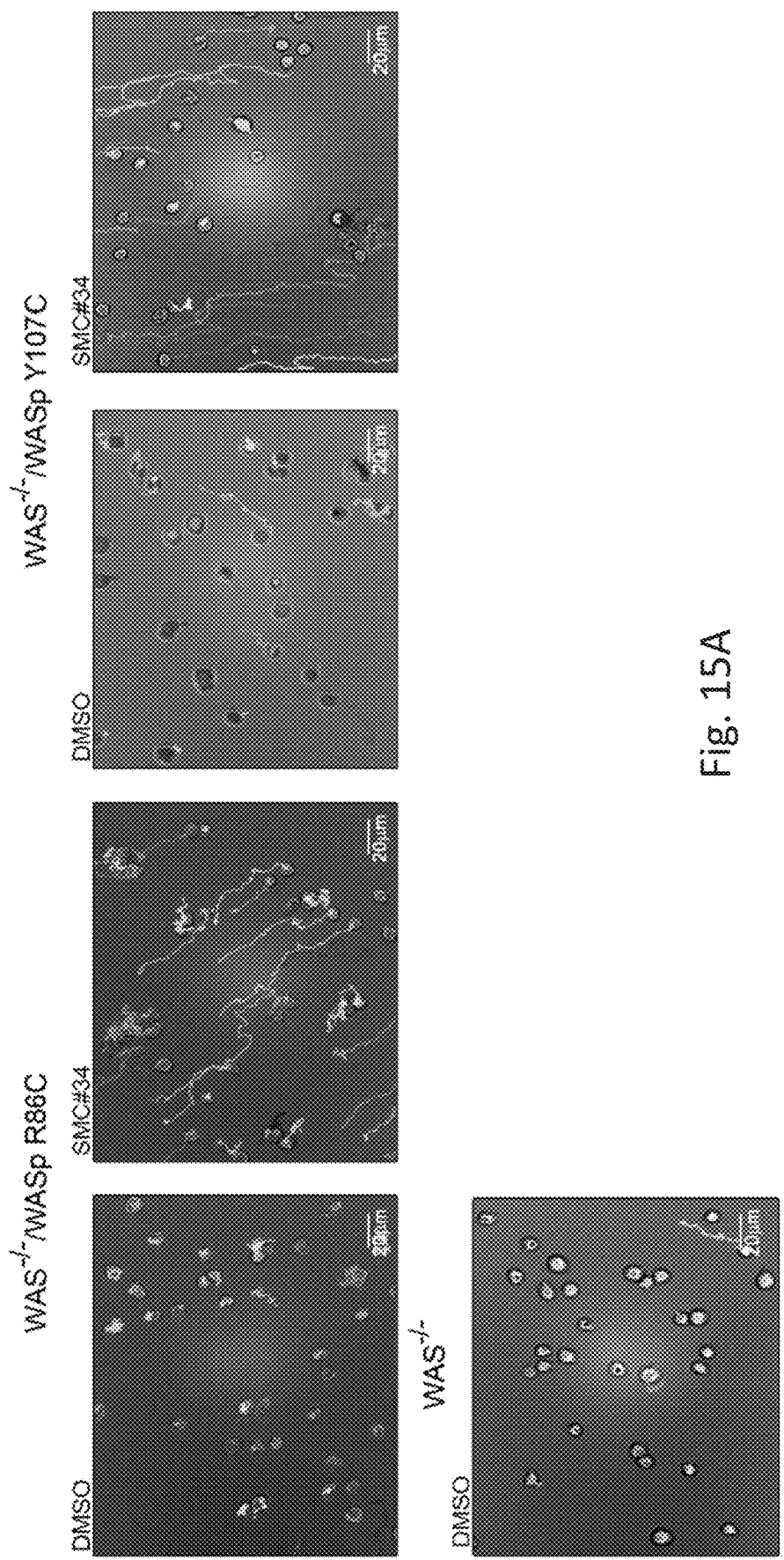
Figure 15B:
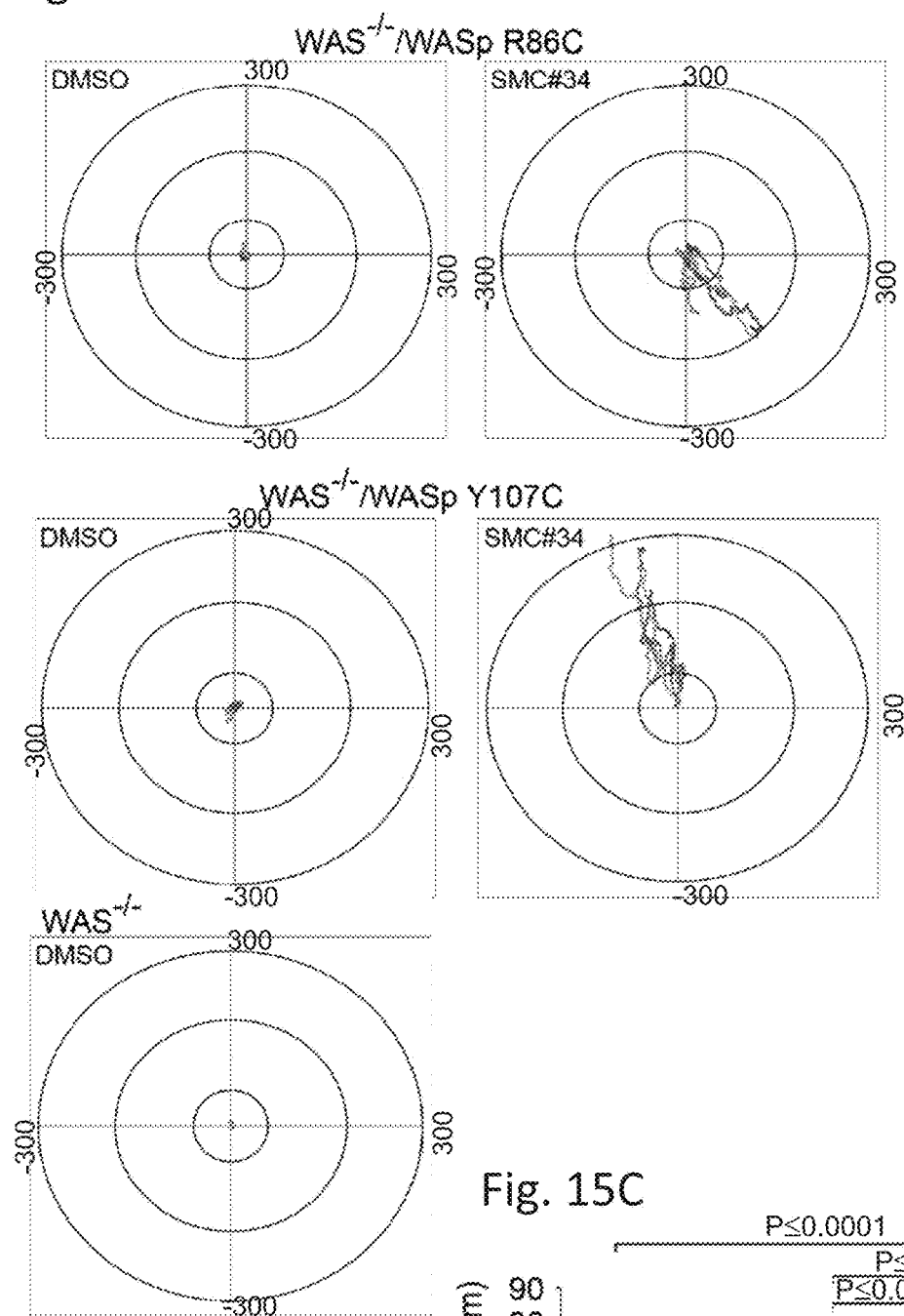
Figure 15C:
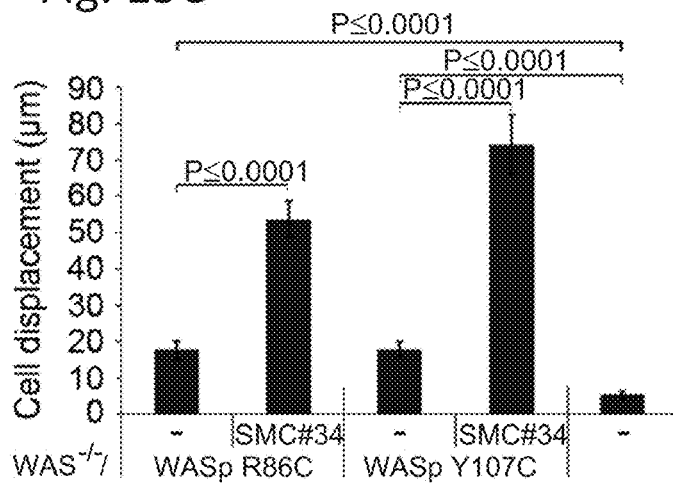

FIG. 15A-15C. WASp-binding SMC #34 enhances the migration of lymphocytes stably expressing common human WAS/XLT WASp mutations WASp knockout Jurkat T-cell lines that express only exogenous YFP-WASp R86C (WAS$^{-/-}$/WASp R86C) or Y107C (WAS$^{-/-}$/WASp Y107C) were pretreated with SMC #34 in comparison to cells treated with the control. Cells that completely lack WASp expression (WAS$^{-/-}$) were also treated with the control. Cellular migration was tracked over a 20-min period on ICAM-1/SDF-1α-coated cover glasses, as described in Experimental procedures.

FIG. 15A. The last frame in the movie of the control or the indicated WASp-binding SMCs.

FIG. 15B. Each line represents one cell. The tracks of five representative cells from each treatment are presented.

FIG. 15C. Mean cell displacement (WAS$^{-/-}$/WASp R86C, DMSO negative control: 17.74±2.46n=110, SMC #34: 53.65±4.88 n=138; WAS$^{-/-}$/WASp Y107C, DMSO negative control: 17.75±2.06 n=138, SMC #34: 74.24±8.16 n=100; WAS$^{-/-}$, DMSO: 5.15±1.09 n=88).

Error bars represent the SE from the mean. P values of SMC-treated cells versus DMSO-treated control cells are presented and were calculated by two-tailed Student's t-test.

Figure 16:
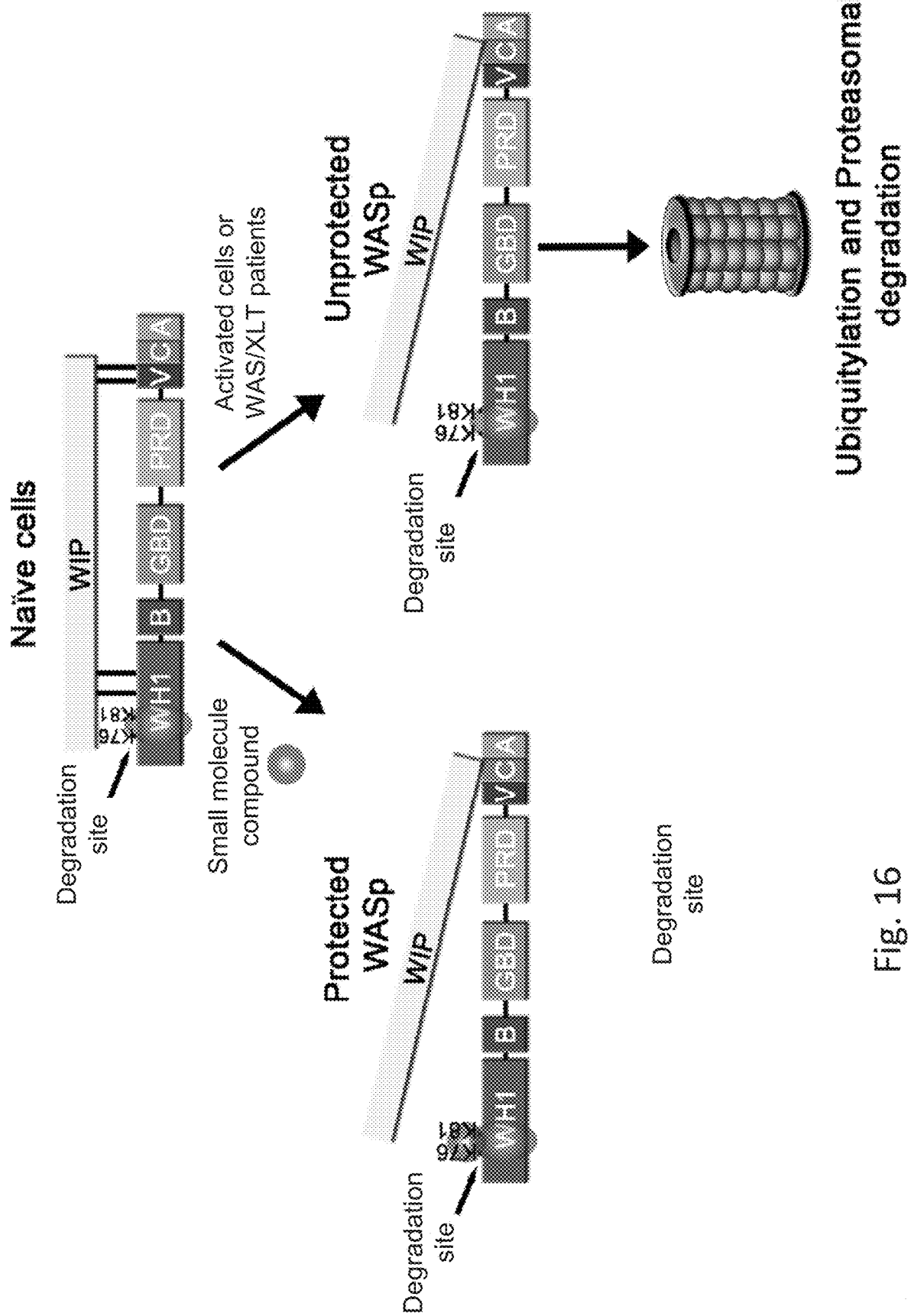

FIG. 16. Proposed model for the mechanism of action by which WASp-binding SMCs protect WASp from degradation WASp degradation sites, lysine residues 76 and 81 are located in a pocket at the N'-terminus of WASp. In normal naïve cells WIP is tightly bound to WASp and protects it from ubiquitylation and degradation (upper scheme). WIP protection is relieved following cellular activation or alternatively due to WAS/XLT mutations, which abrogate the WIP-WASp interaction. Unprotected, lysine residues 76 and 81 are ubiquitylated and WASp is degraded (lower right). WASp-binding SMCs mask WASp degradation sites by binding in the close proximity of the pocket at the N'-terminus. This masking protects WASp from ubiquitylation and degradation (lower left).

DETAILED DESCRIPTION OF THE INVENTION

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed herein before, so far, the attempts for curative treatments for WAS/XLT patients were focused on restoring WASp expression and function in hematopoietic cells, either by hematopoietic stem cell transplantation (HSCT) or gene therapy. Despite being the only approved restorative treatment for WAS, HSCT is a customized treatment, which requires the availability of a matching donor and early intervention. The graft source (bone marrow, cord blood or peripheral blood) and the intensity of preparatory conditioning are also complex consideration that must be taken prior to transplantation. Post-transplant complications may include autoimmunity, malignancies, viral infections, graft-versus-host disease (GVHD) and infertility. Gene therapy, which is in fact an autologous gene-modified HSCT, is an emerging treatment intended to bypass the obstacle of finding a matching donor, and to avoid GVHD. Ex vivo gene correction in this approach is facilitated by various viral vectors that integrate the correct gene to patient-derived hematopoietic progenitor cells, which are then reinfused back to the patient. Unfortunately however, previous clinical studies reported the onset of leukemia in most of the patients who undergone gene therapy with γ-retroviral vectors, due to vector-related insertional oncogenesis (Aiuti et al, 2013). Current efforts at improving safety and efficacy of gene therapy are focusing on lentiviral vectors, which show some clinical improvement with no insertional oncogenesis-associated events recorded to date (Hacein-Bey Abina et al, 2015). However, more time is needed to follow-up patients in order to assess long-term safety and efficacy. Still, gene therapy carries the other risks of allogeneic HSCT, such as infections and infertility due to the preparatory conditioning.

These intensive treatments are considered excessively risky for XLT patients, because XLT patients have good long-term survival, with life expectancy that is not substantially different from the normal population. However, XLT patients suffer from severe disease-related complications, with only 27% of XLT patients reach the age of 60 without experiencing severe disease-related events (Albert et al, 2010). Thus, there is currently no generally accepted treatment policy for XLT patients. Splenectomy is offered to WAS/XLT patients in order to increase platelet count, and, therefore to reduce bleeding events. However, splenectomy is associated with increased risk of infections, requiring the patients to receive life-long antibiotic prophylaxis. Moreover, WAS/XLT patients who underwent splenectomy are not compatible for further HCST because they have an increased morbidity and mortality post-HSCT, due to viral infections (Buchbinder et al, 2014).

The inventors report herein that small molecule compounds (SMCs) restore Wiskott Aldrich Syndrome protein (WASp) expression and function. The inventors further revealed the mechanism underlying this effect of the novel SMCs described herein. More specifically, in normal resting cells WASp is auto inhibited by its tight bond to a protective protein—WIP, which masks WASp degradation sites at lysine residues 76 and 81. In contrast, WAS gene mutations trigger a conformational change that releases WIP protection from the degradation pocket of WASp, subsequently resulting in WASp degradation by uncontrolled ubiquitylation. The resulting WASp deficiency affects a broad spectrum of cell functions, and the severity of the disease is determined by the level of WASp expression. The inventors used an in-silico predictor to screen potential WASp-binding SMCs that protect it from degradation. The binding of potent SMCs was validated using microscale thermophoresis (MST) technology.

Figure 1A:
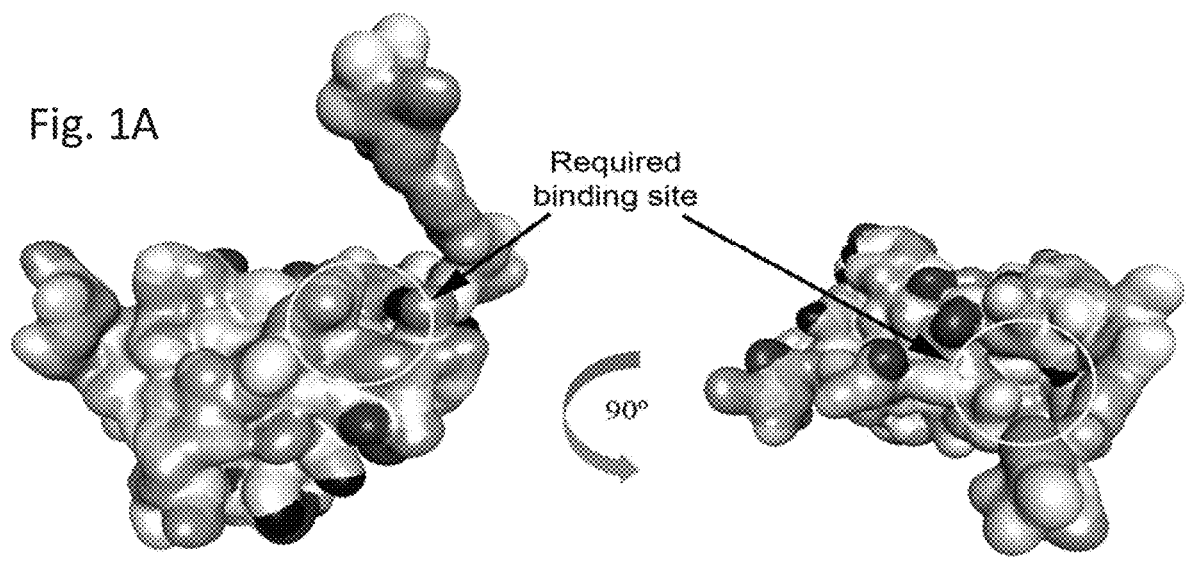
FIG. 1A-1C. Structural model of WASp WH1 for virtual screening of WASp-binding SMCs FIG. 1A. shows an NMR model of the EVH1 domain of rat N-WASp conjugated to a WIP polypeptide (PDB ID: 2IFS) that was virtually modified using virtual mutagenesis tool of Discovery Studio 3.0, allowing the model to be representative of the WH1 domain of human WASp. The required site for SMCs binding is marked with a white circle.
Figure 1B:
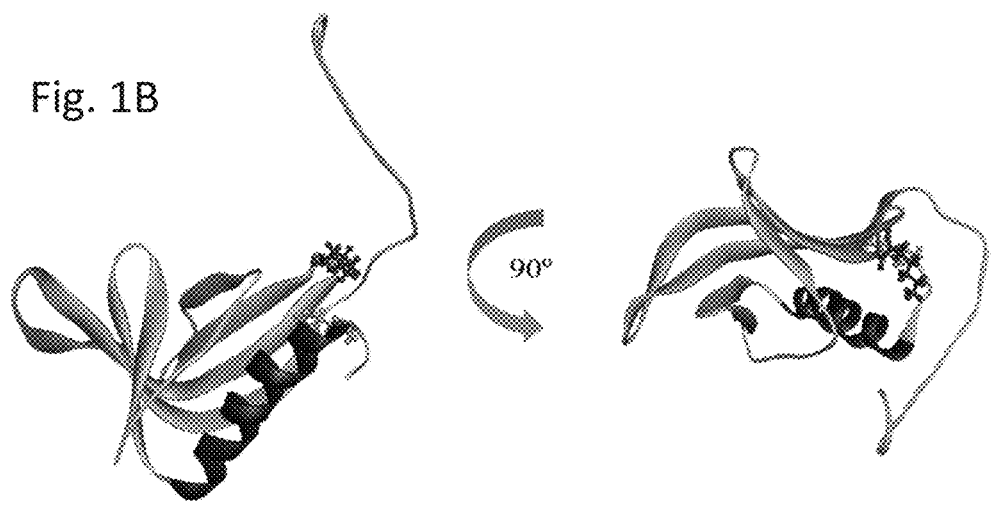
Figure 1C:
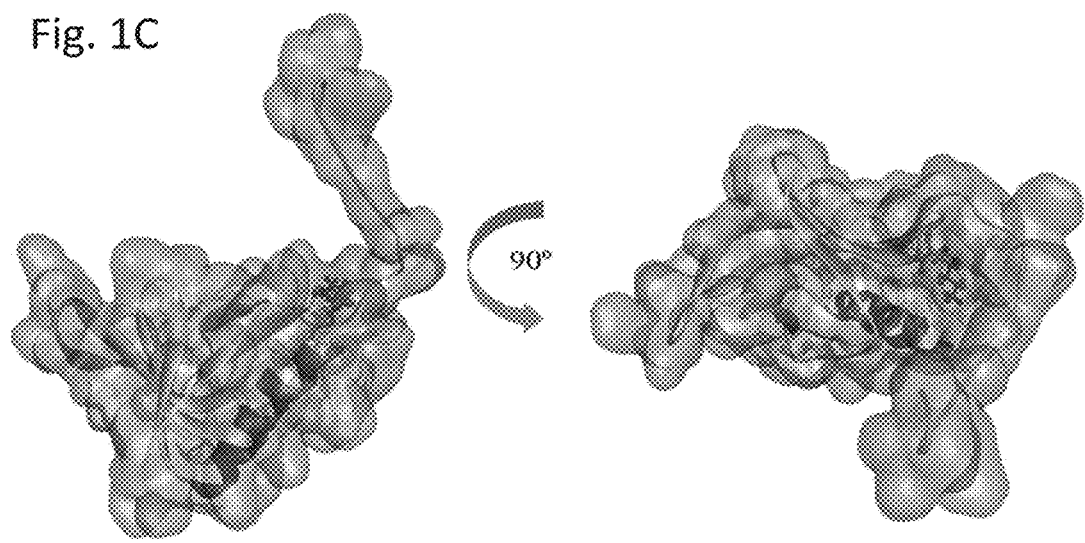
Figure 2:
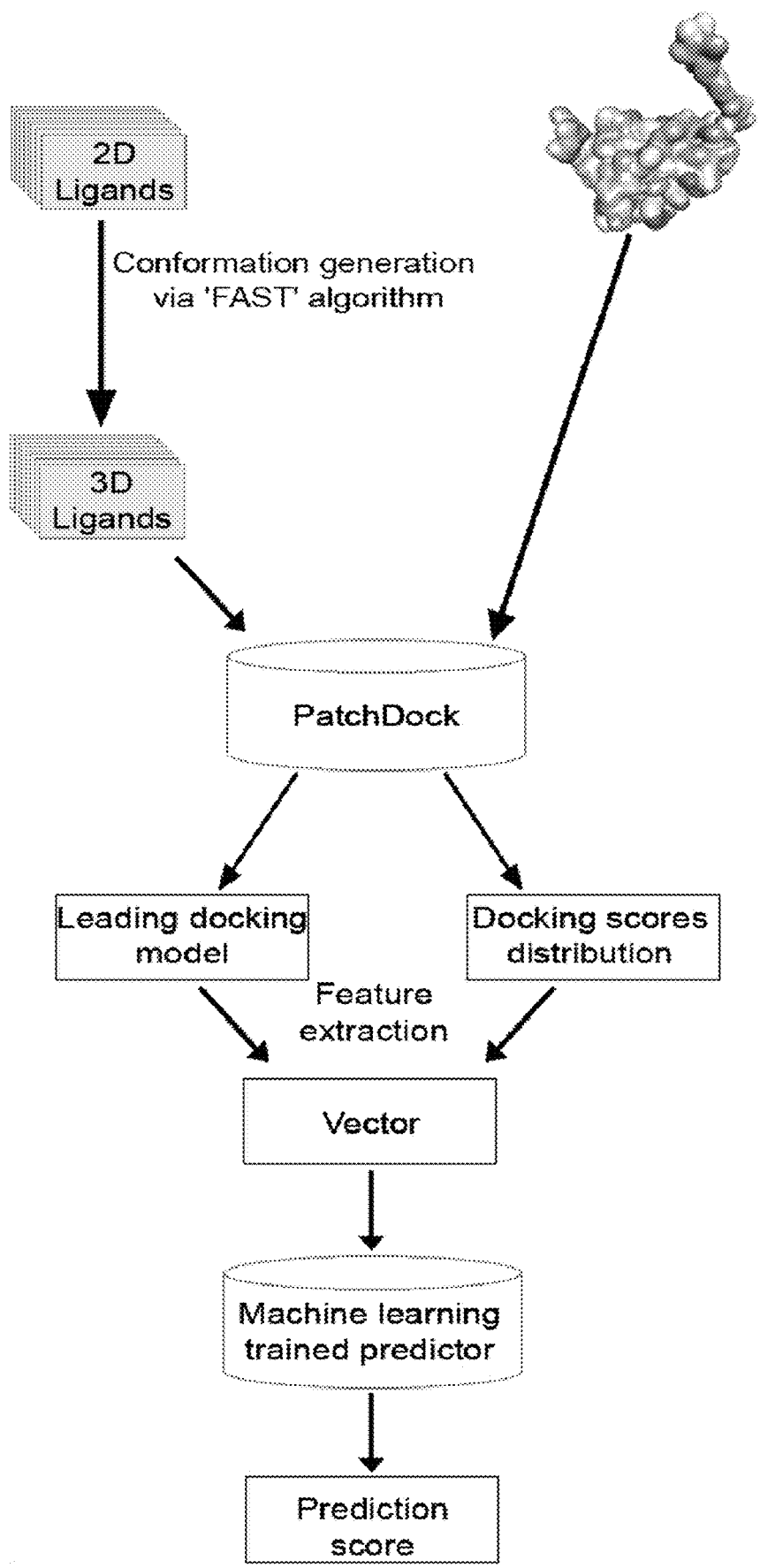
FIG. 2. Schematic workflow of virtual screening for WASp-binding SMCs
Figure 3A:
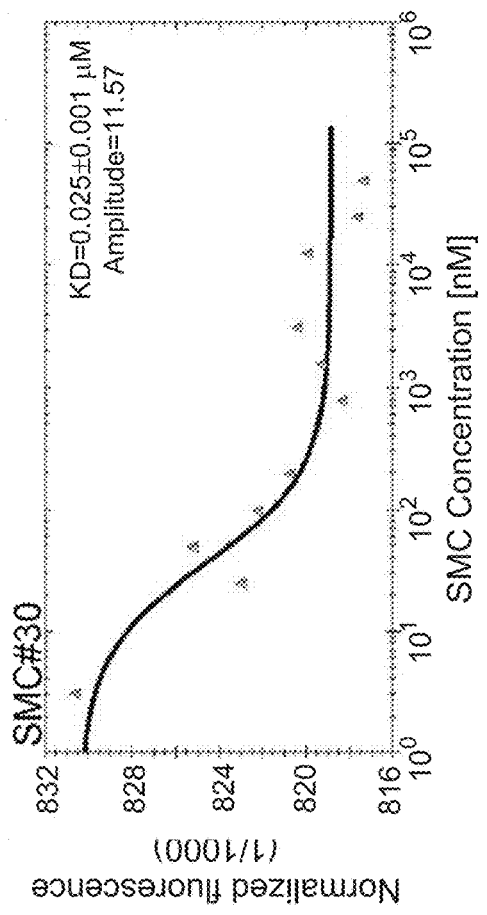
Figure 3B:
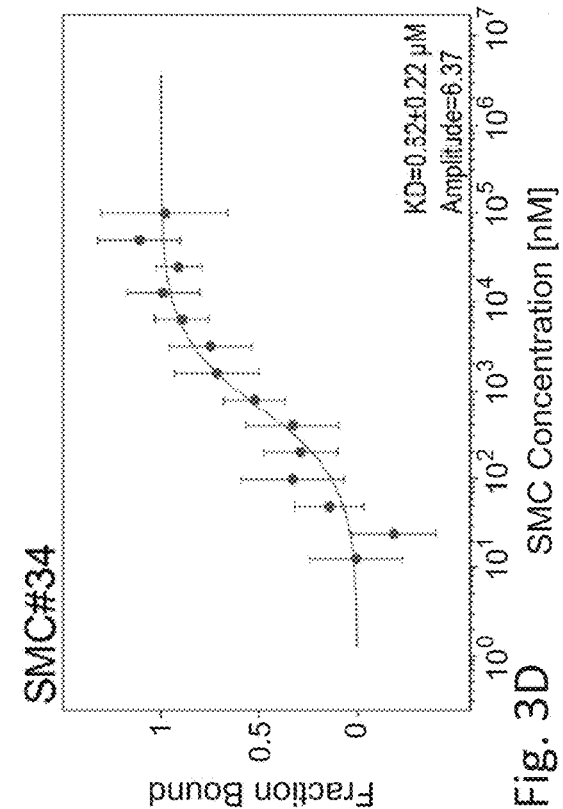
Figure 3C:
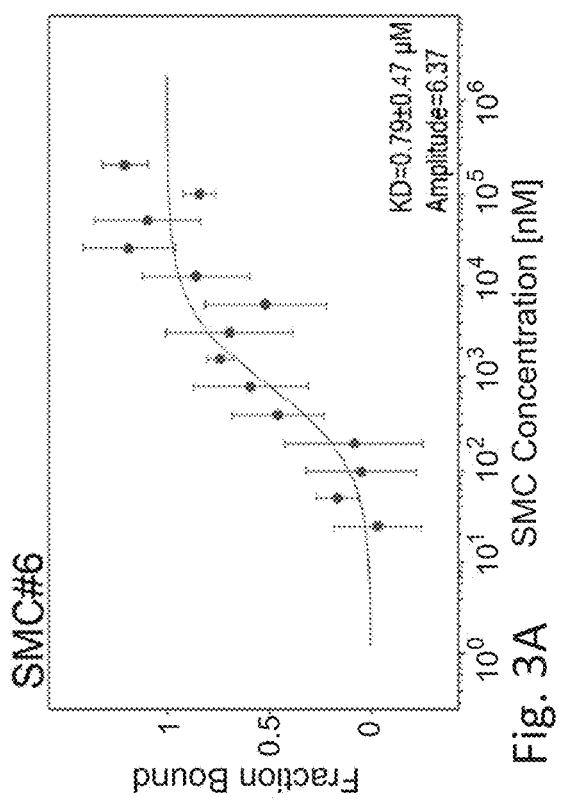
Figure 3D:
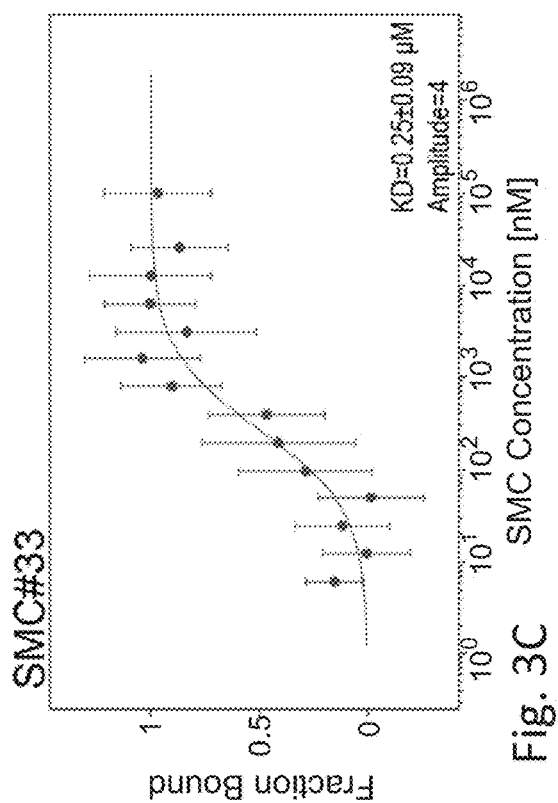
Figure 3G:
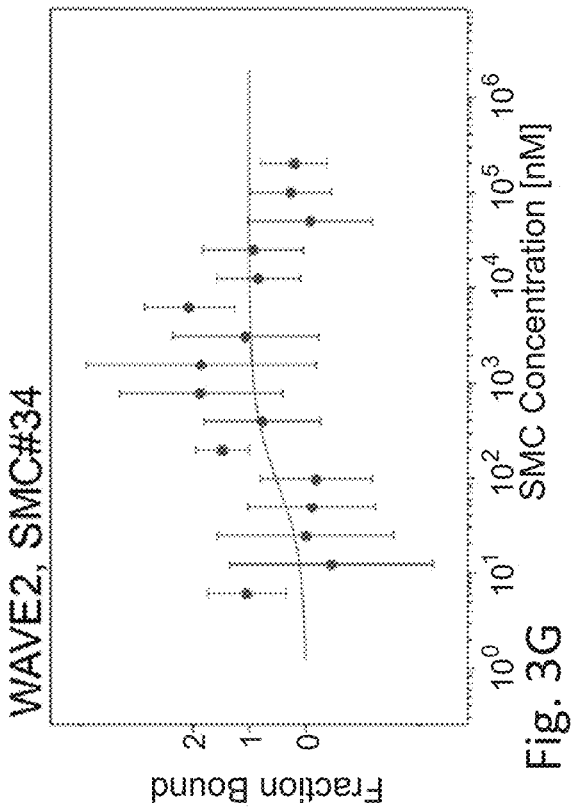
Figure 3E:
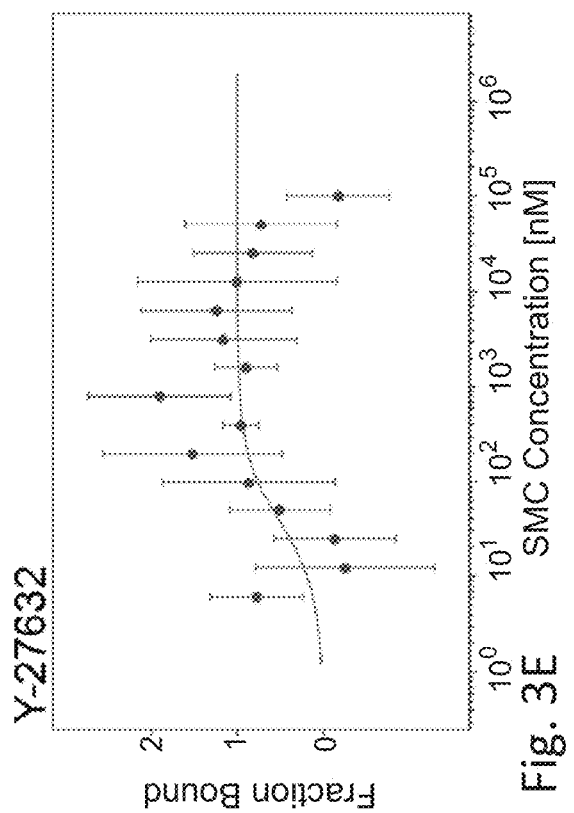
Figure 3F:
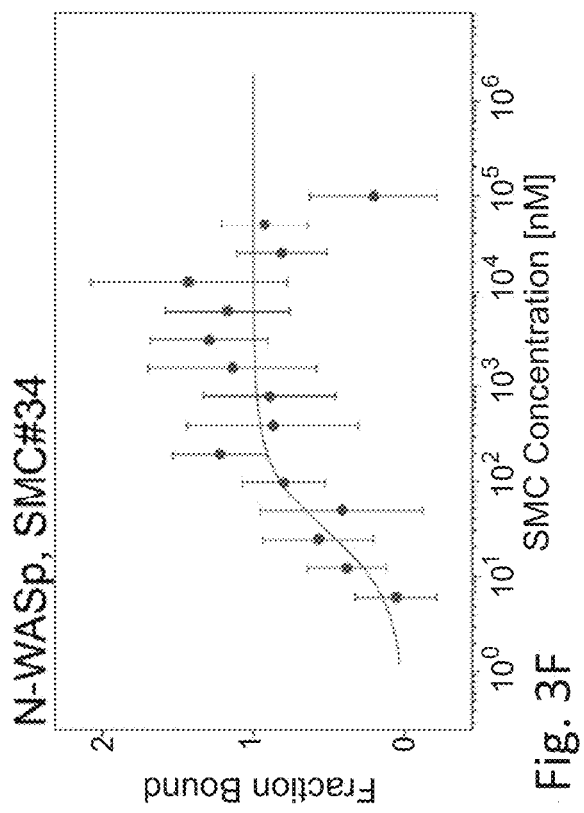

More specifically, in the present disclosure, the inventors provide novel WASp-binding SMCs (EXAMPLE 1, Table 1, FIG. 1, FIG. 3) that potentially protect WASp from degradation, via blocking the ubiquitylation of lysine residues 76 and 81 located in a pocket at WASp WH1 domain. Moreover, the inventors show that by reducing WASp ubiquitylation, the selected SMCs up-regulate WASp expression in T-cell lines, primary lymphocytes and platelets (FIG. 5, FIG. 12). This upregulation of WASp expression by WASp-protecting SMCs, enhanced WASp-dependent cellular function, including cellular activation, intra-cellular calcium influx, proliferation and migration (FIG. 8-FIG. 11). Strikingly, these SMCs restored the function of mutant WASp-expressing cells (FIG. 14-FIG. 15). Therefore, the inventors have revealed a novel function of the selected SMCs, namely, attenuation of WASp degradation by binding to WASp. The findings of the invention are highly valuable and may lead to the development of new therapeutic strategies which target WASp expression. Moreover, these findings form a promising treatment modality for hereditary WASp dysfunction disorders such as WAS/XLT as well as for acquired WASp dysfunction disorders as will be elaborated below.

Thus, a first aspect of the invention relates to an effective amount of at least one small molecule compound (SMC) modulator or any vehicle, matrix, nano- or micro-particle comprising the same, for use in a method for modulating the degradation of Wiskott-Aldrich Syndrome protein (WASp) in a cell. In more specific embodiments, the SMC of the invention may have the general formula (I):

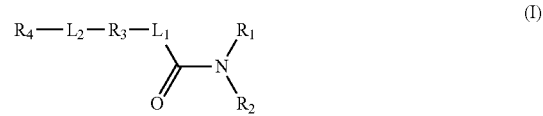

(I)

or a pharmaceutically acceptable salt, solvate, hydrate, stereoisomer or physiologically functional derivative thereof, wherein $R_1$ and $R_2$ are each independently from each other selected from H, straight $C_1$-$C_{12}$ alkyl, branched $C_1$-$C_{12}$ alkyl, $C_2$-$C_{12}$ alkenyl, $C_2$-$C_{12}$alkynyl, straight $C_1$-$C_{12}$ alkoxy, branched $C_1$-$C_{12}$ alkoxy, a ring system containing five to twelve atoms, each optionally substituted by at least one of straight $C_1$-$C_5$ alkyl, branched $C_1$-$C_5$ alkyl, halide, hydroxyl, ester, ether, amide, amine, nitro, $CF_3$, —C(=O)—O—$(CH_2)_n$—$CH_3$, $R_5$, or —NH—C(=O)—$R_5$, $R_5$ is an a ring system containing five to twelve atoms optionally substituted by at least one halide or straight $C_1$-$C_5$ alkyl or branched $C_1$-$C_5$ alkyl;

or $R_1$ and $R_2$ together with the nitrogen atom they are connected to form a five to twelve membered saturated or unsaturated ring that may optionally include N, O, S, NH, C=N, C=O, S=O or $SO_2$ and may be optionally be substituted with at least one of straight or branched $C_1$-$C_5$ alkyl, hydroxyl, halide and cyano;

L1 and L2 are each independently from each other selected to be absent or from —$(CH_2)_n$—, —$(CH_2$—C(O)—N)_n$—, —$(CH_2)_n$—, —$(CH_2)_n$—S—, —$(CH_2)_n$—O—, $S(O)_2$, $S(O)_2$—N—$(CH_2)_n$—, —$(CH_2)_n$—, —$(CH_2)_n$—N—C(=O)—, $S(O)_2$—N—$(CH_2)_n$, —$(CH_2)_n$—S—, NH, —$(CH_2)_n$—S—$(CH_2)_n$—C(O)—NH—$(CH2)_n$-, —(CH$_2$)$_n$—(NH)$_n$—C(=O)—(CH$_2$)$_n$—, —NH—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be each independently from each other optionally substituted with C$_1$-C$_5$ alkyl, a ring system containing five to twelve atoms optionally substituted with C$_1$-C$_5$ alkyl each n, is an integer being independently from each other selected from be 0 to 5;

R$_3$ and R4 are each independently from each other be absent or selected from a ring system containing five to 15 atoms, each optionally substituted with at least one of straight or branched C$_1$-C$_5$ alkyl, (=O), (=S), (O)$_2$, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight C$_1$-C$_5$ alkyl or branched C$_1$-C$_5$ alkyl.

In some embodiments, a ring system containing five to twelve atoms or five to 15 atoms may be substituted with one or more substituents, in certain embodiments one, two, three or four substituents as detailed herein. It should be noted that when referring to ring system five to twelve atoms or five to 15 atoms, it may optionally include least one of N, O, S, NH, C=N, C=O, S=O, or SO$_2$.

In accordance with this aspect, in some specific embodiments, the compound of general Formula I may provide a compound having the general formula (I'):

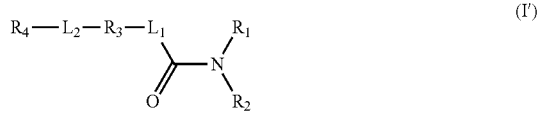

(I')

or a pharmaceutically acceptable salt, solvate, hydrate, stereoisomer or physiologically functional derivative thereof,
wherein
R$_1$ and R$_2$ are each independently from each other selected from H, straight C$_1$-C$_{12}$ alkyl, branched C$_1$-C$_{12}$ alkyl, a ring system containing five to twelve atoms, each optionally substituted by at least one of halide, amide, amine, nitro, —C(=O)—O—(CH$_2$)$_n$—CH$_3$; R$_5$ or —NH—C(=O)—R$_5$, R$_5$ is an a ring system containing five to twelve atoms optionally substituted by at least one halide or straight C$_1$-C$_5$ alkyl or branched C$_1$-C$_5$ alkyl;
or
R$_1$ and R$_2$ together with the nitrogen atom they are connected to form a five to twelve membered saturated or unsaturated ring that may optionally include at least one of N, NH and may be optionally be substituted with at least one of straight or branched C$_1$-C$_5$ alkyl,
L1 and L2 are each independently from each other selected from —(CH$_2$)$_n$—(CH$_2$—C(O)—N)$_n$—(CH$_2$)$_n$, —(CH$_2$)$_n$—S—, NH, —(CH$_2$)$_n$—O—, S(O)$_2$, S(O)$_2$—N—(CH$_2$)$_n$, —(CH$_2$)$_n$—; —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH$_2$)$_n$—, —(CH$_2$)$_n$—(NH)$_n$—C(=O)—(CH$_2$)$_n$—, —NH—(CH$_2$)$_n$—, L1 and L2 may be each independently from each other optionally substituted with C$_1$-C$_5$ alkyl, a ring system containing five to twelve atoms optionally substituted with C$_1$-C$_5$ alkyl, each n, is an integer being independently from each other selected from be 0 to 5;
R$_3$ and R4 are each independently from each other absent or selected from a ring system containing five to 15 atoms, each optionally substituted with at least one of straight or branched C$_1$-C$_5$ alkyl, (=O), (=S), (O)$_2$, or R$_5$, R$_5$ is an a ring system containing five to twelve atoms optionally substituted by at least one halide or straight or branched C$_1$-C$_5$ alkyl.

In accordance with some embodiments, at least one of R$_1$ and R$_2$ is independently from each other selected from H, a ring system containing five to twelve atoms. In accordance with some other embodiments, at least one of R$_1$ and R$_2$ is independently from each other selected from H. In some other embodiments, at least one of R$_1$ and R$_2$ is independently from each other selected from a ring system containing five to twelve atoms, which is optionally substituted with halide, amide, nitro, —C(=O)—O—(CH$_2$)$_n$—CH$_3$, R$_5$, or —NH—C(=O)—R$_5$. In some embodiments, R$_5$ is an aryl or thiophene, optionally substituted with at least one halide.

In some other embodiments, the ring system of at least one of R$_1$ and R$_2$ may be an aryl (aromatic ring) or aliphatic ring (non-aromatic ring). In some further embodiments, at least one of R$_1$ and R$_2$ may be C$_5$-C$_{12}$ saturated cycloalkyl, C$_5$-C$_{12}$ saturated cycloalkylene, C$_5$-C$_{12}$ aryl or C$_5$-C$_{12}$ arylene. In some further embodiments, the ring system of at least one of R$_1$ and R$_2$ may contain at least two carbon atoms and may include at least one heteroatom ring. In some further embodiments, at least one of R$_1$ and R$_2$ may be heteroaryl, heteroarylene, heterocycloalkylene or heterocycloalkyl. In some further embodiments, at least one of R$_1$ and R$_2$ may be C$_2$-C$_{12}$ heterocycloalkyl ring, C$_2$-C$_{12}$ heteroaryl or C$_2$-C$_{12}$ heteroarylene. In some embodiments, the heteroatom may be N, O, S. In some other embodiments, at least one of R$_1$ and R$_2$ may be thiazole, cyclopentane, naphthalene, aryl, each optionally substituted with —C(=O)—O—(CH$_2$)—CH$_3$, halide, nitro or —NH—C(=O)—R$_5$. In some embodiments, R$_5$ is an aryl substituted with at least one halide.

In some other embodiments, at least one of R$_1$ and R$_2$ may be thiazole. In some other embodiments, at least one of R$_1$ and R$_2$ may be cyclopentane. In some other embodiments, at least one of R$_1$ and R$_2$ may be naphthalene. In some other embodiments, at least one of R$_1$ and R$_2$ may be an aryl substituted with —C(=O)—O—(CH$_2$)—CH$_3$. In some other embodiments, at least one of R$_1$ and R$_2$ may be an aryl substituted with at least one halide, preferably F. In some other embodiments, at least one of R$_1$ and R$_2$ may be an aryl substituted with at two F atoms. In some other embodiments, at least one of R$_1$ and R$_2$ may be an aryl substituted with one F and one Cl groups.

In some other embodiments, at least one of R$_1$ and R$_2$ may be an aryl substituted with nitro.

In some other embodiments, at least one of R$_1$ and R$_2$ may be —NH—C(=O)—R$_5$. In some embodiments, R$_5$ is an aryl substituted with at least one halide. In some further embodiments, at least one of R$_1$ and R$_2$ may be benzoic acid methyl ester.

In some other embodiments, R$_1$ and R$_2$ are each independently from each other selected from straight or branched C$_1$-C$_{12}$ alkyl optionally substituted by at least one of amide or thiophene In some other embodiments, at least one of R$_1$ or R$_2$ may be CH$_2$—CH substituted by at least one of dimethyl amine or thiophene.

In some other embodiments, R$_1$ and R$_2$ are each independently from each other selected from straight C$_1$-C$_{12}$ alkyl.

In some embodiments, $R_1$ and $R_2$ are each independently from each other selected from $CH_3$.

In accordance with some embodiments, $R_1$ and $R_2$ together with the nitrogen atom they are connected to form a five or six membered saturated or unsaturated ring that may optionally include at least one of N and may be optionally be substituted with at least one of straight or branched $C_1$-$C_5$ alkyl. In some embodiments, $R_1$ and $R_2$ together with the nitrogen atom they are connected to form piperidine or piperazine, each optionally substituted with at least one straight or branched $C_1$-$C_5$ alkyl. In some embodiments, $R_1$ and $R_2$ together with the nitrogen atom they are connected to form piperidine or piperazine substituted with at least one $CH_3$ group, at times two $CH_3$ groups, at times three $CH_3$ groups.

In some embodiments, $R_1$ and $R_2$ together with the nitrogen atom they are connected to form piperazine substituted with two $CH_3$ groups. In some embodiments, $R_1$ and $R_2$ together with the nitrogen atom they are connected to form piperazine substituted with one $CH_3$ group.

In some embodiments, L1 may be absent or may be selected from —$CH_2$—$CH_2$—C(O)—N—$CH_2$—C(O)—NH—$CH_2$—, —($CH_2$)—S—, —$CH_2$—, —($CH_2$)—N—C(=O)—, —($CH_2$)—S—, —($CH_2$)—S—($CH_2$)$_n$—C(O)—NH—(CH2)-, —($CH_2$)—NH—NH—C(=O)—, —NH—($CH_2$)—, each optionally substituted with ethyl, methyl, an aryl optionally substituted with a methyl or ethyl.

In some embodiments, L2 may be absent or may be selected from —($CH_2$)—O—, S(O)$_2$, S(O)$_2$—N—, $CH_2$, —S(O)$_2$—NH—($CH_2$)—, NH each optionally substituted with a methyl, an ethyl, an aril optionally substituted with a methyl, ethyl.

In some other embodiments, each of $R_3$ and $R_4$ may be absent. In some other embodiments, each of $R_3$ and $R_4$ may be selected from a ring system containing five to 15 atoms, optionally substituted as described herein. In some further embodiments, each of $R_3$ and $R_4$ may be selected from a ring system containing five to twelve atoms, optionally substituted as described herein.

In some other embodiments, the ring system of at least one of $R_3$ and $R_4$ may be an aryl (aromatic ring) or aliphatic ring (non-aromatic ring). In some further embodiments, at least one of $R_3$ and $R_4$ may be $C_5$-$C_{12}$ saturated cycloalkyl, $C_5$-$C_{12}$ saturated cycloalkylene, $C_5$-$C_{12}$ aryl or $C_5$-$C_{12}$ arylene. In some further embodiments, the ring system of at least one of $R_3$ and $R_4$ may contain at least two carbon atoms and may include at least one heteroatom ring. In some further embodiments, at least one of $R_3$ and $R_4$ may be heteroaryl, heteroarylene, heterocycloalkylene or heterocycloalkyl. In some further embodiments, at least one of $R_3$ and $R_4$ may be $C_2$-$C_{12}$ heterocycloalkyl ring, $C_2$-$C_{12}$ heteroaryl or $C_2$-$C_{12}$ heteroarylene. In some embodiments, the heteroatom may be N, O, S.

In some other embodiments, at least one of $R_3$ and $R_4$ may be thiazole, cyclopentane, naphthalene, triazine, triazole, piperidine, piperazine, quinoline, isoquinoline, phthalazine, tetrahydro-quinoline, tetrahydro-quinazoline pyridine, oxadiazole, aryl, each optionally substituted with at least one of $C_1$-$C_5$ alkyl, (=O), (=S), —C(O)—$CH_3$, —C(O)—O—$CH_3$, halide, nitro, aryl, pyridine, morpholine, S(O)$_2$-amide.

In some other embodiments, at least one of $R_3$ and $R_4$ may be triazole, triazine, piperidine, piperazine, quinoline, isoquinoline, phthalazine, pyridine, tetrahydro-quinoline, tetrahydro-quinazole oxadiazole, aryl, each optionally substituted with at least one of $C_1$-$C_5$ alkyl, (=O), (=S), —C(O)—$CH_3$, —C(O)—O—$CH_3$, pyridine, morpholine, S(O)$_2$-amide.

In some other embodiments, $R_3$ may be triazole, triazine, piperidine, phthalazine, oxadiazole, aryl, each optionally substituted with at least one of $CH_3$, (=O), (=S), morpholine.

In some other embodiments, $R_4$ may be piperidine, piperazine, quinoline, isoquinoline, phthalazine, tetrahydroquinoline, pyridine, tetrahydro-quinazoline aryl, each optionally substituted with at least one of $C_1$-$C_5$ alkyl, (=O), (=S), —C(O)—$CH_3$, —C(O)—O—$CH_3$, morpholine, S(O)$_2$-amide.

In some embodiments, L1 is absent and $R_3$ is an aryl, optionally substituted.

In accordance with such embodiments, the present disclosure provides the compound of Formula I that may in some embodiments be presented as a compound having the general formula (II):

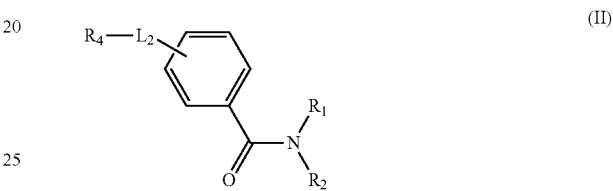

wherein R1, R2, L2 and R4 are as defined above for a compound having the general formula (I) or for a compound having the general formula (I').

In some embodiments, L2 is selected from C(O) and S(O)$_2$. In some embodiments, L1 is absent, $R_3$ is an aryl and L2 is selected from C(O) and S(O)$_2$.

In accordance with such embodiments, the present disclosure provides a compound having the general formula (III), that is derived from the compound of Formula I:

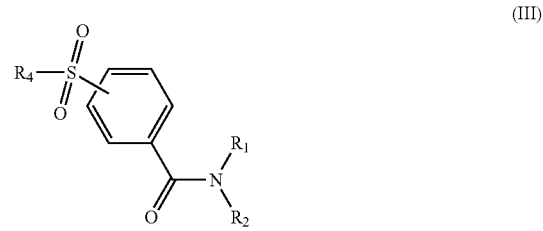

wherein R1, R2 and R4 are as defined above for a compound having the general formula (I) or for a compound having the general formula (I').

Still further aspects of the invention relate to an effective amount of at least one small molecule compound (SMC) modulator or any vehicle, matrix, nano- or micro-particle comprising the same, for use in a method for modulating the degradation of Wiskott-Aldrich Syndrome protein (WASp) in a cell. In more specific embodiments, the modulator of the invention may have the general formula (XI):

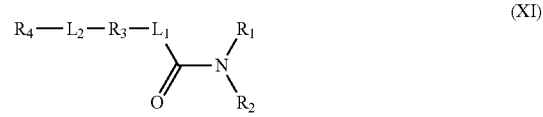

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl
or
$R_1$ and $R_2$ together with the nitrogen atom they are connected to form a five to seven membered saturated or unsaturated ring optionally include at least one of N, O and optionally substituted with at least one of straight $C_1$-$C_5$ alkyl,
L1 and L2 are each independently from each other may be absent or selected from —$CH_2$—($CH_2$—C(O)—N)—($CH_2$)$_2$, —($CH_2$)—S—, —($CH_2$)—, —($CH_2$)—O—, —NH—($CH_2$)—, and each optionally substituted with $C_1$-$C_5$ alkyl, a ring system containing five to twelve atoms optionally substituted with $C_1$-$C_5$ alkyl;
$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl.

In some embodiments, in the SMC modulator for use in accordance with the invention, the $R_1$ and $R_2$ are each independently from each other selected from H, $C_5$-$C_7$ saturated cycloalkyl, $C_5$-$C_7$ saturated cycloalkylene, $C_5$-$C_7$ aryl or $C_5$-$C_7$ arylene, each optionally substituted by at least one a ring system containing five to seven atoms optionally substituted by at least one halide or straight $C_1$-$C_5$ alkyl,
or
$R_1$ and $R_2$ together with the nitrogen atom they are connected to form a five or six membered saturated or unsaturated ring optionally include at least one of N and optionally substituted with at least one of straight $C_3$-$C_5$ alkyl,
L1 may be either absent or may be selected from —$CH_2$—S—, —$CH_2$—$CH_2$—C(O)—N—$CH_2$—C(O)—NH—$CH_2$, —$CH_2$—, each optionally substituted with ethyl, methyl, an aryl optionally substituted with a methyl or ethyl, L2 is absent or —$CH_2$—O—, $CH_2$;
$R_3$ and $R_4$ are each independently from each other absent or selected from $C_5$-$C_{12}$ heterocycloalkyl ring, $C_2$-$C_{15}$ heteroaryl or $C_2$-$C_{15}$ heteroarylene. In some embodiments, the heteroatom may be N, O, S, each optionally substituted with at least one of straight $C_1$-$C_5$ alkyl, (=O), (=S) or $R_5$, $R_5$ is an a ring system containing five to seven atoms optionally substituted by at least one halide or straight $C_1$-$C_5$ alkyl.

In some further embodiments, in the SMC modulator for use in accordance with the invention, the $R_1$ and $R_2$ may be each independently from each other selected from H, cyclopentane, or thiazole. Alternatively, $R_1$ and $R_2$ together with the nitrogen atom they are connected to form a six membered unsaturated ring substituted with at least one methyl,
L1 is absent or is selected from —$CH_2$—S—, —$CH_2$—$CH_2$—C(O)—N—$CH_2$—C(O)—NH—$CH_2$—, substituted with an aryl optionally substituted with a methyl
L2 is absent, $CH_2$, or —$CH_2$—O—,
$R_3$ and $R_4$ are each independently from each other absent or selected from the group consisting of piperidine, piperazine, quinoline, isoquinoline, phthalazine, tetrahydro-quinoline, pyridine, tetrahydro-quinazoline 1, 2, 4-triazole, oxadiazole quinoline, pyridine, phenyl, naphthalene substituted with —C(O)—$CH_3$ or methyl.

In some particular embodiments of the SMC modulator for use in accordance with the invention, the compound of Formula XI, may provide a compound having the general formula (XII):

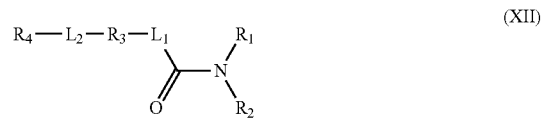

(XII)

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl;
or
$R_1$ and $R_2$ together with the nitrogen atom they are connected to form a five to seven membered unsaturated ring optionally include at least one of N, O and optionally substituted with at least one of straight $C_1$-$C_5$ alkyl,
L1 and L2 each independently from each other may be absent or selected from —$(CH_2)_n$—, $(CH_2)_n$—S—, —$(CH_2)_n$—O—, and may be optionally substituted with $C_1$-$C_5$ alkyl, n may be an integer selected from 0 or 1,
R3 is a ring system containing five atoms, optionally substituted with at least one straight $C_1$-$C_5$ alkyl, or $R_5$, $R_5$ is an a ring system containing five to seven atoms optionally substituted by at least one halide or straight $C_1$-$C_5$ alkyl,
R4 is absent or selected from a ring system containing five to 12 atoms, each optionally substituted with at least one of straight $C_1$-$C_5$ alkyl.

In accordance with some embodiments, of the SMC modulator for use, $R_1$ and $R_2$ are each independently from each other selected from H, straight $C_{2-4}$ alkyl, cycloalkyl, each optionally substituted by at least one a ring system containing five to seven atoms,
or
$R_1$ and $R_2$ together with the nitrogen atom they are connected to form a five or six membered unsaturated ring optionally be substituted with at least one of methyl,
L1 is —$CH_2$—S—, L2 is absent or —$CH_2$—O—,
R3 is a 5-membered aromatic ring, selected from the group consisting of oxazole, 1, 2, 4-triazole, oxadiazole, each optionally substituted by at least one methyl,
R4 is absent or selected from the group consisting of quinoline, pyridine, phenyl, naphthalene.

In yet some further specific embodiments, the SMC modulator for use in accordance with the invention wherein $R_1$ and $R_2$ together with the nitrogen atom they are connected to form a six membered unsaturated ring substituted with at least one methyl,
L1 is —$CH_2$—S—, L2 is absent or —$CH_2$—O—, R3 is 1, 2, 4-triazole, oxadiazole, each optionally substituted by at least one methyl, R4 is absent or selected from the group consisting of quinoline, pyridine.

In some particular embodiments, specific and non-limiting examples of the SMC modulators for use of the invention, or pharmaceutically acceptable salts or hydrates of the compounds of Formula XI, or in some further specific embodiments, pharmaceutically acceptable salts or hydrates of the compounds of Formula XII, may include:

(a)

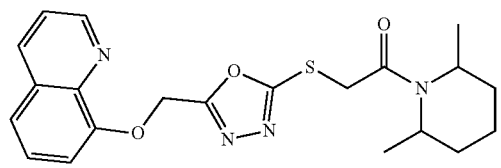 [SMILES: CC1CCCC(C)N1C(=O)CSc1nnc(COc2cccc3cccnc23)o1]

1-(2,6-Dimethyl-piperidin-1-yl)-2-[5-(quinolin-8-yloxymethyl)-[1,3,4]oxadiazol-2-ylsulfanyl]-ethanone (designated herein as SMC 34).

In yet another alternative, the SMC modulators for use of the invention may be (b)

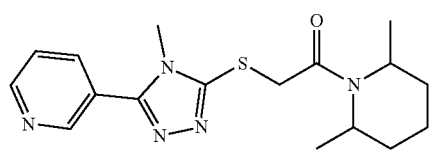 [SMILES: CC1CCCC(C)N1C(=O)CSc1nnc(-c2cccnc2)n1C]

1-(2,6-Dimethyl-piperidin-1-yl)-2-(4-methyl-5-pyridin-3-yl-4H-[1,2,4]triazol-3-ylsulfanyl)-ethanone (designated herein as SMC 34.7).

In yet some further particular embodiments, specific and non-limiting examples of the SMC modulators for use of the invention, or pharmaceutically acceptable salts or hydrates of the compounds of Formula XI, or in some further specific embodiments, pharmaceutically acceptable salts or hydrates of the compounds of Formula XII, may include:

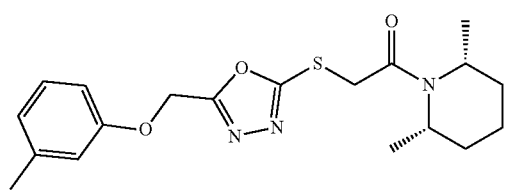 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1)

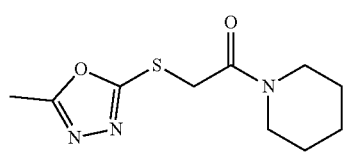 [SMILES: Cc1nnc(SCC(=O)N2CCCCC2)o1]

2-(5-Methyl-[1,3,4]oxadiazol-2-ylsulfanyl)-1-piperidin-1-yl-ethanone (SMC 34.3);

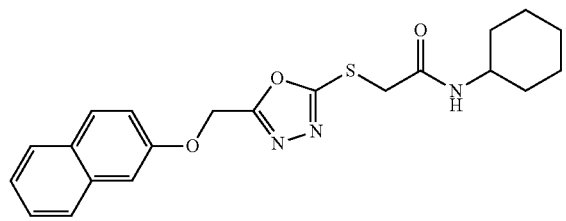 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (SMC 34.4);

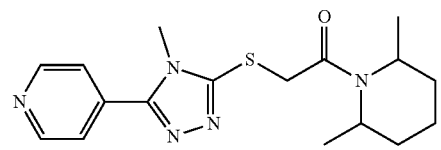 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

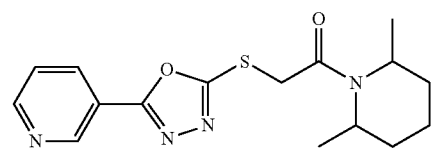 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

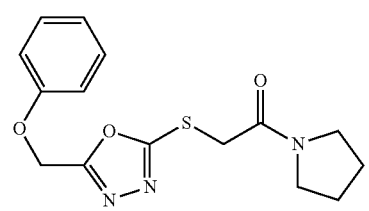 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (SMC 34.8);

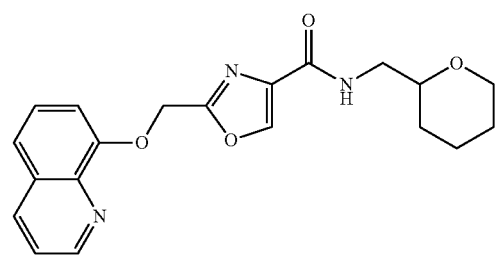 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10)

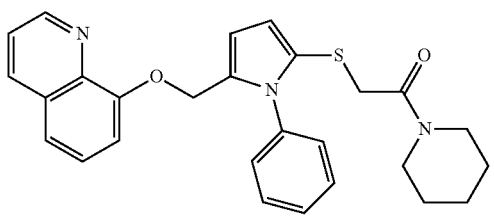 [SMILES: O=C(CSc1ccc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11)

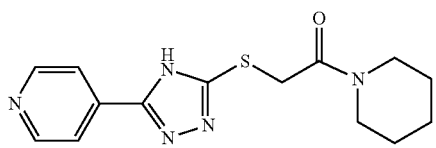 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (SMC 34.12);

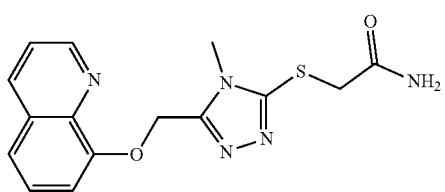 [SMILES: Cn1c(COc2cccc3cccnc23)nnc1SCC(N)=O]

2-[4-Methyl-5-(quinolin-8-yloxymethyl)-4H-[1,2,4]triazol-3-ylsulfanyl]-acetamide (SMC 34.13).

In yet some further particular embodiments, a further example of a SMC modulator that may be used by the invention, may be the compound

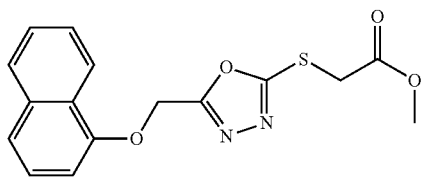 [SMILES: COC(=O)CSc1nnc(COc2cccc3ccccc23)o1]

[5-(Naphthalen-1-yloxymethyl)-[1,3,4]oxadiazol-2-ylsulfanyl]-acetic acid methyl ester (SMC 34.9).

In yet some further particular embodiments, a further example of a SMC modulator that may be used by the invention, may be the compound

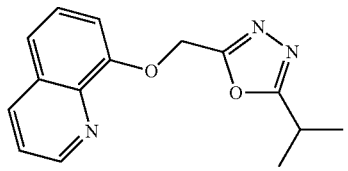 [SMILES: CC(C)c1nnc(COc2cccc3cccnc23)o1]

8-(5-Isopropyl-[1,3,4]oxadiazol-2-ylmethoxy)-quinoline (34.2)

In yet some further particular embodiments, the SMC modulator used by the invention may be any compound defined by Formula XI, Formula XII, with the proviso that the compound is not any of the compounds detailed below:

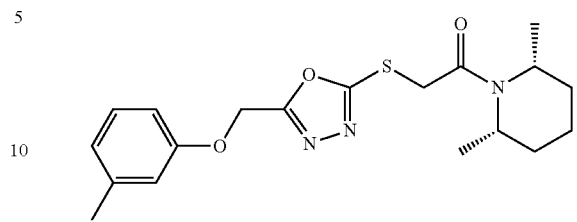

1-(2,6-Dimethyl-piperidin-1-yl)-2-(5-m-tolyloxymethyl-[1,3,4]oxadiazol-2-ylsulfanyl)-ethanone (SMC 34.1)

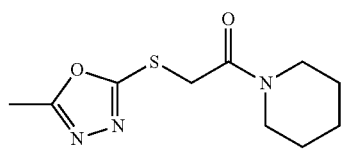 [SMILES: Cc1nnc(SCC(=O)N2CCCCC2)o1]

2-(5-Methyl-[1,34]oxadiazol-2-ylsulfanyl)-1-piperidin-1-yl-ethanone (34.3);

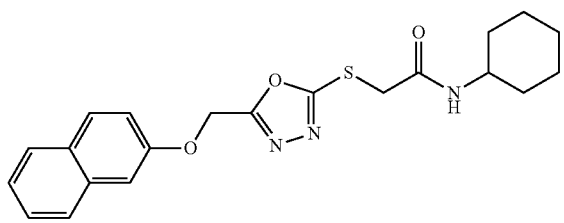 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (34.4);

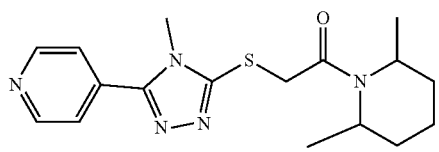 [SMILES: CCC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (34.5);

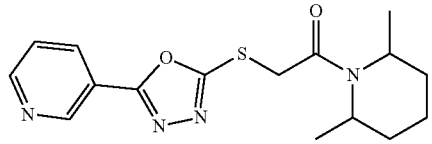 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (34.6);

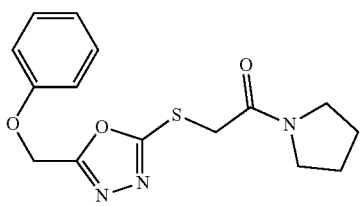 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (34.8);

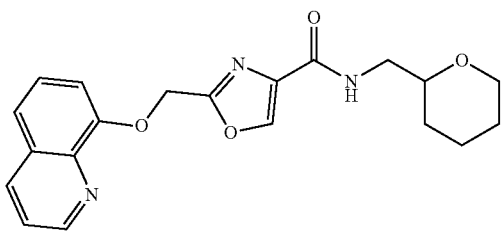 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10);

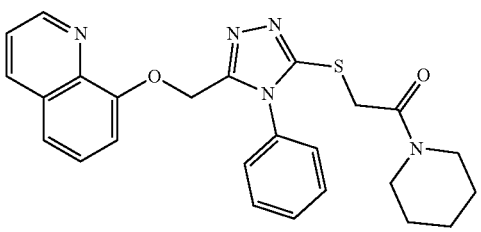 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11);

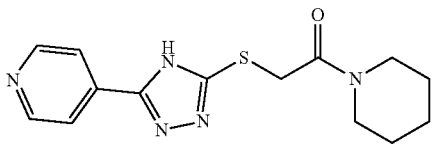 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (34.12);

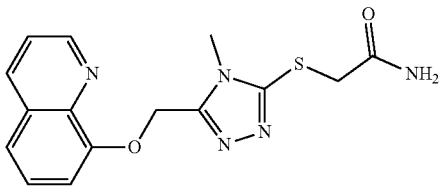 [SMILES: Cn1c(COc2cccc3cccnc23)nnc1SCC(N)=O]

2-[4-Methyl-5-(quinolin-8-yloxymethyl)-4H-[1,2,4]triazol-3-ylsulfanyl]-acetamide (34.13);

In yet some further particular embodiments, the SMC modulator that may be used by the invention, may be any of the compounds disclosed by the invention provided that said compound is not the compound:

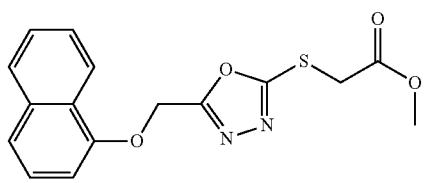 [SMILES: COC(=O)CSc1nnc(COc2cccc3ccccc23)o1]

[5-(Naphthalen-2-yloxymethyl)-[1,3,4]oxadiazol-2-ylsulfanyl]-acetic acid methyl ester (34.9).

In yet some further particular embodiments, the SMC modulator that may be used by the invention, may be any of the compounds disclosed by the invention provided that said compound is not the compound:

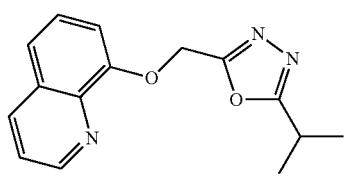 [SMILES: CC(C)c1nnc(COc2cccc3cccnc23)o1]

8-(5-Isopropyl-[1,3,4]oxadiazol-2-ylmethoxy)-quinoline (34.2);

In yet some alternative particular embodiments of the SMC modulator for use in accordance with the invention, the compound of Formula XI, may provide a compound having the general formula (XIV):

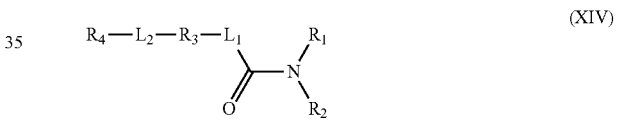

(XIV)

or a pharmaceutically acceptable salt, solvate, hydrate, stereoisomer or physiologically functional derivative thereof,
wherein
$R_1$ and $R_2$ are each independently from each other selected from H and straight $C_1$-$C_5$ alkyl,
L1 and L2 are each independently from each other may be absent or selected from —$(CH_2)$—S—, —$(CH_2)$—, —$(CH_2)$—O—,
$R_3$ and R4 are each independently from each other absent or selected from an aryl or heteroaryl group optionally substituted with at least one of straight or branched $C_1$-$C_5$ alkyl, halide, nitro and cyano.

In some embodiments, in the SMC modulator for use in accordance with the invention, $R_1$ and $R_2$ are each independently from each other selected from H, methyl and ethyl, at times $R_1$ and $R_2$ are each independently from each other selected from H and methyl, L1 may be —$CH_2$—S—, L2 may be —$CH_2$—O—; $R_3$ and R4 are each independently from each other absent or selected from an aryl or heteroaryl group optionally substituted with at least one of straight or branched $C_1$-$C_5$ alkyl, halide, nitro and cyano.

In some further embodiments, in the SMC modulator for use in accordance with the invention, the $R_1$ and $R_2$ may be each independently from each other selected from H and methyl, L1 is —$CH_2$—S—, L2 is, —$CH_2$—O—, $R_3$ is selected from the group consisting of thiazole, [1,3,4]thiadiazole, [1,3,4]oxadiazole, and $R_4$ is phenyl.

In yet some alternative particular embodiments of the SMC modulator for use in accordance with the invention, the compound of Formula I, may provide a compound having the general formula (XV):

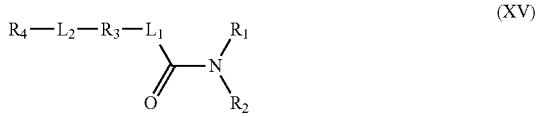

(XV)

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl and branched $C_1$-$C_{12}$ alkyl;
L1 and L2 are each independently from each other selected to be absent or from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$—, —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$—, —(CH$_2$)$_n$—(NH)$_n$—C(=O)—(CH$_2$)$_n$—, —NH—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be each independently from each other optionally substituted with $C_1$-$C_5$ alkyl, a ring system containing five to twelve atoms optionally substituted with $C_1$-$C_5$ alkyl
each n, is an integer being independently from each other selected from be 0 to 5;
$R_3$ and R4 are each independently from each other be absent or selected from a ring system containing five to 15 atoms, each optionally substituted with at least one of straight or branched $C_1$-$C_5$ alkyl, (=O), (=S), (O)$_2$, —C(O)—CH$_3$, —C(O)—O—CH$_3$, halide, CF$_3$, nitro, amide, or $R_5$, $R_5$ is an a ring system containing five to twelve atoms optionally substituted by at least one halide or straight $C_1$-$C_5$ alkyl or branched $C_1$-$C_5$ alkyl.

In some embodiments, $R_1$ and $R_2$ are each independently from each other selected from H or straight $C_1$-$C_5$ alkyl, L1 and L2 are each independently from each other selected to be absent or from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$, —(CH$_2$)$_n$—N—C(=O)—, S(O)$_2$—N—(CH$_2$)$_n$, —(CH$_2$)$_n$—S—, NH, —(CH$_2$), —S—(CH$_2$)$_n$—C(O)—NH—(CH2)$_n$—, —(CH$_2$)$_n$—(NH)$_n$—C(=O)—(CH$_2$)$_n$—, —NH—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; —C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be each independently from each other optionally substituted with $C_1$-$C_5$ alkyl, a ring system containing five to twelve atoms optionally substituted with $C_1$-$C_5$ alkyl; each n, is an integer being independently from each other selected from be 0 to 5;
$R_3$ and R4 are each independently from each other be absent or selected from a ring system containing five to 15 atoms, each optionally substituted with at least one of straight or branched $C_1$-$C_5$ alkyl, (=O), (=S), (O)$_2$, —C(O)—CH$_3$, —C(O)—O—CH$_3$, halide, CF$_3$, nitro, amide, or $R_5$, $R_5$ is an a ring system containing five to twelve atoms optionally substituted by at least one halide or straight $C_1$-$C_5$ alkyl or branched $C_1$-$C_5$ alkyl.

In some other embodiments, $R_1$ and $R_2$ are each independently from each other selected from H, straight $C_1$-$C_5$ alkyl, L1 is absent and L2 is selected from —(CH$_2$)—S—, —(CH$_2$)—O—, —(CH$_2$)—; $R_3$ and R4 are each independently from each other be absent or selected from a ring system containing five to 15 atoms, each optionally substituted with at least one of straight or branched $C_1$-$C_5$ alkyl, —C(O)—CH$_3$, —C(O)—O—CH$_3$, halide, CF$_3$, nitro, amide, or $R_5$, $R_5$ is an a ring system containing five to twelve atoms optionally substituted by at least one halide or straight $C_1$-$C_5$ alkyl or branched $C_1$-$C_5$ alkyl.

In some other embodiments, $R_1$ and $R_2$ are each independently from each other selected from H, straight $C_1$-$C_5$ alkyl, L1 is absent and L2 is selected from —(CH$_2$)—S—, —(CH$_2$)—O—, —(CH$_2$)—;
$R_3$ is a bicyclic ring and R4 is an aryl or a heteroaryl.

In yet some alternative particular embodiments of the SMC modulator for use in accordance with the invention, the compound of Formula XI, may provide a compound having the general formula (XIII):

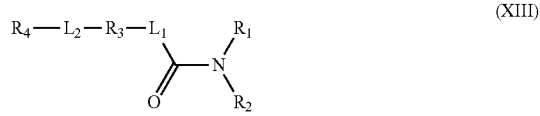

(XIII)

or a pharmaceutically acceptable salt, solvate, hydrate, stereoisomer or physiologically functional derivative thereof,
wherein
$R_1$ and $R_2$ are each independently from each other selected from H, a ring system containing five to seven atoms, each optionally substituted by at least one of halide, amide, amine, nitro;
L1 and L2 if present are each independently may be absent or from each other selected from —CH$_2$—(CH$_2$—C(O)—N)—(CH$_2$)$_2$, —(CH$_2$)—S—, —(CH$_2$)—, —(CH$_2$)—O—, —NH—(CH$_2$)—
each independently from each other optionally substituted with $C_1$-$C_5$ alkyl, a ring system containing five to seven atoms optionally substituted with $C_3$-$C_5$ alkyl;
$R_3$ and R4 are each independently from each other absent or selected from a ring system containing five to 12 atoms, each optionally substituted with at least one of straight $C_1$-$C_5$ alkyl, (=O), (=S), or $R_5$, $R_5$ is an a ring system containing five to seven atoms optionally substituted by at least one halide or straight $C_1$-$C_5$ alkyl.

In more specific embodiments for the compound of Formula XIII, at least one of $R_1$ and $R_2$ is C5-C7 saturated cycloalkyl, C5-C7 saturated cycloalkylene, C5-C7 aryl or C5-C7 arylene, L1 may be absent or selected from —CH$_2$—CH$_2$—C(O)—N—CH$_2$—C(O)—NH—CH$_2$—, —CH$_2$—, each optionally substituted with ethyl, methyl, an aryl optionally substituted with a methyl or ethyl, L2 may be absent or may be selected from CH$_2$, at least one of $R_3$ and $R_4$ may be $C_2$-$C_{12}$ heterocycloalkyl ring, $C_2$-$C_{12}$ heteroaryl or $C_2$-$C_{12}$ heteroarylene. In some embodiments, the heteroatom may be N, O, S.

In still further some embodiments, at least one of $R_1$ and $R_2$ is selected from the group consisting of cyclopentane or thiazole, L1 is absent or —$CH_2$—$CH_2$—C(O)—N—$CH_2$—C(O)—NH—$CH_2$—, substituted with an aryl optionally substituted with a methyl, L2 is absent or selected from $CH_2$, at least one of $R_3$ and $R_4$ is selected from the group consisting of piperidine, piperazine, quinoline, isoquinoline, phthalazine, tetrahydro-quinoline, pyridine, tetrahydro-quinazoline substituted with —C(O)—$CH_3$.

In some particular embodiments, specific and non-limiting examples of the SMC modulators for use of the invention, or pharmaceutically acceptable salts or hydrates of the compounds of Formula XI, or in some further specific embodiments, pharmaceutically acceptable salts or hydrates of the compounds of Formula XIII may include:

(a)

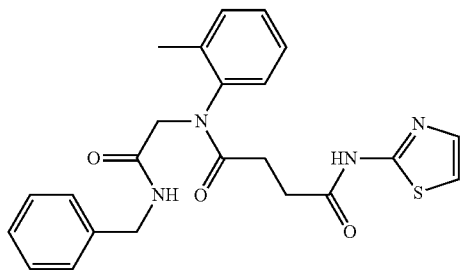

N'-[2-(benzylamino)-2-oxoethyl]-N'-(2-methylphenyl)-N-(1,3-thiazol-2-yl)butanediamide (Designated herein as SMC #33).

In yet another alternative, the compound may be

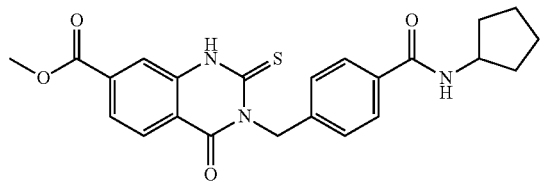 [SMILES: COC(=O)c1ccc2c(=O)n(Cc3ccc(C(=O)NC4CCCC4)cc3)c(=S)[nH]c2c1]

3-(4-Cyclopentylcarbamoyl-benzyl)-4-oxo-2-thioxo-1,2,3,4-tetrahydro-quinazoline-7-carboxylic acid methyl ester (Designated herein as SMC #30).

In yet some further embodiments, specific examples of compounds or pharmaceutically acceptable salts or hydrates of the compounds of Formula I that may be used by the invention include, without limitation:

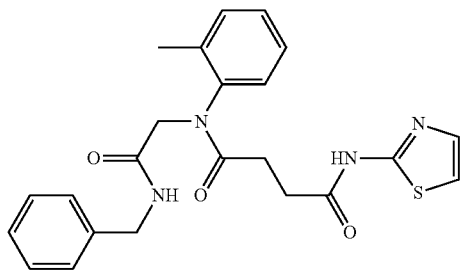 [SMILES: Cc1ccccc1N(CC(=O)NCc1ccccc1)C(=O)CCC(=O)Nc1nccs1]

N'-[2-(benzylamino)-2-oxoethyl]-N'-(2-methylphenyl)-N-(1,3-thiazol-2-yl)butanediamide (Designated herein as SMC #33);

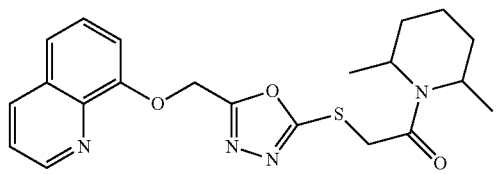 [SMILES: CC1CCCC(C)N1C(=O)CSc1nnc(COc2cccc3cccnc23)o1]

1-(2,6-dimethylpiperidin-1-yl)-2-[[5-(quinolin-8-yloxymethyl)-1,3,4-oxadiazol-2-yl]sulfanyl]ethanone (Designated herein as SMC #34);

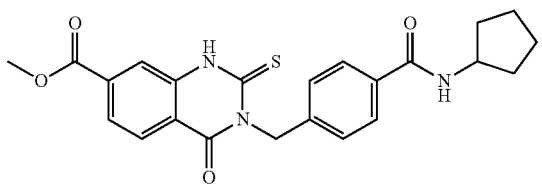 [SMILES: COC(=O)c1ccc2c(=O)n(Cc3ccc(C(=O)NC4CCCC4)cc3)c(=S)[nH]c2c1]

3-(4-Cyclopentylcarbamoyl-benzyl)-4-oxo-2-thioxo-1,2,3,4-tetrahydro-quinazoline-7-carboxylic acid methyl ester (Designated herein as SMC #30);

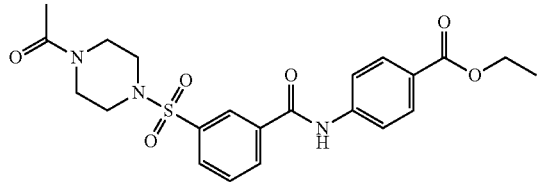 [SMILES: CCOC(=O)c1ccc(NC(=O)c2cccc(S(=O)(=O)N3CCN(C(C)=O)CC3)c2)cc1]

ethyl 4-[[3-(4-acetylpiperazin-1-yl)sulfonylbenzoyl]amino]benzoate (Designated herein as SMC #23);

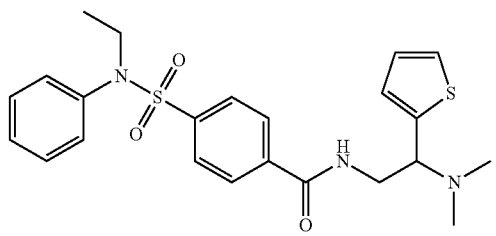 [SMILES: CCN(c1ccccc1)S(=O)(=O)c1ccc(C(=O)NCC(c2cccs2)N(C)C)cc1]

N-[2-(dimethylamino)-2-thiophen-2-ylethyl]-4-[ethyl(phenyl)sulfamoyl]benzamide (Designated herein as SMC #24);

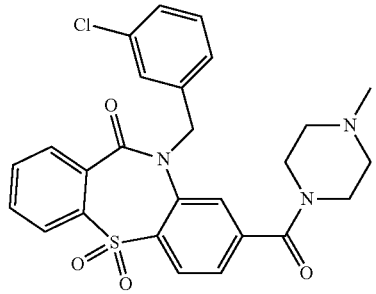 [SMILES: CN1CCN(C(=O)c2ccc3c(c2)N(Cc2cccc(Cl)c2)C(=O)c2ccccc2S3(=O)=O)CC1]

10-(3-Chloro-benzyl)-8-(4-methyl-piperazine-1-carbonyl)-5,5-dioxo-5,10-dihydro-5λ6-dibenzo[b,f][1,4]thiazepin-11-one (Designated herein as SMC #26);

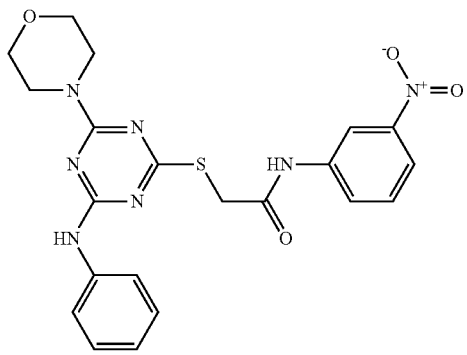

2-(4-Morpholin-4-yl-6-phenylamino-[1,3,5]triazin-2-ylsulfanyl)-N-(3-nitro-phenyl)-acetamide (Designated herein as SMC #15);

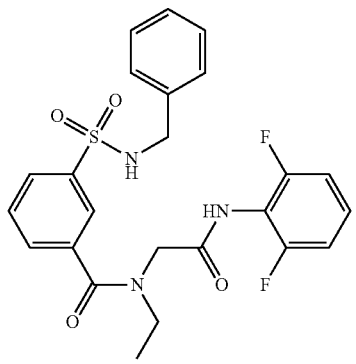 [SMILES: CCN(CC(=O)Nc1c(F)cccc1F)C(=O)c1cccc(S(=O)(=O)NCc2ccccc2)c1]

3-(benzylsulfamoyl)-N-[2-(2,6-difluoroanilino)-2-oxoethyl]-N-ethylbenzamide (Designated herein as SMC #25);

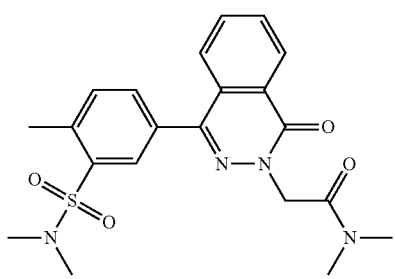

2-[4-[3-(dimethylsulfamoyl)-4-methylphenyl]-1-oxophthalazin-2-yl]-N,N-dimethylacetamide (Designated herein as SMC #16);

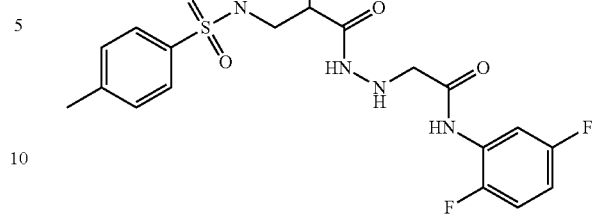

N-(2,5-difluorophenyl)-2-[2-[1-(4-methylphenyl)sulfonylpiperidine-3-carbonyl]hydrazinyl]acetamide (Designated herein as SMC #21);

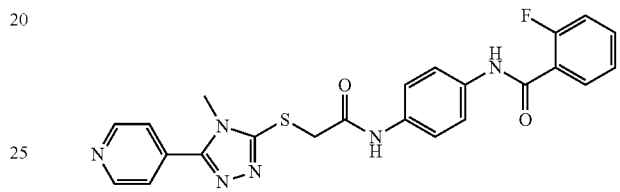

2-fluoro-N-[4-[[2-[(4-methyl-5-pyridin-4-yl-1,2,4-triazol-3-yl)sulfanyl]acetyl]amino]phenyl]benzamide (Designated herein as SMC #31);

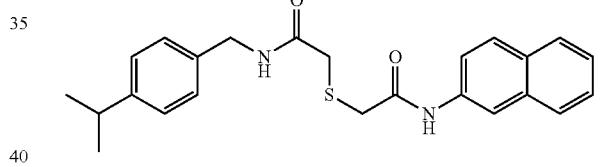

2-[2-(naphthalen-2-ylamino)-2-oxoethyl]sulfanyl-N-[(4-propan-2-ylphenyl)methyl]acetamide (Designated herein as SMC #17);

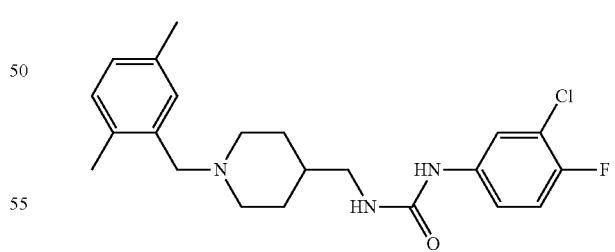

1-(3-chloro-4-fluorophenyl)-3-[[1-[(2,5-dimethylphenyl)methyl]piperidin-4-yl]methyl]urea (Designated herein as SMC #28).

In some alterative embodiments, the compound of the invention may be any compound defined by having general formula (I) above provided that the compound is not any one of the compounds detailed below, specifically:

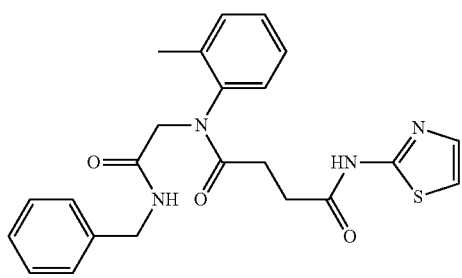

N'-[2-(benzylamino)-2-oxoethyl]-N'-(2-methylphenyl)-N-(1,3-thiazol-2-yl)butanediamide (Designated herein as SMC #33);

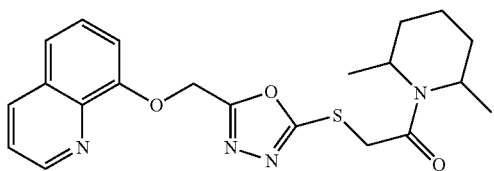 [SMILES: CC1CCCC(C)N1C(=O)CSc1nnc(COc2cccc3cccnc23)o1]

1-(2,6-dimethylpiperidin-1-yl)-2-[[5-(quinolin-8-yloxymethyl)-1,3,4-oxadiazol-2-yl]sulfanyl]ethanone (Designated herein as SMC #34);

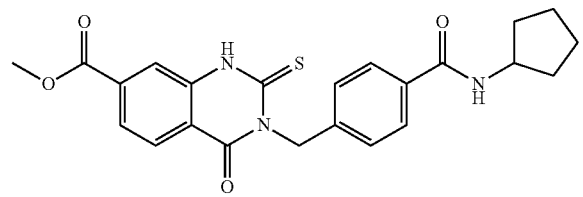 [SMILES: COC(=O)c1ccc2c(=O)n(Cc3ccc(C(=O)NC4CCCC4)cc3)c(=S)[nH]c2c1]

3-(4-Cyclopentylcarbamoyl-benzyl)-4-oxo-2-thioxo-1,2,3,4-tetrahydro-quinazoline-7-carboxylic acid methyl ester (Designated herein as SMC #30);

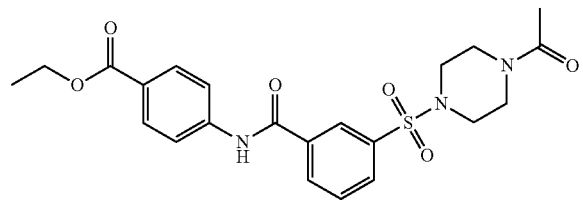 [SMILES: CCOC(=O)c1ccc(NC(=O)c2cccc(S(=O)(=O)N3CCN(C(C)=O)CC3)c2)cc1]

ethyl 4-[[3-(4-acetylpiperazin-1-yl)sulfonylbenzoyl]amino]benzoate (Designated herein as SMC #23);

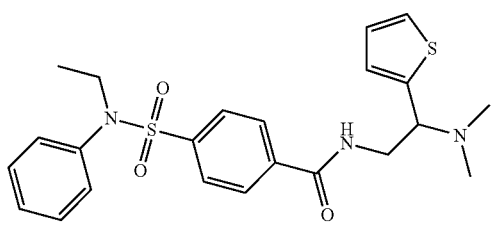 [SMILES: CCN(c1ccccc1)S(=O)(=O)c1ccc(C(=O)NCC(c2cccs2)N(C)C)cc1]

N-[2-(dimethylamino)-2-thiophen-2-ylethyl]-4-[ethyl(phenyl)sulfamoyl]benzamide (Designated herein as SMC #24);

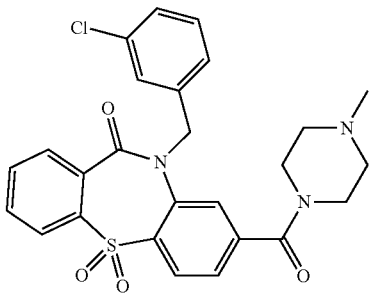 [SMILES: CN1CCN(C(=O)c2ccc3c(c2)N(Cc2cccc(Cl)c2)C(=O)c2ccccc2S3(=O)=O)CC1]

10-(3-Chloro-benzyl)-8-(4-methyl-piperazine-1-carbonyl)-5,5-dioxo-5,10-dihydro-5λ6-dibenzo[b,f][1,4]thiazepin-11-one (Designated herein as SMC #26);

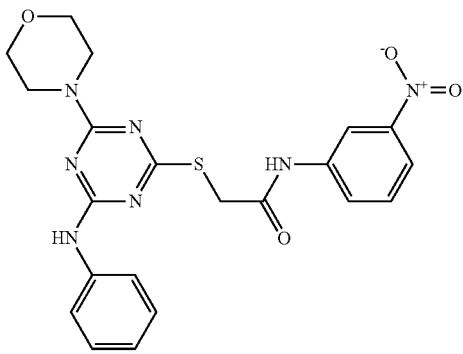

2-(4-Morpholin-4-yl-6-phenylamino-[1,3,5]triazin-2-ylsulfanyl)-N-(3-nitro-phenyl)-acetamide (Designated herein as SMC #15);

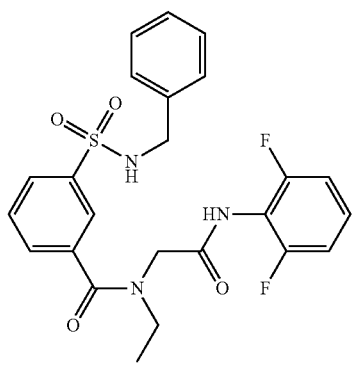 [SMILES: CCN(CC(=O)Nc1c(F)cccc1F)C(=O)c1cccc(S(=O)(=O)NCc2ccccc2)c1]

3-(benzylsulfamoyl)-N-[2-(2,6-difluoroanilino)-2-oxoethyl]-N-ethylbenzamide (Designated herein as SMC #25);

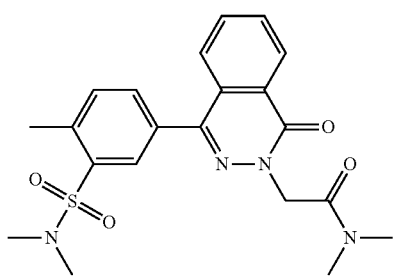

2-[4-[3-(dimethylsulfamoyl)-4-methylphenyl]-1-oxophthalazin-2-yl]-N,N-dimethylacetamide Designated herein as SMC #16);

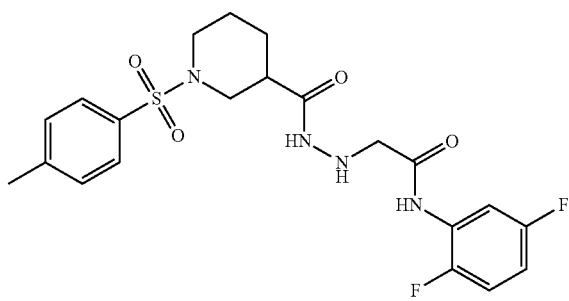 [SMILES: Cc1ccc(S(=O)(=O)N2CCCC(C(=O)NNCC(=O)Nc3cc(F)ccc3F)C2)cc1]

N-(2,5-difluorophenyl)-2-[2-[1-(4-methylphenyl)sulfonylpiperidine-3-carbonyl]hydrazinyl]acetamide (Designated herein as SMC #21);

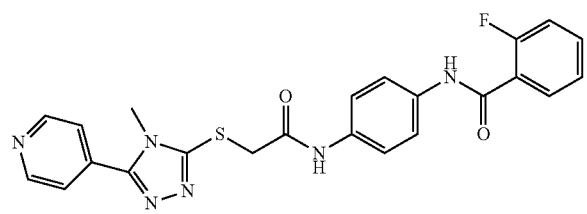 [SMILES: Cn1c(SCC(=O)Nc2ccc(NC(=O)c3ccccc3F)cc2)nnc1-c1ccncc1]

2-fluoro-N-[4-[[2-[(4-methyl-5-pyridin-4-yl-1,2,4-triazol-3-yl)sulfanyl]acetyl]amino]phenyl]benzamide (Designated herein as SMC #31);

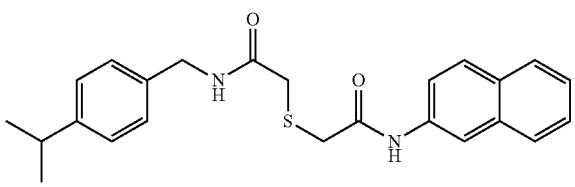 [SMILES: CC(C)c1ccc(CNC(=O)CSCC(=O)Nc2ccc3ccccc3c2)cc1]

2-[2-(naphthalen-2-ylamino)-2-oxoethyl]sulfanyl-N-[(4-propan-2-ylphenyl)methyl]acetamide (Designated herein as SMC #17);

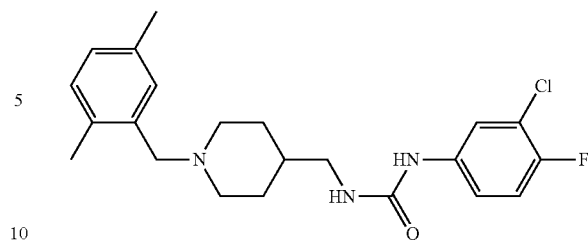

1-(3-chloro-4-fluorophenyl)-3-[[1-[(2,5-dimethylphenyl)methyl]piperidin-4-yl]methyl]urea (Designated herein as SMC #28)

Still further, in some embodiments, the SMC is N'-[2-(benzylamino)-2-oxoethyl]-N'-(2-methylphenyl)-N-(1,3-thiazol-2-yl)butanediamide having a structure:

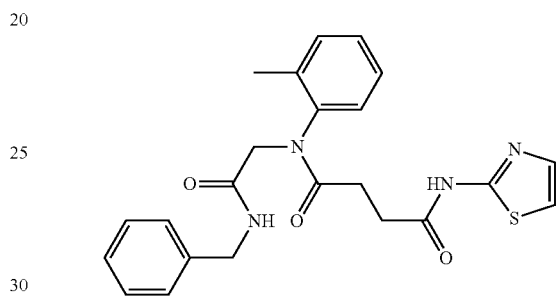

(denoted herein as SMC #33)

In some embodiments, the SMC is 1-(2,6-dimethylpiperidin-1-yl)-2-[[5-(quinolin-8-yloxymethyl)-1,3,4-oxadiazol-2-yl]sulfanyl]ethanone having a structure

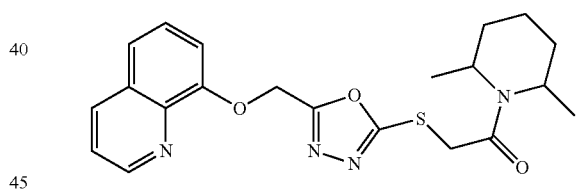

(denoted herein as SMC #34);

In some embodiments, the SMC is ethyl 4-[[3-(4-acetylpiperazin-1-yl)sulfonylbenzoyl]amino]benzoate having a structure

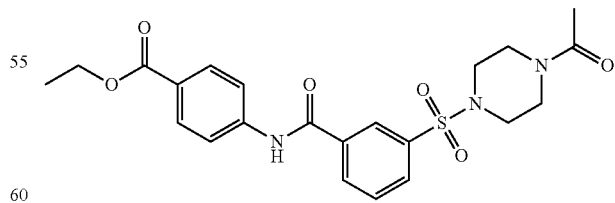

(denoted herein as SMC #23);

In some embodiments, the SMC is 10-(3-Chloro-benzyl)-8-(4-methyl-piperazine-1-carbonyl)-5,5-dioxo-5,10-dihydro-5λ6-dibenzo[b,f][1,4]thiazepin-11-one having a structure

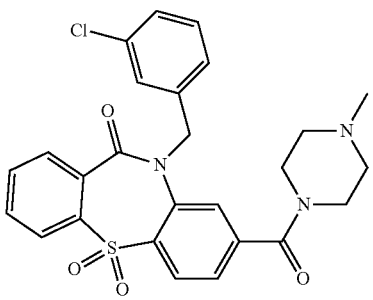 [SMILES: CN1CCN(C(=O)c2ccc3c(c2)N(Cc2cccc(Cl)c2)C(=O)c2ccccc2S3(=O)=O)CC1]

(denoted herein as SMC #26);

In accordance with some other aspects, the present disclosure provides a compound having the general formula (V):

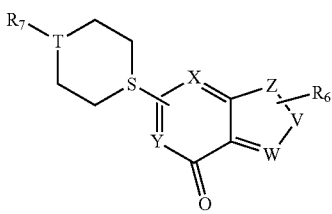

or a pharmaceutically acceptable salt, solvate, hydrate, stereoisomer or physiologically functional derivative thereof,
wherein
each one of X, Y, Z, V, W, T and S may be selected from N, NH and C,
$R_6$ and $R_7$ are the same or are different and are independently selected from each other may be L3-$R_8$,
L3 may be selected from —$(CH_2)n$, —NH—C(O) and C(O)—NH, $S(O)_2$, C(O),
n is an integer between 0 to 5;
$R_8$ may be selected from a ring system containing five to twelve atoms, each optionally substituted by at least one of straight or branched $C_1$-$C_5$ alkyl, halide, hydroxyl, ester, ether, amide, nitro and hydroxyl, $CF_3$.

In accordance with some embodiments, the compound having the general formula (V) may be represented by the general formula (VI):

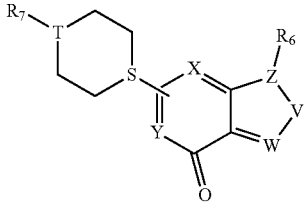

wherein each one of X, Y, Z, V, W, T, S, $R_6$ and $R_7$ are as defined in formula (V).

In accordance with some embodiments, the compound having the general formula (V) may be represented by the general formula (VII):

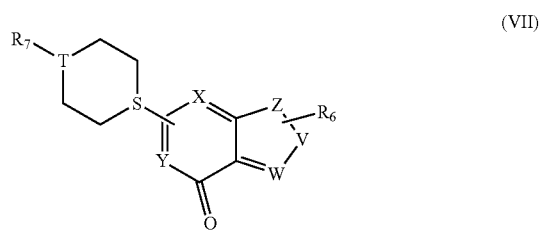

wherein each one of X, Y, Z, V, W, T, S, $R_6$ and $R_7$ are as defined in formula (V).

In accordance with some embodiments, the compound having the general formula (V) may be represented by the general formula (VIII):

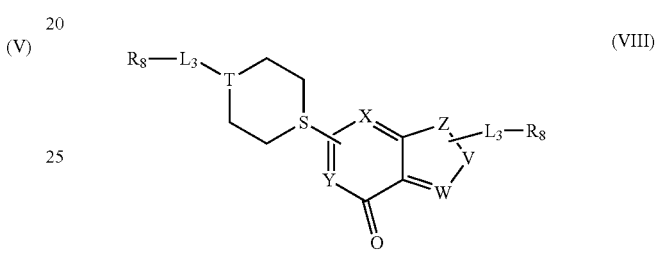

wherein X, Y, Z, W and T may be selected from N and V is selected from NH;
L3 may be selected from —$(CH_2)$—, and —$S(O)_2$;
$R_8$ may be an aryl optionally substituted by at least one halide or $CF_3$.

In some embodiments, specific examples of compounds or pharmaceutically acceptable salts or hydrates of the compounds of Formula V include, without limitation:

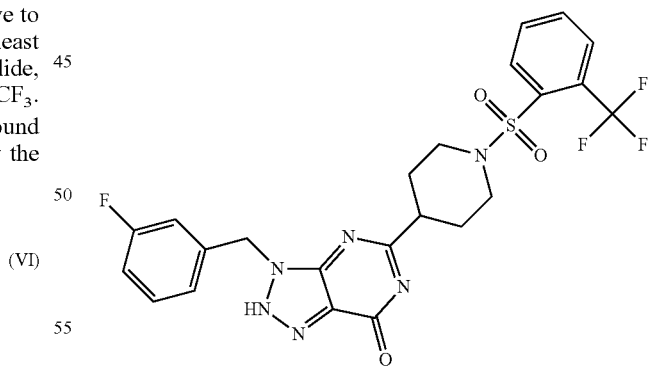

3-[(3-fluorophenyl)methyl]-5-[1-[2-(trifluoromethyl)phenyl]sulfonylpiperidin-4-yl]-2H-triazolo[4,5-d]pyrimidin-7-one (Designated herein as SMC #32);

In some alterative embodiments, the compound of the invention may be any compound defined by having general formula (V) above provided that the compound is not

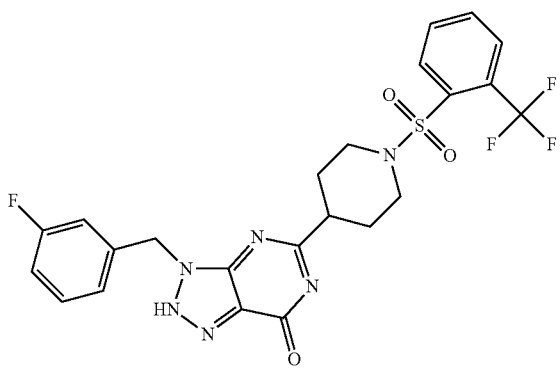

3-[(3-fluorophenyl)methyl]-5-[1-[2-(trifluoromethyl)phenyl]sulfonylpiperidin-4-yl]-2H-triazolo[4,5-d]pyrimidin-7-one
(Designated herein as SMC #32);

In accordance with some other aspects, the present disclosure provides a compound having the general formula (IX):

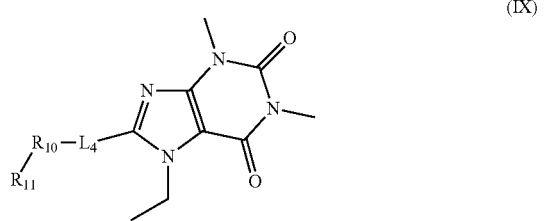

or a pharmaceutically acceptable salt, solvate, hydrate, stereoisomer or physiologically functional derivative thereof,
wherein
L4 may be absent or may be selected from —(CH$_2$)$_n$—, —S—(CH$_2$)$_n$—, —(CH$_2$)$_n$—S—;
n is an integer between 0 and 5;
R$_{10}$ and R11 are each independently from each other absent or selected from a ring system containing five to twelve atoms, each optionally substituted with at least one of straight or branched C$_1$-C$_5$ alkyl, (=O), (=S), —C(O)—CH$_3$, —C(O)—O—CH$_3$, halide, nitro, NH$_2$.

In some embodiments, L4 is selected from —S—(CH$_2$)—. In some other embodiments, R$_{10}$ and R11 are each independently from each other absent or selected from triazine, piperidine each optionally substituted with at least one NH$_2$.

In some embodiments, specific examples of compounds or pharmaceutically acceptable salts or hydrates of the compounds of Formula IX include, without limitation:

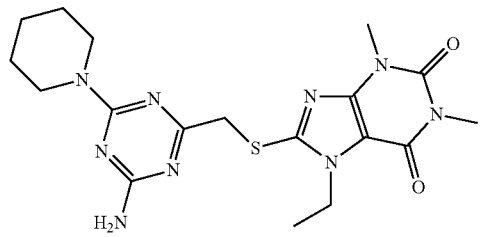 [SMILES: CCn1c(SCc2nc(N)nc(N3CCCCC3)n2)nc2c1c(=O)n(C)c(=O)n2C]

8-[(4-amino-6-piperidin-1-yl-1,3,5-triazin-2-yl)methylsulfanyl]-7-ethyl-1,3-dimethylpurine-2,6-dione (Designated herein as SMC #18).

In yet some alterative embodiments, the compound of the invention may be any compound defined by having general formula (IX) above provided that the compound is not

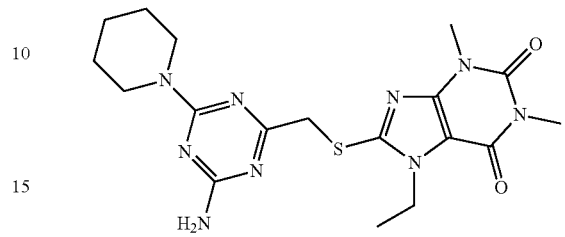

8-[(4-amino-6-piperidin-1-yl-1,3,5-triazin-2-yl)methylsulfanyl]-7-ethyl-1,3-dimethylpurine-2,6-dione (Designated herein as SMC #18).

In accordance with some other aspects, the present disclosure provides a compound having the general formula (X):

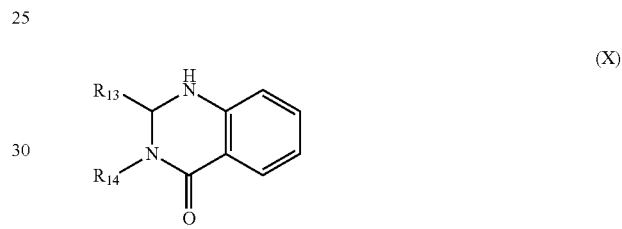

or a pharmaceutically acceptable salt, solvate, hydrate, stereoisomer or physiologically functional derivative thereof,
wherein
R$_{13}$ and R14 are each independently from each other absent or selected from a ring system containing five to twelve atoms, each optionally substituted with at least one of straight or branched C$_1$-C$_5$ alkyl, C$_1$-C$_5$ alkoxy, (=O), (=S), —C(O)—CH$_3$, —C(O)—O—CH$_3$, halide, nitro, NH$_2$, NH—C(O)—CH$_3$.

In some other embodiments, R$_{10}$ and R11 are each independently from each other absent or selected from aryl each optionally substituted with at least one OCH, NH—C(O)—CH$_3$.

In some embodiments, specific examples of compounds or pharmaceutically acceptable salts or hydrates of the compounds of Formula X include, without limitation:

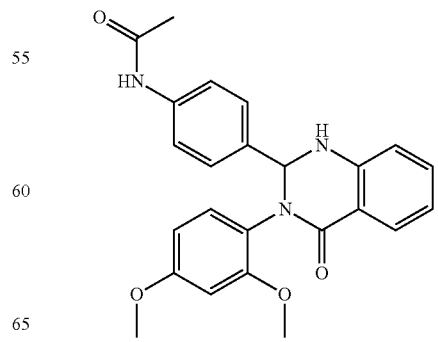

N-[4-[3-(2,4-dimethoxyphenyl)-4-oxo-1,2-dihydroquinazolin-2-yl]phenyl]acetamide (Designated herein as SMC #22).

In yet some alterative embodiments, the compound of the invention may be any compound defined by having general formula (X) above provided that the compound is not

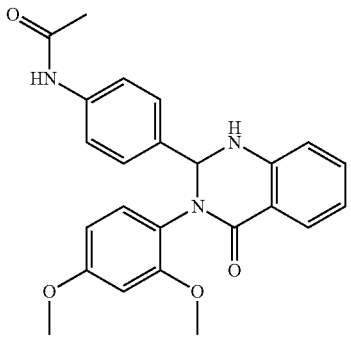

N-[4-[3-(2,4-dimethoxyphenyl)-4-oxo-1,2-dihydroquinazolin-2-yl]phenyl]acetamide (Designated herein as SMC #22).

Still further, in some embodiments, the compound for use in accordance with the uses of the invention may be the SMC #6, specifically. N-[(2R,4R,6S)-2-(4-chlorophenyl)-6-(1-methylbenzotriazol-5-yl)oxan-4-yl]acetamide.

In yet some alternative embodiments, the invention provides the uses of any of the SMCs disclosed herein, provided that said SMC is not SMC #6, specifically, N-[(2R,4R,6S)-2-(4-chlorophenyl)-6-(1-methylbenzotriazol-5-yl)oxan-4-yl]acetamide.

The term "alkyl" as used herein refers to a linear, branched saturated hydrocarbon having from 1 to 20 carbon atoms. The term "$C_1$-$C_{12}$ alkyl" or "$C_1$-$C_{12}$ alkylene" refers to a linear (straight), branched saturated hydrocarbon having from 1 to 12 carbon atoms, in some embodiments, contain from 2 to 8 carbons, in yet some embodiments from 2 to 5 carbons, in yet some further embodiments, from 1 to 3 carbon atoms. It should be noted that alkyl refers to an alkyl end chain and alkylene refers to a middle chain alkyl. Representative $C_1$-$C_{12}$ alkyl groups include, but are not limited to, methyl, ethyl, propyl, isopropyl, cyclopropyl, butyl, sec-butyl, iso-butyl, tert-butyl, cyclobutyl, pentyl, iso-pentyl, neo-pentyl, tert-pentyl, cyclopentyl, hexyl, cyclohexyl, heptyl, cycloheptyl, octyl, sec-octyl (1-methylheptyl), and cyclooctyl.

The term "$C_1$-$C_{12}$ haloalkyl" as used herein refers to a $C_1$-$C_{12}$ alkyl as defined above, with one or more hydrogens substituted by halogen atoms.

The term "alkenyl" as used herein refers to a linear (straight), branched unsaturated hydrocarbon having from 2 to 20 carbon atoms and at least one carbon-carbon double bond. The term "$C_2$-$C_{12}$ alkenyl" or "$C_2$-$C_{12}$ alkenylene" as used herein refers to a linear, branched unsaturated hydrocarbon having from 2 to 12 carbon atoms and at least one carbon-carbon double bond, in some embodiments from 3 to 8 carbons, in yet some further embodiments, from 3 to 5 carbon atoms and at least one double bond. It should be noted that alkenyl refers to an alkyl end chain and alkenylene refers to a middle chain alkyl.

The term "$C_2$-$C_{12}$ haloalkenyl" as used herein refers to a $C_2$-$C_{12}$ alkenyl as defined above, with one or more hydrogens substituted by halogen atoms.

The term "alkynyl" as used herein refers to a linear, branched unsaturated hydrocarbon having from 2 to 20 carbon atoms and at least one carbon-carbon triple bond. The term "$C_2$-$C_{12}$ alkynyl" or "$C_2$-$C_{12}$ alkynylene" as used herein refers to a linear, branched unsaturated hydrocarbon having from 2 to 12 carbon atoms in certain embodiments, from 3 to 8 carbons, and at least one triple bond (at least one carbon-carbon triple bond). It should be noted that alkynyl refers to an alkyl end chain and alkynylene refers to a middle chain alkyl.

The term "$C_2$-$C_{12}$ haloalkynyl" as used herein refers to a $C_2$-$C_{12}$ alkynyl as defined above, with one or more hydrogens substituted by halogen atoms.

As used herein "alkoxy" refers to an alkyl group bonded to an oxygen atom. Similarly, the term "$C_1$-$C_{12}$ alkoxyl" as used herein refers to a $C_1$-$C_{12}$ alkyl group linked to an oxygen. At times, the alkyl group may include one to twelve carbon atoms, at times between one to eight carbon atoms, at times one to five carbon atoms and at times one to three carbon atoms. Representative examples are methoxy, ethoxy, n-propoxy, isopropoxy, butoxy, sec-butoxy, tert-butoxy, pentoxy, isopentoxy, hexoxy, isohexoxy and the like. In certain embodiments, the alkoxy is ethoxy.

The term "halogen" (halo or halide) refers to F, Cl, Br or I.

As used herein, a ring system containing five to twelve atoms refers to a mono- or multi-cyclic ring system having 5 to 12 atoms. The ring system containing five to twelve atoms may be saturated, unsaturated or aromatic rings and the like including for example cycloalkyl, heterocycloalkyl, aryl, arylene, aromatic, heteroaromatic rings. A ring system containing five to twelve atoms may contain two rings (bicyclic, etc.), for example aromatic rings and in such case the aromatic rings of the aryl group may be joined at a single point (e.g., biphenyl), or fused (e.g., naphthyl). In some embodiments, a ring system containing five to twelve atoms is a carbocyclic ring or heterocyclic ring. The term "carbocyclic ring" refers to cyclic compounds containing only carbon atoms. The carbocyclic ring may be optionally substituted by one or more substituents, and may be saturated, unsaturated or aromatic. The term "heterocyclic ring" refers to cyclic compounds where one or more carbons are substituted by heteroatoms. Exemplary heteroatoms include, but not limited to, nitrogen, sulfur, and oxygen. The heterocyclic ring may be optionally substituted, and may be saturated, unsaturated or aromatic. The term "saturated" as used herein means that the compound does not contain double or triple bonds. The term "unsaturated" as used herein means that the compound contains at least one double or triple bond. The term "aromatic" as used herein means that the compound contains alternating double and single bonds.

As used herein, "aryl" refers to aromatic ring systems having between 5 to 12 atoms. Unless otherwise specifically defined, the term "aryl" refers to cyclic, aromatic hydrocarbon groups that have 1 to 2 aromatic rings, including monocyclic or bicyclic groups having between 5 to 12 atoms. Non-limiting examples include phenyl, biphenyl or naphthyl. The aryl group may be optionally substituted by one or more substituents, e.g., 1 to 5 substituents, at any point of attachment. The substituents can themselves be optionally substituted. As used herein, "$C_5$-$C_{12}$ aromatic" refers to aromatic ring systems having 5 to 12 carbon atoms, such as phenyl, naphthalene and the like.

As used herein, the term "heteroaryl" refers to aryls as defined above where one or more carbons are substituted by heteroatoms. Exemplary heteroatoms include, but not limited to, nitrogen, sulfur, and oxygen. As used herein, "heteroaromatic" refers to refers to a monocyclic or multi-cyclic (fused) aromatic ring system, where one or more of the atoms in the ring system is a heteroatom, that is, an element other than carbon, including but not limited to, nitrogen, oxygen or sulfur. The term "heteroaromatic" used interchangeably with the term "heteroaryl" denotes a heterocyclic aromatic ring systems containing 5 to 12 atoms, with at least one, preferably two carbon atoms and one or more heteroatoms selected from nitrogen, oxygen and sulfur. Non-limiting examples include furan, thiophene, pyrrole, oxazole, oxadiazole, thiazole, imidazole, pyrazole, isoxazole, thiazolem benzofuran, indole, benzothiophene, benzoimidazole, indazole, benzoxazole, benzoisoxazole, benzothiazole, isobenzofuran, isoindole, purine, pyridine, pyrazine, pyrimidine, pyridazine, quinoline, quinazoline, quinazoline, isoquinoline, furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, [1,3,4]thiadiazole, thiadiazole, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like.

As used herein, "$C_5$-$C_{12}$ saturated cycloalkyl" refers to a saturated mono- or multi-cyclic ring system having 5 to 12 carbon atoms, preferably having 5 to 7 carbon atoms. Example of "$C_5$-$C_{12}$ cycloalkyl" groups include, but are not limited to cyclopentyl, cyclohexyl and cycloheptyl.

As used herein, "heterocycloalkyl" or "heterocyclyl" or the term "heterocyclic" refers to a monocyclic or multi-cyclic non-aromatic ring system having 5 to 12 members, preferably having 5 to 7 carbon atoms, where one or more, in certain embodiments, 1 to 3, of the atoms in the ring system is a heteroatom, that is, an element other than carbon, including but not limited to, nitrogen, oxygen or sulfur. Examples of "heteroalkyl" include, but are not limited to, pyran, 1,4-dioxane, 1,3-dioxane, piperidine, pyrrolidine, morpholine, tetrahydrothiopyran, tetrahydrothiophene, and the like. The term heterocycloalkyl" also encompasses non-aromatic ring being unsaturated or having one or more degrees of unsaturation containing one or more heteroatomic substitutions selected from S, SO, $SO_2$, O, or N. "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

The term "bicyclic ring" or "bicyclic group" as used herein refers to system or group that features two joined rings and encompasses a carbocyclic (all of the ring atoms are carbons), or heterocyclic (the rings atoms consist of at least two different elements). The bicyclic group can be aromatic, aliphatic or a combination of aliphatic and aromatic. The bicyclic group for example can be any one of the following (i) the two rings share only one single atom, (ii) fused bicyclic compounds, two rings share two adjacent atoms, (iii) bridged bicyclic compounds the two rings share three or more atoms, separating the two bridgehead atoms by a bridge containing at least one atom. The bicyclic group can be optionally substituted as detailed herein.

Non-limiting example of bicyclic group include benzofuran, isobenzofuran, isoindole, benzothiophene, benzo[c] thiophene, benzimidazole, indazole, benzoxazole, benzisoxazole, benzothiazole, naphthalene, quinoline, isoquinoline, quinoxaline, quinazoline, cinnoline, phthalazine.

The term "N-containing group" is used herein a chemical group containing a nitrogen atom for example as amino group. The term "amino" as used herein encompass primary, secondary, tertiary or quaternary amines where the point of attachment is through the nitrogen atom which is substituted. For example, the "N-containing group" include N, NH, $NH_2$, tertiary amine (tertiary alkyl amine), quaternary ammonium (quaternary alkyl ammonium). The nitrogen atom may be substituted with alkyl. In case of a tertiary amine or quaternary amines, the substituent may be the same or may be different.

The term "bond" as used herein denotes a covalent bond. The bond may be between two similar atoms or between different atoms. Non-limiting examples include C—C, C—S, C—O, C—N, S—O, S—N, N—O and the like. It should be noted that a bond as defined above, for example, C—S encompasses both C—S and S—C and this holds for the bonds as defined herein.

The term "optionally substituted" refers to substitution with the named substituent or substituents, multiple degrees of substitution being allowed unless otherwise stated. The term substituted as used herein means that the compounds may contain one or more substituents, including, but not limited to, optionally substituted OH, $CF_3$, halogen, C(=O), —COOH, —$NH_2$, CN, alkyl, alkenyl, alkynyl, alkylene, straight alkenylene, alkynylene, haloalkyl, haloalkenyl, haloalkynyl, alkoxy, carboxyl, halogen, ring system including five to twelve atoms, aromatic or heteroaromatic ring, C(=O)— alkyl.

It should be noted that the carbon number, as used herein, refers to the carbon backbone and carbon branching, but does not include carbon atoms of the substituents, such as alkoxy substitutions and the like.

The invention provides new SMC that act as WASp modulators. A small molecule in the context of the present disclosure refers to a low molecular weight organic compound, having a molecular weight lower than 900 Daltons. In accordance with the present disclosure, when referring to a small molecule it includes also crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" or "polymorph," as used herein include all crystalline and amorphous forms of a small molecule, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

In accordance with the present disclosure, the term "small molecule" may include pharmaceutically acceptable forms of the recited compounds, including chelates, non-covalent complexes, prodrugs, and mixtures thereof. Further and in accordance with the preset disclosure, the term "small molecule" includes also pharmaceutically acceptable forms of a particular molecule and as such the term small molecule also encompasses pharmaceutically acceptable salts.

As detailed above, in accordance with the first aspect, the present disclosure provides small molecule compounds that bind to the N'-terminus of WASp for use in modulating WASp degradation and/or stability in a cell. More specifically, in some embodiments, the SMC modulator of the invention specifically binds to WASp degradation pocket. In more specific embodiments, WASp degradation pocket is located at the N-terminal WASp-homology-1 (WH1) domain of WASp. More specifically, this pocked comprise at least one of lysine residues 76 and 81. Thus, in more specific embodiments, the SMCs of the invention are specifically directed to the N-terminal WH1 domain of WASp.

As used herein, WASp (Wiskott-Aldrich syndrome protein) is a 502-amino acid protein encoded by a gene located at the short arm of the X chromosome (Xp11.22-p11.23.1). WASp serves as an adaptor protein that facilitates actin cytoskeletal rearrangements that are essential for normal immune cell responses. More specifically, WASp is a member of a distinct family of proteins that participate in the transduction of signals from the cell surface to the actin cytoskeleton. This family is characterized by a C-terminal tripartite domain containing a common actin monomer-binding motif, WASp-homology domain 2 (WH2) or verprolin homology domain (V), and a central-acidic (CA) region which is capable of activating the actin related protein (Arp)2/3 complex, a potent nucleator of actin polymerization. The activities of WASp family members are normally tightly controlled within a cell, allowing for both spatial and temporal regulation of actin polymerization. WASp is regulated by several mechanisms including the adoption of an auto inhibited conformation in which the VCA domain forms a hydrophobic interaction with the GTPase binding domain (GBD, residues 230-288) and adjacent C-terminal residues. Binding of GTP-loaded Cdc42 and phosphatidylinositol 4, 5-bisphosphate (PIP2) appears to cooperatively disrupt this interaction, thereby freeing the C-terminus for binding to the Arp2/3 complex. Serine and tyrosine phosphorylation of WASp also acts to directly regulate its activity, although until recently this has been relatively unexplored, particularly in vivo. The N-terminus of WASp/N-WASp contains an Ena/VASP homology 1 (EVH1), which binds the widely expressed verprolin homologue. WIP (WASp interacting protein). The majority of WASp in cells is complexed with WIP, and the WIP/WASp interaction is important for WASp activation by Cdc42 through Toca-1. WIP is a molecular chaperone crucial for the stability of WASp, which otherwise is susceptible to proteolytic cleavage through calpain and possibly the 26S ubiquitin proteasome systems.

As used herein, WASp is a protein exclusively expressed in hematopoietic cells. In some embodiments, said WASp may be a human WASp. In more specific embodiments, said human WAS protein may comprise the amino acid sequence as denoted by Accession number P42768 (CCDS: CCDS14303.1). In more specific embodiments, the amino acid sequence of WASp is as denoted by SEQ ID NO. 1. In some specific embodiments said WASp is encoded by the cDNA of Accession number NM_000377. In more specific embodiments, said cDNA sequence of WASp is denoted by SEQ ID NO. 2.

As demonstrated in FIG. 13, the SMC modulators of the invention, specifically, any of the modulators disclosed by the invention in connection with any aspects thereof, may enhance and stabilize the protective interaction between WASp and WIP. Therefore, in certain embodiments, the SMC modulators of the invention may act as enhancers and stabilizers of the WASp and WIP interaction. In yet some further alternative embodiments, the compounds of the invention may act as WIP mimetic compounds, thereby protecting WASp from proteolysis.

As shown in FIG. 7, by binding to the degradation pocket in WASp, the SMC modulators of the invention modulate WASp ubiquitylation. Thus, in some embodiments, binding of the SMC modulators of the invention (specifically, any of the modulators disclosed by the invention in connection with any aspects thereof), to WASp may lead to modulation of WASp ubiquitylation in a cell. It should be noted that "modulation" as used herein encompasses either "inhibition of ubiquitylation, or alternatively, enhancement".

More specifically, the terms "inhibition", "moderation", "reduction" or "attenuation" as referred to herein, relate to the retardation, restraining or reduction of WASp ubiquitylation by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

Alternatively, the terms "increase", "augmentation" and "enhancement" as used herein relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of WASp ubiquitylation as compared to a suitable control. It should be appreciated that 10%, 50%, 120%, 500%, etc., are interchangeable with "fold change" values, i.e., 0.1, 0.5, 1.2, 5, etc., respectively, 10%, 50%, 120%, 500%, etc., are interchangeable with "fold change" values, i.e., 0.1, 0.5, 1.2, 5, etc., respectively. Therefore, the term increase refers to an increase of about 2, 3, 4, 5, 6, 7, 8, 9, 10, 20, 30, 40, 50, 60, 70, 80, 90, 100, 200, 300, 400, 500, 600, 700, 800, 900, 1000 folds or more.

More specifically, the invention provides different SMCs that following binding to WASp, specifically mask its degradation sites at lysine residues 76 and 81, located in a pocket at the N'-terminal WASp-homology-1 (WH1) domain of WASp. Thus, in some embodiments, SMC binding to WASp induces modulation of ubiquitin proteasome-mediated degradation of WASp in a cell.

"Ubiquitylation-dependent proteosomal degradation" as used herein, is a classical protein degradation pathway within a cell that includes hydrolysis by the proteasome after conjugation of polyubiquitin chains. Before the degradation by the proteasome, a protein undergoes phosphorylation-dependent ubiquitylation. The ubiquitin-proteasome system plays important role in several biological processes such as antigen presentation, endocytosis and cell stress response and represents one of the most important degradation systems in the cell. Misfolded and unfolded proteins are targets for degradation by proteasome in order to maintain cell integrity and survival. Protein ubiquitylation usually requires three processes involving ubiquitin-activating enzyme (E1), ubiquitin-conjugating enzyme (E2s) and ubiquitin ligases (E3s).

As clearly demonstrated in EXAMPLE 3, the prevention of degradation of WASp by the SMC modulators of the invention refers to the ubiquitylation-dependent proteosomal degradation mechanism of WASp in hematopoietic cells, specifically, in platelets, megakaryocytes and lymphocytes.

Thus, in some particular embodiments for the SMC modulator for use in accordance with the invention, any of the described SMC modulator compounds, may attenuate WASp ubiquitylation thereby reducing ubiquitin proteasome-mediated degradation of WASp in a cell.

In more specific embodiments of the SMC modulator of the invention for use, the reduced degradation of WASp caused by the SMC modulator/s may restore, enhance or extend at least one of WASp levels and function in the cell.

It should be understood that where referring to levels of WASp, the invention further encompasses WASp expression and/or stability. "Expression", as used herein generally refers to the process by which gene-encoded information is converted into the structures present and operating in the cell. Therefore, according to the invention "expression" of a gene, specifically, may refer to transcription into a polynucleotide, translation into a protein, or even posttranslational modification of the protein. Protein stability, as used herein, refers to the physical (thermodynamic) stability, and chemical stability of the protein and relates to the net balance of forces, which determine whether a protein will be in its native folded conformation or a denatured state. More specifically, the levels of proteins within cells are determined not only by rates of synthesis as discussed above, but also by rates of degradation and the half-lives of proteins within cells that vary widely, from minutes to several days. In eukaryotic cells, two major pathways mediate protein degradation, the ubiquitin-proteasome pathway, mentioned herein before, and lysosomal proteolysis.

According to some embodiments, wherein indicate "increasing" or "enhancing" the expression or the levels of WASp, it is meant that such increase or enhancement may be an increase or elevation of between about 10% to 100% of the expression and/or stability of WASp. The terms "increase", "augmentation" and "enhancement" as used herein relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of the expression as compared to a suitable control. It should be further noted that increase or elevation may be also an increase of about 2 to $10^6$ folds or more. Still further, it should be appreciated that the increase of the levels or expression of said WASp may be either in translation or the stability of said WASp. With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively. Therefore, the term increase refers to an increase of about 2, 3, 4, 5, 6, 7, 8, 9, 10, 20, 30, 40, 50, 60, 70, 80, 90, 100, 200, 300, 400, 500, 600, 700, 800, 900, 1000 folds or more.

As noted above, WASp is a multifunction protein, acting as an adaptor protein that facilitates actin cytoskeletal rearrangements in response to signals arising at the cell membrane, which are essential for normal immune cell responses. In particular its function includes actin polymerization, sustaining of the immunological synapse, endocytosis, calcium flux, NFAT gene transcription, cellular activation and proliferation.

Moreover, WASp emerges as an important platform for regulating actin polymerization through activation of the Arp2/3 complex, which is a key for cytoskeletal reorganization. It is therefore not surprising that lack of WASp results in a wide range of defects of cellular function involving all hematopoietic cell lineages.

It is thus appreciated that the SMC modulators of the invention may restore WASp function, or phenotype in a cell. The term "phenotype of WASp" as used herein defines the extent of expression of mRNA of WASp, as well as an amount and function of the WAS protein, wherein "restoration of WASp phenotype" means a return of the expression, amount and function to normal levels.

Therefore, in some embodiments, the SMC modulators of the invention protect from WASp degradation and thereby restore the phenotype of WASp in a cell. Specifically the SMCs of the invention restore the expression, amount and function of WASp within a cell. Restore, as used herein in connection with the levels and function of WASp, refers to reinstate, bring back, reinstitute, re-impose, reinstall, reestablish, repair, renovate, recover, elevate, improve, reconstitute, revive, renew, rescue or refresh WAPs levels and/or function, specifically, in a cell displaying abnormal levels of WASp, by the SMCs of the invention in about 5% to 100% or more of the normal WASp levels or function as compared to cells displaying abnormal WASp levels that are not treated with the SMCs of the invention. More specifically, the SMCs of the invention restore about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of WASp levels or function of normal cells as compared to cells displaying abnormal WASp levels that were not treated by the SMCs of the invention.

In certain embodiments, the SMCs of the invention may restore WASp levels and function by attenuating its degradation in hematopoietic cells, for example, leukocytes, platelets and megakaryocytes. As detailed in EXAMPLES 2 and 3, the specific SMC modulators of the invention decreased WASp degradation and thereby restored WASp expression in platelets, peripheral blood mononuclear cells (FIG. 4, FIG. 5, FIG. 6) and T cell lymphocytes (FIG. 5). Retention of WASp levels results in restoration of WASp-mediated cellular function/s.

In some specific embodiment, the cell treated by the SMC modulator/s used in accordance with the invention, may be a hematopoietic cell, more specifically, a non-erythroid hematopoietic cell.

In more specific embodiments, the SMC modulators used by the invention reduce WASp degradation in a non-erythroid hematopoietic cell that may be in some embodiments, at least one of a lymphocyte, platelet, megakaryocyte, granulocyte and monocyte. Thus, in certain specific embodiments, the SMC modulators of the invention may modulate, and specifically, reduce, the WASp ubiquitylation in at least one of lymphocyte, platelet, megakaryocyte, granulocyte and monocyte.

"Hematopoietic cells" are cellular blood components all derived from hematopoietic stem cells in the bone marrow. It should be appreciated that in certain embodiments, hematopoietic cells as used herein include cells of the myeloid and the lymphoid lineages of blood cells. More specifically, myeloid cells include monocytes, (macrophages and dendritic cells (DCs)), granulocytes (neutrophils), basophils, eosinophils, erythrocytes, and megakaryocytes or platelets. The Lymphoid cells include T cells, B cells, and natural killer (NK) cells. Thus, in certain embodiments, the cells treated by the SMC modulators of the invention may be any hematopoietic cell described herein. Generally, blood cells are divided into three lineages: red blood cells (erythroid cells) which are the oxygen carrying, white blood cells (leukocytes, that are further subdivided into granulocytes, monocytes and lymphocytes) and platelets (thrombocytes).

In certain embodiments, the hematopoietic cells treated by the SMC modulators of the invention may be non-erythroid hematopoietic cells. The term "non-erythroid hematopoietic cell" refers to the cells derived from white blood cell precursors and from megakaryocytes and include at least one of granulocytes (neutrophils, basophils, eosinophils), monocytes, lymphocytes, macrophages, dendritic cells and platelets.

In some embodiments, the cell is lymphocyte. In some other embodiments, the cell is T lymphocyte. In some further embodiments, the cell is platelet. In some other embodiments, the cell is megakaryocyte.

Thus, as demonstrated in EXAMPLE 4 (FIG. 8-FIG. 11) addition of the SMC modulators of the invention to lymphocytes, platelets and megakaryocytes not only causes upregulation of WASp expression in these cells but also results in an increase in a specific function of each one of these cells as detailed herein below.

In some specific embodiments, the SMC modulator of the invention may attenuate WASp ubiquitylation in lymphocyte/s, specifically, T lymphocyte/s.

In yet some further specific embodiments, the SMC modulator/s of the invention may attenuate WASp ubiquitylation in platelet/s.

Still further, the SMC modulator/s of the invention may attenuate WASp ubiquitylation in megakaryocyte/s.

As indicated above and demonstrated in the Examples, attenuation of WASp ubiquitylation in a cell restores the levels (FIGS. 4-6) and function (FIGS. 8-11) of WASp in a cell. In more specific embodiments, function of WASp may result in at least one of cell activation, cell proliferation, cell migration, cell homing, cell spreading, cell aggregation, elevation in intracellular calcium concentration, cell adhesion, phagocytosis, and cytolytic activity.

In some specific embodiments, the invention relates to restoring or expending WASp levels and function in lymphocyte/s.

"Lymphocytes" are mononuclear nonphagocytic leukocytes found in the blood, lymph, and lymphoid tissues. They comprise the body's immunologically competent cells and their precursors. They are divided on the basis of ontogeny and function into two classes, B and T lymphocytes, responsible for humoral and cellular immunity, respectively. Most are small lymphocytes 7-10 μm in diameter with a round or slightly indented heterochromatic nucleus that almost fills the entire cell and a thin rim of basophilic cytoplasm that contains few granules. When "activated" by contact with antigen, small lymphocytes begin macromolecular synthesis, the cytoplasm enlarges until the cells are 10-30 μm in diameter, and the nucleus becomes less completely heterochromatic; they are then referred to as large lymphocytes or lymphoblasts. These cells then proliferate and differentiate into B and T memory cells and into the various effector cell types: B cells into plasma cells and T cells into helper, cytotoxic, and suppressor cells.

More specifically, lymphocytes as used herein include T cells, B cells and NK cells. A "T cell" or "T lymphocyte" as used herein is characterized by the presence of a T-cell receptor (TCR) on the cell surface. It should be noted that T-cells include helper T cells ("effector T cells" or "Th cells"), cytotoxic T cells ("Tc," "CTL" or "killer T cell"), memory T cells, and regulatory T cells as well as natural killer T cells, Mucosal associated invariants and Gamma delta T cells.

More specifically, Thymocytes are hematopoietic progenitor cells present in the thymus. Thymocytes are classified into a number of distinct maturational stages based on the expression of cell surface markers. The earliest thymocyte stage is the double negative (DN) stage (negative for both CD4 and CD8), which more recently has been better described as Lineage-negative, and which can be divided into four sub-stages. The next major stage is the double positive (DP) stage (positive for both CD4 and CD8). The final stage in maturation is the single positive (SP) stage (positive for either CD4 or CD8).

B cells or B lymphocytes, develop from hematopoietic stem cells (HSC) that originate from bone marrow. B cells function in the humoral immunity component of the adaptive immune system by secreting antibodies. B cells are characterized by the expression of B cell receptor (BCR) that allows specificity to antigen, against which it will initiate an antibody response. Additionally. B cells present antigen (classified as professional antigen-presenting cells (APCs)) and secrete cytokines. Their development into B cells occurs in several stages, each marked by various gene expression patterns and immunoglobulin H chain and L chain gene loci arrangements, the latter due to B cells undergoing V(D)J recombination as they develop.

Natural killer cells or NK cells are a type of cytotoxic lymphocyte critical to the innate immune system. NK cells (belonging to the group of innate lymphoid cells) are defined as large granular lymphocytes (LGL). The role NK cells play is analogous to that of cytotoxic T cells in the vertebrate adaptive immune response. NK cells provide rapid responses to viral-infected cells, acting at around three days after infection, and respond to tumor formation. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation to kill cells that are missing "self" markers of MHC class 1.

In some specific embodiment, the SMC modulator/s of the invention may up-regulate lymphocyte activation. "Lymphocyte activation" as used herein refers to stimulation of lymphocytes by specific antigen or nonspecific mitogens that result in synthesis of RNA, protein, and DNA and the production of cytokines. This process is followed by proliferation and differentiation of various effector and memory cells. Activation is accompanied by morphologic changes known as lymphocyte transformation, in which small, resting lymphocytes are transformed into large, active lymphocytes (lymphoblasts). As shown by the invention, lymphocyte activation may be evaluated by expression of activation markers. Thus, in some specific embodiments, the SMC modulator/s of the invention may lead to lymphocyte/s activation as demonstrated by expression of lymphocyte activation markers, specifically. CD69 and integrins LFA-1), proliferation and migration.

"Lymphocyte proliferation" relates to the ability of lymphocytes to respond to mitogens, specific antigens, or allogenic cells. More specifically, cell proliferation is the process that results in an increase of the number of cells, and is defined by the balance between cell divisions and cell loss through cell death or differentiation.

As shown in FIG. 10, the SMCs of the invention enhance T lymphocyte migration. Thus, in yet some further embodiments, the SMC modulators of the invention induce lymphocyte migration.

"Lymphocyte Migration" refers to continually re-circulating lymphocytes between the blood and the tissues via the lymph. In order to maintain immune surveillance, the majority of lymphocyte traffic occurs through lymph nodes in vivo. Although a great deal of work has been done to elucidate the molecular mechanisms whereby lymphocytes leave the blood and enter the lymph node, lymphocyte traffic also requires that the lymphocyte successfully transit extravascular tissue and enter the lymph following transendothelial migration.

As part of lymphocyte activation and restoring the functions of WASp, the SMC modulators of the invention may also enhance, participate or induce formation of immunological synapse (IS) by a T lymphocyte. Thus, the present invention may be further articulated from the point view of a lymphocyte forming an immunological synapse (IS) as the target for the presently conceived modulators. The IS model in relating to features such as T cell membrane structure, T cell polarity, signaling pathways, and antigen-presenting cells (APC), provides a comprehensive view on T cells maturation and activation. Originally the term 'IS' denoted a crucial junction between a T cell and APC at which T cell receptors (TCRs) interact with MHC molecules. Today however this term has been expended to include different types of immune cells, as well as non-immune cells. Thus, the term 'IS' herein denotes a specific arrangement of molecules in an immune cell at the interface with another cell. Molecules related to IS formation may include, although not limited to, receptors, signaling molecules, cytoskeletal elements and cellular organelles. When referring to arrangement of said molecules is meant, for example, accumulation of molecules in distinct regions within an activating IS to form a supramolecular activation cluster (SMAC), which may be further segregated into peripheral (pSMAC) and central (cSMAC) zones. This term further encompasses other features, such as engagement of individual receptors, or involvement of microclusters of cell-surface, and signaling molecules that support cell activation and maturation of IS. As indicated herein before, WASp-dependent immune cell functions include actin polymerization, sustaining of the immunological synapse, endocytosis, calcium flux, NFAT gene transcription, cellular activation and proliferation. Thus, in certain embodiments, by restoring WASp levels and function, the SMC modulators of the invention may modulate actin polymerization. The term 'actin' has been articulated herein in various contexts. In the above described aspects and embodiments it was used to convey actin functionality and structural meaning. In most general terms, 'actin' is a ubiquitous globular protein that is one of the most highly-conserved proteins known. Structurally, the term 'actin' refers to the two main states of actin: the G-actin—the globular monomeric form and the F-actin forming helical polymers. Both G- and F-actin are intrinsically flexible structures—a feature vital in actin's role as a dynamic filament network. In terms of functionality, the F-actin polymers form microfilaments—polar intracellular 'tracks' for kinesin motor proteins, allowing the transport of vesicles, organelles and other cargo. Further, actin is a component of the cytoskeleton and links to alpha-actinin. E-cadherin and beta-catenin at adherent junctions. This gives mechanical support to cells and attaches them to each other and the extracellular matrix. Using energy from the hydrolysis of ATP, myofibrils undergo cyclic shortening through actin-myosin head interactions, which represents the mechanics of muscle contraction. Finally, actin has a role in cell motility through polymerization and depolymerization of fibrils.

In further embodiments, the SMC modulators of the invention may upregulate platelet and/or megakaryocyte activation. In yet some other embodiments, the SMC modulators of the invention may activate platelet/s and/or megakaryocyte/s as manifested by at least one of cell spreading, cell aggregation, elevation in intracellular calcium concentration, cell adhesion, phagocytosis, and cytolytic activity.

A megakaryocyte is a large bone marrow cell with a lobulated nucleus responsible for the production of blood thrombocytes (platelets), which are necessary for normal blood clotting. Megakaryocytes are derived from hematopoietic stem cell precursor cells in the bone marrow.

The "platelet/s" as used herein, are one of the key elements of human blood, playing a central role in the process of thrombus formation. The main function of platelets is the formation of mechanical plugs during the normal hemostatic response to the vessel wall injury. Platelets are derived from the megakaryocytes in the bone marrow. These megakaryocytes arise by a process of differentiation from the hemopoietic stem cell and undergo fragmentation of their cytoplasm to produce platelets. Platelet production is under the control of humoral agents such as thrombopoietin. The platelet is an enucleate cell that beside nucleus includes intracellular organelles in the cytoplasm. Resting platelets are discoid and have a smooth, rippled surface. The platelet surface has various receptors to which various stimulants (agonists) bind and thereby activate platelets producing changes within the platelet as well as a change in platelet shape from discoid to spherical, adhesion and aggregation of platelets. One of the methods to evaluate "platelet activation" in response to agonists is by measuring intracellular calcium concentration. Another method is to quantify platelet release products in the plasma. More specifically, resting platelets maintain active calcium efflux via a cyclic AMP activated calcium pump. Intracellular calcium concentration determines platelet activation status, as it is the second messenger that drives platelet conformational change and degranulation. Platelet activation begins seconds after adhesion occurs. Thrombin is a potent platelet activator. Thrombin also promotes secondary fibrin-reinforcement of the platelet plug. Platelet activation in turn degranulates and releases factor V and fibrinogen, potentiating the coagulation cascade. Following their activation and F-actin polymerization, platelets must spread over intact blood vessels in the process of clot formation. Adhesion of platelets to fibrinogen is a key process in platelet aggregation, mediated by integrins, such as $\alpha IIb\beta 3$. WASp is important for $\alpha IIb\beta 3$-mediated-cell adhesion of platelets and megakaryocytes. Platelets contain dense granules, lambda granules and alpha granules. Activated platelets secrete the contents of these granules through their canalicular systems to the exterior.

In yet some further embodiments, the SMCs of the invention may decrease degradation of WASp in any non-erythroid hematopoietic cell, for example, any one of Granulocytes, neutrophils, Eosinophils, Basophils, Monocytes, Macrophages, and Dendritic cells (DCs).

More specifically, Granulocytes are a category of white blood cells characterized by the presence of granules in their cytoplasm. They are also called polymorphonuclear leukocytes (PMN, PML, or PMNL) because of the varying shapes of the nucleus, which is usually lobed into three segments. This distinguishes them from the mononuclear granulocytes.

Neutrophils are normally found in the bloodstream and are the most abundant type of phagocyte, constituting 50% to 60% of the total circulating white blood cells. Once neutrophils have received the appropriate signals, it takes them about thirty minutes to leave the blood and reach the site of an infection. Neutrophils do not return to the blood; they turn into pus cells and die. Mature neutrophils are smaller than monocytes, and have a segmented nucleus with several sections (two to five segments); each section is connected by chromatin filaments. Neutrophils do not normally exit the bone marrow until maturity, but during infection neutrophil precursors called myelocytes and promyelocytes are released.

Neutrophils display three strategies for directly attacking micro-organisms: phagocytosis (ingestion), release of soluble anti-microbials (including granule proteins), and generation of neutrophil extracellular traps (NETs). The intracellular granules of the human neutrophil have long been recognized for their protein-destroying and bactericidal properties.

Eosinophils play a crucial part in the killing of parasites (e.g., enteric nematodes) because their granules contain a unique, toxic basic protein and cationic protein (e.g., cathepsin). These cells also have a limited ability to participate in phagocytosis, but are professional antigen-presenting cells. They are able to regulate other immune cell functions (e.g., CD4+ T cell, dendritic cell, B cell, mast cell, neutrophil, and basophil functions) and are involved in the destruction of tumor cells. In addition, they promote the repair of damaged tissue.

Basophils are one of the least abundant cells in bone marrow and blood. The cytoplasm of basophils contains a varied amount of granules; these granules are usually numerous enough to partially conceal the nucleus. Granule contents of basophils are abundant with histamine, heparin, chondroitin sulfate, peroxidase, platelet-activating factor, and other substances. When an infection occurs, mature basophils will be released from the bone marrow and travel to the site of infection. When basophils are injured, they will release histamine, which contributes to the inflammatory response that helps fight invading organisms. Mast cells also contain many granules rich in histamine and heparin. Although best known for their role in allergy and anaphylaxis, mast cells play an important protective role as well, being intimately involved in wound healing, angiogenesis, immune tolerance, defense against pathogens, and blood-brain barrier function. The mast cell is very similar in both appearance and function to the basophil.

Monocyes are a type of white blood cell, or leukocyte. They are the largest type of leukocyte and can differentiate into macrophages and myeloid lineage dendritic cells.

Macrophages are a type of white blood cell that engulfs and digests cellular debris, foreign substances, microbes, cancer cells, and anything else that does not have the types of proteins specific to healthy body cells on its surface in a process called phagocytosis. These large phagocytes are found in essentially all tissues, where they patrol for potential pathogens by amoeboid movement. They take various forms (with various names) throughout the body (e.g., histiocytes, Kupffer cells, alveolar macrophages, microglia, and others), but all are part of the mononuclear phagocyte system. Besides phagocytosis, they play a critical role in nonspecific defense (innate immunity) and also help initiate specific defense mechanisms (adaptive immunity) by recruiting other immune cells such as lymphocytes. For example, they are important as antigen presenting cells to T cells.

Dendritic cells (DCs) as used herein are antigen-presenting cells (also known as accessory cells) of the mammalian immune system. Their main function is to process antigen material and present it on the cell surface to the T cells of the immune system. They act as messengers between the innate and the adaptive immune systems. Dendritic cells are present in the skin (where there is a specialized dendritic cell type called the Langerhans cell) and the inner lining of the nose, lungs, stomach and intestines. Once activated, DCs migrate to the lymph nodes where they interact with T cells and B cells to initiate and shape the adaptive immune response.

As noted above and exemplified by the following examples, WASp is a key regulator of immune cell function. By promoting cytoskeletal polymerization and reshaping, WASp is critical for immune cell stimulation, allowing a rapid and effective immune response. WASp is exclusively expressed in hematopoietic cells, and as such, may serve as a specific target for boosting the immune response. Activities supported by WASp include but are not limited to immune cell activation, proliferation, chemotaxis, migration and cell-cell interactions. Most importantly, WASp is a master regulator of leukocyte effector functions including, phagocytosis, cytolytic activity and cytokine transcription and secretion. Cells that are regulated by WASp include the lymphoid cells (T, B and Natural Killer cells), monocytes/macrophages, dendritic cells (DCs) and neutrophils as discussed above. WASp is also present in platelets and in their precursors, the megakaryocytes. WASp expression was found to be crucial for both platelet production by megakaryocytes, as well as for their activation and effector function. WASp levels are regulated by two degradative pathways, proteolysis by the calpain cysteine protease, and ubiquitin-mediated proteolysis. The SMCs of the invention were shown as effective agents for blocking WASp degradation and increasing its levels and function. Thus, in addition to the use of this strategy as therapeutic approach for treating the primary, innate immuno-deficiencies such as WAS/XLT, the SMCs of the invention also offers a powerful approach for boosting the immune response in acquired immune deficiencies or other immune disorders. Increasing WASp expression and function could be useful for increasing white blood cell (WBC) number and activity in immunopathologies such as leukopenia, neutropenia and thrombocytopenia. Remedying these hematological disorders may be helpful following or during conventional cancer treatments such as chemotherapy and radiotherapy, diseases caused by viral, bacterial and parasitic pathogens, thrombocytopenia caused by blood loss or autoimmunity e.g. immune thrombocytopenic purpura (ITP). Furthermore, such a strategy could serve as supportive therapy for rapid reconstitution following bone marrow (BM) transplantation, ex vivo and/or in vivo expansion of hematopoietic cells for use in autologous or allogenic hematopoietic stem cell transplantation (HSCT), gene therapy or adoptive cell transfer, and upregulating the immune response against cancers of non-hematopoietic origin.

Thus, in some embodiments, the SMC modulator of the invention may be used to restore, enhance and/or increase WASp levels and activity in a cell of a subject suffering from an innate or acquired immune-related disorder or condition. Thus, the aforementioned SMCs are suitable for the treatment, prevention an amelioration of immune-related disorder. An "Immune-related disorder" or "Immune-mediated disorder", as used herein encompasses any condition that is associated with the immune system of a subject, more specifically through inhibition of the immune system, or that can be treated, prevented or ameliorated by reducing degradation of a certain component of the immune response in a subject, such as the adaptive or innate immune response. An immune-related disorder may include infectious condition (e.g., viral infections), metabolic disorders and a proliferative disorder, specifically, cancer.

In some specific embodiments wherein the immune-related disorder or condition may be a primary or a secondary immunodeficiency.

Thus, due to the wide range of activities of WASp, WASp-stabilizing SMCs are a promising therapeutic modality for a variety of innate and acquired immunodeficiencies caused by immunosuppressive treatments (chemo- and radiotherapy), pathogenic infections, cancer and HSCT.

More specifically, Immunodeficiency (or immune deficiency) is a state in which the immune system's ability to fight infectious disease and cancer is compromised or entirely absent. Most cases of immunodeficiency are acquired ("secondary") due to extrinsic factors that affect the patient's immune system. Examples of these extrinsic factors include viral infection, specifically, HIV, extremes of age, and environmental factors, such as nutrition. In the clinical setting, the immunosuppression by some drugs, such as steroids, can be either an adverse effect or the intended purpose of the treatment. Examples of such use are in organ transplant surgery as an anti-rejection measure and in patients suffering from an overactive immune system, as in autoimmune diseases. Immunodeficiency also decreases cancer immunosurveillance, in which the immune system scans the cells and kills neoplastic ones.

Still further, Primary immunodeficiencies (PID), also termed innate immunodeficiencies, are disorders in which part of the organism immune system is missing or does not function normally. To be considered a primary immunodeficiency, the cause of the immune deficiency must not be caused by other disease, drug treatment, or environmental exposure to toxins). Most primary immune-deficiencies are genetic disorders; the majority is diagnosed in children under the age of one, although milder forms may not be recognized until adulthood. While there are over 100 recognized PIDs, most are very rare. About 1 in 500 people in the United States are born with a primary immunodeficiency. Immune deficiencies can result in persistent or recurring infections, autoinflammatory disorders, tumors, and disorders of various organs.

There are several types of immunodeficiency that include, Humoral immune deficiency (including B cell deficiency or dysfunction), which generally includes symptoms of hypogammaglobulinemia (decrease of one or more types of antibodies) with presentations including repeated mild respiratory infections, and/or agammaglobulinemia (lack of all or most antibody production) and results in frequent severe infections (mostly fatal); T cell deficiency, often causes secondary disorders such as acquired immune deficiency syndrome (AIDS); Granulocyte deficiency, including decreased numbers of granulocytes (called as granulocytopenia or, if absent, agranulocytosis) such as of neutrophil granulocytes (termed neutropenia); granulocyte deficiencies also include decreased function of individual granulocytes, such as in chronic granulomatous disease; Asplenia, where there is no function of the spleen; and Complement deficiency in which the function of the complement system is deficient.

WASp was first discovered as the protein mutated in patients of Wiskott-Aldrich syndrome (WAS). WAS-mutations were found to cause the rapid degradation of WASp, strongly reducing WASp expression in patient cells. WAS is characterized by severe clinical characteristics including immunodeficiency, recurrent infections, eczema, and susceptibility to autoimmune diseases and cancer, highlighting the importance of WASp for immune cell function. Additionally, WAS, as well the milder WAS variant, X-linked thrombocytopenia (XLT), are characterized by severe bleeding caused by reduced platelet number and size, and by disrupted blood clotting, demonstrating the importance of WASp for platelet generation and function. WASp degradation in WAS and XLT was found to be linked to the mechanism by which WASp levels and activity are regulated. Normally, when activated, WASp undergoes partial detachment from its chaperone, WASp Interacting Protein (WIP), allowing it to be ubiquitylated on lysine residues 76 and 81 by the Cbl E3 ubiquitin ligases, leading to its proteasomal degradation. In the primary immunodeficiencies, WAS/XLT, mutations on WASp disrupt its interaction with WIP, causing WASp to be readily ubiquitylated and degraded, regardless of its activation state.

In some embodiments, the SMC modulator of the invention may be used to restore, enhance or increase WASp levels and activity in a cell of a subject suffering from a primary immunodeficiency. It should be appreciated that in certain embodiments, the SMCs of the invention may be applicable for any of the PIDs disclosed herein. In yet some more specific embodiments, such immunodeficiency may be a hereditary or acquired disorder associated with WASp dysfunction.

In more specific embodiments, hereditary disorder associated with WASp dysfunction may be at least one of Wiskott Aldrich Syndrome (WAS) and X-linked thrombocytopenia (XLT), or any condition or disorder associated therewith.

Increasing WASp levels can be of significant benefit not only for primary immunodeficiency diseases (PIDD) caused by inherited or genetic defects but also for secondary immunodeficiencies that occur when the immune system is compromised due to environmental factors. Such factors include but are not limited to radiotherapy as well as chemotherapy. While often used as fundamental anti-cancer treatments, these modalities are known to suppress immune function, leaving patients with an increased risk of infection; indeed, infections were found to be a leading cause of patient death during cancer treatment. Neutropenia was specifically associated with vulnerability to life-threatening infections following chemotherapy and radiotherapy. WASp plays key roles in upregulating the proliferation and function of lymphocytes, and in enhancing the function of myeloid cells. Increasing myeloid cell activity as well as lymphoid cell proliferation and activation by using a WASp-stabilizing SMC treatment offers a promising approach for ameliorating radiotherapy and chemotherapy-induced immune suppression and to protect recovering cancer patients from opportunistic pathogens. Such a strategy is also expected to be generally useful in the treatment of infections; increasing WASp expression and activity is likely to enhance key immune cell functions required for robust immune responses. These include chemotaxis and immune cell infiltration to inflammatory sites (by all WBCs), phagocytosis (by neutrophils, monocytes/macrophages, and dendritic cells (DCs)), and cell-mediated cytotoxicity (by cytotoxic T lymphocytes (CTLs), or natural killer (NK) cells). Thus, this novel approach for stabilizing WASp using SMCs is expected to improve clinical outcomes of secondary immune deficiencies by (1) increasing the proliferation and survival of all lymphoid cell populations (T, B and NK cells), and by (2) boosting the activation and function of both lymphoid and myeloid cells (monocytes, macrophages, dendritic cells).

Thus, in some embodiments, the SMC modulator/s of the invention may be used to restore, enhance or increase WASp levels and activity in a cell of a subject suffering from a secondary immunodeficiency. In more specific embodiments, such secondary immunodeficiency may be caused by at least one of chemotherapy, radiotherapy, biological therapy, bone marrow transplantation, gene therapy, adoptive cell transfer or any combinations thereof.

More specifically, WASp was shown to promote lymphocyte growth and survival in both mice and humans. Proliferation of T or B lymphocytes in response to stimulation by anti-T cell antigen receptor (TCR) or anti-IgM, respectively, are impaired in WASp-deficient lymphocytes. Furthermore, similar proliferation defects were detected following interaction of WAS KO DCs with normal CD4+ and CD8+ T lymphocytes. Restoration of WASp expression has been shown to significantly mitigate these defects. Still further, reduced leukocyte number is a common side effect of chemotherapy and radiotherapy, which exposes cancer patients to life threatening infections. The approach of the present invention of increasing WASp levels and function using the SMCs of the invention has the potential to expedite hematopoietic rejuvenation following chemo- and radiotherapies by enhancing lymphocyte growth and survival.

Thus, in some embodiments, the SMC modulator of the invention may be used to restore, enhance or increase WASp levels and activity in a cell of a subject suffering from a secondary immunodeficiency caused by at least one of chemotherapy, radiotherapy, biological therapy or any combinations thereof.

Still further, WASp is a key regulator of actin cytoskeleton polymerization and reshaping in all white blood cells, as well as in platelets. As such, WASp is involved in multiple immune cell functions such as cellular activation, migration, cell to cell interaction, proliferation, and phagocytosis, all of which are actin dependent processes. Indeed, the restructuring of the actin cytoskeleton was found to be a fundamental process controlling immune cell function. The formation of actin filaments (F-actin) from actin monomers (G-actin) and the complementary process of actin filament breakdown enable the actin cytoskeleton to dynamically adapt to facilitate a variety of cellular activities.

Actin filament formation is a highly regulated process, the spontaneous generation of filaments is prevented by the intrinsic instability of actin dimers, necessitating the simultaneous association of three or more actin subunits to establish a stable anchor from which polymerization can proceed. These initial polymers are called actin nuclei, and their formation is mediated by actin nucleation proteins. Arp2/3 is an actin nucleation complex that promotes actin filament branching from an existing filament, allowing the formation of complex actin structures. Arp2/3 activity depends on binding to proteins of the nucleation-promoting factor (NPF) family and WASp is a central NPF.

In some embodiments, the SMCs used by the invention may enhance leukocyte migration and homing in subjects suffering from a secondary immunodeficiency caused by at least one of chemotherapy, radiotherapy, biological therapy or any combinations thereof.

In yet some further embodiments, the SMCs of the invention may induce and enhance migration and adhesion of neutrophils in a subject suffering from a secondary immunodeficiency caused by at least one of chemotherapy, radiotherapy, biological therapy or any combinations thereof.

In yet some further embodiments, the SMCs of the invention may enhance or increase recruitment of phagocytes in a subject suffering from a secondary immunodeficiency caused by at least one of chemotherapy, radiotherapy, biological therapy or any combinations thereof.

In some further embodiments, the SMCs of the invention may induce polarization and migration of monocytes, specifically, dendritic cells (DC) in response to inflammatory chemokines in a subject suffering from a secondary immunodeficiency caused by at least one of chemotherapy, radiotherapy, biological therapy or any combinations thereof.

WASp deficiency, either in humans or mice, results in multiple dysfunctions in most immune cell lineages, giving rise to combined cellular and humoral immune deficiencies. These dysfunctions include significantly impaired formation of membrane structures such as lamelliopodia, fillopodia and podosomes in all myeloid and lymphoid immune cells. Impaired assembly of these structures results in diminished growth and/or survival of hematopoietic cells, defective phagocytosis due to the reduced formation of the actin-rich phagocytic cup, impaired polarization and migration, impaired homing to sites of inflammation and compromised initiation of the adaptive immune response in secondary lymphoid tissues. For example, abnormal homing of DCs prevent appropriate priming and activation of key effector cells such as NK cells, T cells and B cells, thereby diminishing the overall efficiency of the immune response.

Still further, it should be noted that podosomes play a crucial role in cellular motility and invasion. These structures are localized in close proximity with the leading edge of migrating cells, and their formation and function are dependent on WASp activity.

Thus, in some embodiments, the SMCs of the invention may enhance or increase podosome formation and function in macrophages and DCs in a subject suffering from a secondary immunodeficiency caused by at least one of chemotherapy, radiotherapy, biological therapy or any combinations thereof.

More specifically, Podosomes are conical, actin-rich structures found on the outer surface of the plasma membrane of animal cells. While usually situated on the periphery of the cellular membrane, these unique structures display a polarized pattern of distribution in migrating cells, situating at the front border between the lamellipodium and lamellum. Their primary purpose is connected to cellular motility and invasion; therefore, they serve as both sites of attachment and degradation along the extracellular matrix. Many different specialized cells exhibit these dynamic structures such as certain immune cells like macrophages and dendritic cells, endothelial cells, osteoclasts, vascular smooth muscle cells and also invasive cancer cells.

In some embodiments, the SMCs of the invention may reduce degradation of WASp, thereby enhancing formation of membrane structures such as lamelliopodia and fillopodia in all myeloid and lymphoid immune cells. The lamellipodium as used herein is a cytoskeletal protein actin projection on the leading edge of the cell. It contains a quasi-two-dimensional actin mesh; the whole structure propels the cell across a substrate. Within the lamellipodia are ribs of actin called microspikes, which, when they spread beyond the lamellipodium frontier, are called filopodia.

In yet some further embodiments, the SMCs of the invention may enhance, increase or induce secretion of cytokines upon TCR activation in a subject suffering from a secondary immunodeficiency caused by at least one of chemotherapy, radiotherapy, biological therapy or any combinations thereof.

In certain embodiments, the SMCs of the invention may rescue NK cell function, specifically, the ability of NK cells to lyse susceptible target cells, in a subject suffering from a secondary immunodeficiency caused by at least one of chemotherapy, radiotherapy, biological therapy or any combinations thereof.

In yet some further embodiments, the SMCs used by the invention may restore and enhance phagocytosis and the formation of phagocytic cup. Still further, Phagocytosis is the process by which a cell engulfs a solid particle to form an internal compartment known as a phagosome. In an organism's immune system, phagocytosis is a major mechanism used to remove pathogens and cell debris. For example, when a macrophage ingests a pathogenic microorganism, the pathogen becomes trapped in a phagosome which then fuses with a lysosome to form a phagolysosome. Within the phagolysosome, enzymes and toxic peroxides digest the pathogen.

In yet some further embodiments, the SMCs of the invention may enhance, increase or rescue macrophages or DC functions following chemotherapy or radiotherapy (phagocytic activity of bone marrow macrophages or DCs) in a subject suffering from a secondary immunodeficiency caused by at least one of chemotherapy, radiotherapy, biological therapy or any combinations thereof.

Still further, in some embodiments, the SMCs of the invention may reverse the chemotherapy or radiotherapy damage to the B-cell follicle, as well as the marginal zone (MZ) architecture in a subject suffering from a secondary immunodeficiency caused by at least one of chemotherapy, radiotherapy, biological therapy or any combinations thereof.

In some further embodiments, the SMCs of the invention may lead to reduced secretion of inflammatory cytokines, specifically, IFNγ and IL-2 by the T cells upon restoration of Treg suppressive function in a subject suffering from a secondary immunodeficiency caused by at least one of chemotherapy, radiotherapy, biological therapy or any combinations thereof.

Still further, it should be noted that additional secondary immuno-deficiencies may result following bone marrow (BM) transplantation, gene therapy or adoptive cell transfer. The success of hematopoietic stem cell transplantation (HSCT) is dependent on the timely establishment of the graft and the reconstitution of the immune system, which is preceded by a period characterized by high risk for complications and infections, prior to engraftment. By enhancing immune cell proliferation, migration and function, the use of a WASp stabilizing SMCs of the invention to enhance the host immune system may provide crucial protection for recovering hematopoietic stem cell transplantation patients during this critical time frame.

Thus, in some further embodiments, the SMCs of the invention may induce and enhance migration and adhesion of neutrophils in a subject suffering from a secondary immunodeficiency caused by bone marrow (BM) transplantation, gene therapy or adoptive cell transfer.

In some specific embodiments, SMCs of the invention may induce and enhance hematopoietic system reconstitution in a subject suffering from a secondary immunodeficiency caused by bone marrow (BM) transplantation, gene therapy or adoptive cell transfer.

Still further, in some embodiments, the SMCs of the invention may induce and enhance treatment of neutropenia in a subject suffering from a secondary immunodeficiency caused by bone marrow (BM) transplantation, gene therapy or adoptive cell transfer.

In yet some further embodiments, the SMCs of the invention may induce and enhance expansion of hematopoietic cells in culture, e.g., for bone marrow transplant and use in ex vivo expansion of hematopoietic cells. In yet some further embodiments, the SMCs of the invention may be useful in increasing the number of hematopoietic stem cells in a donor subject in case of allogeneic HSCT.

Moreover, infectious diseases constitute a major risk to human health. It is estimated that the yearly death toll of infectious diseases is 15 million. Moreover, pathogenic infections disrupt regular life routines, resulting in decreased productivity; influenza alone is estimated to cause, on average, the loss of 3.7 to 5.9 workdays per employee, annually. In the US alone, influenza is estimated to result in 140,000 to 710,000 hospitalizations per year. Limiting the number of required hospitalizations and/or reducing hospitalization times can decrease healthcare costs. Reducing the burden of infectious diseases can thus be expected to have a significant economic potential.

Thus, in some embodiments, the SMC modulators of the invention may be used to restore, enhance and/or increase WASp levels and activity in a cell of a subject suffering from immune-related disorder or condition, specifically, a pathologic condition caused by at least one pathogen.

By restoring WASp levels and activity, the SMCs of the invention improve the ability of the immune system to deal with pathogenic challenges (viral, (e.g. CMV, EBV, influenza), or bacterial antigens [e.g. *Mycobacterium tuberculosis*, MTB; *Streptococcus pneumoniae*, pneumococcus or *S. pneumoniae*).]

In some further specific embodiments, the SMCs of the invention may improve ability to phagocytose pathogens (for pathogen clearance, and also presenting foreign antigens to the adaptive arm of the immune system) of a subject suffering from a pathologic condition caused by at least one pathogen.

In certain specific embodiments, the SMCs of the invention may induce formation of actin-based membrane invaginations, called phagocytic cups in a subject suffering from a pathologic condition caused by at least one pathogen.

In further embodiments, the SMCs of the invention may increase or enhance the ability of macrophages and DCs to phagocytose apoptotic cells in a subject suffering from a pathologic condition caused by at least one pathogen.

Still further, in some embodiments, the SMCs of the invention may enhance B cell activation against a pathogenic antigen (increasing IgM levels) infectious diseases and related conditions, specifically, sepsis in a subject suffering from a pathologic condition caused by at least one pathogen. It should be appreciated that pathogens described in more detail hereinafter in connection with other aspects of the invention, are applicable in connection with the present aspect as well.

WASp was found to also affect platelets, as demonstrated by severe bleeding in WAS/XLT patients caused by reduced platelet number, size and function. Consistent with these findings, WASp-stabilizing SMCs efficiently increased WASp expression levels and enhanced human platelet activation responsible for their adhesion and coagulation (FIG. 4A-4B, FIG. 5C-5D and FIG. 11). Thus, a WASp-stabilizing SMC-based treatment may provide a potent therapeutic approach for thrombocytopenia. Specifically, in idiopathic thrombocytopenic purpura (ITP), SMC treatment may be used to enhance platelet function as well as the production of new platelets by megakaryocytes in order to offset antibody-mediated platelet destruction, improving clinical outcomes.

Thus, in some embodiments, the SMC modulators of the invention may be used to restore, enhance and/or increase WASp levels and activity in a cell of a subject suffering from immune-related disorder or condition, specifically, thrombocytopenia.

In some further embodiments, the SMC modulators of the invention may be used to restore, enhance and/or increase WASp levels and activity in a cell of a subject suffering from thrombocytopenia cause by bleeding, chemo- or radiotherapy, or autoimmunity (ITP).

In some specific embodiments, the SMC modulators of the invention may be used to restore, enhance and/or increase WASp levels and activity in a cell of a subject suffering from ITP.

Still further, in some embodiments, the SMCs of the invention may lead to increase in platelet number (production from megakaryocytes), aggregation and activation in a subject suffering from thrombocytopenia, specifically, ITP.

In yet some further embodiments, the SMCs of the invention may enhance F-actin content in a subject suffering from thrombocytopenia, specifically, ITP.

In certain embodiments, the SMCs of the invention may lead to increased αIIbβ3 integrin activation in a subject suffering from thrombocytopenia, specifically, ITP.

Still further, in some embodiments, the SMCs of the invention may enhance platelets adhesion and spreading capacity in a subject suffering from thrombocytopenia, specifically, ITP.

In certain embodiments, the SMCs of the invention may reduce platelet clearance by macrophages and the premature release of platelets from their precursors into the BM in a subject suffering from thrombocytopenia, specifically, ITP.

Still further, SMC-based treatment in accordance with the invention may also be used to enhance anti-tumor immunity. CTLs, as well as NK cells serve as the primary mediators of immune response against cancer cells. WASp was shown to be essential for NK-cancer cell conjugate formation and cytotoxic capacity. NK cells from WAS patients exhibit defective cytotoxicity. Thus, WASp enhancing SMCs may increase the potency of this response by improving the ability of the cells to migrate into the tumor, as well as improving activation and cytotoxic granule release. Furthermore, the tumor microenvironment induces suppression and reduced activity of NK and T cells, through the secretion of inhibitory factors suppressing the anti-tumor response, a phenomenon known as exhaustion. Increasing WASp, a mediator of activating immune signaling may counteract this increased inhibitory signaling and allow a robust T cell and NK cell mediated cytotoxic response.

Thus, in some further embodiments, the SMC modulators of the invention may be used to restore, enhance or increase WASp levels and activity in a cell of a subject suffering from an immune-related disorder or condition that may be a cancer of a non-hematopoietic origin.

In yet some further embodiments, the SMCs of the invention may be used as a supportive treatment for boosting the immune-system, specifically, cytotoxic lymphocytes activity in a subject suffering from a cancer of a non-hematopoietic origin.

In certain embodiments, the SMCs of the invention may enhance activation and function of cytotoxic lymphocytes, thereby enhancing tumor surveillance in a subject suffering from a cancer of a non-hematopoietic origin.

In some further embodiments, the SMC modulator used by the invention may restore or enhance WASp function and/or levels in a cell of a subject suffering from immune-related disorder or condition, for example, cancer of a non-hematopoietic origin. It should be understood that in some embodiments, the SMCs of the invention may be used as a supportive treatment for boosting the immune-system, specifically, cytotoxic lymphocytes activity against the cancer.

The SMC modulators of the invention may be used in some embodiments, in a method for treating, preventing, inhibiting, reducing, eliminating, protecting or delaying the onset of a an innate or acquired immune-related disorder or condition in a subject in need thereof.

In some embodiments, the immune-related disorder or condition may be a primary or a secondary immunodeficiency.

In yet some further embodiments, the subjects may suffer of a primary immunodeficiency that may be a hereditary or acquired disorder associated with WASp dysfunction. In further embodiments, the subjects may suffer of a hereditary disorder associated with WASp dysfunction is at least one of Wiskott Aldrich Syndrome (WAS) and X-linked thrombocytopenia (XLT), or any condition or disorder associated therewith.

In yet some further embodiments, the subjects may suffer of a secondary immunodeficiency that may be caused by at least one of chemotherapy, radiotherapy, biological therapy, bone marrow transplantation, gene therapy, adoptive cell transfer or any combinations thereof.

Still further, in some embodiments, the subjects may suffer of a pathologic condition caused by at least one pathogen.

In further embodiments, the subjects may suffer from thrombocytopenia. In more particular embodiments, the thrombocytopenia may be cause by bleeding or as a result of chemo- or radiotherapy. Alternatively, such thrombocytopenia may be an autoimmune disease, specifically, ITP.

In yet some additional embodiments, the SMC modulators of the invention may be used in treating subjects that may suffer of a cancer of a non-hematopoietic origin. In more specific embodiments, the SMCs of the invention may be thus used as a supportive treatment for boosting the immune-system, specifically, cytotoxic lymphocytes activity.

In yet a further aspect, the invention relates to a method for modulating degradation and/or stability of WASp in a cell. More specifically, the method may comprise in some embodiments the step of contacting the cell with an effective amount of at least one SMC modulator of WASp degradation, or any vehicle, matrix, nano- or micro-particle or any composition comprising the same. More specifically, the method comprises the step of contacting the cell with an effective amount of at least one of any of the SMC modulators of WASp as described herein.

In some aspects, the method of the invention may comprise the step of contacting the cell with an effective amount of at least one SMC modulator of WASp having the general formula (I)

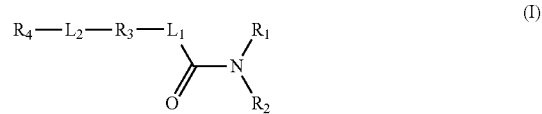

or a pharmaceutically acceptable salt, solvate, esters, hydrate, stereoisomer or physiologically functional derivative thereof, any combination thereof, or any vehicle, matrix, nano- or micro-particle, or composition comprising the same, wherein $R_1$ and $R_2$ are each independently from each other selected from H, straight or branched $C_1$-$C_{12}$ alkyl, $C_2$-$C_{12}$ alkenyl, $C_2$-$C_{12}$ alkynyl, straight or branched $C_1$-$C_{12}$ alkoxy, a ring system containing five to twelve atoms, each optionally substituted by at least one of halide, hydroxyl, ester, ether, amide, amine, nitro, —C(=O)—O—(CH$_2$)$_n$—CH$_3$, R$_5$, or —NH—C(=O)—R$_5$, R$_5$ is an a ring system containing five to twelve atoms optionally substituted by at least one halide or straight or branched C$_1$-C$_5$ alkyl;

or

R$_1$ and R$_2$ together with the nitrogen atom they are connected to form a five to twelve membered saturated or unsaturated ring that may optionally include N, O, S, NH, C=N, C=O, S=O, or SO$_2$ and may be optionally be substituted with at least one of straight or branched C$_1$-C$_5$ alkyl, hydroxyl, halide and cyano;

L1 and L2 are each independently from each other to be absent or to be selected from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$, —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$-, —(CH$_2$)$_n$—(NH)$_n$—C(=O)—(CH$_2$)$_n$—, —NH—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be are each independently from each other optionally substituted with C$_1$-C$_5$ alkyl, a ring system containing five to twelve atoms substituted with C$_1$-C$_5$ alkyl each n, is an integer being independently from each other selected from be 0 to 5;

R$_3$ and R4 are each independently from each other be absent or selected from a ring system containing five to 15 atoms, each optionally substituted with at least one of straight or branched C$_1$-C$_5$ alkyl, (=O), (=S), (O)$_2$, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight or branched C$_1$-C$_5$ alkyl.

The invention further provides in some aspects thereof, a method for modulating degradation of WASp in a cell. More specifically, the method may comprise in some embodiments the step of contacting the cell with an effective amount of at least one SMC modulator of WASp degradation, or any vehicle, matrix, nano- or micro-particle or any composition comprising the same. In more specific embodiments, the SMC/s used by the methods of the invention may have the general formula (XI):

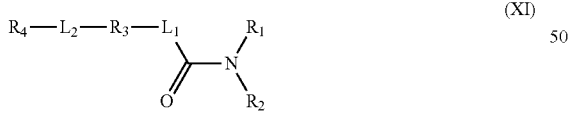

(XI)

or a pharmaceutically acceptable salt, solvate, hydrate, stereoisomer or physiologically functional derivative thereof, wherein R$_1$ and R$_2$ are each independently from each other selected from H, straight C$_1$-C$_{12}$ alkyl, a ring system containing five to seven atoms, each optionally substituted by at least one a ring system containing five to seven atoms optionally substituted by at least one halide or straight C$_1$-C$_5$ alkyl or R$_1$ and R$_2$ together with the nitrogen atom they are connected to form a five to seven membered saturated or unsaturated ring optionally include at least one of N, O and optionally substituted with at least one of straight C$_1$-C$_5$ alkyl, L1 and L2 are each independently from each other may be absent or selected from —CH$_2$—(CH$_2$—C(O)—N)—(CH$_2$)$_2$, —(CH$_2$)—S—, —(CH$_2$)—, —(CH$_2$)—O—, —NH—(CH$_2$)—, and each optionally substituted with C$_1$-C$_5$ alkyl, a ring system containing five to twelve atoms optionally substituted with C$_1$-C$_5$ alkyl;

R$_3$ and R4 are each independently from each other absent or selected from a ring system containing five to 12 atoms, each optionally substituted with at least one of straight or branched C$_1$-C$_5$ alkyl, (=O), (=S) or R$_5$, R$_5$ is an a ring system containing five to seven atoms optionally optionally substituted by at least one halide or straight C$_1$-C$_5$ alkyl.

In some specific embodiments, the SMC modulator used by the methods of the invention may be at least one pharmaceutically acceptable salts or hydrates of the compounds of Formula XI, or in some further specific embodiments, pharmaceutically acceptable salts or hydrates of the compounds of Formula XII. In more specific and non-limiting example, such compounds may include:

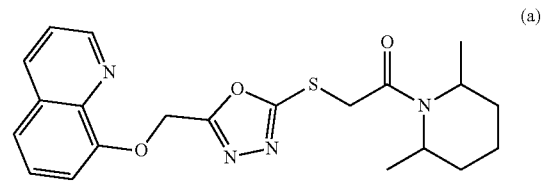 [SMILES: CC1CCCC(C)N1C(=O)CSc1nnc(COc2cccc3cccnc23)o1]

(a)

1-(2,6-Dimethyl-piperidin-1-yl)-2-[5-(quinolin-8-yloxymethyl)-[1,3,4]oxadiazol-2-ylsulfanyl]-ethanone (designated herein as SMC 34); or

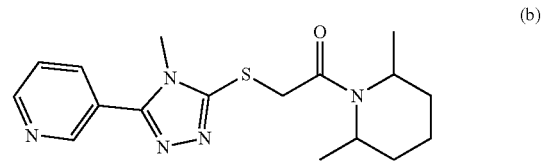 [SMILES: CC1CCCC(C)N1C(=O)CSc1nnc(-c2cccnc2)n1C]

(b)

1-(2,6-Dimethyl-piperidin-1-yl)-2-(4-methyl-5-pyridin-3-yl-4H-[1,2,4]triazol-3-ylsulfanyl)-ethanone (designated herein as SMC 34.7).

In yet some further particular embodiments, specific and non-limiting examples of the SMC modulators that may be used by the methods of the invention, may be pharmaceutically acceptable salts or hydrates of the compounds of Formula XI, or in some further specific embodiments, pharmaceutically acceptable salts or hydrates of the compounds of Formula XII, that may include:

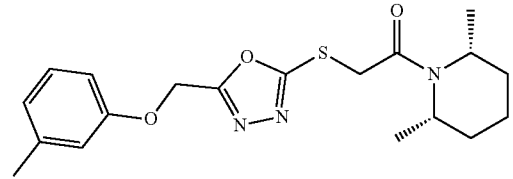 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1);

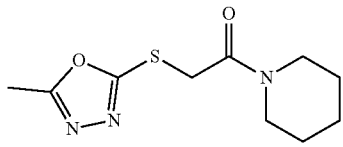 [SMILES: Cc1nnc(SCC(=O)N2CCCCC2)o1]

2-(5-Methyl-[1,3,4]oxadiazol-2-ylsulfanyl)-1-piperidin-1-yl-ethanone (SMC 34.3);

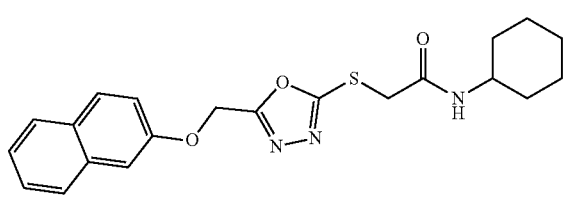 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (SMC 34.4);

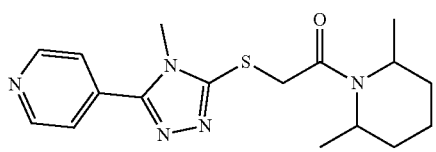 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

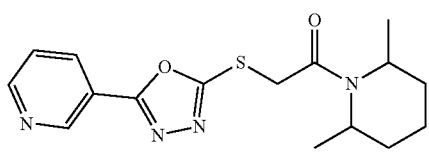 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

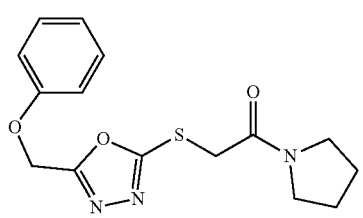 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (34.8 SMC);

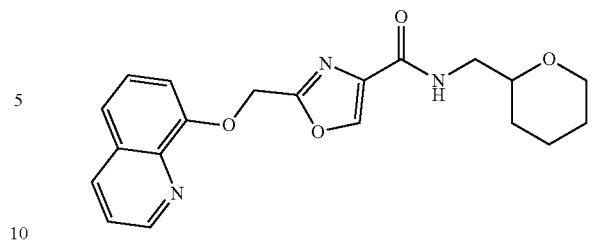

2-(Quinolin-8-yloxymethyl)-oxazole-4-carboxylic acid (tetrahydro-pyran-2-ylmethyl)-amide (SMC 34.10)

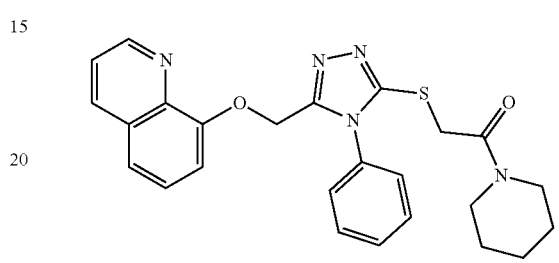

2-[4-Phenyl-5-(quinolin-8-yloxymethyl)-4H-[1,2,4]triazol-3-ylsulfanyl]-1-piperidin-1-yl-ethanone (SMC 34.11);

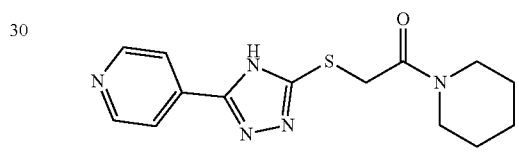

1-Piperidin-1-yl-2-(5-pyridin-4-yl-4H-[1,2,4]triazol-3-ylsulfanyl)-ethanone (SMC 34.12);

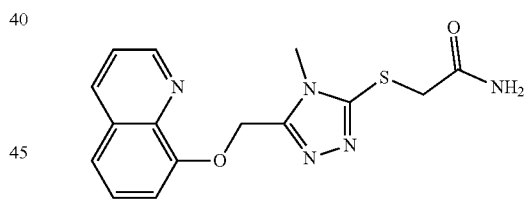

2-[4-Methyl-5-(quinolin-8-yloxymethyl)-4H-[1,2,4]triazol-3-ylsulfanyl]-acetamide (SMC 34.13).

In yet some further particular embodiments, an additional example of a SMC modulator that may be used by the method of the invention, may be the compound:

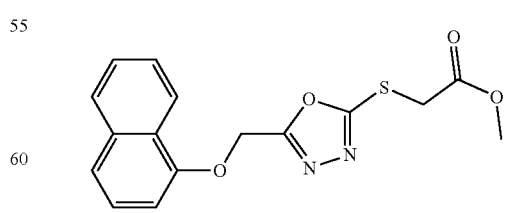

[5-(Naphthalen-2-yloxymethyl)-[1,3,4]oxadiazol-2-ylsulfanyl]-acetic acid methyl ester (SMC 34.9).

In yet some further alternative and particular embodiments, the SMC modulator used by the method invention may be any compound defined by Formula XI, Formula XII, with the proviso that the compound is not any of the compounds detailed below:

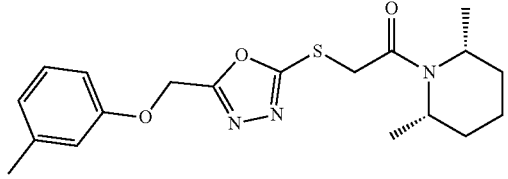 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1).

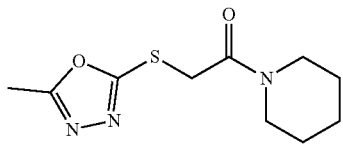 [SMILES: Cc1nnc(SCC(=O)N2CCCCC2)o1]

2-(5-Methyl-[1,3,4]oxadiazol-2-ylsulfanyl)-1-piperidin-1-yl-ethanone (SMC 34.3)

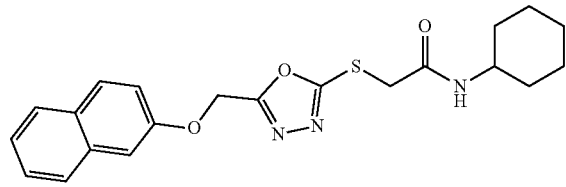 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (SMC 34.4);

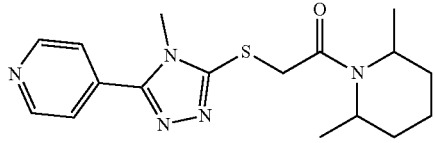 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

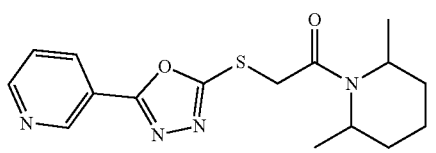 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

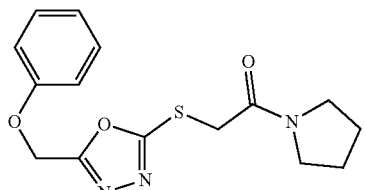

2-(5-Phenoxymethyl-[1,3,4]oxadiazol-2-ylsulfanyl)-1-pyrrolidin-1-yl-ethanone (SMC 34.8)

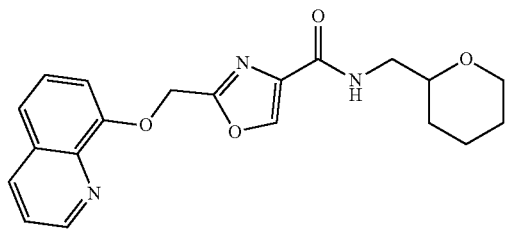 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl-amide (SMC 34.10).

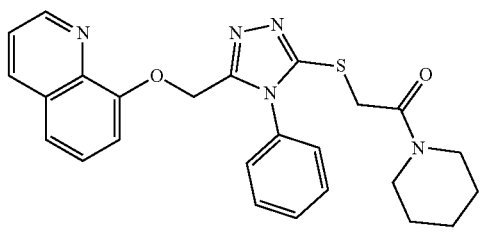 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11).

1-Piperidin-1-yl-2-(5-pyridin-4-yl-4H-[1,2,4]triazol-3-ylsulfanyl)-ethanone (SMC 34.12).

2-[4-Methyl-5-(quinolin-8-yloxymethyl)-4H-[1,2,4]triazol-3-ylsulfanyl]-acetamide (SMC 34.13).

In yet some further particular embodiments, the SMC modulator that may be used by the method of the invention, may be any of the compounds disclosed by the invention provided that said compound is not the compound:

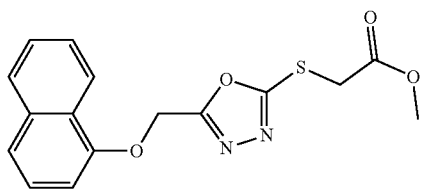 [SMILES: COC(=O)CSc1nnc(COc2cccc3ccccc23)o1]

[5-(Naphthalen-2-yloxymethyl)-[1,3,4]oxadiazol-2-ylsulfanyl]-acetic acid methyl ester (SMC 34.9).

In yet some further particular embodiments, the SMC modulator that may be used by the method of the invention, may be any of the compounds disclosed by the invention provided that said compound is not the compound:

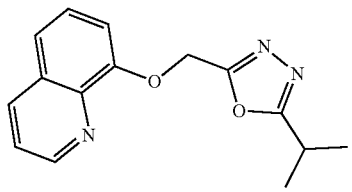 [SMILES: CC(C)c1nnc(COc2cccc3cccnc23)o1]

8-(5-Isopropyl-[1,3,4]oxadiazol-2-ylmethoxy)-quinoline (34.2).

In yet some further specific embodiments, the SMC modulator used by the methods of the invention may be at least one pharmaceutically acceptable salts or hydrates of the compounds of Formula XI, or in some further specific embodiments, pharmaceutically acceptable salts or hydrates of the compounds of Formula XIII. In more specific and non-limiting example, such compounds may include:

(a)

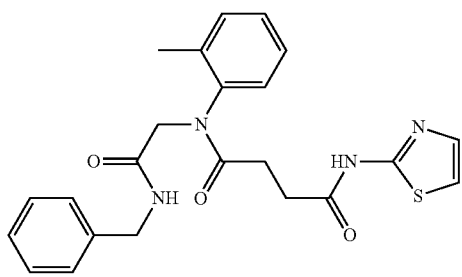

N'-[2-(benzylamino)-2-oxoethyl]-N'-(2-methylphenyl)-N-(1,3-thiazol-2-yl)butanediamide (Designated herein as SMC #33); or (b)

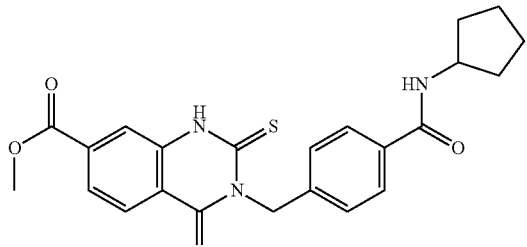

3-(4-Cyclopentylcarbamoyl-benzyl)-4-oxo-2-thioxo-1,2,3,4-tetrahydro-quinazoline-7-carboxylic acid methyl ester (Designated herein as SMC #30).

In yet some further embodiments, the method comprises the step of contacting the cell with an effective amount of N'-[2-(benzylamino)-2-oxoethyl]-N'-(2-methylphenyl)-N-(1,3-thiazol-2-yl)butanediamide having a structure:

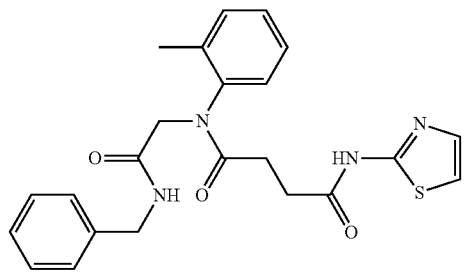 [SMILES: Cc1ccccc1N(CC(=O)NCc1ccccc1)C(=O)CCC(=O)Nc1nccs1]

(Denoted herein as SMC #33)

In some other embodiments, the method comprises the step of contacting the cell with an effective amount of 1-(2,6-dimethylpiperidin-1-yl)-2-[[5-(quinolin-8-yloxymethyl)-1,3,4-oxadiazol-2-yl]sulfanyl]ethanone having a structure:

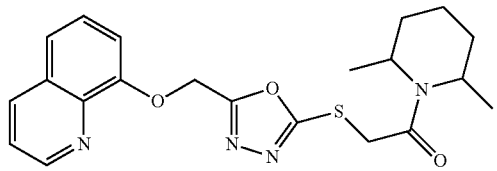 [SMILES: CC1CCCC(C)N1C(=O)CSc1nnc(COc2cccc3cccnc23)o1]

(Denoted herein as SMC #34)

In some embodiments, the method comprises the step of contacting the cell with an effective amount of ethyl 4-[[3-(4-acetylpiperazin-1-yl)sulfonylbenzoyl]amino]benzoate having a structure:

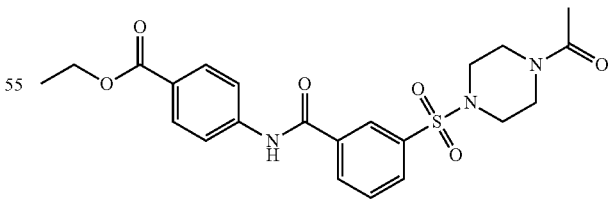

(Denoted herein as SMC #23)

In some embodiments, the method comprises the step of contacting the cell with an effective amount of 10-(3-Chloro-benzyl)-8-(4-methyl-piperazine-1-carbonyl)-5,5-dioxo-5,10-dihydro-5λ6-dibenzo[b,f][1,4]thiazepin-11-one having a structure

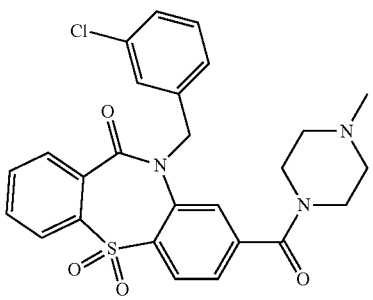 [SMILES: CN1CCN(C(=O)c2ccc3c(c2)N(Cc2cccc(Cl)c2)C(=O)c2ccccc2S3(=O)=O)CC1]

(Denoted herein as SMC #26)

In accordance with some other aspects, the method comprises the step of contacting the cell with an effective amount of at least one SMC modulator of WASp having the general formula (V):

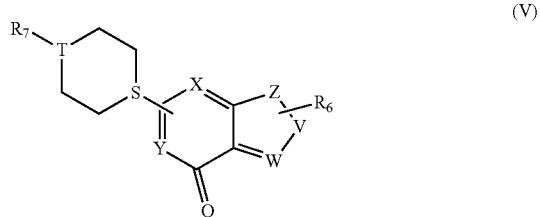

or a pharmaceutically acceptable salt, solvate, hydrate, stereoisomer or physiologically functional derivative thereof,
wherein
each one of X, Y, Z, V, W, T and S may be selected from N, NH and C,
$R_6$ and $R_7$ are the same or are different and are independently selected from each other may be L3-$R_8$,
L3 may be selected from —(CH$_2$)n, —NH—C(O) and C(O)—NH, S(O)$_2$, C(O),
n is an integer between 0 to 5;
$R_8$ may be selected from a ring system containing five to twelve atoms, each optionally substituted by at least one of straight or branched $C_1$-$C_5$ alkyl, halide, hydroxyl, ester, ether, amide, nitro and hydroxyl, $CF_3$.

In some embodiments, the method comprises the step of contacting the cell with an effective amount of

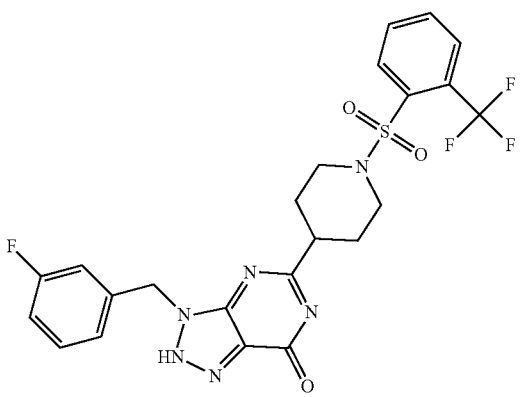 [SMILES: O=c1nc(C2CCN(S(=O)(=O)c3ccccc3C(F)(F)F)CC2)nc2n(Cc3cccc(F)c3)[nH]nc1-2]

3-[(3-fluorophenyl)methyl]-5-[1-[2-(trifluoromethyl)phenyl]sulfonylpiperidin-4-yl]-2H-triazolo[4,5-d]pyrimidin-7-one (Designated herein as SMC #32).

In accordance with some other aspects, the method comprises the step of contacting the cell with an effective amount of at least one SMC modulator of WASp having the general formula (IX):

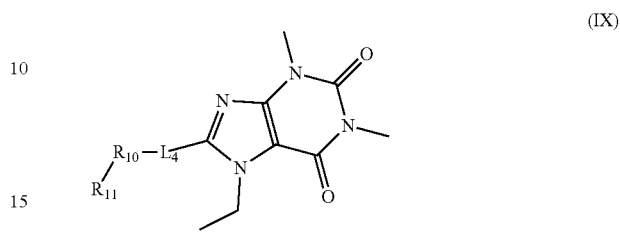

or a pharmaceutically acceptable salt, solvate, hydrate, stereoisomer or physiologically functional derivative thereof,
wherein
L4 may be absent or may be selected from —(CH$_2$)$_n$—, —S—(CH$_2$)$_n$—, —(CH$_2$)$_n$—S—;
n is an integer between 0 and 5;
$R_{10}$ and R11 are each independently from each other absent or selected from a ring system containing five to twelve atoms, each optionally substituted with at least one of straight or branched $C_1$-$C_5$ alkyl, (=O), (=S), —C(O)—CH$_3$, —C(O)—O—CH$_3$, halide, nitro, NH$_2$.

In some embodiments, L4 is selected from —S—(CH$_2$)—. In some other embodiments, $R_{10}$ and R11 are each independently from each other absent or selected from triazine, piperidine each optionally substituted with at least one NH$_2$.

In accordance with some other aspects, the method comprises the step of contacting the cell with an effective amount of at least one SMC modulator of WASp having the general formula (X):

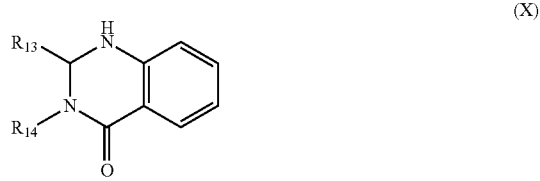

or a pharmaceutically acceptable salt, solvate, hydrate, stereoisomer or physiologically functional derivative thereof,
wherein
$R_{13}$ and R14 are each independently from each other absent or selected from a ring system containing five to twelve atoms, each optionally substituted with at least one of straight or branched $C_1$-$C_5$ alkyl, $C_1$-$C_5$ alkoxy, (=O), (=S), —C(O)—CH$_3$, —C(O)—O—CH$_3$, halide, nitro, NH$_2$, NH—C(O)—CH$_3$.

In some other embodiments, $R_{10}$ and R11 are each independently from each other absent or selected from aryl each optionally substituted with at least one OCH, NH—C(O)—CH$_3$.

Still further, in some embodiments, the compound used in the methods of the invention may be the SMC #6, specifically, N-[(2R,4R,6S)-2-(4-chlorophenyl)-6-(1-methylbenzotriazol-5-yl)oxan-4-yl]acetamide.

In yet some alternative embodiments, the invention provides methods using of any of the SMCs disclosed herein, provided that said SMC is not SMC #6, specifically, N-[(2R, 4R,6S)-2-(4-chlorophenyl)-6-(1-methylbenzotriazol-5-yl) oxan-4-yl]acetamide.

In more specific embodiments, the method of the invention may use any of the SMC modulator/s of the invention as defined herein, or any combinations thereof.

In some specific embodiments, the modulation of WAPs degradation by the methods of the invention may result in reduced WASp degradation in a cell.

In more specific embodiments, the methods of the invention may lead to reduced degradation of WASp and thereby restores, enhances and/or extends at least one of WASp levels and function in the treated cell.

In some specific embodiments, the cell modulated by the method of the invention may be a hematopoietic cell, more specifically, any cell of the lymphoid or the myeloid lineages. In yet some further embodiments, the hematopoietic cell according to the invention may be a non-erythroid hematopoietic cell.

In yet some further embodiments, the SMCs used by the methods of the invention may modulate WASp levels and/or function in a non-erythroid hematopoietic cell that may be least one of a lymphocyte, platelet, megakaryocyte, granulocyte and monocyte.

In some embodiments, the WASp function in a cell restored, extended or enhanced by the SMCs used by the methods of the invention may be at least one of cell activation, cell proliferation, cell migration, cell homing, cell spreading, cell aggregation, elevation in intracellular calcium concentration, cell adhesion, phagocytosis, and cytolytic activity.

In yet some further embodiments, the SMCs used by the methods of the invention may modulate, specifically, enhance and/or restore WASp levels and/or function as described above, in a cell of a subject suffering from an innate or acquired immune-related disorder or condition.

In some embodiments, the immune-related disorder or condition may be a primary or a secondary immunodeficiency. In yet some further specific embodiments, the primary immunodeficiency may be a hereditary or acquired disorder associated with WASp dysfunction. Still further, in some embodiments, the hereditary disorder associated with WASp dysfunction may be at least one of WAS and XLT, or any condition or disorder associated therewith.

In yet some further embodiments, acquired disorders or conditions associated with WAS and XLT, may include autoimmune disorders, inflammatory disorders, atopic eczema.

As shown by the EXAMPLES, application of the WASp-binding SMC modulators of the invention that potentially protect WASp from degradation, lead to increased WASp expression in T-cell lines, primary lymphocytes, megakaryocytes and platelets by reducing WASp ubiquitylation (FIGS. 4, 6, 7, 12, 14 and 15). This increase in WASp levels by the SMC modulators enhanced WASp-dependent cellular functions, including cellular activation, intra-cellular calcium influx, proliferation and migration (FIG. 8, 9-11). In addition, treatment with SMCs not only reconstituted the expression of common WASp mutants but also restored the function of mutant WASp-expressing cells. (FIG. 14, 15).

As therapeutic agents, SMCs have several advantages over proteins and peptides, including superior bio-availability and less immunogenicity. Currently MSCs cannot be tested in vivo due to the lack of valid animal models. The only available animal model for studying WAS is the WAS knockout mouse, which is completely devoid of the WAS gene and as such is not a suitable model for testing post translational pathways. Because the rarity of WAS/XLT, the inventors established WASp-deficient T cell lines, reconstituted with WAS/XLT mutant WASp, as a mid-step towards evaluation of WASp-protecting SMCs. The data presented in EXAMPLES 4, 5 and 6 provide proof of concept for using rationally-selected WASp-binding SMCs as a suitable treatment for WASp dysfunction disorders.

Therefore, attenuation of WASp degradation by WASp-binding SMC modulators of the invention is suggested as a promising treatment option for Wiskott-Aldrich Syndrome and X-linked thrombocytopenia.

In yet some alternative embodiments, the secondary immunodeficiency may be caused by at least one of chemotherapy, radiotherapy, biological therapy, bone marrow transplantation, gene therapy, adoptive cell transfer or any combinations thereof.

It should be appreciated that in case of bone marrow transplantations, by restoring, enhancing and/or extending at least one of WASp levels and function in a cell using the SMC modulators described herein, the invention further encompasses an in vitro method for expansion of cells in culture, e.g., for bone marrow transplant and use in ex vivo expansion of hematopoietic cells.

In yet some further embodiments, the method of the invention may be applicable in restoring, enhancing or extending at least one of WASp levels and function in a cell of a subject suffering from a pathologic condition caused by at least one pathogen.

In yet some further embodiments, the method of the invention may be applicable in restoring, enhancing or extending at least one of WASp levels and function in a cell of a subject suffering from thrombocytopenia. More specifically, thrombocytopenia cause by bleeding, chemo- or radiotherapy, or autoimmunity (ITP).

In yet some certain embodiments, the method of the invention may be applicable in restoring, enhancing and/or extending at least one of WASp levels and function in a cell of a subject suffering from cancer of a non-hematopoietic origin. In more specific embodiments, such method may be used as a supportive treatment for boosting the immune-system, specifically, cytotoxic lymphocytes activity in the treated subjects.

Still further, in some embodiments, for modulating the WASp levels/activity in a cell, the SMC modulators of the invention may be contacted with the cell. The term "contacting" as used herein, means to bring, put, incubate or mix together. As such, a first item is contacted with a second item when the two items are brought or put together, e.g., by touching them to each other or combining them. In the context of the present invention, the term "contacting" includes all measures or steps, which allow interaction between the compounds of the invention and the cells or subjects to be modulated, as specified herein after.

As indicated above, the present invention provides methods for modulating WASp degradation levels in a cell. The term modulation as used herein refers to reduction or alternatively, to elevation of WASp degradation in said cell.

In yet more specific embodiments, the SMC of the invention may lead to decrease, reduction, elimination, attenuation or inhibition of the WASp degradation of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% in a cell contacted with, or in a subject administered with the SMC of the invention as compared with a cell or a subject not treated with the SMC of the invention.

In yet a further aspect, the invention relates to a method for treating, preventing, inhibiting, reducing, eliminating, protecting or delaying the onset of an innate or acquired immune-related disorder or condition in a subject in need thereof. More specifically, the method may comprise administering to the subject a therapeutically effective amount of at least one SMC modulator of WASp as described herein.

In accordance with some aspects, the method for treating, preventing, inhibiting, reducing, eliminating, protecting or delaying the onset of an innate or acquired immune-related disorder or condition in a subject in need comprise administering to the subject a therapeutically effective amount of at least one SMC modulator of WASp having the general formula (I)

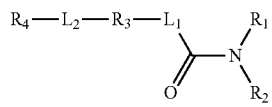

(I)

or a pharmaceutically acceptable salt, solvate, esters, hydrate, stereoisomer or physiologically functional derivative thereof, any combinations thereof, or of any vehicle, matrix, nano- or micro-particle or composition comprising the same, wherein $R_1$ and $R_2$ are each independently from each other selected from H, straight or branched $C_1$-$C_{12}$ alkyl, $C_2$-$C_{12}$ alkenyl, $C_2$-$C_{12}$ alkynyl, straight or branched $C_1$-$C_{12}$ alkoxy, a ring system containing five to twelve atoms, each optionally substituted by at least one of halide, hydroxyl, ester, ether, amide, amine, nitro, —C(=O)—O—(CH$_2$)$_n$—CH$_3$, $R_5$, or —NH—C(=O)—$R_5$, $R_5$ is an a ring system containing five to twelve atoms optionally substituted by at least one halide or straight or branched $C_1$-$C_5$ alkyl;

or $R_1$ and $R_2$ together with the nitrogen atom they are connected to form a five to twelve membered saturated or unsaturated ring that may optionally include N, O, S, NH, C=N, C=O, S=O or SO$_2$ and may be optionally be substituted with at least one of straight or branched $C_1$-$C_5$ alkyl, hydroxyl, halide and cyano;

L1 and L2 are each independently from each other selected to be absent or from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$—(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$-, —(CH$_2$)$_n$—(NH)$_n$—C(=O)—(CH$_2$)$_n$—, —NH—(CH$_2$)$_n$—, —C(=O)—NH—(CH$_2$)$_n$—, —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be are each independently from each other optionally substituted with $C_1$-$C_5$ alkyl, a ring system containing five to twelve atoms substituted with $C_1$-$C_5$ alkyl each n, is an integer being independently from each other selected from be 0 to 5;

$R_3$ and R4 are each independently from each other be absent or selected from a ring system containing five to 15 atoms, each optionally substituted with at least one of straight or branched $C_1$-$C_5$ alkyl, (=O), (=S), (O)$_2$, —C(O)—CH$_3$, —C(O)—O—CH$_3$, halide, CF$_3$, nitro, amide, or $R_5$, $R_5$ i an a ring system containing five to twelve atoms optionally substituted by at least one halide or straight or branched $C_1$-$C_5$ alkyl.

In some specific embodiments, the method of the invention may use any of the SMC modulator/s defined by the invention or any combinations thereof.

In some embodiments of this aspect, the SMC is N'-[2-(benzylamino)-2-oxoethyl]-N'-(2-methylphenyl)-N-(1,3-thiazol-2-yl)butanediamide having a structure:

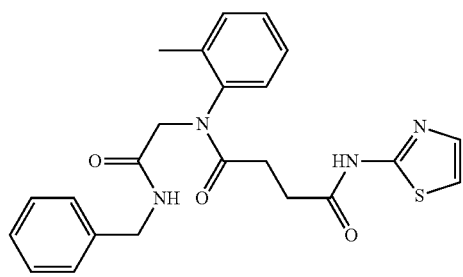 [SMILES: Cc1ccccc1N(CC(=O)NCc1ccccc1)C(=O)CCC(=O)Nc1nccs1]

(denoted herein as SMC #33);

In some embodiments of this aspect, the SMC is 1-(2,6-dimethylpiperidin-1-yl)-2-[[5-(quinolin-8-yloxymethyl)-1,3,4-oxadiazol-2-yl]sulfanyl]ethanone having a structure

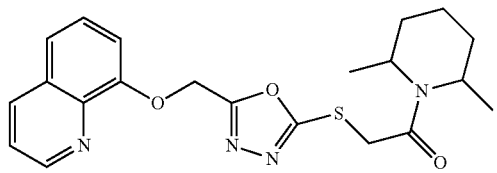 [SMILES: CC1CCCC(C)N1C(=O)CSc1nnc(COc2cccc3cccnc23)o1]

(denoted herein as SMC #34);

In some embodiments of this aspect, the SMC is ethyl 4-[[3-(4-acetylpiperazin-1-yl)sulfonylbenzoyl]amino]benzoate having a structure

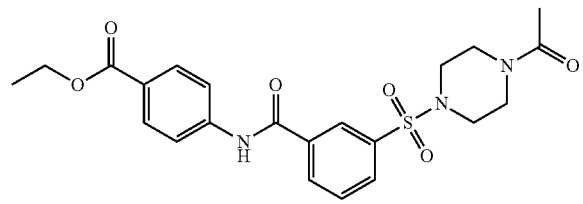 [SMILES: CCOC(=O)c1ccc(NC(=O)c2cccc(S(=O)(=O)N3CCN(C(C)=O)CC3)c2)cc1]

(denoted herein as SMC #23);

In some embodiments of this aspect, the SMC is 10-(3-Chloro-benzyl)-8-(4-methyl-piperazine-1-carbonyl)-5,5-di-oxo-5,10-dihydro-5λ6-dibenzo[b,f][1,4]thiazepin-11-one having a structure

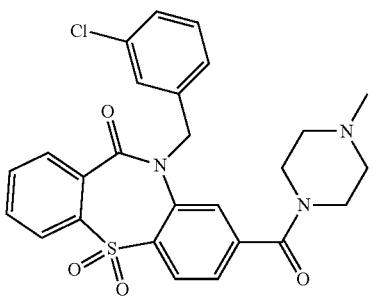 [SMILES: CN1CCN(C(=O)c2ccc3c(c2)N(Cc2cccc(Cl)c2)C(=O)c2ccccc2S3(=O)=O)CC1]

(denoted herein as SMC #26);

In still some further aspects thereof, the invention provides a method for treating, preventing, inhibiting, reducing, eliminating, protecting or delaying the onset of an innate or acquired immune-related disorder or condition in a subject in need thereof. More specifically, the method may comprise administering to the treated subject a therapeutically effective amount of at least one SMC modulator of WASp having the general formula (XI):

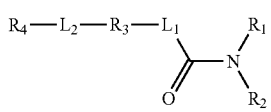

(XI)

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl
or
$R_1$ and $R_2$ together with the nitrogen atom they are connected to form a five to seven membered saturated or unsaturated ring optionally include at least one of N, O and optionally substituted with at least one of straight $C_1$-$C_5$ alkyl,
L1 and L2 are each independently from each other may be absent or selected from —CH$_2$—(CH$_2$—C(O)—N)—(CH$_2$)$_2$, —(CH$_2$)—S—, —(CH$_2$)—, —(CH$_2$)—O—, —NH—(CH$_2$)—, and each optionally substituted with $C_1$-$C_5$ alkyl, a ring system containing five to twelve atoms optionally substituted with $C_1$-$C_5$ alkyl;
$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl.

In some particular embodiments, specific and non-limiting examples of the SMC modulators used by the methods of the invention, may be pharmaceutically acceptable salts or hydrates of the compounds of Formula XI, or in some further specific embodiments, pharmaceutically acceptable salts or hydrates of the compounds of Formula XII, that may include:

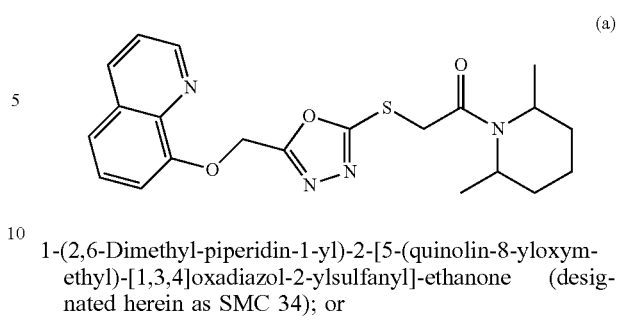

(a)

1-(2,6-Dimethyl-piperidin-1-yl)-2-[5-(quinolin-8-yloxymethyl)-[1,3,4]oxadiazol-2-ylsulfanyl]-ethanone (designated herein as SMC 34); or

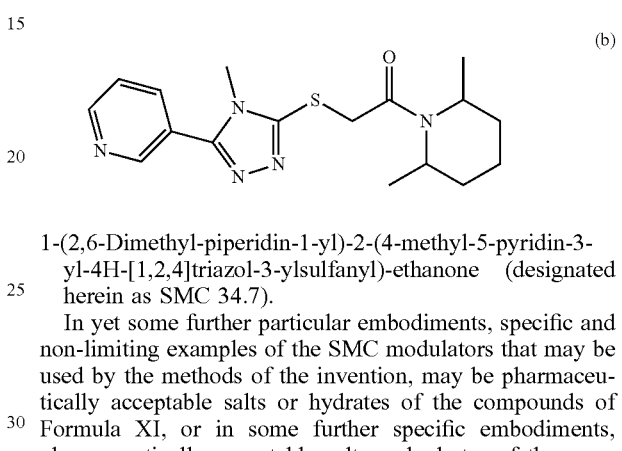

(b)

1-(2,6-Dimethyl-piperidin-1-yl)-2-(4-methyl-5-pyridin-3-yl-4H-[1,2,4]triazol-3-ylsulfanyl)-ethanone (designated herein as SMC 34.7).

In yet some further particular embodiments, specific and non-limiting examples of the SMC modulators that may be used by the methods of the invention, may be pharmaceutically acceptable salts or hydrates of the compounds of Formula XI, or in some further specific embodiments, pharmaceutically acceptable salts or hydrates of the compounds of Formula XII, that may include:

1-(2,6-Dimethyl-piperidin-1-yl)-2-(5-m-tolyloxymethyl-[1,3,4]oxadiazol-2-ylsulfanyl)-ethanone (SMC 34.1);

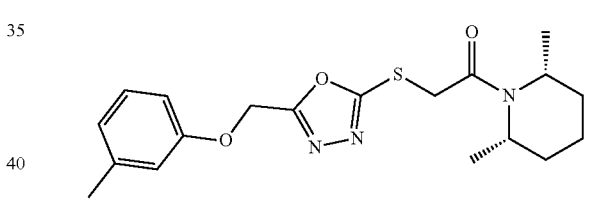

2-(5-Methyl-[1,3,4]oxadiazol-2-ylsulfanyl)-1-piperidin-1-yl-ethanone (SMC 34.3);

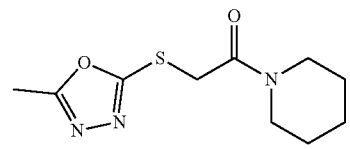 [SMILES: Cc1nnc(SCC(=O)N2CCCCC2)o1]

N-Cyclohexyl-2-[5-(naphthalen-2-yloxymethyl)-[1,3,4]oxadiazol-2-ylsulfanyl]-acetamide (SMC 34.4);

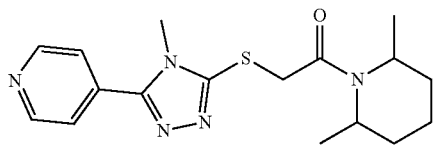 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

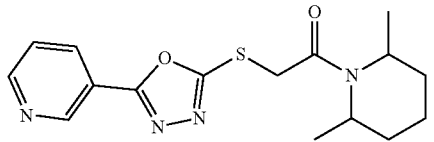 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

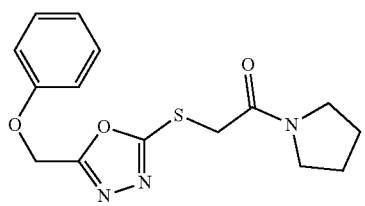 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (SMC 34.8);

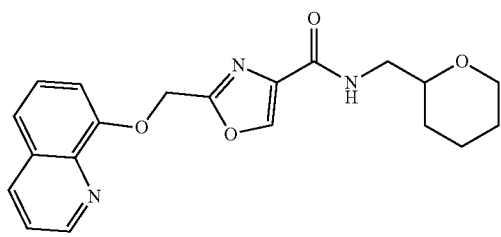 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10);

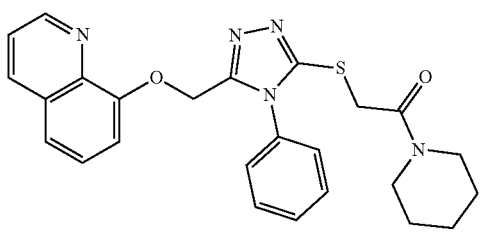 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11);

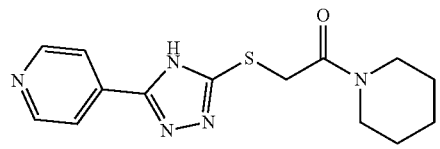 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (SMC 34.12);

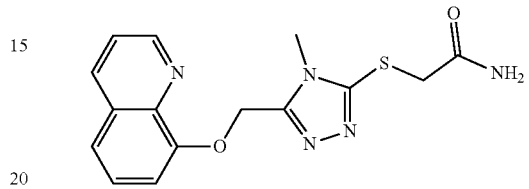

2-[4-Methyl-5-(quinolin-8-yloxymethyl)-4H-[1,2,4]triazol-3-ylsulfanyl]-acetamide (SMC 34.13);

In yet some further particular embodiments, an additional example of a SMC modulator that may be used by the method of the invention, may be the compound:

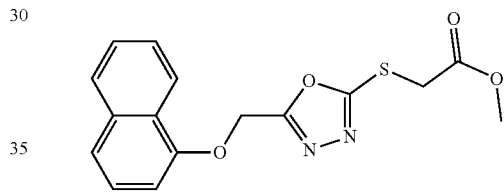

[5-(Naphthalen-2-yloxymethyl)-[1,3,4]oxadiazol-2-ylsulfanyl]-acetic acid methyl ester (SMC 34.9).

In yet some further particular embodiments, an additional example of a SMC modulator that may be used by the method of the invention, may be the compound:

In yet some further particular embodiments, an additional example of a SMC modulator that may be used by the method of the invention, may be the compound:

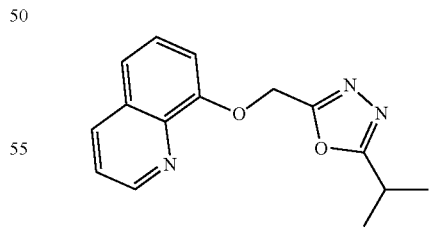

8-(5-Isopropyl-[1,3,4]oxadiazol-2-ylmethoxy)-quinoline (34.2).

In yet some further alternative and particular embodiments, the SMC modulator used by the method invention may be any compound defined by Formula XI, Formula XII, with the proviso that the compound is not any of the compounds detailed below:

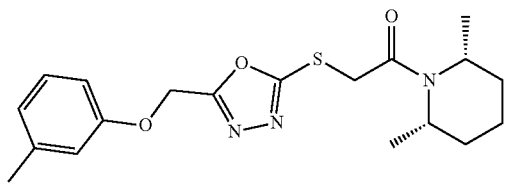 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1);

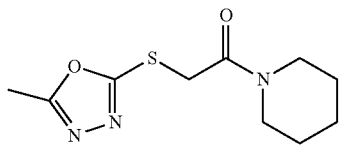 [SMILES: Cc1nnc(SCC(=O)N2CCCCC2)o1]

2-(5-Methyl-[1,3,4]oxadiazol-2-ylsulfanyl)-1-piperidin-1-yl-ethanone (SMC 34.3);

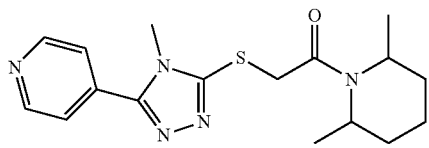 [SMILES: CC1CCCC(C)N1C(=O)CSc1nnc(-c2ccncc2)n1C]

N-Cyclohexyl-2-[5-(naphthalen-2-yloxymethyl)-[1,3,4]oxadiazol-2-ylsulfanyl]-acetamide (SMC 34.4);

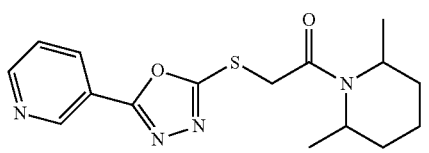 [SMILES: CC1CCCC(C)N1C(=O)CSc1nnc(-c2cccnc2)o1]

1-(2,6-Dimethyl-piperidin-1-yl)-2-(4-methyl-5-pyridin-4-yl-4H-[1,2,4]triazol-3-ylsulfanyl)-ethanone (SMC 34.5);

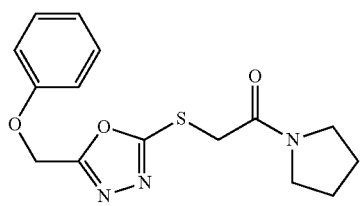 [SMILES: O=C(CSc1nnc(COc2ccccc2)o1)N1CCCC1]

1-(2,6-Dimethyl-piperidin-1-yl)-2-(5-pyridin-3-yl-[1,3,4]oxadiazol-2-ylsulfanyl)-ethanone (SMC 34.6);

2-(5-Phenoxymethyl-[1,3,4]oxadiazol-2-ylsulfanyl)-1-pyrrolidin-1-yl-ethanone (SMC 34.8);

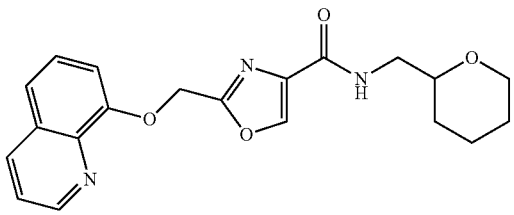 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10);

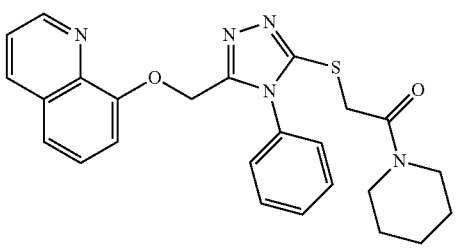 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11);

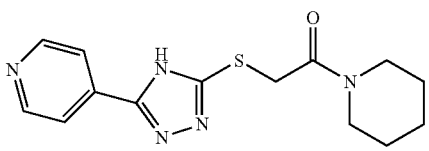 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (SMC 34.12);

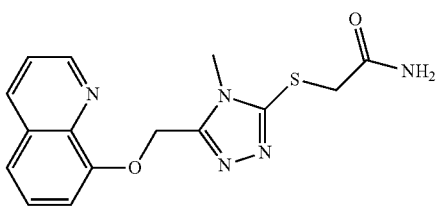 [SMILES: Cn1c(COc2cccc3cccnc23)nnc1SCC(N)=O]

2-[4-Methyl-5-(quinolin-8-yloxymethyl)-4H-[1,2,4]triazol-3-ylsulfanyl]-acetamide (SMC 34.13).

In yet some further particular embodiments, the SMC modulator that may be used by the method of the invention, may be any of the compounds disclosed by the invention provided that said compound is not the compound:

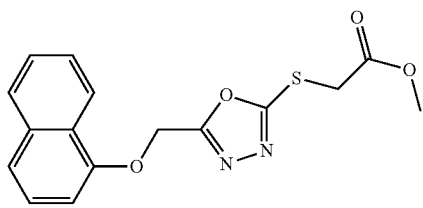 [SMILES: COC(=O)CSc1nnc(COc2cccc3ccccc23)o1]

[5-(Naphthalen-2-yloxymethyl)-[1,3,4]oxadiazol-2-ylsulfanyl]-acetic acid methyl ester (SMC 34.9).

In yet some further particular embodiments, the SMC modulator that may be used by the method of the invention, may be any of the compounds disclosed by the invention provided that said compound is not the compound:

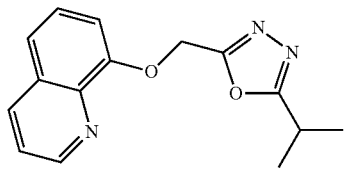 [SMILES: CC(C)c1nnc(COc2cccc3cccnc23)o1]

8-(5-Isopropyl-[1,3,4]oxadiazol-2-ylmethoxy)-quinoline (34.2).

In some particular embodiments, specific and non-limiting examples of the SMC modulators used by the methods of the invention, may be pharmaceutically acceptable salts or hydrates of the compounds of Formula XI, or in some further specific embodiments, pharmaceutically acceptable salts or hydrates of the compounds of Formula XIII, that may include:

(a)

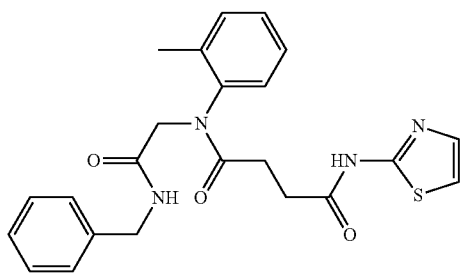 [SMILES: Cc1ccccc1N(CC(=O)NCc1ccccc1)C(=O)CCC(=O)Nc1nccs1]

N'-[2-(benzylamino)-2-oxoethyl]-N'-(2-methylphenyl)-N-(1,3-thiazol-2-yl)butanediamide (Designated herein as SMC #33); or (b)

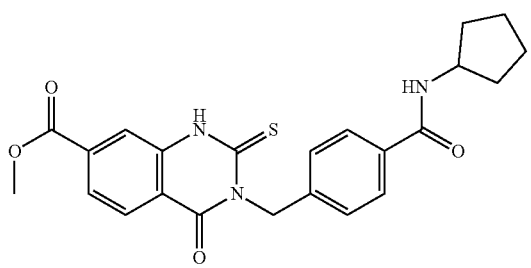 [SMILES: COC(=O)c1ccc2c(=O)n(Cc3ccc(C(=O)NC4CCCC4)cc3)c(=S)[nH]c2c1]

3-(4-Cyclopentylcarbamoyl-benzyl)-4-oxo-2-thioxo-1,2,3,4-tetrahydro-quinazoline-7-carboxylic acid methyl ester (Designated herein as SMC #30).

In accordance with some other aspects, the method for treating, preventing, inhibiting, reducing, eliminating, protecting or delaying the onset of an innate or acquired immune-related disorder or condition in a subject in need comprise administering to the subject a therapeutically effective amount of at least one SMC modulator of WAS having the general formula (V):

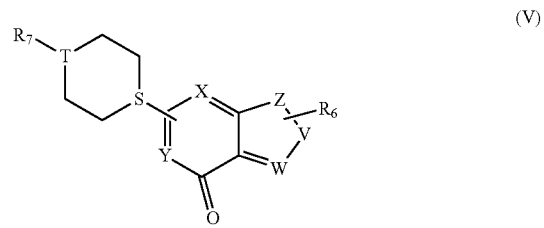

(V)

or a pharmaceutically acceptable salt, solvate, hydrate, stereoisomer or physiologically functional derivative thereof, wherein each one of X, Y, Z, V, W, T and S may be selected from N, NH and C, $R_6$ and $R_7$ are the same or are different and are independently selected from each other may be L3-$R_8$, L3 may be selected from —(CH$_2$)n, —NH—C(O) and C(O)—NH, S(O)$_2$, C(O), n is an integer between 0 to 5;

$R_8$ may be selected from a ring system containing five to twelve atoms, each optionally substituted by at least one of straight or branched $C_1$-$C_5$ alkyl, halide, hydroxyl, ester, ether, amide, nitro and hydroxyl, CF$_3$.

In some embodiments of this aspect, the method comprises administering to the subject a therapeutically effective amount of

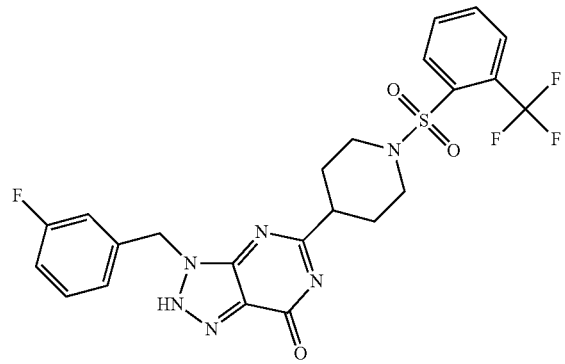 [SMILES: O=c1nc(C2CCN(S(=O)(=O)c3ccccc3C(F)(F)F)CC2)nc2n(Cc3cccc(F)c3)[nH]nc1-2]

3-[(3-fluorophenyl)methyl]-5-[1-[2-(trifluoromethyl)phenyl]sulfonylpiperidin-4-yl]-2H-triazolo[4,5-d]pyrimidin-7-one (Designated herein as SMC #32).

In accordance with some other aspects, the method for treating, preventing, inhibiting, reducing, eliminating, protecting or delaying the onset of an innate or acquired immune-related disorder or condition in a subject in need comprise administering to the subject a therapeutically effective amount of at least one SMC modulator of WASp having the general formula (IX):

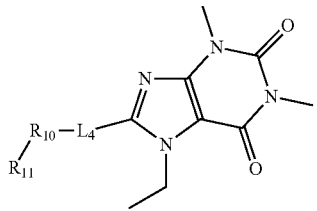

(IX)

or a pharmaceutically acceptable salt, solvate, hydrate, stereoisomer or physiologically functional derivative thereof,
wherein
L4 may be absent or may be selected from —$(CH_2)_n$—, —S—$(CH_2)_n$—, —$(CH_2)_n$—S—;
n is an integer between 0 and 5;
$R_{10}$ and R11 are each independently from each other absent or selected from a ring system containing five to twelve atoms, each optionally substituted with at least one of straight or branched $C_1$-$C_5$ alkyl, (=O), (=S), —C(O)—$CH_3$, —C(O)—O—$CH_3$, halide, nitro, $NH_2$.

In some embodiments, L4 is selected from —S—$(CH_2)$—. In some other embodiments, $R_{10}$ and R11 are each independently from each other absent or selected from triazine, piperidine each optionally substituted with at least one $NH_2$.

In accordance with some other aspects, the method for treating, preventing, inhibiting, reducing, eliminating, protecting or delaying the onset of an innate or acquired immune-related disorder or condition in a subject in need comprise administering to the subject a therapeutically effective amount of at least one SMC modulator of WASp having the general formula (X):

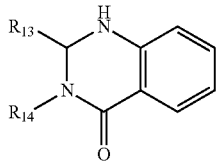

(X)

or a pharmaceutically acceptable salt, solvate, hydrate, stereoisomer or physiologically functional derivative thereof,
wherein
$R_{13}$ and R14 are each independently from each other absent or selected from a ring system containing five to twelve atoms, each optionally substituted with at least one of straight or branched $C_1$-$C_5$ alkyl, $C_1$-$C_5$ alkoxy, (=O), (=S), —C(O)—$CH_3$, —C(O)—O—$CH_3$, halide, nitro, $NH_2$, NH—C(O)—$CH_3$.

In some other embodiments, $R_{10}$ and R11 are each independently from each other absent or selected from aryl each optionally substituted with at least one OCH, NH—C(O)—$CH_3$. Still further, in some embodiments, the compound used in the methods of the invention may be the SMC #6, specifically, N-[(2R,4R,6S)-2-(4-chlorophenyl)-6-(1-methylbenzotriazol-5-yl)oxan-4-yl]acetamide.

In yet some alternative embodiments, the invention provides methods using of any of the SMCs disclosed herein, provided that said SMC is not SMC #6, specifically, N-[(2R,4R,6S)-2-(4-chlorophenyl)-6-(1-methylbenzotriazol-5-yl) oxan-4-yl]acetamide.

In some embodiments, the methods of the invention may be particularly applicable for treating an immune-related disorder or condition that may be a primary or a secondary immunodeficiency. Specifically, any of the primary or a secondary immunodeficiency disorders described herein before in connection with other aspects of the invention.

In yet some further specific embodiments, the methods of the invention may be applicable in the treatment of a primary immunodeficiency, specifically, a hereditary or acquired disorder associated with WASp dysfunction.

In more specific embodiments, such hereditary disorder associated with WASp dysfunction may be at least one of WAS and XLT, or any condition or disorder associated therewith.

In some specific embodiments the SMC modulators of the invention may be suitable for treating Wiskott-Aldrich Syndrome.

The "Wiskott-Aldrich syndrome" (WAS) is a rare (affects 4 of every 1 million males worldwide) X-linked disorder characterized by thrombocytopenia, small platelets, eczema, recurrent infections, immunodeficiency, and a high incidence of autoimmune diseases and malignancies. A classic WAS phenotype is generally associated with null-mutations of the WAS gene located on the short arm of the X chromosome (Xp11.22) that encode the WAS protein (WASp).

It should be appreciated that in certain embodiments, the SMCs of the invention may be relevant for the treatment of any disease caused by a mutation in the WAS gene. In yet some further embodiments, the SMCs of the invention may be applicable for any WASp mutant, wherein the translated WAS protein maintains or retains, at least in part, the WASp-homology-1 (WH1) domain corresponding to the interaction site with WIP also named WASp degradation pocket.

The term "mutation" is used herein to describe any inherited or sporadic change in the nucleotide sequence or arrangement of DNA that results in a dysfunctional or absent protein including, but not limited to the following: nucleotide substitutions (e.g. missense mutations, nonsense mutations, non-stop mutations, RNA processing mutations, splice-site mutations, regulatory mutations, nucleotide transitions and nucleotide transversions), insertions or deletions of one or more nucleotides, truncations, duplications of any nucleotide sequence, repeat expansion mutations (e.g. trinucleotide repeats, etc.) and frameshift mutations. In some embodiments, the SMCs of the invention are particularly relevant for reducing degradation of WASp with a missense mutation. In other embodiments, the SMCs of the invention are particularly relevant for reducing degradation of WASp with any mutation as discussed above. In yet some further embodiments, the SMCs of the invention may be applicable for any known WASp mutation, specifically any of the WASp mutations disclosed herein after or any combinations thereof. In some specific embodiments, the SMCs of the invention are particularly relevant for reducing degradation of WASp R86C mutant (specifically, substitution of Arginine to Cysteine in position 86 of WASp as denoted by the amino acid sequence of SEQ ID NO. 1). In other specific embodiments, the SMCs of the invention are particularly relevant for reducing degradation of WASp Y107C mutant (specifically, substitution of Tyrosine to Cysteine in position 107 of WASp as denoted by the amino acid sequence of SEQ ID NO. 1). In some specific embodiments, the SMCs of the invention are particularly relevant for reducing degradation of WASp A134T mutant (specifically, substitution of Alanine to Threonine in position 134 of WASp as denoted by the amino acid sequence of SEQ ID NO. 1). In some specific embodiments, the SMCs of the invention are particularly relevant for reducing degradation of WASp T45M mutant. In some specific embodiments, the SMCs of the invention are particularly relevant for reducing degradation of WASp R86S mutant. In some specific embodiments, the SMCs of the invention are particularly relevant for reducing degradation of WASp R86G mutant. In some specific embodiments, the SMCs of the invention are particularly relevant for reducing degradation of WASp R86H mutant. In some specific embodiments, the SMCs of the invention are particularly relevant for reducing degradation of WASp R86L mutant. In some specific embodiments, the SMCs of the invention are particularly relevant for reducing degradation of WASp R211 stop codon mutant (truncation). In some specific embodiments, the SMCs of the invention are particularly relevant for reducing degradation of WASp mutant with deletion of Exon 8. In some specific embodiments, the SMCs of the invention are particularly relevant for reducing degradation of WASp E31K mutant. In some specific embodiments, the SMCs of the invention are particularly relevant for reducing degradation of WASp E133K mutant. In some specific embodiments, the SMCs of the invention are particularly relevant for reducing degradation of WASp E133D mutant. In some specific embodiments, the SMCs of the invention are particularly relevant for reducing degradation of WASp C73Y mutant. In some specific embodiments, the SMCs of the invention are particularly relevant for reducing degradation of WASp C73W mutant. In some specific embodiments, the SMCs of the invention are particularly relevant for reducing degradation of WASp V75M mutant. In some specific embodiments, the SMCs of the invention are particularly relevant for reducing degradation of WASp V51F mutant. In some specific embodiments, the SMCs of the invention are particularly relevant for reducing degradation of WASp W97C mutant. In some specific embodiments, the SMCs of the invention are particularly relevant for reducing degradation of WASp C43W mutant. In some specific embodiments, the SMCs of the invention are particularly relevant for reducing degradation of WASp A56V mutant. In some specific embodiments, the SMCs of the invention are particularly relevant for reducing degradation of WASp P58A mutant. In some specific embodiments, the SMCs of the invention are particularly relevant for reducing degradation of the WASp S24P mutant. In some specific embodiments, the SMCs of the invention are particularly relevant for reducing degradation of the WASp S24F mutant. In some specific embodiments, the SMCs of the invention are particularly relevant for reducing degradation of the WASp L27F mutant. In some specific embodiments, the SMCs of the invention are particularly relevant for reducing degradation of the WASp L35H mutant. In some specific embodiments, the SMCs of the invention are particularly relevant for reducing degradation of the WASp L39P mutant. In some specific embodiments, the SMCs of the invention are particularly relevant for reducing degradation of the WASp A47D mutant. In some specific embodiments, the SMCs of the invention are particularly relevant for reducing degradation of the WASp T48I mutant. In some specific embodiments, the SMCs of the invention are particularly relevant for reducing degradation of the WASp P58R mutant. In some specific embodiments, the SMCs of the invention are particularly relevant for reducing degradation of the WASp W64R mutant. In some specific embodiments, the SMCs of the invention are particularly relevant for reducing degradation of the WASp F74S mutant. In some specific embodiments, the SMCs of the invention are particularly relevant for reducing degradation of the WASp K76T mutant. In some specific embodiments, the SMCs of the invention are particularly relevant for reducing degradation of the WASp D77H mutant. In some specific embodiments, the SMCs of the invention are particularly relevant for reducing degradation of the WASp D77G mutant. In some specific embodiments, the SMCs of the invention are particularly relevant for reducing degradation of the WASp S82P mutant. In some specific embodiments, the SMCs of the invention are particularly relevant for reducing degradation of the WASp W97X mutant. In some specific embodiments, the SMCs of the invention are particularly relevant for reducing degradation of the WASp Q99X mutant. In some specific embodiments, the SMCs of the invention are particularly relevant for reducing degradation of the WASp E100D mutant. In some specific embodiments, the SMCs of the invention are particularly relevant for reducing degradation of the WASp L105P mutant. In some specific embodiments, the SMCs of the invention are particularly relevant for reducing degradation of the WASp G119E mutant. In some specific embodiments, the SMCs of the invention are particularly relevant for reducing degradation of the WASp C122X mutant. In some specific embodiments, the SMCs of the invention are particularly relevant for reducing degradation of the WASp G125R mutant. In some specific embodiments, the SMCs of the invention are particularly relevant for reducing degradation of the WASp L126P mutant. In some specific embodiments, the SMCs of the invention are particularly relevant for reducing degradation of the WASp F128L mutant. In some specific embodiments, the SMCs of the invention are particularly relevant for reducing degradation of the WASp F128S mutant. In some specific embodiments, the SMCs of the invention are particularly relevant for reducing degradation of the WASp E131K, E133K double mutant. In some specific embodiments, the SMCs of the invention are particularly relevant for reducing degradation of the WASp E131K, R86K double mutant. In some specific embodiments, the SMCs of the invention are particularly relevant for reducing degradation of the WASp A134V mutant. In some specific embodiments, the SMCs of the invention are particularly relevant for reducing degradation of the WASp S228X mutant. In some specific embodiments, the SMCs of the invention are particularly relevant for reducing degradation of the WASp A236G mutant. In some specific embodiments, the SMCs of the invention are particularly relevant for reducing degradation of the WASp E285X mutant. In some specific embodiments, the SMCs of the invention are particularly relevant for reducing degradation of the WASp Q297X mutant. In some specific embodiments, the SMCs of the invention are particularly relevant for reducing degradation of the WASp M307V mutant. In some specific embodiments, the SMCs of the invention are particularly relevant for reducing degradation of the WASp R321X mutant. In some specific embodiments, the SMCs of the invention are particularly relevant for reducing degradation of the WASp P361T mutant. In some specific embodiments, the SMCs of the invention are particularly relevant for reducing degradation of the WASp R364X mutant. In some specific embodiments, the SMCs of the invention are particularly relevant for reducing degradation of the WASp I481N mutant. In some specific embodiments, the SMCs of the invention are particularly relevant for reducing degradation of the WASp X503S mutant. In some specific embodiments, the SMCs of the invention are particularly relevant for reducing degradation of the WASp V75L mutant. In some specific embodiments, the SMCs of the invention are particularly relevant for reducing degradation of the WASp V75L mutant. In some specific embodiments, the SMCs of the invention are particularly relevant for reducing degradation of the WASp S2T mutant. In some specific embodiments, the SMCs of the invention are particularly relevant for reducing degradation of the WASp M6I mutant. In some specific embodiments, the SMCs of the invention are particularly relevant for reducing degradation of the WASp L39P mutant. In some specific embodiments, the SMCs of the invention are particularly relevant for reducing degradation of the WASp D58A mutant. In some specific embodiments, the SMCs of the invention are particularly relevant for reducing degradation of the WASp E67K mutant. In some specific embodiments, the SMCs of the invention are particularly relevant for reducing degradation of the WASp Q80R mutant. In some specific embodiments, the SMCs of the invention are particularly relevant for reducing degradation of the WASp Y83X mutant. In some specific embodiments, the SMCs of the invention are particularly relevant for reducing degradation of the WASp Y88C mutant. In some specific embodiments, the SMCs of the invention are particularly relevant for reducing degradation of the WASp G89D mutant. In some specific embodiments, the SMCs of the invention are particularly relevant for reducing degradation of the WASp G119R mutant. In some specific embodiments, the SMCs of the invention are particularly relevant for reducing degradation of the WASp N169X mutant. In some specific embodiments, the SMCs of the invention are particularly relevant for reducing degradation of the WASp H180N mutant. In some specific embodiments, the SMCs of the invention are particularly relevant for reducing degradation of the WASp S242C mutant. In some specific embodiments, the SMCs of the invention are particularly relevant for reducing degradation of the WASp G334X mutant. In some specific embodiments, the SMCs of the invention are particularly relevant for reducing degradation of the WASp G363X mutant. In some specific embodiments, the SMCs of the invention are particularly relevant for reducing degradation of the WASp G477K mutant. In some specific embodiments, the SMCs of the invention are particularly relevant for reducing degradation of the WASp D485N mutant. In some specific embodiments, the SMCs of the invention are particularly relevant for reducing degradation of the WASp D485G mutant.

It should be appreciated that the specific WASp mutants referred to herein are indicated using the conventional nomenclature for one letter code of the substituted amino acid residue. Specifically, Ala or A for alanine, Arg or R for arginine, Asn or N for Asparagine, Asp or D for Aspartic acid, Cys or C for Cysteine, Glu or E for Glutamic acid, Gln or Q for Glutamine, Gly or G for Glycine, His or H for Histidine, Ile or I for Isoleucine, Leu or L for Leucine, Lys or K for Lysine, Met or M for Methionine, Phe or F for Phenylalanine, Pro or P for Proline, Ser or S for Serine, Thr or T for Threonine, Trp or W for Tryptophan, Tyr or Y for Tyrosine and Val or V for Valine. Still further, Asx or B for aspartic acid or aspargine, Llx or Z for Glutamine or Glutamic acid, Xle or J for Leucine or Isoleucine, and Xaa or X, for any amino acid. The substituted position is referred to herein in relation to the wild type sequence of the human WASp as denoted by the amino acid sequence of SEQ ID NO. 1.

In some specific embodiments, SMC #34, is particularly relevant for reducing degradation of the WASp R86C mutant or the WASp Y107C mutant or the WASp A134T mutant.

In further specific embodiments, SMC #6 is particularly relevant for reducing degradation of the WASp R86C mutant or the WASp Y107C mutant or the WASp A134T mutant. In other specific embodiments, SMC #30 is particularly relevant for reducing degradation of the WASp R86C mutant or the WASp Y107C mutant or the WASp A134T mutant.

In more specific embodiments, SMC #33 is particularly relevant for reducing degradation of the WASp R86C mutant or the WASp Y107C mutant or the WASp A134T mutant.

It should be appreciated that the method of the invention may be applicable also to disorders or conditions associated with WAS. More specifically, the intrinsic defects in phagocytosis, chemotaxis, cytotoxicity, apoptosis and cell signaling appear to contribute to more than just the immunodeficiency observed in WAS that has high incidence of autoimmunity, inflammatory conditions and vasculitis. Still further, WAS results from a hematopoietic-cell-specific defect in actin reorganization and cell signaling due to WASp deficiency. Patients lacking WASp expression or expressing abnormal WASp have NK cells with decreased cytolytic capacity. Clinically, patients with WAS are susceptible to herpes viruses and can develop HLH.

Clinically, the genetic defect produces cellular and humoral immunodeficiency, high susceptibility to autoimmune diseases, and increased risk for developing hematologic malignancies. This is the classic presentation, but the disease has a broad clinical spectrum that tends to correlate with the location and nature of the causative mutation. More than 300 mutations have been described, and the clinical picture varies from mild microthrombocytopenia alone (also called X-linked thrombocytopenia) to the full-blown syndrome.

Still further, in other specific embodiments the SMC modulators of the invention may be suitable for treating X-linked thrombocytopenia.

More specifically, a milder phenotype, "X-linked thrombocytopenia" (XLT), is often associated with mutations that result in expression of mutated protein. XLT patients have either no or very mild eczema and few problems, if any, with infections, autoimmunity, and malignancy. Amino acid substitutions within the guanosine triphosphatase-binding domain of WASP interfere with the intramolecular autoinhibitory mechanism, resulting in gain of function impaired actin polymerization, causing X-linked neutropenia. By definition, WAS and XLT patients have congenital thrombocytopenia in the range of 20,000 to 60,000/L and microplatelets, but normal numbers of megakaryocytes. Hemorrhagic problems may be mild, consisting of bruises and petechiae, or serious, including gastrointestinal and central nervous system hemorrhages. Patients with classic WAS acquire bacterial, fungal, and viral infections.

Because of the poor long-term outcome, early allogeneic hematopoietic stem cell transplantation is the treatment of choice, however, this procedure is associated with many risks. Haploidentical transplantation is not recommended. Splenectomy ameliorates the bleeding tendency by increasing the number of blood platelets. However, splenectomy substantially increases the risk of septicemia, sometimes in spite of antibiotic prophylaxis, and often results in fatal bacterial infections. Patients with XLT have better prognosis, but may develop complications including serious bleeding, autoimmune diseases, and malignancies. Furthermore patients that are treated by splenectomy are not chosen for bone marrow transplantation or gene therapy due to their impaired immune response.

Still further, as indicated above, it should be appreciated that the invention further encompasses methods for treating WAS, XLT and any conditions or disorders associated therewith. Such disorders or conditions may include but are not limited to Microthrombocytopenia, inflammatory skin chronic conditions such as eczema, autoimmune conditions, immunodeficiency and tumors.

The term "Microthrombocytopenia" as used herein, refers to a decrease in thrombocyte (platelet) number and to a small size of generating platelets, which is the most consistent feature of WASP-associated disease. The mechanism of the abnormal size remains incompletely understood. Mutant WASP is uniformly absent in platelets, even in the mildest patient phenotypes, suggesting a direct role of WASP deficiency in producing thrombocytopenia (a decrease in platelet number) and microthrombocytopenia.

Among clinical manifestations, hemorrhages are frequent (80% incidence) in WAS and XLT patients and range from non-life-threatening bleeding to severe bleedings, such as intestinal and intracranial bleeding. Bleeding is the result of severe thrombocytopenia. Platelets of WAS and XLT have reduced size, which is the most common finding (100% incidence). Thrombocytopenia occurs irrespectively of the severity of the mutation and is possibly caused by instability of mutated WASp in platelets. Despite intensive research, the mechanisms underlying WASp-related thrombocytopenia and hemorrhages are not completely understood. Peripheral destruction of platelets in the spleen is thought to play an important role in inducing thrombocytopenia because a substantial correction of the platelet count and size after splenectomy has been reported. Overall, a full comprehension of the mechanisms causing thrombocytopenia still needs to be achieved.

In yet some more specific embodiments, the method of the invention may be applicable for treating inflammatory chronic skin conditions, specifically, eczema. The typical skin lesions in WAS and XLT patients resemble acute or chronic eczema in appearance and distribution. Eczema develops in 80% of the patients and is heterogeneous in severity and persistence. Indeed, in its most severe form, eczema is resistant to therapy, persists into adulthood, and facilitates opportunistic skin infections (Molluscum contagiosum, herpes simplex, or bacteria). The incidence and severity of eczema are significantly lower in patients with residual WASp expression. The causes of eczema in WAS patients are currently unknown.

Still further embodiments, related to the method of the invention that may be suitable for treating autoimmune conditions. WAS-associated autoimmune complications are frequently observed. The incidence of autoimmunity in classic WAS is high in the US and European populations (40%-72%), whereas a lower incidence was reported in Japan (22%). The most common manifestations are autoimmune hemolytic anemia, cutaneous vasculitis, arthritis, and nephropathy. Less common autoimmune manifestations include inflammatory bowel disease, idiopathic thrombocytopenic purpura, and neutropenia. Patients frequently have multiple autoimmune manifestations at the same time. Development of autoimmunity can have a prognostic value. Indeed, it has been reported that WAS patients who develop autoimmune hemolytic anemia or autoimmune thrombocytopenia early (180 days) after splenectomy have a poor prognosis. Moreover, autoimmunity is associated with a higher risk of a later development of tumors and an increased risk of mortality. Until now, the mechanisms of WAS-associated autoimmunity have not been clarified. It has been proposed that autoimmunity could be the result of a bystander tissue damage originating from the chronic inflammatory state that is established after incomplete pathogen clearance.

Still further embodiments relate to the applicability of the methods of the invention in the treatment of tumors in WAS patients. Recent surveys reported an increased tumor incidence in WAS patients. Tumors can arise during childhood (especially myelodysplasia) but are more frequent in adolescents and young adults. WAS-associated tumors are mainly lymphoreticular malignancies, with leukemia, myelodysplasia, and lymphoma resulting in up to 90% of the cases. WAS-associated malignancies have a poor prognosis because less than 5% of patients survive 2 years after diagnosis, and result in up to 25% of death cases. Immune deficiency can contribute to the genesis of tumors.

One of the known abnormalities associated with WAS are dysfunction of dendritic cells (DC), which are bone marrow-derived antigen presenting cells that are required for the initiation of immune responses. A prominent role for DC has been proposed in many clinical situations including autoimmunity, transplantation, malignancy and vaccination. It is probable that other molecularly undefined immunodeficiencies have defects in this cell population, and that disruption of DC polarization and motility, involving WASp could contribute to more common inflammatory conditions such as atopic eczema and autoimmunity. Intrinsic dysfunction of the DC population may also have an important role in the pathogenesis of other primary immunodeficiency syndromes, while changes in DC cytoskeletal signaling pathways may contribute to the initiation of acquired immunological and inflammatory disorders.

It was also found that WASP has a role in regulating IL-2 production, which is independent of its role in immune synapse formation. Therefore, disorders associated with impaired IL2 production may benefit from WASp upregulation. Thus, in some embodiments, the invention may further provide methods for treating disorders associated with impaired IL-2 production.

As noted above, acquired disorders associated with WASp dysfunction may include autoimmune disorders, inflammatory disorders and atopic eczema. Therefore, in further embodiments the pharmaceutical compositions and methods of the invention may be suitable for treatment of acquired disorders related to WASp dysfunction.

Still further, in certain embodiments, the methods and compositions of the invention may be applicable for treating disorders associated with immunodeficiency. 'Immunodeficiency', primary or secondary, meaning inherited or acquired, respectively. The term 'immunodeficiency' is intended to convey a state of an organism, wherein the immune system's ability for immuno-surveillance of infectious disease or cancer is compromised or entirely absent.

According to the International Union of Immunological Societies, more than 150 primary immunodeficiency diseases (PIDs) have been characterized, and the number of acquired (or secondary) immuno-deficiencies exceeds the number of PIDs. PIDs are those caused by inherited genetic mutations. Secondary immuno-deficiencies are caused by various conditions, aging or agents such as viruses or immune suppressing drugs.

Thus, in certain embodiments, the methods of the invention may be applicable for subjects suffering from secondary immunodeficiency. In yet some further embodiments, such immunodeficiency may be caused by at least one of chemotherapy, radiotherapy, biological therapy, bone marrow transplantation, gene therapy, adoptive cell transfer or any combinations thereof.

As indicated above, the in some further embodiments, the SMCs of the invention may be applicable in boosting the immune response of a subject suffering from a secondary immunosuppression caused by chemotherapy, specifically, treatment with a chemotherapeutic agent.

"chemotherapeutic agent" or "chemotherapeutic drug" (also termed chemotherapy) as used herein refers to a drug treatment intended for eliminating or destructing (killing) cancer cells or cells of any other proliferative disorder. The mechanism underlying the activity of some chemotherapeutic drugs is based on destructing rapidly dividing cells, as many cancer cells grow and multiply more rapidly than normal cells. As a result of their mode of activity, chemotherapeutic agents also harm cells that rapidly divide under normal circumstances, for example bone marrow cells, digestive tract cells, and hair follicles. Insulting or damaging normal cells result in the common side-effects of chemotherapy: myelosuppression (decreased production of blood cells, hence also immuno-suppression), mucositis (inflammation of the lining of the digestive tract), and alopecia (hair loss).

Various different types of chemotherapeutic drugs are available. A chemotherapeutic drug may be used alone or in combination with another chemotherapeutic drug or with other forms of cancer therapy, such as a biological drug, radiation therapy or surgery.

Certain chemotherapy agents have also been used in the treatment of conditions other than cancer, including ankylosing spondylitis, multiple sclerosis, hemangiomas, Crohn's disease, psoriasis, psoriatic arthritis, rheumatoid arthritis, lupus and scleroderma.

Chemotherapeutic drugs affect cell division or DNA synthesis and function and can be generally classified into groups, based on their structure or biological function. The present invention generally pertains to chemotherapeutic agents that are classified as alkylating agents, anti-metabolites, anthracyclines, plant alkaloids, topoisomerase inhibitors, and other anti-tumor agents such as DNA-alkylating agents, anti-tumor antibiotic agents, tubulin stabilizing agents, tubulin destabilizing agents, hormone antagonist agents, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial or exotoxic agents.

However, several chemotherapeutic drugs may be classified as relating to more than a single group. It is noteworthy that some agents, including monoclonal antibodies and tyrosine kinase inhibitors, which are sometimes referred to as "chemotherapy", do not directly interfere with DNA synthesis or cell division but rather function by targeting specific components that differ between cancer cells and normal cells and are generally referred to as "targeted therapies", "biological therapy" or "immunotherapeutic agent" as detailed below.

More specifically, as their name implies, alkylating agents function by alkylating many nucleophilic functional groups under conditions present in cells. Examples of chemotherapeutic agents that are considered as alkylating agents are cisplatin and carboplatin, as well as oxaliplatin. Alkylating agents impair cell function by forming covalent bonds with amino, carboxyl, sulfhydryl, and phosphate groups in various biologically-significant molecules. Examples of agents which function by chemically modifying DNA are mechlorethamine, cyclophosphamide, chlorambucil and ifosfamide. An additional agent acting as a cell cycle non-specific alkylating antineoplastic agent is the alkyl sulfonate agent busulfan (also known as Busulfex).

alkylating chemotherapeutic agent cyclophosphamide

In some particular embodiments, the immune-suppressive condition may be caused by treatment with oxaliplatin. More specifically, Oxaliplatin is a platinum-based chemotherapy drug in the same family as cisplatin and carboplatin. It is typically administered in combination with fluorouracil and leucovorin in a combination known as Folfox for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Oxaliplatin is marketed by Sanofi-Aventis under the trademark Eloxatin®.

Still Further, anti-metabolites (also termed purine and pyrimidine analogues) mimic the structure of purines or pyrimidines which are the building blocks of DNA and may thus be incorporated into DNA. The incorporation of anti-metabolites into DNA interferes with DNA syntheses, leading to abnormal cell development and division. Anti-metabolites also affect RNA synthesis. Examples of anti-metabolites include 5-fluorouracil (5-FU), azathioprine and mercaptopurine, fludarabine, cladribine (2-chlorodeoxyadenosine, 2-CdA), pentostatin (2'-deoxycoformycin, 2'-DCF), nelarabine, Floxuridine (FUDR), gemcitabine (Gemzar, a synthetic pyrimidine nucleoside) and Cytosine arabinoside (Cytarabine).

In yet some further embodiments, the SMCs of the invention may be applicable for boosting an immune-response in a subject treated with a chemotherapeutic agent that may be at least one Plant alkaloid and terpenoid. Plant alkaloids and terpenoids are agents derived from plants that block cell division by preventing microtubule function, thereby inhibiting the process of cell division (also known as "mitotic inhibitors" or "anti-mitotic agents"). Examples of alkaloids include the vinca alkaloids (e.g. vincristine, vinblastine, vinorelbine and vindesine) and terpenoids include, for example, taxanes (e.g. paclitaxel and docetaxel). Taxanes act by enhancing the stability of microtubules, preventing the separation of chromosomes during anaphase.

In further embodiments, the SMCs of the invention may be applicable for boosting an immune-response in a subject treated with chemotherapeutic agent that may be at least one Topoisomerase inhibitor. Topoisomerases are essential enzymes that maintain DNA topology (i.e. the overall three dimensional structure of DNA). Inhibition of type I or type II topoisomerases interferes with both transcription and replication of DNA by inhibiting proper DNA supercoiling. Type I topoisomerase inhibitors include camptothecins [e.g. irinotecan and topotecan (CPT11)] and examples of type II inhibitors include amsacrine, etoposide, etoposide phosphate, and teniposide.

Still further, Anthracyclines (or anthracycline antibiotics) are a class of drugs used in cancer chemotherapy that are derived from the *Streptomyces* bacterium. These compounds are used to treat many cancers, including leukemias, lymphomas, breast, uterine, ovarian, and lung cancers. These agents include, inter alia, the drugs daunorubicin (also known as Daunomycin), and doxorubicin and many other related agents (e.g., Valrubicin and Idarubicin). For example, the anthracycline agent Idarubicin acts by interfering with the enzyme topoisomerase II.

In further embodiments, the SMCs of the invention may be applicable for boosting an immune-response in a subject treated with Doxorubicin. The chemotherapeutic agent Doxorubicin (also known by the trade name Adriamycin and by the name hydroxydaunorubicin) is an anthracycline antibiotic that is closely related to the natural product daunomycin, and like all anthracyclines, it works by intercalating DNA. The most serious adverse side effect of using this agent is the life-threatening heart damage. It is commonly used in the treatment of a wide range of cancers, including hematological malignancies, many types of carcinoma, and soft tissue sarcomas.

In certain embodiments, the SMCs of the invention may be applicable for boosting an immune-response in a subject treated with chemotherapeutic agent that may be at least one Cytotoxic antibiotics. The anthracyclines agents described above are also classified as "cytotoxic antibiotics". Cytotoxic antibiotics also include the agent actinomycin D (also known generically as Actinomycin or Dactinomycin), which is the most significant member of the actinomycines class of polypeptide antibiotics (that were also isolated from *Streptomyces*). Actinomycin D is shown to have the ability to inhibit transcription by binding DNA at the transcription initiation complex and preventing elongation of RNA chain by RNA polymerase. Other cytotoxic antibiotics include bleomycin, epirubicin and mitomycin.

Still further, in some embodiments the SMCs of the invention may be applicable for subjects suffering from immune-deficiency caused by immune-therapy or a biological therapy. More specifically, cancer vaccines, antibody treatments, and other "immunotherapies" are potentially more specific and effective and less toxic than the current approaches of cancer treatment and are generally termed "immunotherapy", and therefore, an agent used for immunotherapy, is defined herein as an immuno-therapeutic agent. The term immunotherapy as herein defined (also termed biologic therapy or biotherapy) is a treatment that uses certain components of the immune system to fight diseases (e.g. cancer), by, inter alia, stimulating the immune system to become more efficient in attacking cancer cells (e.g., by administering vaccines) or by administering components of the immune system (e.g., by administering cytokines, antibodies, etc.).

In the last few decades immunotherapy has become an important part of treating several types of cancer with the main types of immunotherapy used being monoclonal antibodies (either naked or conjugated), cancer vaccines (i.e. that induce the immune system to mount an attack against cancer cells in the body) and non-specific immunotherapies.

Antibody-mediated therapy as referred to herein refers to the use of antibodies that are specific to a cancer cell or to any protein derived there-from for the treatment of cancer. As a non-limiting example, such antibodies may be monoclonal or polyclonal which may be naked or conjugated to another molecule. Antibodies used for the treatment of cancer may be conjugated to a cytotoxic moiety or radioactive isotope, to selectively eliminate cancer cells.

It should be noted that the term "biological treatment" or "biological agent", as used herein refers to any biological material that affects different cellular pathways. Such agent may include antibodies, for example, antibodies directed to cell surface receptors participating in signaling, that may either activate or inhibit the target receptor. Such biological agent may also include any soluble receptor, cytokine, peptides or ligands. Non limiting examples for monoclonal antibodies that are used for the treatment of cancer include bevacizumab (also known as Avastin), rituximab (anti CD20 antibody), cetuximab (also known as Erbitux), anti-CTLA4 antibody and panitumumab (also known as Vectibix) and anti Gr1 antibodies.

More specifically, cancer vaccines as referred to herein are vaccines that induce the immune system to mount an attack against cancer cells in the body. A cancer treatment vaccine uses cancer cells, parts of cells, or pure antigens to increase the immune response against cancer cells that are already in the body. These cancer vaccines are often combined with other substances or adjuvants that enhance the immune response.

Non-specific immunotherapies as referred to herein do not target a certain cell or antigen, but rather stimulate the immune system in a general way, which may still result in an enhanced activity of the immune system against cancer cells. A non-limiting example of non-specific immunotherapies includes cytokines (e.g. interleukins, interferons). It should be thus appreciated that in some embodiments, the SMCs of the invention may be used as a combined supportive treatment for patients suffering from immune suppression. This supportive treatment may be combined with other supportive therapies as discussed herein.

Thus, in yet other embodiments, SMCs of the invention may be applicable for subjects undergoing at least one of adoptive cell transfer, a cancer vaccine, antibody-based therapy, a hormone, a cytokine or any combination thereof.

As indicated above, in some embodiments, the SMCs of the invention may be used for hematopoietic cell reconstitution in subjects undergoing radiotherapy. Radiation therapy or radiotherapy, often abbreviated RT, RTx, or XRT, is therapy using ionizing radiation, generally as part of cancer treatment to control or kill malignant cells and normally delivered by a linear accelerator. Radiation therapy may be curative in a number of types of cancer if they are localized to one area of the body. It may also be used as part of adjuvant therapy, to prevent tumor recurrence after surgery to remove a primary malignant tumor (for example, early stages of breast cancer). According to some specific embodiment, the radiation is ionizing radiation, which may be any one of X-rays, gamma rays and charged particles. In other embodiments, the radiation may be employed in the course of total body irradiation, brachytherapy, radioisotope therapy, external beam radiotherapy, stereotactic radio surgery (SRS), stereotactic body radiation therapy, particle or proton therapy, or body imaging using the ionizing radiation.

As indicated above, in some embodiments, the SMCs of the invention may be used for hematopoietic cell reconstitution in subjects undergoing gene therapy. Gene therapy is the therapeutic delivery of nucleic acid polymers into a patient's cells as a drug to treat disease. The most common form uses DNA, optionally packed in a vector, that encodes a functional, therapeutic gene to replace a mutated gene.

In yet some further embodiments, the SMCs of the invention may be used for enhancing reconstitution of leukocyte and megakaryocyte populations in a subject that undergoes adoptive transfer. The term "adoptive transfer" as herein defined applies to all the therapies that consist of the transfer of components of the immune system that are already capable of mounting a specific immune response. Examples of adoptive transfer include both the transfer of antibodies and also, in adoptive cell transfer, specific types of cells that are capable of mediating antigen-specific tumor regression such as LAK and T cells. Cell-based therapies with various lymphocytes and antigen-presenting cells are promising approaches for cancer immunotherapy. The transfusion of T lymphocytes, also called adoptive cell therapy (ACT), is an effective treatment for viral infections and has induced regression of cancer in early stage clinical trials.

As noted above, conditions alleviated or modulated by the administration of the SMCs are typically those characterized by a reduced hematopoietic or immune function and more specifically, a reduced neutrophil count. Such conditions may be induced as a course of therapy for other purposes, such as chemotherapy or radiation therapy. Such conditions may result from infectious disease, such as bacterial, viral, fungal, or other infectious disease. For example, sepsis results from bacterial infection. Or, such condition may be hereditary or environmentally caused, such as severe chronic neutropenia. Age may also play a factor, as in the geriatric setting; patients may have a reduced neutrophil mobilization, reduced hematopoietic function, reduced immune function, reduced neutrophil count, reduced platelets count, sepsis, severe chronic neutropenia, infectious diseases, leukopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome.

Leukopenia is a decrease in the number of white blood cells (leukocytes) found in the blood, which places individuals at increased risk of infection. Neutropenia, a subtype of leukopenia, refers to a decrease in the number of circulating neutrophil granulocytes, the most abundant white blood cells. Low white cell count may be due to acute viral infections. It has been associated with chemotherapy, radiation therapy, myelofibrosis, aplastic anemia (failure of white cell, red cell and platelet production), stem cell transplant, bone marrow transplant, AIDS, and steroid use.

Other causes of low white blood cell count include systemic lupus erythematosus, Hodgkin's lymphoma and some types of cancer, typhoid, malaria, tuberculosis, dengue, rickettsial infections, enlargement of the spleen, folate deficiencies, psittacosis, sepsis, Sjögren's syndrome and Lyme disease. It has also been shown to be caused by deficiency in certain minerals, such as copper and zinc. The SMCs of the invention may be applicable for any of the conditions disclosed above.

In some further embodiments, the methods of the invention may be applicable for immune-related disorder or condition that may be a pathologic condition caused by at least one pathogen.

It should be appreciated that an infectious disease as used herein also encompasses any infectious disease caused by a pathogenic agent, specifically, a pathogen. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Pseudomonas* sp. (e.g., *P. aeruginosa*). *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., (e.g., *Streptococcus pneumonia*). *Bacillus* sp., *Clostridium* sp., *Corynebacterium* sp., *Proprionibacterium* sp., *Mycobacterium* sp., (e.g., *Mycobacteria tuberculosis*). *Ureaplasma* sp. and *Listeria* sp.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum*.

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*.

In yet some further embodiments, the SMCs of the invention may be applicable in boosting the immune response against a pathogen that may be in further specific embodiment, a viral pathogen or a virus. The term "viruses" is used in its broadest sense to include viruses of the families adenoviruses, papovaviruses, herpesviruses: simplex, varicella-zoster, Epstein-Barr (EBV), Cytomegalo virus (CMV), pox viruses: smallpox, vaccinia, hepatitis B (HBV), rhinoviruses, hepatitis A (HBA), poliovirus, rubella virus, hepatitis C (HBC), arboviruses, rabies virus, influenza viruses A and B, measles virus, mumps virus, human deficiency virus (HIV), HTLV I and II and Zika virus.

Of particular relevance for acquired immunodeficiency caused by a viral pathogen, is any immunodeficiency caused by HIV. More specifically, in some further embodiments, the SMCs of the invention may be applicable for AIDS. Acquired immunodeficiency syndrome (AIDS) is defined in terms of either a CD4+ T cell count below 200 cells per μL or the occurrence of specific diseases in association with an HIV infection. In the absence of specific treatment, around half of people infected with HIV develop AIDS within ten years. The most common initial conditions that alert to the presence of AIDS are *Pneumocystis* pneumonia (40%), cachexia in the form of HIV wasting syndrome (20%), and esophageal candidiasis. Other common signs include recurring respiratory tract infections.

In yet some further embodiments, the SMCs of the invention may be applicable in boosting the immune response against a pathogen that may be a fungal pathogen. The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

Still further, the term parasite includes, but not limited to, infections caused by somatic tapeworms, blood flukes, tissue roundworms, ameba, and *Plasmodium, Trypanosoma, Leishmania,* and *Toxoplasma* species.

In certain additional embodiments, the methods of the invention may be applicable for immune-related disorder or condition that may be thrombocytopenia. More particularly, thrombocytopenia cause by bleeding, chemo- or radio-therapy, or autoimmunity (ITP).

The proposed therapeutic approaches can also benefit several orphan diseases such as Idiopathic thrombocytopenic purpura (ITP). ITP is a type of thrombocytopenic purpura defined as isolated low platelet count (thrombocytopenia) with normal bone marrow and the absence of other causes of thrombocytopenia. It causes a characteristic purpuric rash and an increased tendency to bleed. ITP is an autoimmune disease with antibodies detectable against several platelet surface antigens. ITP is diagnosed by a low platelet count in a complete blood count (a common blood test).

As shown by the examples, the SMCs of the invention induce platelets activation and as such may modulate and enhance coagulation processes. Induction of coagulation may be applicable in prevention and ameliorating conditions that may involve bleeding. Thus, in some embodiments, the SMCs of the invention may be applicable for treating acquired hemostatic disorders. The acquired hemostatic disorder may be at least one of surgery-induced bleeding, trauma-induced bleeding, acute gastrointestinal bleeding, bleeding associated with burns, hemorrhagic stroke, lung injury associated with emphysema and chronic obstructive pulmonary disease (COPD), bleeding associated with childbirth, disseminated intravascular coagulation (DIC), and bleeding resulting from fibrinolytic or thrombolytic therapy.

In some specific embodiments, the SMCs of the invention may be applicable for treating, preventing, reducing, attenuating, and inhibiting bleeding associated with surgical procedures, specifically, minor or major surgical procedures.

In a further specific embodiment the method of the invention may be suitable for treating trauma-induced bleeding (traumatic bleeding). Traumatic bleeding can be caused by any type of injury, for example any injury caused by, work and car accidents, combats or falls. There are different types of traumatic wounds which may cause bleeding. In general, trauma causes damage to a blood vessels that in turn causes blood to flow externally outside the body or internally into body organs such as brain, lung, liver, kidney, spleen or into body cavities, such as thorax and abdomen.

In some specific embodiments the SMCs of the invention may be suitable for treatment of acute or chronic gastrointestinal bleeding, that may include upper gastrointestinal bleeding and lower gastrointestinal bleeding.

In yet further embodiments the SMCs of the invention may be applicable for the treatment of hemorrhagic stroke or any other brain injury or trauma.

In certain specific embodiments, the SMCs the invention may be suitable for treating, preventing, reducing, attenuating, and inhibiting bleeding associated with surgical intervention, specifically, a minor or a major surgery. More specifically, it should be understood that in cases the surgical procedures are elective, expected or not urgent (e.g., cesarean surgery, or any other major surgery that allow sufficient time for pre-operative preparations), the SMCs of the invention may be used for pre-operative treatment to facilitate prevention or reduction of excessive bleeding during the surgical intervention.

Major surgery is defined as any surgical procedure that involves anesthesia or respiratory assistance. In more specific embodiments, major surgery may be an open heart surgery. In yet some other embodiments a major surgery may be liver transplantation surgery.

It should be further recognized that the treatment with the SMCs of the invention may be particularly applicable for treating the bleeding manifestations induced by thrombolytic/fibrinolytic therapy. As used herein, the term "anticoagulant agent" is intended to mean any agent which interferes with the clotting of blood. Some anticoagulants, such as the coumarin derivatives bishydroxycoumarin (Dicumarol) and warfarin (Coumadin) inhibit synthesis of prothrombin, a clot-forming substance, and other clotting factors. Anticoagulants can include but are not limited to compounds acting as beta2 Adrenoreceptor Antagonists, Neuropeptide V2 Antagonists, prostacyclin analogs, thromboxane synthase inhibitors, calcium agonists, coumarin derivatives, elastase inhibitors, Non-steroidal anti-inflammatories thrombin inhibitors, lipoxygenase inhibitors, Factor VIIa inhibitors, Factor Xa inhibitors, phosphodiesterase III inhibitors, Heparins, and fibrinogen glucoprotein IIb/IIIa Antagonists.

SMC-based treatment may also be used to enhance anti-tumor immunity. CTLs, as well as NK cells serve as the primary mediators of immune response against cancer cells. WASp was shown to be essential for NK-cancer cell conjugate formation and cytotoxic capacity. NK cells from WAS patients exhibit defective cytotoxicity. Thus, WASp enhancing SMCs may increase the potency of this response by improving the ability of the cells to migrate into the tumor, as well as improving activation and cytotoxic granule release.

The term "anti-tumor immunity" refers to innate and adaptive immune responses which may lead to tumor control.

The immune system can be activated by tumor antigens and, once primed, can elicit an antitumor response. Activated tumor specific cytotoxic T lymphocytes (CTLs) can seek out and destroy metastatic tumor cells and reduce tumor lesions. Natural Killer (NK) cells are a front-line defense against drug-resistant tumors and can provide tumoricidal activity to enhance tumor immune surveillance. Cytokines like IFN-γ or TNF play a crucial role in creating an immunogenic microenvironment and therefore are key players in the fight against metastatic cancer. Critical aspects in the tumor-immune system interface include the processing and presentation of released antigens by antigen-presenting cells (APCs), interaction with T lymphocytes, subsequent immune/T-cell activation, trafficking of antigen-specific effector cells, and, ultimately, the engagement of the target tumor cell by the activated effector T cell.

Nevertheless, although often successful in preventing tumor outgrowth, this "cancer-immunity cycle" can be disrupted by artifices involved in immune escape and development of tolerance, culminating with the evasion and proliferation of malignant cells.

Furthermore, the tumor microenvironment induces suppression and reduced activity of NK and T cells, through the secretion of inhibitory factors suppressing the anti-tumor response, a phenomena known as exhaustion. Increasing WASp, a mediator of activating immune signaling may counteract this increased inhibitory signaling and allow a robust T cell and NK cell mediated cytotoxic response.

In still some further embodiments, the methods of the invention may be applicable for immune-related disorder or condition that may be a cancer. In some embodiments, such cancer may be either of a non-hematopoietic origin or alternatively, of a hematological origin. It should be appreciated that is some embodiments, the methods of the invention may be used as a supportive treatment for boosting the immune-system, specifically, cytotoxic lymphocytes activity.

As used herein to describe the present invention, "cancer", "proliferative disorder", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the SMC modulators and methods of the present invention may be applicable for the treatment of a patient suffering from any one of non-solid and solid tumors.

Malignancy, as contemplated in the present invention may be any one of carcinomas, melanomas, sarcomas and also in some embodiments, may include lymphomas, leukemia and myeloma.

More specifically, carcinoma as used herein refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

Melanoma as used herein, is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Further malignancies that may find utility in the present invention can comprise but are not limited to various solid tumors including GI tract, colon, lung, liver, breast, prostate, pancreas and Kaposi's sarcoma. The invention may be applicable as well for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

As noted above, in some specific embodiments, the SMC modulators of the invention may be applicable in upregulating the immune-response against cancers of non-hematopoietic origin. Specifically, any of the caner disorders disclosed above. More specifically, cancer that is of a non-hematologic origin or non-hematological cancer or malignancy may be any cancer originated from any cell that is not of a lymphoid or myeloid origin. In some embodiments however, the SMCs of the invention may be applicable for hematological cancers, specifically, leukemia, lymphoma and myeloma.

More specifically, leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. The term lymphoma as used herein encompasses T cell as well as B cell lymphoma. Non limiting examples for lymphoma include Hodgkin's disease, non-Hodgkin's lymphomas and Burkitt's lymphoma.

Hematological malignancies (including lymphoma, leukemia and myeloproliferative disorders, as described above), may further include hypoplastic and aplastic anemia (both virally induced and idiopathic), myelodysplastic syndromes, all types of paraneoplastic syndromes (both immune mediated and idiopathic).

In yet some further embodiments, where the SMCs of the invention are used for boosting the immune-system of a subject that suffers of a secondary-immunosuppression caused by chemo- or radiotherapy. In more specific embodiments, such radio- or chemotherapy may be applied on a subject suffering from a malignant disorder. In yet some further embodiments the subject may be affected by a non-hematopoietic malignancy. In yet some further embodiments, the subject may be affected by a hematopoietic malignancy. It should be noted that any of the malignancies discussed herein above are relevant for any aspect of the invention and for any use of the SMCs, specifically, any of the uses disclosed by the invention.

In yet some further embodiments, embodiments, the methods of the invention may be applicable for a subject that suffers from a cancer and undergoes at least one of chemotherapy, radiotherapy, biological therapy, or any combinations thereof. In some specific embodiments, such subject may be suffering from a non-hematologic cancer and undergoes a chemotherapy, radiotherapy, a biological therapy or any combinations thereof. Alternatively, the subject may be suffering from hematologic cancer and undergoes a chemotherapy, radiotherapy, a biological therapy or any combinations thereof. In yet some further specific embodiments, such method may further comprise the step of administering to the treated subject before, simultaneously with, after or any combination thereof, the administration of the SMC modulator/s of the invention, at least one agent that induces differentiation of hematopoietic progenitor cells. In some specific and non-limiting embodiments, such treatment may be any supportive treatment. In yet some further particular embodiments, such treatment may include G-CSF and/or any analogs thereof.

As indicated above, the methods of the invention may be used in some embodiments, for treating any autoimmune disorder. It should be noted that an "autoimmune disorder" is a condition associated with dysfunction of the immune system of a subject, either through activation or suppression of the immune system or that can be treated, prevented or diagnosed by targeting a certain component of the immune response in a subject, such as the adaptive or innate immune response. Such disorder may be any one of an inflammatory disease or an autoimmune disease.

In other embodiments, the pharmaceutical compositions and methods of the invention can be suitable for treatment of inflammatory disorders. Based on the insufficient availability of specific anti-inflammatory treatments and the awareness of the roles of WASp in the pathogenesis of several groups of disorders, the development of new anti-inflammatory treatments is anticipated. Thus, there is a current need for the employment of the present invention in therapy.

The general term "inflammatory disorder" relates to disorders where an inflammation is a main response to harmful stimuli, such as pathogens, damaged cells, or irritants. Inflammation is a protective response that involves immune cells, blood vessels, and molecular mediators, as well as the end result of long-term oxidative stress. More specifically, inflammatory disorders are a large group of disorders that underlie a vast variety of human diseases. Also, the immune system can be involved in inflammatory disorders, stemming from abnormal immune response of the organism against substances of its own, or initiation the inflammatory process for unknown reason, i.e. autoimmune and auto-inflammatory disorders, respectively. Non-immune diseases with etiological origins in inflammatory processes include cancer, atherosclerosis, and ischemic heart disease.

The term "inflammatory disorders associated with WASp dysfunction" as used herein relates to at least one but not limited to the following: arthritis (ankylosing spondylitis, systemic lupus erythematosus, osteoarthritis, rheumatoid arthritis, psoriatic arthritis), asthma, atherosclerosis, inflammatory bowel disease (Crohn's disease, ulcerative colitis) and dermatitis (including psoriasis).

In more specific embodiments, the SMC modulators of the invention or any pharmaceutical compositions thereof, as well as methods of the invention may be applicable for preventing, treating, ameliorating or inhibiting inflammatory bowel disease (IBD), specifically, ulcerative colitis and Crohn's disease.

Inflammatory bowel diseases (IBD) are common gastrointestinal disorders, that can be perceived as being the result of a disbalance between Th1-pro-inflammatory and Th2-anti-inflammatory subtypes of immune responses. IBD is a group of inflammatory conditions of the colon and small intestine. The major types of IBD are Crohn's disease and ulcerative colitis (UC). Other forms of IBD account for far fewer cases. These are collagenous colitis, lymphocytic colitis, ischemic colitis, diversion colitis, and indeterminate colitis, in cases where it is impossible to make a definitive diagnosis distinguishing Crohn's disease from ulcerative colitis.

The main difference between Crohn's disease and UC is the location and nature of the inflammatory changes. Crohn's disease can affect any part of the gastrointestinal tract, from mouth to anus (skip lesions), although a majority of the cases start in the terminal ileum. Ulcerative colitis, in contrast, is restricted to the colon and the rectum. Microscopically, ulcerative colitis is restricted to the mucosa (epithelial lining of the gut), while Crohn's disease affects the whole bowel wall. Finally, Crohn's disease and ulcerative colitis present with extra-intestinal manifestations (such as liver problems, arthritis, skin manifestations and eye problems) in different proportions. Crohn's disease and ulcerative colitis share the same symptoms such as diarrhea, vomiting, weight loss, fever and abdominal pain.

According to other unlimited embodiments, the SMC modulators, compositions, and methods of the invention may be used for preventing, treating, ameliorating or inhibiting atopic eczema.

"Atopic eczema", also known as atopic dermatitis, is the most common form of eczema. It mainly affects children, but can also affect adults. Eczema is a condition that causes the skin to become itchy, red, dry and cracked. It is a long-term (chronic) condition in most people, although it can improve over time, especially in children. Atopic eczema can affect any part of the body, but the most common areas to be affected are: backs or fronts of the knees, outside or inside of the elbows, around the neck, hands, cheeks and scalp. The exact cause of atopic eczema is unknown, but it's clear it's not down to one single thing. It often occurs in people who get allergies—"atopic" means sensitivity to allergens. There is currently no cure for atopic eczema, but symptomatic treatment can help relieve the symptoms and many cases improve over time. However, severe eczema often has a significant impact on daily life and may be difficult to cope with physically and mentally.

In yet another aspect thereof, the invention provides the use of an effective amount of at least one SMC modulator of WASp having the general formula (I)

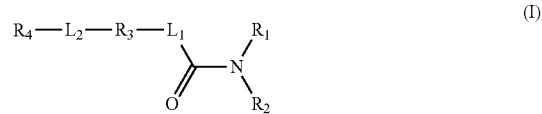

or a pharmaceutically acceptable salt, solvate, esters, hydrate, stereoisomer or physiologically functional derivative thereof, or any combination thereof, or any vehicle, matrix, nano- or micro-particle comprising the same, in the preparation of a composition or medicament for treating, preventing, inhibiting, reducing, eliminating, protecting or delaying the onset of an innate or acquired immune-related disorder or condition in a subject in need thereof, wherein $R_1$ and $R_2$ are each independently from each other selected from H, straight or branched $C_1$-$C_{12}$ alkyl, $C_2$-$C_{12}$ alkenyl, $C_2$-$C_{12}$ alkynyl, straight or branched $C_1$-$C_{12}$ alkoxy, a ring system containing five to twelve atoms, each optionally substituted by at least one of halide, hydroxyl, ester, ether, amide, amine, nitro, —C(=O)—O—(CH$_2$)$_n$—CH$_3$, $R_5$, or —NH—C(=O)—$R_5$, $R_5$ is an a ring system containing five to twelve atoms optionally substituted by at least one halide or straight or branched $C_1$-$C_5$ alkyl;

or $R_1$ and $R_2$ together with the nitrogen atom they are connected to form a five to twelve membered saturated or unsaturated ring that may optionally include N, O, S, NH, C=N, C=O S=O, or SO$_2$ and may be optionally be substituted with at least one of straight or branched $C_1$-$C_5$ alkyl, hydroxyl, halide and cyano;

L1 and L2 are each independently from each other be absent or selected from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$, —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$-, —(CH$_2$)$_n$—(NH)$_n$—C(=O)—(CH$_2$)$_n$—, —NH—(CH$_2$)$_n$—, —C(=O)—NH$_4$CH$_2$)$_n$—; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$, —N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be are each independently from each other optionally substituted with $C_1$-$C_5$ alkyl, a ring system containing five to twelve atoms substituted with $C_1$-$C_5$ alkyl each n, is an integer being independently from each other selected from be 0 to 5;

$R_3$ and R4 are each independently from each other be absent or selected from a ring system containing five to 15 atoms, each optionally substituted with at least one of straight or branched $C_1$-$C_5$ alkyl, (=O), (=S), (O)$_2$, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight or branched C$_1$-C$_5$ alkyl.

Still further, the invention in some other aspects thereof, provides the use of an effective amount of at least one SMC modulator of WASp having the general formula (XI):

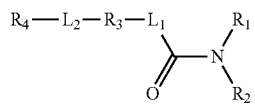
(XI)

or a pharmaceutically acceptable salt, solvate, esters, hydrate, stereoisomer or physiologically functional derivative thereof, or any combination thereof, or any vehicle, matrix, nano- or micro-particle comprising the same, in the preparation of a composition for treating, preventing, inhibiting, reducing, eliminating, protecting or delaying the onset of an innate or acquired immune-related disorder or condition in a subject in need thereof. In more specific embodiments, R$_1$ and R$_2$ are each independently from each other selected from H, straight C$_1$-C$_{12}$ alkyl, a ring system containing five to seven atoms, each optionally substituted by at least one a ring system containing five to seven atoms optionally substituted by at least one halide or straight C$_1$-C$_5$ alkyl or R$_1$ and R$_2$ together with the nitrogen atom they are connected to form a five to seven membered saturated or unsaturated ring optionally include at least one of N, O and optionally substituted with at least one of straight C$_1$-C$_5$ alkyl, L1 and L2 are each independently from each other may be absent or selected to be absent or from —CH$_2$— (CH$_2$—C(O)—N)—(CH$_2$)$_2$, —(CH$_2$)—S—, —(CH$_2$)—, —(CH$_2$)—O—, —NH—(CH$_2$)—, and each optionally substituted with C$_1$-C$_5$ alkyl, a ring system containing five to twelve atoms optionally substituted with C$_1$-C$_5$ alkyl;

R$_3$ and R4 are each independently from each other absent or selected from a ring system containing five to 12 atoms, each optionally substituted with at least one of straight or branched C$_1$-C$_5$ alkyl, (═O), (═S) or R$_5$, R$_5$ is an a ring system containing five to seven atoms optionally substituted by at least one halide or straight C$_1$-C$_5$ alkyl.

In more specific embodiments, the invention provides the use of any of the SMC modulators as defined by the invention and described herein before or of any combinations thereof.

As used herein, "disease", "disorder", "condition" and the like, as they relate to a subject's health, are used interchangeably and have meanings ascribed to each and all of such terms. It should be appreciated that the invention provides therapeutic methods applicable for any of the disorders disclosed above, as well as to any condition or disease associated therewith. It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

The terms "treat, treating, treatment" as used herein and in the claims mean ameliorating one or more clinical indicia of disease activity by administering a pharmaceutical composition of the invention in a patient having a pathologic disorder.

"The term "treatment" as used herein refers to the administering of a therapeutic amount of the composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

The term "amelioration" as referred to herein, relates to a decrease in the symptoms, and improvement in a subject's condition brought about by the compositions and methods according to the invention, wherein said improvement may be manifested in the forms of inhibition of pathologic processes associated with the immune-related disorders described herein, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the invention described below.

The terms "delay", "delaying the onset", "retard" and all variations thereof are intended to encompass the slowing of the progress and/or exacerbation of a pathologic disorder or an infectious disease and their symptoms slowing their progress, further exacerbation or development, so as to appear later than in the absence of the treatment according to the invention.

More specifically, treatment or prevention include the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

The present invention as defined by the claims, the contents of which are to be read as included within the disclosure of the specification, and will now be described by way of example with reference to the accompanying Figures.

The present invention relates to the treatment of subjects, or patients, in need thereof. By "patient" or "subject in need" it is meant any organism who may be infected by the above-mentioned pathogens, and to whom the preventive and prophylactic kit/s, system/s and methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the kit/s and method/s of the invention are intended for preventing pathologic condition in mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral lavage and directly into the digestive tract of subjects in need thereof. The present invention relates to the treatment of subjects, or patients, in need thereof. It should be further noted that particularly in case of human subject, administering of the compositions of the invention to the patient includes both self-administration and administration to the patient by another person.

In yet a further aspect, the invention provides a SMC modulator of WASp degradation having the general formula (XI):

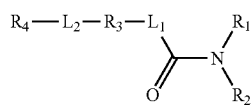

(XI)

or a pharmaceutically acceptable salt, solvate, hydrate, stereoisomer or physiologically functional derivative thereof,
wherein
$R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl
or
$R_1$ and $R_2$ together with the nitrogen atom they are connected to form a five to seven membered saturated or unsaturated ring optionally include at least one of N, O and optionally substituted with at least one of straight $C_1$-$C_5$ alkyl, L1 and L2 are each independently from each other may be absent or selected from —$CH_2$—($CH_2$—C(O)—N)—($CH_2$)$_2$, —($CH_2$)—S—, —($CH_2$)—, —($CH_2$)—O—, —$NH_4CH_2$)—, and each optionally substituted with $C_1$-$C_5$ alkyl, a ring system containing five to twelve atoms optionally substituted with $C_1$-$C_5$ alkyl;

$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl.

In some particular embodiments, specific and non-limiting examples of the SMC modulators of the invention, may be pharmaceutically acceptable salts or hydrates of the compounds of Formula XI, or in some further specific embodiments, pharmaceutically acceptable salts or hydrates of the compounds of Formula XII. More specifically, such compounds may include:

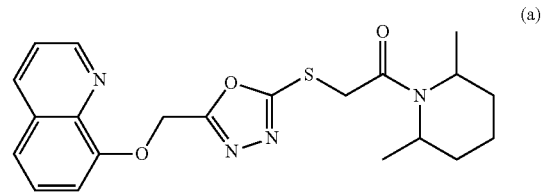 [SMILES: CC1CCCC(C)N1C(=O)CSc1nnc(COc2cccc3cccnc23)o1]

(a)

1-(2,6-Dimethyl-piperidin-1-yl)-2-[5-(quinolin-8-yloxymethyl)-[1,3,4]oxadiazol-2-ylsulfanyl]-ethanone (designated herein as SMC 34); or

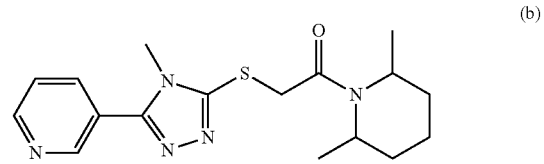 [SMILES: CC1CCCC(C)N1C(=O)CSc1nnc(-c2cccnc2)n1C]

(b)

1-(2,6-Dimethyl-piperidin-1-yl)-2-(4-methyl-5-pyridin-3-yl-4H-[1,2,4]triazol-3-ylsulfanyl)-ethanone (designated herein as SMC 34.7).

In yet some further particular embodiments, specific and non-limiting examples of the SMC modulators of the invention, or pharmaceutically acceptable salts or hydrates of the compounds of Formula XI, or in some further specific embodiments, pharmaceutically acceptable salts or hydrates of the compounds of Formula XII, may include:

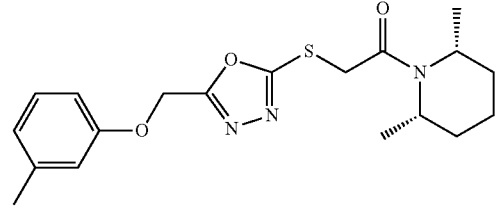 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1);

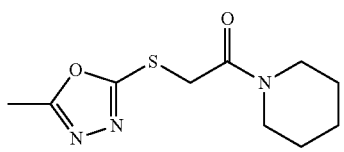 [SMILES: Cc1nnc(SCC(=O)N2CCCCC2)o1]

2-(5-Methyl-[1,3,4]oxadiazol-2-ylsulfanyl)-1-piperidin-1-yl-ethanone (SMC 34.3);

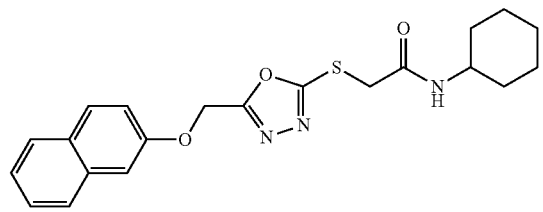 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (SMC 34.4);

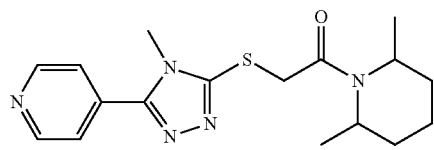 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

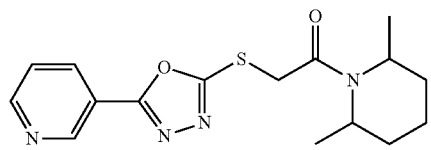 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

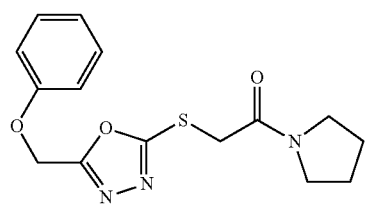 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (SMC 34.8);

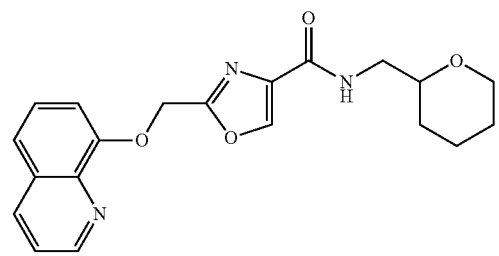 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl amide (SMC 34.10);

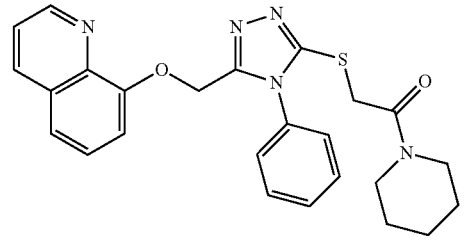 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11);

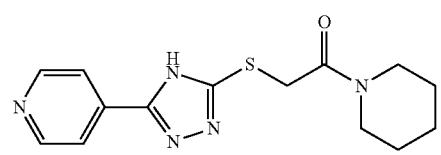 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (SMC 34.12);

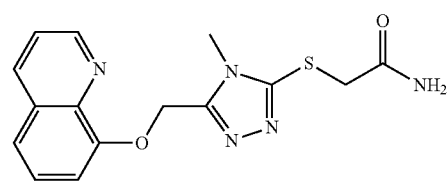 [SMILES: Cn1c(COc2cccc3cccnc23)nnc1SCC(N)=O]

2-[4-Methyl-5-(quinolin-8-yloxymethyl)-4H-[1,2,4]triazol-3-ylsulfanyl]-acetamide (SMC 34.13).

In yet some further particular embodiments, a further example of a SMC modulator that may be used by the invention, may be the compound

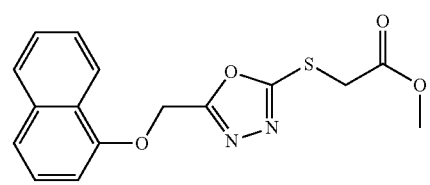 [SMILES: COC(=O)CSc1nnc(COc2cccc3ccccc23)o1]

[5-(Naphthalen-2-yloxymethyl)-[1,3,4]oxadiazol-2-ylsulfanyl]-acetic acid methyl ester (SMC 34.9).

In yet some further particular embodiments, a further example of a SMC modulator that may be used by the invention, may be the compound

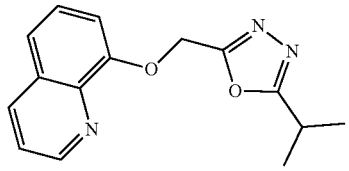 [SMILES: CC(C)c1nnc(COc2cccc3cccnc23)o1]

8-(5-Isopropyl-[1,3,4]oxadiazol-2-ylmethoxy)-quinoline (34.2);

In some particular embodiments, specific and non-limiting examples of the SMC modulators of the invention, may be pharmaceutically acceptable salts or hydrates of the compounds of Formula XI, or in some further specific embodiments, pharmaceutically acceptable salts or hydrates of the compounds of Formula XIII. More specifically, such compounds may include:

(a)

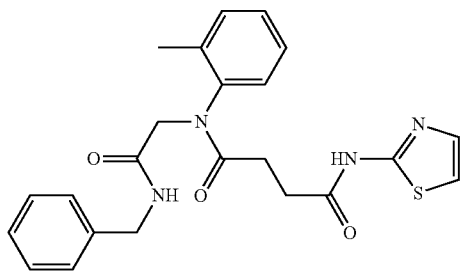

N'-[2-(benzylamino)-2-oxoethyl]-N'-(2-methylphenyl)-N-(1,3-thiazol-2-yl)butanediamide (Designated herein as SMC #33); or (b)

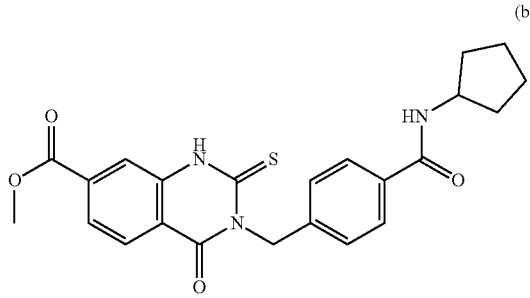

3-(4-Cyclopentylcarbamoyl-benzyl)-4-oxo-2-thioxo-1,2,3,4-tetrahydro-quinazoline-7-carboxylic acid methyl ester (Designated herein as SMC #30).

In some further embodiments, the invention provides an SMC that may be ethyl 4-[[3-(4-acetylpiperazin-1-yl)sulfonylbenzoyl]amino]benzoate having a structure

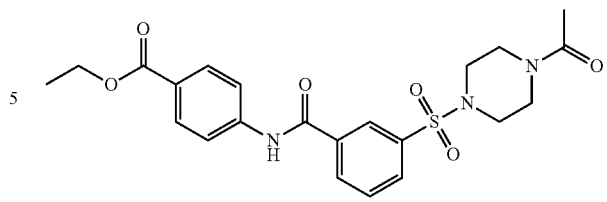

(Denoted herein as SMC #23)

In yet some other embodiments, the invention provides an SMC that may be 10-(3-Chloro-benzyl)-8-(4-methyl-piperazine-1-carbonyl)-5,5-dioxo-5,10-dihydro-5λ6-dibenzo[b,f][1,4]thiazepin-11-one having a structure

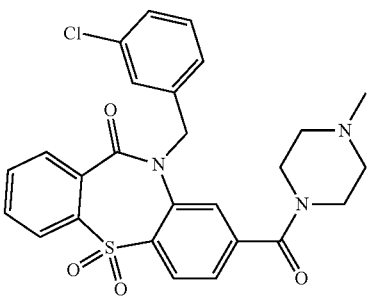 [SMILES: CN1CCN(C(=O)c2ccc3c(c2)N(Cc2cccc(Cl)c2)C(=O)c2ccccc2S3(=O)=O)CC1]

(Denoted herein as SMC #26).

In yet some alternative particular embodiments of the SMC modulator for use in accordance with the invention, the compound of Formula XI, may provide a compound having the general formula (XIV):

(XIV)

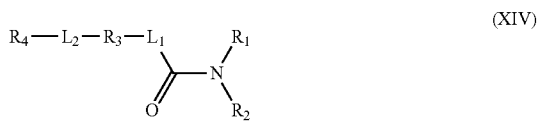

or a pharmaceutically acceptable salt, solvate, hydrate, stereoisomer or physiologically functional derivative thereof,
wherein
$R_1$ and $R_2$ are each independently from each other selected from H and straight $C_1$-$C_5$ alkyl,
L1 and L2 are each independently from each other may be absent or selected from —$(CH_2)$—S—, —$(CH_2)$—, —$(CH_2)$—O—,
$R_3$ and R4 are each independently from each other absent or selected from an aryl or heteroaryl group optionally substituted with at least one of straight or branched $C_1$-$C_5$ alkyl, halide, nitro and cyano.

In some embodiments, in the SMC modulator for use in accordance with the invention. $R_1$ and $R_2$ are each independently from each other selected from H, methyl and ethyl, at times $R_1$ and $R_2$ are each independently from each other selected from H and methyl, L1 may be —$CH_2$—S—, L2 may be —$CH_2$—O—; $R_3$ and R4 are each independently from each other absent or selected from an aryl or heteroaryl group optionally substituted with at least one of straight or branched $C_1$-$C_5$ alkyl, halide, nitro and cyano.

In some further embodiments, in the SMC modulator for use in accordance with the invention, the $R_1$ and $R_2$ may be each independently from each other selected from H and methyl, L1 is —CH$_2$—S—, L2 is, —CH$_2$—O—, R$_3$ is selected from the group consisting of thiazole, [1,3,4]thiadiazole, [1,3,4]oxadiazole, and R$_4$ is phenyl.

In yet some alternative particular embodiments of the SMC modulator for use in accordance with the invention, the compound of Formula I, may provide a compound having the general formula (XV):

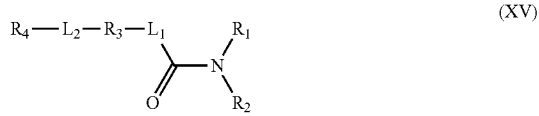

(XV)

or a pharmaceutically acceptable salt, solvate, hydrate, stereoisomer or physiologically functional derivative thereof,
wherein
R$_1$ and R$_2$ are each independently from each other selected from H, straight C$_1$-C$_{12}$ alkyl and branched C$_1$-C$_{12}$ alkyl;
L1 and L2 are each independently from each other selected to be absent or from —(CH$_2$)$_n$—(CH$_2$—C(O)—N)$_n$—(CH$_2$)$_n$, —(CH$_2$)$_n$—S—, —(CH$_2$)$_n$—O—, S(O)$_2$, S(O)$_2$—N—(CH$_2$)$_n$, —(CH$_2$)$_n$, —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$—, —(CH$_2$)$_n$—(NH)$_n$—C(=O)—(CH$_2$)$_n$—, —NH—(CH$_2$)$_n$—, —C(=O)—NH—(CH$_2$)$_n$; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—, CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C(=O)— L1 and L2 may be each independently from each other optionally substituted with C$_1$-C$_5$ alkyl, a ring system containing five to twelve atoms optionally substituted with C$_1$-C$_5$ alkyl
each n, is an integer being independently from each other selected from be 0 to 5;
R$_3$ and R4 are each independently from each other be absent or selected from a ring system containing five to 15 atoms, each optionally substituted with at least one of straight or branched C$_1$-C$_5$ alkyl, (=O), (=S), (O)$_2$, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight C$_1$-C$_5$ alkyl or branched C$_1$-C$_5$ alkyl.

In some embodiments, R$_1$ and R$_2$ are each independently from each other selected from H or straight C$_1$-C$_5$ alkyl, L1 and L2 are each independently from each other selected to be absent or from —(CH$_2$)$_n$—(CH$_2$—C(O)—N)$_n$—(CH$_2$)$_n$, —(CH$_2$), —S—, —(CH$_2$), —O—, S(O)$_2$, S(O)$_2$—N—(CH$_2$)$_n$, —(CH$_2$)$_n$, —(CH$_2$)$_n$—N—C(=O)—, S(O)$_2$—N—(CH$_2$)$_n$, —(CH$_2$)$_n$—S—, NH, —(CH$_2$)$_n$—S—(CH$_2$)$_n$—C(O)—NH—(CH2)$_n$-, —(CH$_2$)$_n$—(NH)$_n$—C(=O)—(CH$_2$)$_n$—, —NH—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S(CH$_2$)$_n$—; —NH—S(=O)$_n$—(CH$_2$)$_n$—, —CH$_2$—S—C(O)—NH—CH$_2$—, —(CH$_2$)$_n$—(NH)$_n$—C(=O)—(CH$_2$)$_n$—N—C(=O)—, S(O)$_2$—N—(CH$_2$)$_n$, —(CH$_2$)$_n$—(NH)$_n$—C(=O)—, —(CH$_2$)$_n$—N—C (=O)— L1 and L2 may be each independently from each other optionally substituted with C$_1$-C$_5$ alkyl, a ring system containing five to twelve atoms optionally substituted with C$_1$-C$_5$ alkyl; each n, is an integer being independently from each other selected from be 0 to 5;
R$_3$ and R4 are each independently from each other be absent or selected from a ring system containing five to 15 atoms, each optionally substituted with at least one of straight or branched C$_1$-C$_5$ alkyl, (=O), (=S), (O)$_2$, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight C$_1$-C$_5$ alkyl or branched C$_1$-C$_5$ alkyl.

In some other embodiments, R$_1$ and R$_2$ are each independently from each other selected from H, straight C$_1$-C$_5$ alkyl, L1 is absent and L2 is selected from —(CH$_2$)—S—, —(CH$_2$)—O—, —(CH$_2$)—; R$_3$ and R4 are each independently from each other be absent or selected from a ring system containing five to 15 atoms, each optionally substituted with at least one of straight or branched C$_1$-C$_5$ alkyl, —C(O)—CH$_3$, —C(O)—O—CH$_3$, halide, CF$_3$, nitro, amide, or R$_5$, R$_5$ is an a ring system containing five to twelve atoms optionally substituted by at least one halide or straight C$_1$-C$_5$ alkyl or branched C$_1$-C$_5$ alkyl.

In some other embodiments, R$_1$ and R$_2$ are each independently from each other selected from H, straight C$_1$-C$_5$ alkyl, L1 is absent and L2 is selected from —(CH$_2$)—S—, —(CH$_2$)—O—, —(CH$_2$)—;

R$_3$ is a bicyclic ring and R4 is an aryl or a heteroaryl.

In accordance with some other aspects, the invention relates to at least one SMC modulator of WASp having the general formula (V):

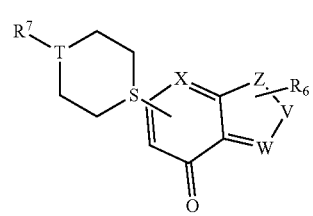

(V)

or a pharmaceutically acceptable salt, solvate, hydrate, stereoisomer or physiologically functional derivative thereof,
wherein
each one of X, Y, Z, V, W, T and S may be selected from N, NH and C,
R$_6$ and R$_7$ are the same or are different and are independently selected from each other may be L3-R$_8$,
L3 may be selected from —(CH$_2$)$_n$, —NH—C(O) and C(O)—NH, S(O)$_2$, C(O),
n is an integer between 0 to 5;
R$_8$ may be selected from a ring system containing five to twelve atoms, each optionally substituted by at least one of straight or branched C$_1$-C$_5$ alkyl, halide, hydroxyl, ester, ether, amide, nitro and hydroxyl, CF$_3$.

In some embodiments, the invention provides an SMC that may be any one of:

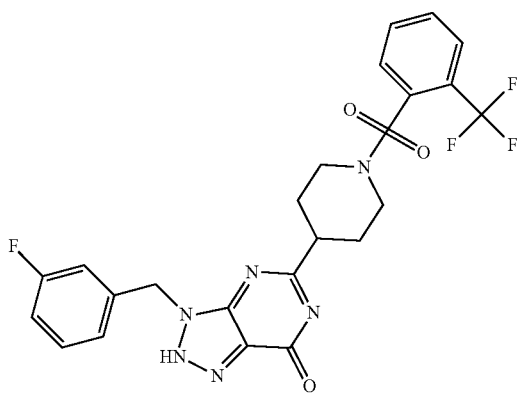

3-[(3-fluorophenyl)methyl]-5-[1-[2-(trifluoroethyl)phenyl]
sulfonylpiperidin-4-yl]-2H-triazolo[4,5-d]pyrimidin-7-
one
(Designated herein as SMC #32);

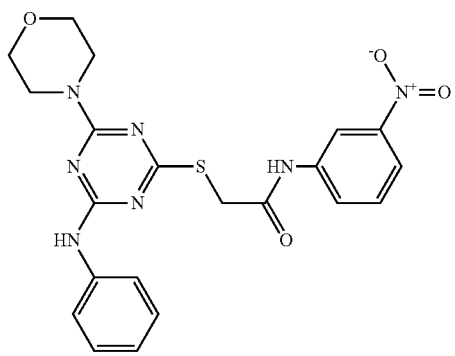

2-(4-Morpholin-4-yl-6-phenylamino-[1,3,5]triazin-2-ylsul-
fanyl)-N-(3-nitro-phenyl)-acetamide Designated herein
as SMC #15);

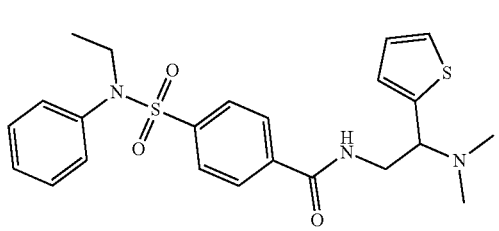 [SMILES: CCN(c1ccccc1)S(=O)(=O)c1ccc(C(=O)NCC(c2cccs2)N(C)C)cc1]

N-[2-(dimethylamino)-2-thiophen-2-ylethyl]-4-[ethyl(phe-
nyl)sulfamoyl]benzamide (Designated herein as SMC
24);

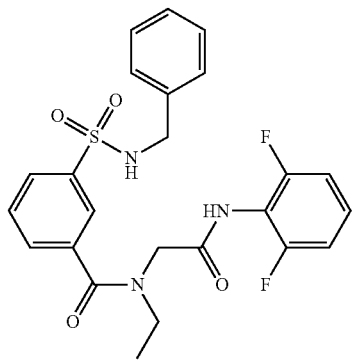

3-(benzylsulfamoyl)-N-[2-(2,6-difluoroanilino)-2-oxo-
ethyl]-N-ethylbenzamide (Designated herein as SMC
25);

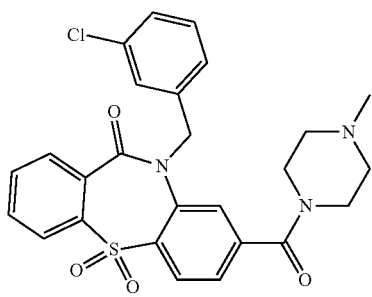 [SMILES: CN1CCN(C(=O)c2ccc3c(c2)N(Cc2cccc(Cl)c2)C(=O)c2ccccc2S3(=O)=O)CC1]

10-(3-Chloro-benzyl)-8-(4-methyl-piperazine-1-carbonyl)-
5,5-dioxo-5,10-dihydro-5λ6-dibenzo[b,f][1,4]thiazepin-
11-one (Designated herein as SMC #26);

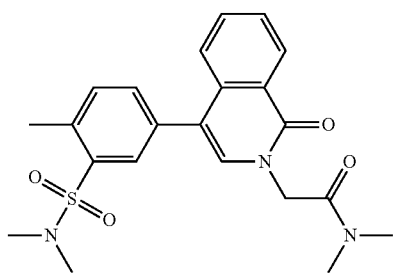

2-[4-[3-(dimethylsulfamoyl)-4-methylphenyl]-1-oxophtha-
lazin-2-yl]-N,N-dimethylacetamide (Designated herein as
SMC #16);

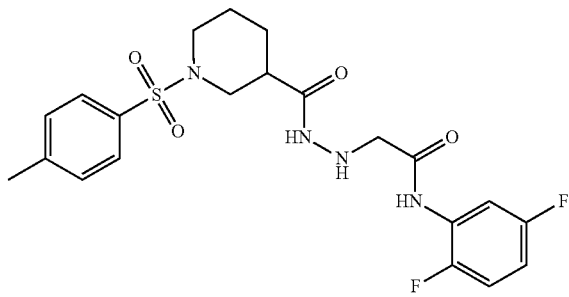 [SMILES: Cc1ccc(S(=O)(=O)N2CCCC(C(=O)NNCC(=O)Nc3cc(F)ccc3F)C2)cc1]

N-(2,5-difluorophenyl)-2-[2-[1-(4-methylphenyl)sulfonylpiperidin-3-carbonyl]hydrazinyl]acetamide (Designated herein as SMC #21);

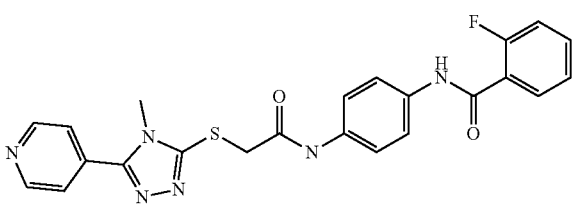 [SMILES: Cn1c(SCC(=O)Nc2ccc(NC(=O)c3ccccc3F)cc2)nnc1-c1ccncc1]

2-fluoro-N-[4-[[2-[(4-methyl-5-pyridin-4-yl-1,2,4-triazol-3-yl)sulfanyl]acetyl]amino]phenyl]benzamide (Designated herein as SMC #31);

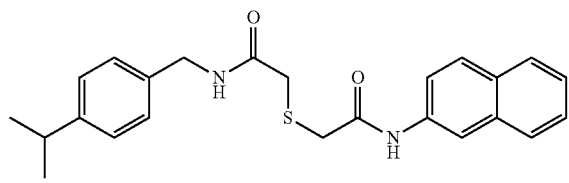 [SMILES: CC(C)c1ccc(CNC(=O)CSCC(=O)Nc2ccc3ccccc3c2)cc1]

2-[2-(naphthalen-2-ylamino)-2-oxoethyl]sulfanyl-N-[(4-propan-2-ylphenyl)methyl]acetamide (Designated herein as SMC #17)

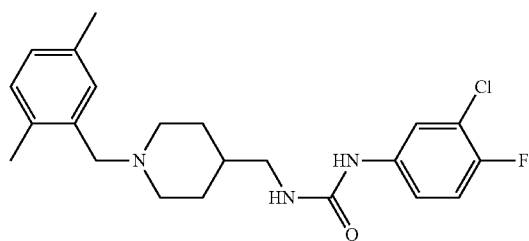 [SMILES: Cc1ccc(C)c(CN2CCC(CNC(=O)Nc3ccc(F)c(Cl)c3)CC2)c1]

1-(3-chloro-4-fluorophenyl)-3-[[1-[(2,5-dimethylphenyl)methyl]piperidin-4-yl]methyl]urea (Designated herein as SMC #28).

It should be appreciated that the invention encompasses any of the SMCs modulators disclosed herein.

In yet a further aspect, the invention relates to a pharmaceutical composition comprising a therapeutically effective amount of at least one SMC modulator of WASp as described herein. It should be noted that the composition of the invention may optionally further comprise at least one pharmaceutically acceptable carrier/s, excipient/s, auxiliaries, and/or diluent/s.

Some aspects of the invention relate to a pharmaceutical composition comprising a therapeutically effective amount of at least one SMC modulator of WASp having the general formula (I)

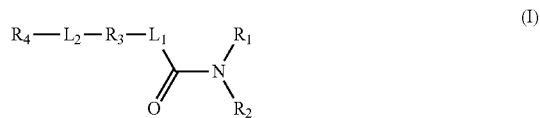

(I)

or a pharmaceutically acceptable salt, solvate, esters, hydrate, stereoisomer or physiologically functional derivative thereof, or any vehicle, matrix, nano- or micro-particle comprising the same, said composition optionally further comprises at least one pharmaceutically acceptable carrier/s, excipient/s, auxiliaries, and/or diluent/s, wherein $R_1$ and $R_2$ are each independently from each other selected from H, straight or branched $C_1$-$C_{12}$ alkyl, $C_2$-$C_{12}$ alkenyl, $C_2$-$C_{12}$ alkynyl, straight or branched $C_1$-$C_{12}$ alkoxy, a ring system containing five to twelve atoms, each optionally substituted by at least one of halide, hydroxyl, ester, ether, amide, nitro, —C(═O)—O—$(CH_2)_n$—$CH_3$, $R_5$, or —NH—C(═O)—$R_5$, $R_5$ is an a ring system containing five to twelve atoms optionally substituted by at least one halide or straight or branched $C_1$-$C_5$ alkyl;

or $R_1$ and $R_2$ together with the nitrogen atom they are connected to form a five to twelve membered saturated or unsaturated ring that may optionally include N, O, S, NH, C═N, C═O, S═O, or $SO_2$ and may be optionally be substituted with at least one of straight or branched $C_1$-$C_5$ alkyl, hydroxyl, halide and cyano;

L1 and L2 are each independently from each other may be absent or selected from —$(CH_2)_n$—$(CH_2$—C(O)—N$)_n$—$(CH_2)_n$, —$(CH_2)_n$—S—, —$(CH_2)_n$—O—, $S(O)_2$, $S(O)_2$—N—$(CH_2)_n$, —$(CH_2)_n$, —$(CH_2)_n$—N—C(═O)—, $S(O)_2$—N—$(CH_2)_n$, —$(CH_2)_n$—S—, NH, —$(CH_2)_n$—S—$(CH_2)_n$—C(O)—NH—$(CH2)_n$-, —$(CH_2)_n$—$(NH)_n$—C(═O)—$(CH_2)_n$—, —NH—$(CH_2)_n$—, —C(═O)—NH—$(CH_2)_n$—; —S—S—$(CH_2)_n$—; —O—$(CH_2)_n$—; —NH—$(CH_2)_n$—; C(═O)—$(CH_2)_n$—; —S—$(CH_2)_n$—; —NH—S(═O)$_n$—$(CH_2)_n$—, —$CH_2$—S—C(O)—NH—$CH_2$—, —$(CH_2)_n$—$(NH)_n$—C(═O)—$(CH_2)_n$—N—C(═O)—, $S(O)_2$—N—$(CH_2)_n$, —$(CH_2)_n$—$(NH)_n$—C(═O)—, —$(CH_2)_n$—N—C(═O)— L1 and L2 may be are each independently from each other optionally substituted with $C_1$-$C_5$ alkyl, a ring system containing five to twelve atoms substituted with $C_1$-$C_5$ alkyl each n, is an integer being independently from each other selected from be 0 to 5;

$R_3$ and R4 are each independently from each other be absent or selected from a ring system containing five to 15 atoms, each optionally substituted with at least one of straight or branched $C_1$-$C_5$ alkyl, (═O), (═S), (O)$_2$, —C(O)—$CH_3$, —C(O)—O—$CH_3$, halide, $CF_3$, nitro, amide, or $R_5$, $R_5$ is an a ring system containing five to twelve atoms optionally substituted by at least one halide or straight or branched $C_1$-$C_5$ alkyl.

In yet some further aspects thereof, the composition of the invention may comprise at least one SMC modulator of WASp degradation having the general formula (XI):

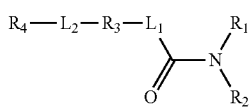 (XI)

or a pharmaceutically acceptable salt, solvate, hydrate, stereoisomer or physiologically functional derivative thereof,
wherein
R$_1$ and R$_2$ are each independently from each other selected from H, straight C$_1$-C$_{12}$ alkyl, a ring system containing five to seven atoms, each optionally substituted by at least one a ring system containing five to seven atoms optionally substituted by at least one halide or straight C$_1$-C$_5$ alkyl
or
R$_1$ and R$_2$ together with the nitrogen atom they are connected to form a five to seven membered saturated or unsaturated ring optionally include at least one of N, O and optionally substituted with at least one of straight C$_1$-C$_5$ alkyl,
L1 and L2 are each independently from each other selected to be absent or from —CH$_2$—(CH$_2$—C(O)—N)—(CH$_2$)$_2$, —(CH$_2$)—S—, —(CH$_2$)—, —(CH$_2$)—O—, —NH—(CH$_2$)—, and each optionally substituted with C$_1$-C$_5$ alkyl, a ring system containing five to twelve atoms optionally substituted with C$_1$-C$_5$ alkyl;
R$_3$ and R4 are each independently from each other absent or selected from a ring system containing five to 12 atoms, each optionally substituted with at least one of straight or branched C$_1$-C$_5$ alkyl, (=O), (=S) or R$_5$, R$_5$ is an a ring system containing five to seven atoms optionally substituted by at least one halide or straight C$_1$-C$_5$ alkyl.

In some particular embodiments, specific and non-limiting examples of the SMC modulators of the compositions of the invention, may be pharmaceutically acceptable salts or hydrates of the compounds of Formula XI, or in some further specific embodiments, pharmaceutically acceptable salts or hydrates of the compounds of Formula XII. More specifically, such compounds may include:

(a)

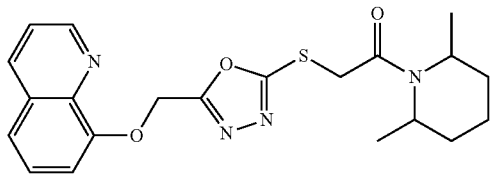

1-(2,6-Dimethyl-piperidin-1-yl)-2-[5-(quinolin-8-yloxymethyl)-[1,3,4]oxadiazol-2-ylsulfanyl]-ethanone (designated herein as SMC 34); or (b)

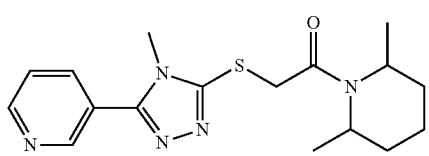

1-(2,6-Dimethyl-piperidin-1-yl)-2-(4-methyl-5-pyridin-3-yl-4H-[1,2,4]triazol-3-ylsulfanyl)-ethanone (designated herein as SMC 34.7).

In yet some further particular embodiments, specific and non-limiting examples of the SMC modulators of the compositions of the invention, or pharmaceutically acceptable salts or hydrates of the compounds of Formula XI, or in some further specific embodiments, pharmaceutically acceptable salts or hydrates of the compounds of Formula XII, may include:

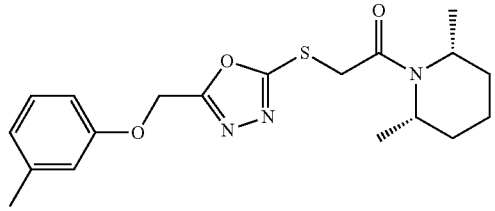 [SMILES: Cc1cccc(OCc2nnc(SCC(=O)N3[C@H](C)CCC[C@@H]3C)o2)c1]

1-(2,6-Dimethyl-piperidin-1-yl)-2-(5-m-tolyloxymethyl-[1,3,4]oxadiazol-2-ylsulfanyl)-ethanone (SMC 34.1);

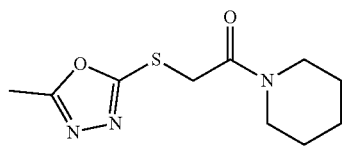 [SMILES: Cc1nnc(SCC(=O)N2CCCCC2)o1]

2-(5-Methyl-1,3,4 oxadiazol-2-ylsulfanyl)-1-piperidin-1-yl-ethanone (SMC 34.3);

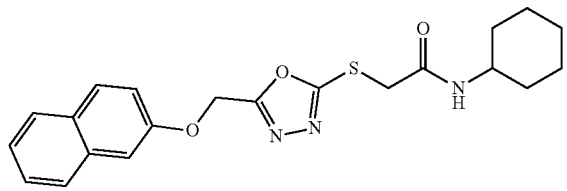 [SMILES: O=C(CSc1nnc(COc2ccc3ccccc3c2)o1)NC1CCCCC1]

N-Cyclohexyl-2-[5-(naphthalen-2-yloxymethyl)-[1,3,4]oxadiazol-2-ylsulfanyl]-acetamide (SMC 34.4);

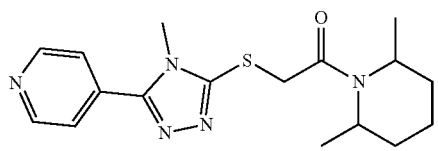 [SMILES: CC1CCCC(C)N1C(=O)CSc1nnc(-c2ccncc2)n1C]

1-(2,6-Dimethyl-piperidin-1-yl)-2-(4-methyl-5-pyridin-4-yl-4H-[1,2,4]triazol-3-ylsulfanyl)-ethanone (SMC 34.5);

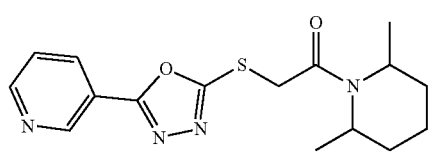 [SMILES: CC1CCCC(C)N1C(=O)CSc1nnc(-c2cccnc2)o1]

1-(2,6-Dimethyl-piperidin-1-yl)-2-(5-pyridin-3-yl-[1,3,4]oxadiazol-2-ylsulfanyl)-ethanone (SMC 34.6);

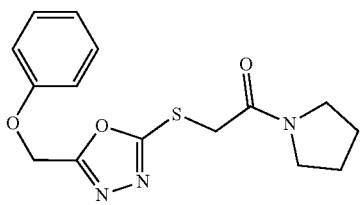 [SMILES: O=C(CSc1nnc(COc2ccccc2)o1)N1CCCC1]

2-(5-Phenoxymethyl-[1,3,4]oxadiazol-2-ylsulfanyl)-1-pyrrolidin-1-yl-ethanone (SMC 34.8);

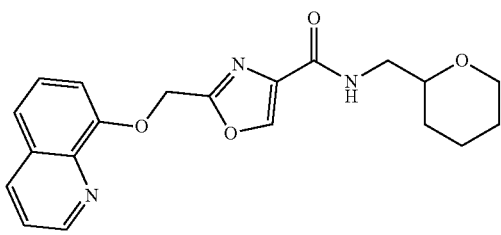 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10);

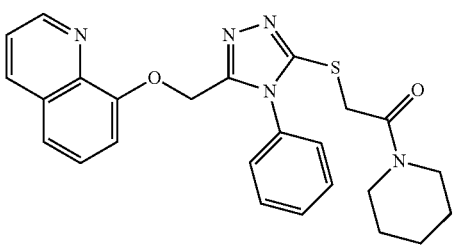 [SMILES: O=C(CSc1nnc(COc2cccc3cccnc23)n1-c1ccccc1)N1CCCCC1]

2-[4-Phenyl-5-(quinolin-8-yloxymethyl)-4H-[1,2,4]triazol-3-ylsulfanyl]-1-piperidin-1-yl-ethanone (SMC 34.11);

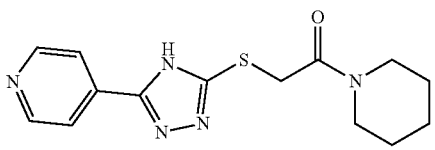 [SMILES: O=C(CSc1nnc(-c2ccncc2)[nH]1)N1CCCCC1]

1-Piperidin-1-yl-2-(5-pyridin-4-yl-4H-[1,2,4]triazol-3-ylsulfanyl)-ethanone (SMC 34.12);

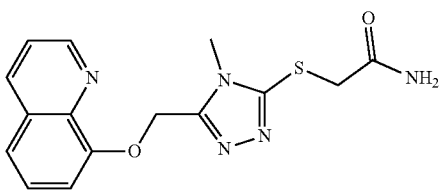 [SMILES: Cn1c(COc2cccc3cccnc23)nnc1SCC(N)=O]

2-[4-Methyl-5-(quinolin-8-yloxymethyl)-4H-[1,2,4]triazol-3-ylsulfanyl]-acetamide (SMC 34.13)

In yet some further particular embodiments, a further example of a SMC modulator that may be used by the invention, may be the compound

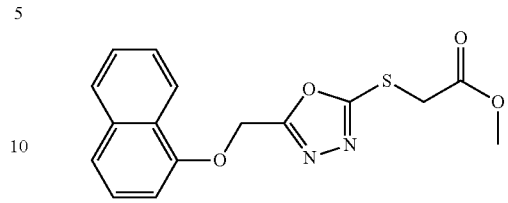

[5-(Naphthalen-2-yloxymethyl)-[1,3,4]oxadiazol-2-ylsulfanyl]-acetic acid methyl ester (SMC 34.9).

In yet some further particular embodiments, a further example of a SMC modulator that may be used by the invention, may be the compound

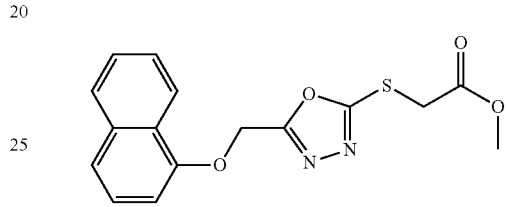

[5-(Naphthalen-2-yloxymethyl)-[1,3,4]oxadiazol-2-ylsulfanyl]-acetic acid methyl ester (SMC 34.9).

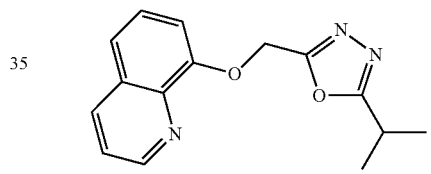

8-(5-Isopropyl-[1,3,4]oxadiazol-2-ylmethoxy)-quinoline (34.2)

In some other particular embodiments, specific and non-limiting examples of the SMC modulators of the compositions of the invention may be pharmaceutically acceptable salts or hydrates of the compounds of Formula XI, or in some further specific embodiments, pharmaceutically acceptable salts or hydrates of the compounds of Formula XIII. More specifically, such compounds may include:

(a)

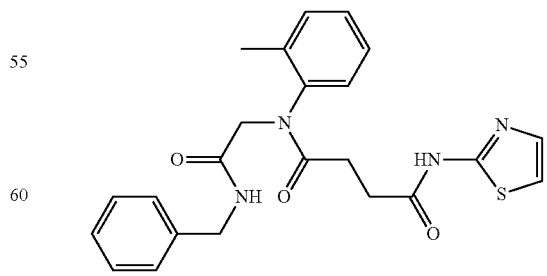

N'-[2-(benzylamino)-2-oxoethyl]-N'-(2-methylphenyl)-N-(1,3-thiazol-2-yl)butanediamide (Designated herein as SMC #33); or

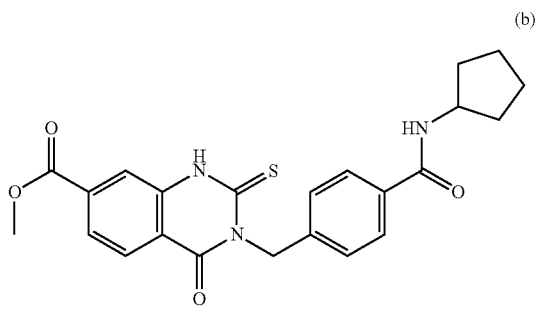 [SMILES: COC(=O)c1ccc2c(=O)n(Cc3ccc(C(=O)NC4CCCC4)cc3)c(=S)[nH]c2c1]

3-(4-Cyclopentylcarbamoyl-benzyl)-4-oxo-2-thioxo-1,2,3,4-tetrahydro-quinazoline-7-carboxylic acid methyl ester (Designated herein as SMC #30).

In some embodiments, the pharmaceutical composition comprising a therapeutically effective amount of N'-[2-(benzylamino)-2-oxoethyl]-N'-(2-methylphenyl)-N-(1,3-thiazol-2-yl)butanediamide having a structure:

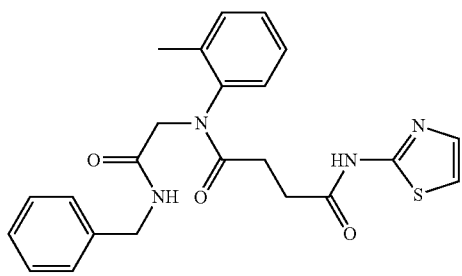 [SMILES: Cc1ccccc1N(CC(=O)NCc1ccccc1)C(=O)CCC(=O)Nc1nccs1]

(Denoted herein as SMC #33)

In some other embodiments, the pharmaceutical composition comprising a therapeutically effective amount of 1-(2,6-dimethylpiperidin-1-yl)-2-[[5-(quinolin-8-yloxymethyl)-1,3,4-oxadiazol-2-yl]sulfanyl]ethanone having a structure

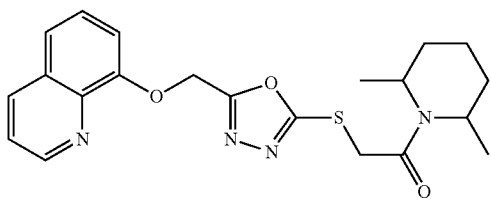 [SMILES: CC1CCCC(C)N1C(=O)CSc1nnc(COc2cccc3cccnc23)o1]

(Denoted herein as SMC #34);

In some further embodiments, the pharmaceutical composition comprising a therapeutically effective amount is ethyl 4-[[3-(4-acetylpiperazin-1-yl)sulfonylbenzoyl]amino]benzoate having a structure

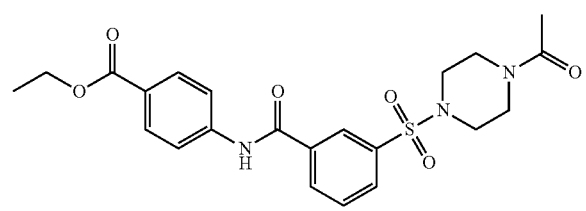 [SMILES: CCOC(=O)c1ccc(NC(=O)c2cccc(S(=O)(=O)N3CCN(C(C)=O)CC3)c2)cc1]

(Denoted herein as SMC #23);

In yet some other embodiments, the pharmaceutical composition comprising a therapeutically effective amount of 10-(3-Chloro-benzyl)-8-(4-methyl-piperazine-1-carbonyl)-5,5-dioxo-5,10-dihydro-5λ6-dibenzo[b,f][1,4]thiazepin-11-one having a structure

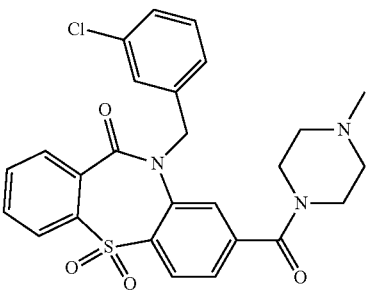 [SMILES: CN1CCN(C(=O)c2ccc3c(c2)N(Cc2cccc(Cl)c2)C(=O)c2ccccc2S3(=O)=O)CC1]

(Denoted herein as SMC #26);

In accordance with some other aspects, the invention relates to a pharmaceutical composition comprising a therapeutically effective amount of at least one SMC modulator of WASp having the general formula (V):

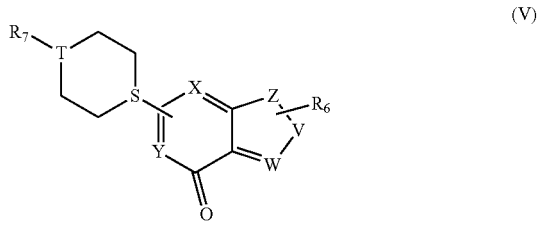

(V)

or a pharmaceutically acceptable salt, solvate, hydrate, stereoisomer or physiologically functional derivative thereof, wherein each one of X, Y, Z, V, W, T and S may be selected from N, NH and C, $R_6$ and $R_7$ are the same or are different and are independently selected from each other may be L3-$R_8$, L3 may be selected from —(CH$_2$)n, —NH—C(O) and C(O)—NH, S(O)$_2$, C(O), n is an integer between 0 to 5;

$R_8$ may be selected from a ring system containing five to twelve atoms, each optionally substituted by at least one of straight or branched $C_1$-$C_5$ alkyl, halide, hydroxyl, ester, ether, amide, nitro and hydroxyl, CF$_3$.

In some embodiments, the pharmaceutical composition comprising a therapeutically effective amount of

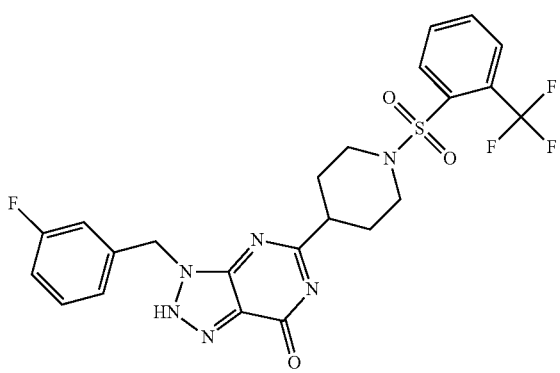 [SMILES: O=c1nc(C2CCN(S(=O)(=O)c3ccccc3C(F)(F)F)CC2)nc2n(Cc3cccc(F)c3)[nH]nc1-2]

3-[(3-fluorophenyl)methyl]-5-[1-[2-(trifluoromethyl)phenyl]sulfonylpiperidin-4-yl]-2H-triazolo[4,5-d]pyrimidin-7-one (Designated herein as SMC #32)

In accordance with some other aspects, the invention relates to a pharmaceutical composition comprising a therapeutically effective amount of at least one SMC modulator of WASp having the general formula (IX):

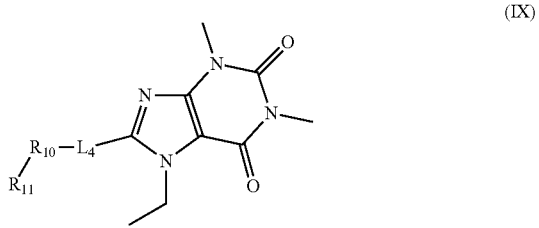

(IX)

or a pharmaceutically acceptable salt, solvate, hydrate, stereoisomer or physiologically functional derivative thereof,
wherein
L4 may be absent or may be selected from —(CH$_2$)$_n$—, —S—(CH$_2$)$_n$—, —(CH$_2$)$_n$—S—;
n is an integer between 0 and 5;
R$_{10}$ and R11 are each independently from each other absent or selected from a ring system containing five to twelve atoms, each optionally substituted with at least one of straight or branched C$_1$-C$_5$ alkyl, (=O), (=S), —C(O)—CH$_3$, —C(O)—O—CH$_3$, halide, nitro, NH$_2$.

In some embodiments, L4 is selected from —S—(CH$_2$)—. In some other embodiments, R$_{10}$ and R11 are each independently from each other absent or selected from triazine, piperidine each optionally substituted with at least one NH$_2$.

In accordance with some other aspects, the invention relates to a pharmaceutical composition comprising a therapeutically effective amount of at least one SMC modulator of WASp having the general formula (X):

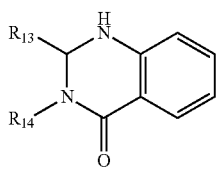

(X)

or a pharmaceutically acceptable salt, solvate, hydrate, stereoisomer or physiologically functional derivative thereof,
wherein
R$_{13}$ and R14 are each independently from each other absent or selected from a ring system containing five to twelve atoms, each optionally substituted with at least one of straight or branched C$_1$-C$_5$ alkyl, C$_1$-C$_5$ alkoxy, (=O), (=S), —C(O)—CH$_3$, —C(O)—O—CH$_3$, halide, nitro, NH$_2$, NH—C(O)—CH$_3$.

In some other embodiments, R$_{10}$ and R11 are each independently from each other absent or selected from aryl each optionally substituted with at least one OCH, NH—C(O)—CH$_3$.

In some specific embodiments, the pharmaceutical composition may comprise any of the SMC modulator/s as described by the invention or any vehicle, matrix, nano- or micro-particle comprising the same.

In yet some further embodiments, the invention provides the pharmaceutical compositions as described herein for use in a method for treating, preventing, inhibiting, reducing, eliminating, protecting or delaying the onset of an innate or acquired immune-related disorder or condition.

In some embodiments, the pharmaceutical composition for use in a method for treating, preventing, inhibiting, reducing, eliminating, protecting or delaying the onset of an innate or acquired immune-related disorder or condition, comprising a therapeutically effective amount of N'-[2-(benzylamino)-2-oxoethyl]-N'-(2-methylphenyl)-N-(1,3-thiazol-2-yl)butanediamide having a structure:

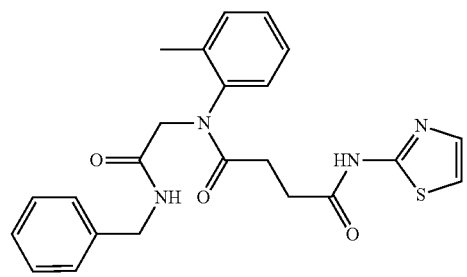 [SMILES: Cc1ccccc1N(CC(=O)NCc1ccccc1)C(=O)CCC(=O)Nc1nccs1]

(denoted herein as #33)

In some other embodiments, the pharmaceutical composition for use in a method for treating, preventing, inhibiting, reducing, eliminating, protecting or delaying the onset of an innate or acquired immune-related disorder or condition, comprising a therapeutically effective amount of 1-(2,6-dimethylpiperidin-1-yl)-2-[[5-(quinolin-8-yloxymethyl)-1,3,4-oxadiazol-2-yl]sulfanyl]ethanone having a structure

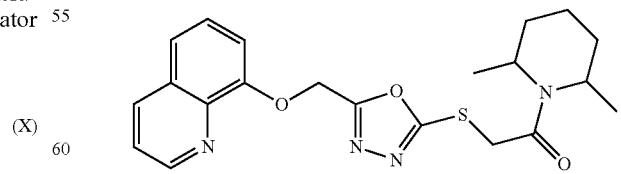

(denoted herein as SMC #34).

In some further embodiments, the pharmaceutical composition for use in a method for treating, preventing, inhibiting, reducing, eliminating, protecting or delaying the onset of an innate or acquired immune-related disorder or condition, comprising a therapeutically effective amount is ethyl 4-[[3-(4-acetylpiperazin-1-yl)sulfonylbenzoyl]amino]benzoate having a structure

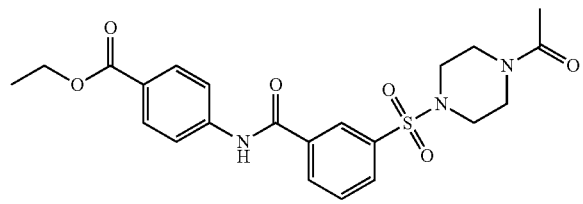 [SMILES: CCOC(=O)c1ccc(NC(=O)c2cccc(S(=O)(=O)N3CCN(C(C)=O)CC3)c2)cc1]

(denoted herein as SMC #23).

In yet some other embodiments, the pharmaceutical composition for use in a method for treating, preventing, inhibiting, reducing, eliminating, protecting or delaying the onset of an innate or acquired immune-related disorder or condition, comprising a therapeutically effective amount of 10-(3-Chloro-benzyl)-8-(4-methyl-piperazine-1-carbonyl)-5,5-dioxo-5,10-dihydro-5λ6-dibenzo[b,f][1,4]thiazepin-11-one having a structure

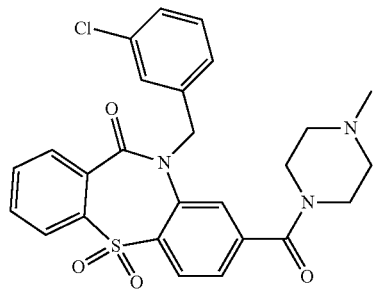 [SMILES: CN1CCN(C(=O)c2ccc3c(c2)N(Cc2cccc(Cl)c2)C(=O)c2ccccc2S3(=O)=O)CC1]

(denoted herein as SMC #26).

It should be appreciated that the small molecule compounds (SMCs) of the invention are referred to either by their formula or by their numbers, for example, compound #34 may be referred to herein as SMC 34, SMC #34 or #34.

In some specific embodiments, the compositions of the invention may be used for treating hereditary disorder associated with WASp dysfunction. In more specific embodiments, such disorders may be at least one of Wiskott Aldrich Syndrome (WAS) and X-linked thrombocytopenia (XLT), or any condition or disorder associated therewith.

In some specific embodiments, condition or disorder associated with WAS and/or XLT, may be also defined as an acquired disorder related to WASp dysfunction. Such conditions or disorders may include but are not limited to at least one of autoimmune disorders, inflammatory disorders and atopic eczema.

It should be appreciated that in some embodiments, the composition of the invention may be used for any immune-related disorders, in some embodiments, any innate or acquired immunodeficiency as detailed in connection with other aspects of the invention. Specifically, any primary (e.g., WAS, XLT and associated conditions) or secondary immunodeficiency (e.g., caused by at least one of chemotherapy, radiotherapy, biological therapy, bone marrow transplantation, gene therapy, adoptive cell transfer or any combinations thereof).

It should be appreciated that the SMC modulators used by the methods of the invention may be formulated in any vehicle, matrix, nano- or micro-particle, or composition. Of particular relevance are formulations of the SMC modulators of the invention adapted for use as a nano- or micro-particles. Nanoscale drug delivery systems using micellar formulations, liposomes and nanoparticles are emerging technologies for the rational drug delivery, which offers improved pharmacokinetic properties, controlled and sustained release of drugs and, more importantly, lower systemic toxicity. A particularly desired solution allows for externally triggered release of encapsulated compounds. Externally controlled release can be accomplished if drug delivery vehicles, such as micelles, liposomes or polyelectrolyte multilayer capsules, incorporate nanoparticle (NP) actuators. More specifically, Controlled drug delivery systems (DDS) have several advantages compared to the traditional forms of drugs. A drug is transported to the place of action, hence, its influence on vital tissues and undesirable side effects can be minimized. Accumulation of therapeutic compounds in the target site increases and, consequently, the required doses of drugs are lower. This modern form of therapy is especially important when there is a discrepancy between the dose or the concentration of a drug and its therapeutic results or toxic effects. Cell-specific targeting can be accomplished by attaching drugs to specially designed carriers.

It should be therefore understood that the invention further encompasses the use of various nanostructures, including micellar formulations, liposomes, polymers, dendrimers, silicon or carbon materials, polymeric nanoparticles and magnetic nanoparticles, as carriers in drug delivery systems. The term "nanostructure" or "nanoparticle" is used herein to denote any microscopic particle smaller than about 100 nm in diameter. In some other embodiments, the carrier is an organized collection of lipids. When referring to the structure forming lipids, specifically, micellar formulations or liposomes, it is to be understood to mean any biocompatible lipid that can assemble into an organized collection of lipids (organized structure). In some embodiments, the lipid may be natural, semi-synthetic or fully synthetic lipid, as well as electrically neutral, negatively or positively charged lipid. In some embodiments, the lipid may be a naturally occurring phospholipid. Examples of lipids forming glycerophospholipids include, without being limited thereto, glycerophospholipid, phosphatidylglycerols (PG) including dimyristoyl phosphatidylglycerol (DMPG), phosphatidylcholine (PC), including egg yolk phosphatidylcholine, dimyristoyl phosphatidylcholine (DMPC), 1-palmitoyl-2-oleoylphosphatidyl choline (POPC), hydrogenated soy phosphatidylcholine (HSPC), distearoylphosphatidylcholine (DSPC); phosphatidic acid (PA), phosphatidylinositol (PI), phosphatidylserine (PS). Examples of cationic lipids may include, for example, 1,2-dimyristoyl-3-trimethylammonium propane (DMTAP) 1,2-dioleyloxy-3-(trimethylamino) propane (DOTAP); N-[1-(2,3-ditetradecyloxy)propyl]-N,N-dimethyl-N-hydroxyethylammonium bromide (DMRIE); N-[1-(2,3-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3β[N—(N',N'-dimethylaminoethane) carbamoly] cholesterol (DC-Chol); and dimethyl-dioctadecylammonium (DDAB), N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS), or the neutral lipid dioleoylphosphatidyl ethanolamine (DOPE) derivatized with polylysine to form a cationic lipopolymer.

The lipids may be combined with other lipid compatible substances, such as, sterols, lipopolymers etc. A lipopolymer may be a lipid modified by inclusion in its polar headgroup a hydrophilic polymer. The polymer headgroup of a lipopolymer may be preferably water-soluble. In some embodiments, the hydrophilic polymer has a molecular weight equal or above 750 Da. There are numerous polymers which may be attached to lipids to form such lipopolymers, such as, without being limited thereto, polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers. The lipids derivatized into lipopolymers may be neutral, negatively charged, as well as positively charged. The most commonly used and commercially available lipids derivatized into lipopolymers are those based on phosphatidyl ethanolamine (PE), usually, distearoylphosphatidylethanolamine (DSPE).

In some embodiments, the structure forming lipids may be combined with other lipids, such as a sterol. Sterols and in particular cholesterol are known to have an effect on the properties of the lipid's organized structure (lipid assembly), and may be used for stabilization, for affecting surface charge, membrane fluidity.

In some embodiments, a sterol, e.g. cholesterol is employed in order to control fluidity of the lipid structure. The greater the ratio sterol:lipids (the structure forming lipids), the more rigid the lipid structure is.

Liposomes are often distinguished according to their number of lamellae and size. The liposomes employed in the context of the present disclosure may be multilamellar vesicles (MLVs), multivesicular vesicles (MVVs), small unilamellar vesicles (SUVs), large unilamellar vesicles (LUVs) or large multivesicular vesicles (LMVV).

It should be appreciated that the at least one SMCs of the invention may be associated with any of the nanostructures described above, specifically, any of the micellar formulations, liposomes, polymers, dendrimers, silicon or carbon materials, polymeric nanoparticles and magnetic nanoparticles disclosed herein above. The term "association" may be used interchangeably with the term "entrapped", "attachment", "linked", "embedded", "absorbed" and the like, and contemplates any manner by which the at least one SMCs of the invention is held. This may include for example, physical or chemical attachment to the carrier. Chemical attachment may be via a linker, such as polyethylene glycol. The association provides capturing of the at least one SMCs of the invention by the nanostructure such that the release of the at least one SMCs of the invention may be controllable. Still further, it should be appreciated that in some embodiments, the nanostructure in accordance with the present disclosure may further comprise at least one targeting moiety on the surface. Such targeting moiety may facilitate targeting the SMCs-nanostructures of the invention into a particular target cell, target tissue, target organ or particular cellular organelle target. The transporting or targeting moiety may be attached directly or indirectly via any linker, and may comprise affinity molecules, for example, antibodies that specifically recognize target antigen on specific hematopoietic cells. As noted above, the pharmaceutical composition of the invention may optionally further comprise at least one pharmaceutically acceptable carrier/s, excipient/s, auxiliaries, and/or diluent/s. "Pharmaceutically or therapeutically acceptable carrier" refers to a carrier medium which does not interfere with the effectiveness of the biological activity of the active ingredients. As mentioned herein, the compositions provided by the invention optionally further comprise at least one pharmaceutically acceptable excipient or carrier. As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

As used herein "pharmaceutically acceptable carrier/diluents/excipient" includes any and all solvents, dispersion media, coatings and the like. The use of such media and agents for pharmaceutical active substances is well known in the art. Except as any conventional media or agent is incompatible with the active ingredient, its use in the therapeutic composition is contemplated.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

In various embodiments, the final solution of any of the compositions of the invention may be adjusted with a pharmacologically acceptable acid, base or buffer.

The pharmaceutical composition of the invention can be administered and dosed by the methods of the invention, in accordance with good medical practice, systemically, for example by parenteral, e.g. intravenous, intraperitoneal or intramuscular injection. In another example, the pharmaceutical composition can be introduced to a site by any suitable route including intravenous, subcutaneous, transcutaneous, topical, intramuscular, intraarticular, subconjunctival, or mucosal, e.g. oral, intranasal, or intraocular administration.

In some embodiments, the SMCs of the invention as well as pharmaceutical compositions thereof may be suitable for systemic administration. The pharmaceutical composition of the invention can be administered and dosed by the methods of the invention, in accordance with good medical practice. More specifically, the compositions used in the methods and kits of the invention, described herein after, may be adapted for administration by systemic, parenteral, intraperitoneal, transdermal, oral (including buccal or sublingual), rectal, topical (including buccal or sublingual), vaginal, intranasal and any other appropriate routes. Such formulations may be prepared by any method known in the art of pharmacy, for example by bringing into association the active ingredient with the carrier(s) or excipient(s).

The phrases "systemic administration", "administered systemically" as used herein mean the administration of a compound, drug or other material other than directly into the central blood system, such that it enters the patient's system and, thus, is subject to metabolism and other like processes.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Systemic administration includes parenteral injection by intravenous bolus injection, by intravenous infusion, by sub-cutaneous, intramuscular, intraperitoneal injections or by suppositories, by patches, or by any other clinically accepted method, including tablets, pills, lozenges, pastilles, capsules, drinkable preparations, ointment, cream, paste, encapsulated gel, patches, boluses, or sprayable aerosol or vapors containing these complexes and combinations thereof, when applied in an acceptable carrier. Alternatively, to any pulmonary delivery as by oral inhalation such as by using liquid nebulizers, aerosol-based metered dose inhalers (MDI's), or dry powder dispersion devices.

In other embodiments the pharmaceutical composition is adapted for topical administration. By "topical administration" it is meant that the pharmaceutical composition and the carrier may be adapted to any mode of topical administration including: epicutaneous, oral, bronchoalveolar lavage, ophthalmic administration, enema, nasal administration, administration to the ear, administration by inhalation.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, and suitable mixtures thereof. The proper fluidity can be maintained, for example, by the use of a coating, such as lecithin, by the maintenance of the required particle size in the case of dispersion and by the use of surfactants.

In some embodiments the SMCs of the invention and pharmaceutical composition thereof, can be administered either alone or in combination with other SMC or with any additional therapeutic agent/s. Combined compositions as well as combined treatment regimens are thus encompassed by the invention as will be also detailed in connection with the kit of the invention.

More specifically, it should be appreciated that in some embodiments, the SMCs of the invention may be used in a combined therapeutic regimen. In non-limiting embodiments, the SMCs may be combined with at least one of the chemotherapeutic agents discussed above, and/or optionally with any compound that induces differentiation of hematopoietic progenitor cells (e.g., G-CSF), or any biological therapeutic agent. Thus, in some embodiments, the SMCs of the invention may be added in combination with any of the above treatment regimens. The term "in combination with" such as when used in reference to a therapeutic regimen, refers to administration or two or more therapies over the course of a treatment regimen, where the therapies may be administered together or separately, and, where used in reference to drugs, may be administered in the same or different formulations, by the same or different routes, and in the same or different dosage form type.

Alternatively, the SMCs treatment may precede or follow the other agent treatment by intervals ranging from minutes to weeks. In embodiments where the second therapeutic agent and the SMCs are administered separately, one would generally ensure that a significant period of time did not expire between the time of each delivery, such that the second agent and the SMCs would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

The combined treatment regimen encompassed by the invention may require different compositions and administration modes for each of the compounds and as such be facilitated by the provision of the different components (e.g., the SMCs as well as an additional therapeutic agent) in a kit format.

Thus, a further aspect of the invention relates to a kit comprising:

(a) at least one SMC modulator of WASp having the general formula (XI):

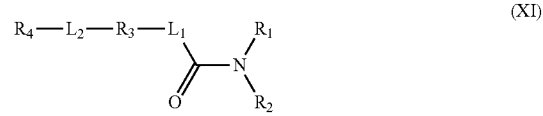

or a pharmaceutically acceptable salt, solvate, hydrate, stereoisomer or physiologically functional derivative thereof, wherein $R_1$ and $R_2$ are each independently from each other selected from H, straight $C_1$-$C_{12}$ alkyl, a ring system containing five to seven atoms, each optionally substituted by at least one a ring system containing five to seven atoms optionally substituted by at least one halide or straight $C_1$-$C_5$ alkyl or $R_1$ and $R_2$ together with the nitrogen atom they are connected to form a five to seven membered saturated or unsaturated ring optionally include at least one of N, O and optionally substituted with at least one of straight $C_1$-$C_5$ alkyl, L1 and L2 are each independently from each other selected to be absent or from —$CH_2$—($CH_2$—C(O)—N)—($CH_2$)$_2$, —($CH_2$)—S—, —($CH_2$)—, —($CH_2$)—O—, —NH—($CH_2$)—, and each optionally substituted with $C_1$-$C_5$ alkyl, a ring system containing five to twelve atoms optionally substituted with $C_1$-$C_5$ alkyl;

$R_3$ and R4 are each independently from each other absent or selected from a ring system containing five to 12 atoms, each optionally substituted with at least one of straight or branched $C_1$-$C_5$ alkyl, (=O), (=S) or $R_5$, $R_5$ is an a ring system containing five to seven atoms optionally substituted by at least one halide or straight $C_1$-$C_5$ alkyl;

and at least one of:
(b) at least one chemotherapeutic agent;
(c) at least one biological therapy agent; and
(d) at least one agent that induces differentiation of hematopoietic progenitor cells.

Still further, in addition to therapies based solely on the delivery of the SMCs, combination therapy is specifically contemplated. In the context of the present invention, it is contemplated that the SMCs therapy could be used similarly in conjunction with other agents commonly used for the treatment of neutropenia, leucopenia and thrombocytopenia.

To achieve the appropriate therapeutic outcome, using the methods and compositions of the present invention, one would generally provide a composition comprising the SMCs and at least one other therapeutic agent (second therapeutic agent). In the present invention, it is contemplated that the second therapeutic agent may involve the administration or inclusion of at least one additional factor that may in some specific embodiments be selected from among EPO, G-CSF, M-GDF, SCF, GM-CSF, M-CSF, CSF-1, IL-1, IL-2, IL-3, IL-4, IL-5, IL-6, IL-7, IL-8, IL-9, IL-10, IL-11, IL-12, or other various interleukins, IGF-1, LIF, interferon (such as a, beta, gamma or consensus), neurotrophic factors (such as BDNF, NT-3, CTNF or noggin), other multi-potent growth factors (such as, to the extent these are demonstrated to be such multi-potent growth factors, flt-3/flk-2 ligand, stem cell proliferation factor, and totipotent stem cell factor), fibroblast growth factors (such as FGF), and analogs, fusion molecules, or other derivatives of the above.

As noted above, the present invention further encompasses a combined treatment with further agents that may induce differentiation of hematopoietic stem cells. Of particular interest is the G-CSF. Granulocyte-colony simulating factor (G-CSF), also known as colony-stimulating factor 3 (CSF 3), is a glycoprotein that stimulates the bone marrow to produce granulocytes and stem cells and release them into the bloodstream. Functionally, it is a cytokine and hormone, a type of colony-stimulating factor, and is produced by a number of different tissues. G-CSF also stimulates the survival, proliferation, differentiation, and function of neutrophil precursors and mature neutrophils. The recombinant human G-CSF (rhG-CSF) synthesized in an *E. coli* expression Filgrastim, was first marketed by Amgen with the brand name Neupogen. Filgrastim (Neupogen) and PEG-filgrastim or lenograstim (Neulasta) are two commercially-available forms of rhG-CSF. Several bio-generic versions are now also available in markets such as Europe and Australia, and are all applicable for the combined treatment regimen encompassed by the present invention. In oncology and hematology, a recombinant form of G-CSF is used with certain cancer patients to accelerate recovery and reduce mortality from neutropenia after chemotherapy, allowing higher-intensity treatment regimens.

According to some embodiments, the kit of the invention may further comprise container means for containing the different components of the kit of the invention or any dosage forms thereof. The term "container" as used herein refers to any receptacle capable of holding at least one component of a pharmaceutical composition of the invention. Such a container may be any jar, vial or box known to a person skilled in the art and may be made of any material suitable for the components contained therein and additionally suitable for short or long term storage under any kind of temperature. More specifically, the kit includes container means for containing separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It should be appreciated that the invention further encompasses in further aspects thereof, any of the nucleic acid constructs described herein, specifically, any of the mutated WASp constructs described in the Examples, that encode the different WASp mutants or any fusion proteins thereof. More specifically, any nucleic acid construct that comprises the nucleic acid sequence encoding the WASp mutant R86C, specifically, the mutant comprising the amino acid sequence as denoted by SEQ ID NO. 13. In yet some further specific embodiments, the invention refers to a nucleic acid construct comprising the nucleic acid sequence as denoted by SEQ ID NO. 14, encoding the R86C mutant. In yet some further embodiments, the invention provides any construct comprising the nucleic acid sequence encoding the WASp mutant Y107C, specifically, the mutant comprising the amino acid sequence as denoted by SEQ ID NO. 15. In yet some further specific embodiments, the invention refers to a nucleic acid construct comprising the nucleic acid sequence as denoted by SEQ ID NO. 16, encoding the Y107C mutant. In still further embodiments, the invention provides any construct comprising the nucleic acid sequence encoding the WASp mutant A134T, specifically, the mutant comprising the amino acid sequence as denoted by SEQ ID NO. 17. In yet some further specific embodiments, the invention refers to a nucleic acid construct comprising the nucleic acid sequence as denoted by SEQ ID NO. 18, encoding the A134T mutant. In yet some further embodiments, the invention further pertains to any cell line or transgenic animal expressing the constructs of the invention. Particular specific embodiments for cell lines provided by the invention relate to the WASp knockout Jurkat T-cell lines that further express any of the mutated WASps of the invention or any derivative or fusion proteins thereof, specifically, WASp knockout Jurkat T-cell line expressing the Yellow fluorescent protein (YEP) fusion protein with the WASp mutants. More specifically, WASp knockout Jurkat T-cell line expressing the YEP-WASp R86C mutant, in yet some further embodiments the WASp knockout Jurkat T-cell line expressing the YEP-WASp Y107C mutant. Still further, in some embodiments, the invention provides the WASp knockout Jurkat T-cell line expressing the YEP-A134T mutant.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Other purposes and advantages of the invention will become apparent as the description proceeds. While in the foregoing description describes in detail only a few specific embodiments of the invention, it will be understood by those skilled in the art that the invention is not limited thereto and that other variations in form and details may be possible without departing from the scope and spirit of the invention herein disclosed or exceeding the scope of the claims.

The present invention as defined by the claims, the contents of which are to be read as included within the disclosure of the specification, and will now be described by way of example with reference to the accompanying Figures.

All scientific and technical terms used herein have meanings commonly used in the art unless otherwise specified. The definitions provided herein are to facilitate understanding of certain terms used frequently herein and are not meant to limit the scope of the present disclosure.

Various embodiments and aspects of the present invention as delineated herein above and as claimed in the claims section below find experimental support in the following examples.

It must be noted that, as used in this specification and the appended claims, the singular forms "a", "an" and "the" include plural referents unless the content clearly dictates otherwise.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

EXAMPLES

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Maryland (1988).

Standard organic synthesis protocols known in the art not specifically described herein are generally followed essentially as in Organic syntheses: Vol. 1-79, editors vary, J. Wiley, New York, (1941-2003); Gewert et al., Organic synthesis workbook, Wiley-VCH, Weinheim (2000); Smith & March, Advanced Organic Chemistry, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Vanderkerken K. The 5T2MM murine model of multiple myeloma: maintenance and analysis. [Methods Mol. Med. 113:191-205 (2005); Epstein J. The SCID-hu myeloma model. Methods Mol. Med. 113:183-90 (2005)].

Reference is now made to the following examples, which together with the above descriptions illustrate some embodiments of the invention in a non-limiting fashion.

Materials and Reagents

Antibodies:

The following antibodies were used for imaging: mouse anti-CD3ε (UCHT). The following primary antibodies were used for immunoprecipitations and western blotting: rabbit anti-Ub (DAKO), mouse anti-GFP (Roche), mouse anti-WASp D1 and rabbit anti-WASp H-250 (Santa Cruz), rabbit anti-WIP (Santa Cruz), rabbit anti-PKCθ (Epitomics), and mouse anti-GAPDH (Biodesign, and Santa Cruz). The following primary antibodies were used for flow-cytometry: PE-Cy5™-conjugated mouse anti-human CD69 (Biolegend) and purified anti-activated human LFA-1 antibody from KIM127 hybridoma (Sigma-Aldrich). HRP-conjugated secondary antibodies used include goat anti-mouse (Jackson) and goat anti-rabbit (Jackson). For flow-cytometry, secondary Alexa 488-conjugated goat anti-mouse IgG1 antibody was used (Jackson).

Reagents:

Small molecule compounds (SMCs) used for the following experiments were purchased from ChemBridge Corporation, Sigma-Aldrich Corporation and AKos GmbH, were dissolved in DMSO as per the manufacturer's instructions and diluted gradually in matching cell medium containing 25 mM HEPES for cell incubation.

Pools of three independent RNA duplexes specific for human PKCθ were obtained from Invitrogen and have the following sequences:

GAGUCUCCGUUGGAUGAGGUGGAUA, (denoted by SEQ ID NO. 3)

GCAUCCGUUUCUGACGCACAUGUUU (denoted by SEQ ID NO. 4)
and

CCGGCCGAAAGUGAAAUCACCAUUU, . (denoted by SEQ ID NO. 5)

Pools of non-targeting (nonspecific) negative control siRNA duplexes were obtained from Dharmacon and have the following sequences: UAGCGACUAAACACAUCAA (denoted by SEQ ID NO. 6), UAAGGC-UAUGAAGAGAUAC (denoted by SEQ ID NO. 7), AUGUAUUGGCCUGUAUUAG (denoted by SEQ ID NO. 8), AUGAACGUGAAUUGCUCAA (denoted by SEQ ID NO. 9), and UGGUUUACAUGUCGACUAA (denoted by SEQ ID NO. 10).

Expression Vectors and Plasmid Construction

YFP-WIP, YFP-WASp and CFP-WASp plasmids were obtained as was previously described (Fried et al, 2014; Reicher et al, 2012). Exogenous plasmids solely encoding the CDS of WASp. The expression vectors pEYFP-C1, pEYFP-N1, pECFP-C1, and pECFPN1 were obtained from Clontech, and pcDNA3.1+/Hygro was obtained from Invitrogen. Complementary DNA (cDNA) encoding human WASp or WIP were cloned into the expression vectors pECFP or pEYFP to obtain the cyan fluorescent protein (CFP)- or yellow fluorescent protein (YFP)-tagged proteins. *Aequorea* GFP derivatives were rendered monomeric by the A206K substitution.

YFP tagged WASp plasmid, solely encoding the CDS of WASp was utilized to create the common WASp mutants (R86C, Y107C or A134T). Molecular WASp mutants were prepared using the QuikChange II XL site-directed mutagenesis kit (Stratagene). Establishing T-cell lines exclusively expressing human WAS/XLT WASp mutants tagged to YFP was achieved by using addgene PX458 CRISPR/CAS9 plasmid with custom guide RNAs targeting the WAS locus.

Experimental Procedures

Adaptation of an Existing PDB Model for Virtual Screening of SMCs

An NMR model of the EVH1 domain of N-WASp (PDB ID: 2IFS) (Peterson (2007), the closest homologue of WASp, was downloaded from RCSB protein data bank. This model was linked to a fragment of WIP. The model was rendered suitable for virtual screening by deletion of the WIP fragment and the linking residues, and additional virtual mutagenesis near the ubiquitylation sites using Discovery Studio 3.0 software (Accelrys). Thirty four molecules were selected for further evaluation.

CRISPR/CAS9 Gene Knockdown

CRISPR/CAS9 knockdown of endogenous WASp in T-cells was conducted according to published protocol (Ran F A et al, 2013). The vector pSpCas9 (BB)-2A-GFP (PX458) was purchased from Addgene, plasmid #48138. RNA guides were designed to target an intron/exon junction in the WAS gene, in order to eliminate gene silencing of exogenous YFP-WASp. RNA guide sequences aimed for WASp locus were constructed using the online CRISPR design tool algorithm (Zhang Lab) and NCBI gene. The guides which received the highest score were selected to be subcloned into the pSpCas9 (BB)-2A-GFP (PX458) vector.

The RNA guides have the following sequences:

aaacTCGCTGGAGATGTAAGTGGATc as denoted by SEQ ID NO. 11
and caccgATCACTTACATCTCCAGCGA as denoted by SEQ ID NO. 12.

The sequence present in WASp exons is bold. The sequence that is complementary to WASp intron (chromosome X, GRCh38.p7 nucleotides 1883-1890) is underlined.

Knockout of endogenous WASp was conducted in Jurkat cells alone or in Jurkat cells stably expressing YFP-WASp containing the following mutations, R86C (as denoted by SEQ ID NO. 13 and encoded by SEQ ID NO. 14) or Y107C (as denoted by SEQ ID NO. 15 and encoded by SEQ ID NO. 16).

Cell Transfection, Generation of Stable Cells and FACS Analysis

Jurkat E6.1 T cells were transfected with a Lonza Nucleofector™ 2b Device using the manufacturer's protocol H-10. Stable clones were derived from transiently transfected cells with a combination of drug selection and cell sorting. Cells transiently expressing chimeric proteins were selected in Neomycin. Fluorescence analysis and cell sorting were performed using the FACSARIA (Becton Dickinson Biosciences) and FlowJo software (Pauker M H, et al, 2011).

For the establishment of T-cell lines exclusively expressing human WAS/XLT WASp mutants tagged to YFP, after transfection, cells were seeded onto a 96 wells plate, diluted to a concentration of 1 cell per well. After colony growth, individual colonies were screened via western blot using anti-WASp antibody. Desired colonies were those that expressed only exogenous YFP-WASp at a higher molecular weight (92 kDa) and which demonstrated no expression of endogenous WASp (65 kDa).

MicroScale Thermophoresis (MST) Measurements

YFP-tagged WASp was obtained from cell lysates of Human Embryonic Kidney (HEK) 293T, transiently transfected with YFP-WASp/WAVE2/N-WASp by DNA-calcium phosphate co-precipitation as previously described (Reicher et al, 2012). MST measurements were performed using the protein purification-free method described by Khavrutskii et al. (Khavrutskii et al, 2013). Briefly, SMCs were serially diluted over three orders of magnitude (100 μM-3 nM) in 1×PBS supplemented with 0.05% Tween-20 in 200 μL PCR-tubes. Then, YFP-WASp/WAVE2/N-WASp-containing cell lysate was added from a doubly diluted sample in the same buffer and the samples were gently mixed. The samples were allowed to incubate at room temperature for 30 min before being loaded into standard-treated Monolith™ capillaries (NanoTemper). After loading into the instrument (Monolith NT.115, NanoTemper), the samples were measured by standard protocols at 60% MST power. The changes of the fluorescent thermophoresis signals were plotted against the concentration of the serially diluted SMCs. $K_D$ values were determined using the NanoTemper analysis software (NT Analysis 1.5.37 or 2.2.31).

Primary PBMC and Platelet Isolation and Stimulation

Human primary PBMCs were isolated from whole blood of healthy donors, as previously described (Barda-Saad et al, 2005). The cells were activated with anti-CD3ε (OKT3, 10 μg/ml) and anti-CD28 (10 μg/ml) for 30 min on ice. The cells were then warmed to 37° C. for 10 min and stimulated with anti-human IgG (50 μg/ml) for 2 min. Human primary platelets were isolated from thrombocyte-enriched platelet rich plasma peripheral blood of healthy donors, as previously described by Abcam. Briefly, platelet rich plasma (PRP) was diluted with HEP buffer (140 mM NaCl, 2.7 mM KCl, 3.8 mM HEPES, 5 mM EGTA, pH 7.4) at 1:1 ratio (v/v) and centrifuged at 100×g for 15 min at room temperature (with no brake applied) to pellet contaminating red and white blood cells. Platelets were then pelleted through plasma by centrifugation at 800×g for 15 min at room temperature (with no brake applied). The washed platelets were resuspended in Tyrode's buffer (134 mM NaCl, 12 mM NaHCO$_3$, 2.9 mM KCl, 0.34 mM Na$_2$HPO$_4$, 1 mM MgCl$_2$, 10 mM HEPES, 5 mM glucose, 3 mg/ml BSA, pH 7.4). Platelets and Meg-01 cells were stimulated with TRAP-6 (10 μM and 100 μM, respectively) at room temperature and at 37° C., respectively, for indicated times.

In Vitro Incubation of Hematopoietic Cells with SMCs

DMSO-soluble stock solutions of SMCs were gradually hydrated with the matching cell medium, containing 25 mM HEPES, by repeated cycles of introducing and mixing less than 20% (v/v) hydrous buffer to the DMSO-soluble SMCs. The hydrated SMCs were then added directly to the target cells, at final concentration of 40 μM or 100 μM, for indicated times.

Immunoprecipitation and Western Blotting

Immunoprecipitations and western blotting analysis were performed as previously described (Reicher et al, 2012). Briefly, platelets (2×10$^8$ cells per sample) were lysed by the addition of an equal volume of 2× lysis buffer (30 mM HEPES pH7.4, 300 mM NaCl, 2 mM phenylmethyl sulfonyl fluoride (PMSF), 2 mM sodium orthovanadate, 2% Triton X-100 and complete protease inhibitor tablets (Roche)). MEG-01 cells (2×10$^7$ cells per sample) were lysed in 1.25× lysis buffer. Proteasome activity was blocked by addition of MG132 (AdooQ) to platelets and Meg-01 cell medium at final concentration of 10 μM, for 1 h before the cells were harvested. Densitometric analysis of band intensities was performed with ImageJ software, with final results normalized with WASp or GAPDH as loading controls for immunoprecipitated samples and whole-cell lysates, respectively. Relative protein abundance or relative extent of co-precipitated protein was compared to the relevant control.

Extracellular Staining of Lymphocytes for Flow Cytometry

PBMCs or Jurkat cells (about 3×10$^5$ cells) were incubated for 4 h, at 37° C. with 50 ng/ml PMA and 250 ng/ml Ionomycin, or 40 ng/ml PMA and 6 μM Ionomycin, respectively, or left untreated. After incubation, the cells were collected and stained with 1 μg/ml anti-active human LFA-1 antibody (purified from KIM127 hybridoma sup, ATCC Cat #: CRL-2838, Sigma) for 30 min in 37° C., followed by staining with Alexa488-Fluor goat anti-mouse IgG1 secondary antibody (Molecular Probes, Cat #: A-21121), 30 min on ice. Cells were then co-stained with PE-Cy5™-conjugated mouse anti-human CD69 (BD Pharmingen, Cat #: 555532) to measure lymphocyte activation.

Cell Proliferation Assay

Lymphocyte proliferation was assessed using an XTT-based Cell Proliferation Kit (Biological Industries Ltd.) according to the manufacturer's instructions.

Lymphocyte Migration Assay

Approximately 1×10$^5$ lymphocytes were seeded over chambered coverslips (LabTek) pre-coated with 6 μg/ml ICAM-1 and 2 μg/ml SDF-1α. Cells were incubated at 37° C., 5% CO$_2$ and DIC images were acquired with the Zeiss Observer Z1 inverted microscope every 5 s for 20 min under a 20× objective lens using Zen software. The random movement (Displacement and velocity) of the cells was automatically tracked and analyzed using TrackMate plugin of ImageJ software. An individual trace was assigned to each of the analyzed cells.

Spreading Assay

Spreading assays were performed as previously described (Fried et al, 2014; Barda-Saad 2005). Briefly, T cells (2×10$^6$ cells/ml) were seeded on the bottom of chambered cover glasses (LabTek) that were pre-coated with anti-CD3 stimulatory monoclonal antibodies (10 μg/ml). The cells were incubated in imaging buffer [RPMI without phenol red containing 10% fetal calf serum (FCS) and 25 mM HEPES] at 37° C., 5% CO$_2$, for the times indicated in the figure legends. Cells were fixed for 25 min with 4% paraformaldehyde in phosphate-buffered saline (PBS) and then were washed three times with PBS.

Measurement of Platelet Intra-Cellular Calcium Concentration

Cells were incubated with 5 μM Indo-1-acetoxymethyl-ester (Indo-1-AM, Teflabs) in Tyrode's buffer at 37° C. for 20 min. The cells were washed once, resuspended in Tyrode's buffer containing 10 mM HEPES and maintained at room temperature for 20 min. The cells were incubated at 37° C. for 5 min before measurements and then stimulated with 10 μM TRAP-6. The Ca$^{2+}$ influx was measured by spectrofluorometer using the Synergy 4 Microplate Reader (Bio Tek).

FRET Correction and Calculation

Double-color FRET was performed as described previously (Barda-Saad et al, 2005; Pauker, 2011, Pauker, 2012). The inventors used CFP (excitation wavelength: 468 nm; emission filter wavelength: 465 to 510 nm) as a donor, and YFP (excitation wavelength: 514 nm; emission filter wavelength: 530 nm long-pass, LP) as an acceptor. The non-FRET components were calculated and removed with calibration curves derived from images of single-labeled cells containing CFP or YFP, as previously described (Barda-Saad et al, 2005). Sets of reference images were obtained with the same acquisition parameters as those used for the FRET experimental images. Bleed-through components were calculated as a function of the intensity of the expressed fluorescent proteins with data gathered from single-labeled cell lines. By using the intensity measured pixel by pixel through the different filter sets, as well as cross-talk elements that were isolated from the control, single-labeled cells, the measured FRET was corrected and the actual FRET efficiency at every pixel was determined. The relative FRET efficiency (FRETeff) was calculated on a pixel-by-pixel basis with the following equation: FRETeff=FRETcorr/(FRETcorr+donor)×100%, where FRETcorr is the pixel intensity in the corrected FRET image, and donor is the intensity of the corresponding pixel in the appropriate donor channel image. To increase the reliability of the calculations and to prevent low-level noise from distorting the calculated ratio, the inventors excluded pixels below 50 intensity units, as well as saturated pixels from the calculations, and set their intensities to zero. These pixels are shown in black in the pseudo-colored FRET efficiency images. To estimate the reliability of the obtained FRET efficiency values and to exclude the possibility of obtaining false-positive FRET, the inventors prepared cells expressing free CFP and free YFP as negative controls. The FRET efficiency in the negative control system was measured and calculated in the same manner as that in the main experiment. FRET efficiency values obtained from the negative control samples were subtracted from the values obtained in the main experiments.

Example 1

Virtual Screening Enables the Identification of WASp-Binding SMCs

In order to find promising SMCs candidates capable of preventing WASp ubiquitylation-dependent degradation, an NMR model of a recombinant EVH1 domain of N-WASp fused to a short WIP peptide (PDB ID: 2IFS) was adapted (FIG. 1) (Peterson, F C et al. 2007). The WIP and the linker fragments was removed, and in silico mutagenesis was performed in order to simulate a WASp model. Three-dimensional structures of SMCs were constructed from chemical formulae using the FAST algorithm. Using Patch-Dock molecular docking software (D. Schneidman-Duhovny, et al, 2005), models of putative SMC-WASp binding structures were generated, and were filtered taking only the highest scoring model for each SMC 3D structure-WASp pair. These models were then further filtered by discarding any structure depicting a binding not in close proximity to WASp degradation site (defined as more than 5 Å between the SMC and either of the lysine residues 76 or 81). Finally, the remaining models were scored by a machine learning trained classifier as illustrated in FIG. 2).

Following this in silico screening, the inventors identified eight SMCs (#6, #23, #24, #25, #30, #32, #33, #34, see Table 1). The inventors validated their binding to human WASp, using MST, as described in Experimental procedures. As demonstrated in FIG. 3, four of these SMCs (#6, #30, #33, #34) showed binding to WASp, with dissociation constants ($K_D$) that ranged between 25 nM to 0.79 μM (FIG. 3A-3D), while an irrelevant SMC, Y-27632 (Rho-associated protein kinase inhibitor) did not show binding to WASp (FIG. 3E). Strikingly, no binding was demonstrated between WASp-binding SMC #34 to the ubiquitously expressed WASp paralogs, i.e. N-WASp (FIG. 3F) and WAVE2 (FIG. 3G), indicating its specificity and precluding off-target effects. The SMCs that specifically bind the degradation pocket of WASp were further evaluated by the inventors.

TABLE 1

The SMC molecules

| Molecule | IUPAC name |
|---|---|
| SMC #6 | N-[(2R, 4R, 6S)-2-(4-chlorophenyl)-6-(1-methylbenzotriazol-5-yl)oxan-4-yl]lacetantide |
| SMC #23 | ethyl 4-[[3-(4-acetylpiperazin-1-yl)sulfonylbenzoyl]amino] benzoate |
| SMC #24 | N-[2-(dimethylamino)-2-thiophen-2-ylethyl]-4-[ethyyl(phenyl)sulfamoyl]benzamide |
| SMC #25 | 3-(benzylsulfamoyl)-N-[2-(2,6-difluoroanilino)-2-oxoethyl]-N-ethlylbenzamide |
| SMC #30 | Methyl3-[[4-(cyclopentylcarbamoyl)phenyl]methyl]-4-oxo-2-sulfanylidene-1H-quinazoline-7-carboxylate |
| SMC #32 | 3-[(3-fluorophenyl)methyl]-5-[1-[2-(trifluoromethyl)phenyl]sulfonylpiperidin-4-yl]-2H-triazolo [4,5-d]pyrimidin-7-one |
| SMC #33 | N'-[2-(benzylamino)-2-oxoethyl]-N'-(2-methylphenyl)-N-(1,3-thiazol-2-yl)butanediamide |
| SMC #34 | 1-(2,6-dimethylpiperidin-1-yl)-2-[[5-(quinolin-8-yloxymethyl)-1,3,4-oxadiazol-2-yl]sulfanyl]ethanone |

Example 2

WASp-Binding SMCs Upregulate WASp Expression

Having identified SMCs that were experimentally validated to bind WASp in the proximity of WASp degradation site, the inventors examined whether these SMCs can increase WASp expression in hematopoietic cells. Platelets from healthy donors were pre-incubated with SMC #6 (40 μM) or non-treated control (DMSO) for 15 min followed by stimulation and western blot analysis. As shown in FIG. 4A and illustrated in the summarizing graph of FIG. 4B, stimulation of non-treated control platelets consistently resulted in downregulation of WASp, confirming previous observations that WASp in platelets is degraded following platelet activation (Lutskiy et al, 2007, Shcherbina et al, 2001). More specifically, incubation with SMC #6 attenuated WASp degradation in activated platelets, compared with control platelets, with prominent effect observed following 15 min of incubation (FIG. 4A, 4B). These results demonstrate a WASp-upregulating activity in active platelets during 15 min of incubation, which is facilitated by SMC #6.

In freshly isolated peripheral blood mononuclear cells (PBMCs), treatment with SMC #6 also attenuated WASp degradation after 15 min of incubation, and this effect was more pronounced after 2 h (FIG. 4C) and illustrated in the summarizing graph of FIG. 4D. These results demonstrate an optimal WASp-upregulating activity, which is facilitated by SMC #6 during 15 min or 2 h of incubation, in active platelets and PBMCs, respectively. Encouraged by these results, the inventors next examined the effect of the other WASp-binding SMCs on WASp expression in activated Jurkat T-cell line, PBMCs and platelets that is illustrated in FIG. 5. Strikingly, under these conditions, treatment with each of the indicated SMCs resulted in WASp upregulation, up to 4.5, 3.3, 2-fold, comparing to non-treated platelets, PBMCs or T-cells, respectively (FIG. 5A-5D).

Similar results were shown in FIG. 6A-6D for further SMCs, as indicated therein. Therefore, targeting the degradation pocket of WASp by the SMCs of the invention provides protection and may therefore restore WASp functions.

Example 3

WASp Undergoes Ubiquitylation-Dependent Proteasomal Degradation in Megakaryocytes and Platelets

Insufficient WASp expression in platelets and megakaryocytes is the cause of microthrombocytopenia of WAS/XLT patients (Albert et al 2010, Lutskiy et al, 2007). It is established that WASp is degraded in platelets and megakaryocytes following their activation (Lutskiy et al, 2007, Shcherbina et al, 2001). However, it is unclear whether this downregulation mechanism is executed via the ubiquitin-proteasome pathway, as previously demonstrated for lymphocytes (Fried et al, 2014; Reicher et al, 2012). Because the mechanism of action of WASp-binding SMCs is via blocking the ubiquitylation pathway of WASp, the inventors hypothesized that this degradation pathway may be relevant to platelets/megakaryocytes as well. The inventors previously demonstrated that in lymphocytes PKCθ associates with the WIP-WASp complex early in the activation process, and later, phosphorylation of WIP by PKCθ results in WIP-WASp slight dissociation and subsequent WASp ubiquitylation (Fried et al, 2014). To examine whether similar pathways exist in platelets, the inventors stimulated freshly-isolated platelets from healthy donor peripheral blood, lysed the platelets 30 sec, 2 min and 15 min post-stimulation and analyzed the interactions between WIP, WASp and PKCθ using co-immunoprecipitation analysis. As presented in FIG. 7A, both WASp and PKCθ co-precipitated with WIP after 30 sec and 2 min of activation, and this interaction was substantially decreased after 15 min of activation. Similarly, reciprocal co-precipitation was detected between WASp and WIP during the first two minutes of activation when WASp was immunoprecipitated (FIG. 7B). The inventors then tested whether this triplet interaction in platelets leads to WASp ubiquitylation. Following activation, WASp was immunoprecipitated from the lysates of freshly-isolated platelets, and the lysates were probed by western blot for ubiquitin and WASp. WASp ubiquitylation was detected as a ladder of bands above 65 kDa, with a prominent band at ~81 kDa, representing ubiquitylated WASp (Reicher et al, 2012) (FIG. 7C). This ubiquitylation was more intense after 2 min and 15 min of activation. In order to examine whether WASp ubiquitylation in platelets marks it for proteasomal degradation, WASp expression was analyzed in platelets after 15 min of activation, with or without the addition of MG132 proteasome inhibitor. Western blot analysis revealed more than 2-fold increase in WASp expression when the platelets were treated with the proteasome inhibitor (FIG. 7D), suggesting that in platelets WASp is downregulated in the ubiquitin-proteasome pathway. As megakaryocytes may also be a future target for WASp-protecting SMCs, the inventors next examined whether ubiquitylation-mediated proteasomal degradation of WASp occurs also in megakaryocytes. Therefore, Meg-01 cells were either treated with MG132 or left untreated, lysed following stimulation and the lysates were immunoprecipitated with anti-WASp antibody. As shown in FIG. 7E, probing immunoprecipitates of WASp with anti-ubiquitin and anti-WASp antibodies revealed WASp ubiquitylation pattern similar to that of lymphocytes (Fried et al, 2014; Reicher et al, 2012) and platelets. WASp ubiquitylation occurred following activation and was more intense in cells that were treated with MG132, suggesting that WASp enters the proteasomal pathway following its ubiquitylation in megakaryocytes. Accordingly, more WASp was detected in the whole cell lysates (W.C.L) of Meg-01 cells that were treated with MG132 (FIG. 7G). The possible involvement of PKCθ in WASp degradation in megakaryocytes was next examined in stimulated Meg-01 cells that were either transfected with PKCθ-specific siRNA or non-specific scrambled siRNA. As shown in FIG. 7F, PKCθ siRNA achieved 70% silencing of PKCθ in the treated cells, which in turn resulted in 1.35-fold increase of WASp expression in the treated megakaryocytes. Taken together, these data suggest a ubiquitylation-dependent degradation mechanism of WASp in platelets and megakaryocytes, which is similar to that of lymphocytes.

Example 4

WASp-Binding SMCs Effectively Upregulate Cellular Function of Lymphocytes and Platelets

WASp plays a key role in various functions of hematopoietic cells, including cellular activation, proliferation and migration. These cellular functions are impaired in WASp-deficient mice and WAS/XLT patients (Matalon et al 2013). Without being bound by any theory, the inventors hypothesized that upregulating WASp expression by SMCs may potentially restore normal immune function. Accordingly, upregulation of WASp expression by SMCs in normal immune cells is expected to enhance cellular function of these cells. To test this hypothesis, the inventors set up an array of in vitro biological assays, in which several cellular functions of lymphocytes and platelets were examined, following incubation with WASp-binding SMCs.

Lymphocyte activation is a hallmark of a normal immune response. To test whether treatment with WASp-binding SMCs could upregulate lymphocyte activation, freshly-isolated PBMCs were incubated with SMCs or control (solvent only) and stimulated with PMA and Ionomycin. The cells were then stained with two different antibodies, which recognize two lymphocyte activation markers, CD69 and an epitope exposed at the active conformation of the integrin LFA-1 (KIM127). Both were detected by flow-cytometry. In comparison to control cells, treatment with SMC #6, #30, #33 and #34 led to an upregulation of lymphocyte activation, as detected by FACS (FIG. 8A-8D and FIG. 9C).

Once activated, lymphocytes proliferate to effectively amplify the immune response. To examine the possible effect of WASp-protecting SMCs on the proliferation of lymphocytes, T cell line (Jurkat) or freshly isolated PBMCs were treated with SMCs and assayed for their proliferation, using an XTT-based assay. In accordance with the upregulation of lymphocyte activation, treatment with each of the indicated SMCs enhanced cellular proliferation of the treated cells, up to 2-fold, compared to the non-treated cells (FIG. 9D-9E). In line with these findings, FACS analysis shown in FIG. 9 reveals an upregulation of Jurkat T cells (FIG. 9A, 9B) and PBMCs (FIG. 9C) activation incubated with SMC #6.

A common theme of active lymphocytes is their high migratory ability. This enables them to move within tissues and reach and engage target cells (Burkhardt et al, 2008). Because WASp plays a role in cellular motility, the ability of WASp-binding SMCs to effectively enhance the migration of lymphocytes was tested. The random movement of SMC-treated or control cells was automatically tracked and analyzed using live microscopy, as described in Experimental procedures. As observed, measured and presented by FIG. 10A-10C, treatment with SMC #6, #30, #33 and #34 resulted in a significant 1.7- to 2.83-fold increase in the migration of these cells in comparison to the DMSO-treated cells. Therefore, specific upregulation of WASp expression with the SMCs efficiently enhanced the migration of T lymphocytes.

Unlike lymphocytes, platelets, which are non-nuclear cells, do not undergo proliferation following their activation. However, following receptor-mediated stimulation, platelets dramatically elevate their intra-cellular calcium concentrations, which in turn serve as signaling cues that evoke platelet effector functions, including platelet spreading, adhesion and aggregation (Varga-Sabo et al, 2009). Therefore, the ability of WASp-protecting SMCs to upregulate intra-cellular calcium accumulation in activated platelets was next tested. Freshly-isolated human platelets were incubated with SMC #6, #30, #33 and #34 or with the solvent (negative control). Following incubation, platelets were stimulated with thrombin receptor activator peptide TRAP-6 (10 µM) and calcium levels were measured by spectrofluorometer, using Indo-1-AM-based calcium assay as described in Experimental procedures. FIG. 11A-11D shows that in accordance with the WASp-upregulating activity of SMCs in lymphocytes, treatment with any of the tested SMCs dramatically enhanced intra-cellular calcium concentration in activated platelets (FIG. 11A-11D). These results clearly demonstrate the potential therapeutic effect of WASp-protecting SMCs in platelets.

Example 5

WASp Protection by WASp-Binding SMCs is Achieved Via Attenuation of WASp Ubiquitylation WASp-protecting SMCs were screened and selected according to their predicted ability to bind and block the degradation sites of WASp. In order to validate that this indeed the mechanism of action by which these SMCs work, it was examined whether treatment with WASp-binding SMCs affect the ubiquitylation of WASp in activated platelets and lymphocytes. Freshly-isolated activated or non-activated platelets were preincubated for 15 min with SMC #6, and #33 or with the solvent (neg. control), and lysed. WASp was then immunoprecipitated from the lysates, and the co-immunoprecipitation of ubiquitin and WASp was assayed by western blot. WASp ubiquitylation in active platelets, treated with WASp-binding SMCs was considerably decreased in comparison to activated untreated cells (FIG. 12A-12B). Similarly, treatment of PBMCs with WASp-binding SMC #6 and #33 downregulated the ubiquitylation of WASp in treated active lymphocytes in comparison to activated negative control cells (FIG. 12C-12D).

Additional mechanism by which WASp-binding SMCs could protect WASp from ubiquitylation is to strengthen the WIP-WASp interaction, as WIP protects WASp from proteasomal degradation (Fried et al, 2014; Reicher et al, 2012). To monitor the WIP-WASp interaction the inventors next employed the Förster resonance energy transfer, also known as fluorescence resonance energy transfer technology or FRET, which is widely used to detect molecular interactions in the nanometer resolution (Fried et al, 2014; Barda-Saad et al 2005). The wild type human WASp and WIP were fluorescently tagged with cyan fluorescent protein (CFP) and yellow fluorescent protein (YFP), respectively. T-cells stably expressing CFP-WASp and YFP-WIP were treated with SMC #6, #30, #33 and #34 or with the negative control. The cells were plated on stimulatory coverslips (pre-coated with an anti-CD3 antibody), and then were fixed after 5 min (FIG. 13A is a confocal micro image and FIG. 13B represents the percentage of FRET efficiency). Under these conditions, low FRET efficiency was detected in activated T cells that were treated with the solvent (9.9±1.5. FIG. 13), indicating a very weak interaction between WIP and WASp following cellular activation, as expected and previously published (Fried S, et al. 2014). Interestingly, SMC-treated cells displayed very high average FRET efficiency (SMC #6: 22.7±1.4%, SMC #30: 24.4±1.4%, SMC #33: 21.4±1.4%, SMC #34: 23.8±1.1%), typical of a stable WIP-WASp interaction, which is usually observed in non-activated cells (FIG. 13). This unexpected result indicates that WASp-binding SMCs could directly or indirectly stabilize the WIP-WASp interaction.

Example 6

WASp-Binding SMCs Restore WASp Expression in Lymphocytes Expressing Common Human WAS/XLT Mutations Having established the effect of WASp-binding SMCs in the upregulation of WASp expression and cellular function in T lymphocytes and platelets, the inventors explored whether these SMCs could restore WASp expression of known human common WASp mutants that cause to WAS/XLT immunodeficiencies. For this purpose, Jurkat T-cells were initially generated stably expressing YFP-WASp wt or common WASp mutants including WASp R86C, WASp Y107C and WASp A134T, as denoted by the amino acid sequences of SEQ ID NO. 13, 14 and 15, respectively, and encoded by the nucleic acid sequence as denoted by SEQ ID NO. 14, 16 AND 18, respectively. As expected, exogenous WASp mutants (R86C, Y107C, A134T) demonstrated lower expression than exogenous WASp wt due to the fact that these mutations have a deleterious impact on WASp stabilization (FIG. 14A). Lymphocytes stably expressing the YFP-WASp mutants were then incubated with SMCs or control, stimulated and analyzed by western blot. Treatment with WASp-binding SMCs increased WASp expression compared to control-treated cells in YFP-WASp mutant expressing cells (FIG. 14B).

In order to study the effect of WASp-binding SMCs on the prevention of WASp degradation, it is necessary to establish a physiologically relevant model which accurately resembles the phenotypic characteristics of defective WASp expression. A limitation to this approach is that selected SMCs cannot be tested in vivo due to the lack of a valid animal model. The only available animal model for studying WAS is the WAS knockout mouse, which is completely devoid of the WAS gene and as such, is not a suitable model for testing post translational pathways (Snapper S B, et al. 1998). Hence, generating WASp knockout human cell lines, solely expressing exogenous WASp mutants can serve as invaluable tools to test the efficacy of SMC mediated therapy. These lines would have the benefit of exclusively expressing tagged mutant WASp, potentially serving as ideal templates to study SMC stabilizing effects without endogenous WASp background interference.

To this end, human WASp knockout Jurkat T-cell lines were generated which have no expression of endogenous WASp wt ($WAS^{-/-}$) (FIG. 14C) and solely express exogenous WASp harboring the common human WAS and XLT mutations. R86C ($WAS^{-/-}$/WASp R86C) or Y107C ($WAS^{-/-}$/WASp Y107C), utilizing the CRISPR/CAS9 genome editing system, an emerging powerful tool for custom genomic modification including genomic deletions and point mutations (Doudna J A, et al. 2014).

Cells exclusively expressing the YFP-WASp mutants were incubated with SMC #34 or solvent, stimulated and analyzed by western blot. Treatment with WASp-binding SMC increased WASp expression compared to control-treated cells (FIG. 14D). These results demonstrate that WASp-binding SMCs can successfully restore WASp levels in WAS/XLT mutant cells, thus may become a novel therapeutic approach to treat these diseases.

Finally, the inventors examined the ability of WASp-binding SMC to restore the cellular function of cells that completely lack WASp expression (WAS$^{-/-}$) or to upregulate the cellular function of cells that exclusively express WASp mutant forms and are deficient to endogenous WASp.

In comparison to control treated cells, treatment with SMC #34 led to an upregulation of lymphocyte activation in cells exclusively expressing YFP-WASp R86C and restored the activation of WAS$^{-/-}$ cells (FIG. 14E). Furthermore, treatment with SMC #34 significantly increased the migration of WAS$^{-/-}$/WASp R86C and WAS$^{-/-}$/WASp Y107C cells and completely restored the migration of WAS$^{-/-}$ cells (FIG. 15A-15C).

Collectively, these results clearly demonstrate the mechanism of action and therapeutic potential of WASp-binding SMCs. In normal resting lymphocytes, megakaryocytes and platelets, WASp is protected from ubiquitylation and degradation via its interaction with WIP. Following cellular activation, this interaction is partially released, WASp degradation sites are uncovered which leads to proteasomal degradation. Alternatively, in WAS/XLT patients the WIP-WASp interaction is compromised due to mutations in WASp N'-terminus. In the absence of, or comprised WIP protection. WASp is constitutively ubiquitylated and degraded. The addition of carefully selected SMCs, which bind in a close proximity to WASp degradation pocket, blocks the exposed degradation sites of WASp, protecting it from ubiquitylation and degradation as illustrated in FIG. 16. Thus, WASp-binding SMCs protect WASp from degradation and can upregulate the expression and normal function of WASp in the hematopoietic cells of WAS/XLT patients.

Example 7

Treating Immunosuppression Caused by Chemotherapy and Radiotherapy
The Effect of WASp-Stabilizing SMC in Improving Leukocyte Proliferation and Hematopoietic Cell Reconstitution.

WASp was shown to promote lymphocyte growth and survival in both mice and humans. Proliferation of T or B lymphocytes in response to stimulation by anti-T cell antigen receptor (TCR) or anti-IgM, respectively, are impaired in WASp-deficient lymphocytes. Restoration of WASp expression has been shown to significantly mitigate these defects (Charrier S. et al. *Gene therapy* 2007). Reduced leukocyte number is a common side effect of chemotherapy and radiotherapy, which exposes cancer patients to life threatening infections. Increasing WASp expression enables to expedite hematopoietic rejuvenation following chemo- and radiotherapies by enhancing lymphocyte growth and survival.

To determine the ability of the WASp-stabilizing SMC to improve lymphocyte proliferation, primary hematopoietic cells including T, B, and NK cells are isolated from peripheral blood of healthy donors, using magnetic cell separation kits (commercially available EasySep, StemCell). Freshly isolated cells are incubated with the WASp-stabilizing SMCs of the invention and compared to control-SMC. The cells are then activated with anti-CD3 for T cells, anti-IgM for B cells, and anti-CD16 for NK cells. Unstimulated cells are examined as a control. Cellular proliferation are determined using XTT proliferation assay or by a FACS-based CFSE staining assay, which measures proliferation by dilution of the fluorescent signal upon cellular divisions. A significant increase in lymphocyte proliferation upon WASp-stabilizing SMC treatment is expected. To assess whether the WASp-stabilizing-SMCs of the invention could restore normal lymphoid cell counts, mice are subjected to chemotherapy or radiotherapy and hematopoietic recovery is monitored. To determine the effect of SMC treatment on the immune response following chemotherapy, C57BL/6 mice are treated with the chemotherapeutic agents oxaliplatin (5 mg/kg), or doxorubicin (2 mM in 100 ml PBS) injected intraperitoneally (IP).

For radiotherapy experiments, C57BL/6 mice are briefly anesthetized using isoflurane, and subjected to total body X-irradiation at a dose of 7.5 Gray (Gy). Mice are used at 6 to 20 weeks of age. The mice are injected intravenously (IV) with the WASp-stabilizing SMCs of the invention vs. control and monitored by complete blood cell counts to determine the absolute numbers of T, B, and NK cells. Blood sample are withdrawn from the tail vein and the cells are counted primarily using a blood analyzer (KX21N, Sysmex, Kobe, Japan) followed by Giemsa-staining of blood smears.

Additionally, total cell counts in bone marrow, thymus, and spleen are evaluated after preparation of single-cell suspensions and elimination of red blood cells.

To confirm normal reconstitution of the hematopoietic system, as compared of proliferation of specific populations at the expense of others, the relative distribution of white blood cell subsets is analyzed by FACS. Specifically, the following subsets is analyzed: SSClowCD11b-CD90+ (T cells), SSClowCD11b– B220+ (B cells), SSClowCD11b (monocytes), SSChighCD11b+ (granulocytes). Although WASp-stabilizing SMCs are not expected to affect monocyte and granulocyte numbers but rather their functions, these cells are analyzed to determine the distribution of lymphocytes relatively to the entire hematopoietic cell population. Moreover, due to the specific effect of WASp on lymphocyte proliferation and survival, the number and relative distribution of T (CD3+), NK (CD3–CD56+) and B (CD19+) cells is specifically determined using FACS. Focusing on these markers enables to determine the distribution of the major hematopoietic populations. The absolute blood counts of these cells is calculated by multiplying the relative percentages by the total white blood cell counts.
The Use of WASp-Stabilizing SMC in Enhancing Leukocyte Migration and Homing.

Aside from increasing cellular proliferation, which results in the expansion of specific leukocyte populations, secondary immuno-deficiencies can also be treated by boosting the activity and effector function of mature leukocytes within existing populations. The efficacy of an immune response is dependent on the timely recruitment of immune cells to sites of inflammation. A hallmark of a suppressed immune system, as evident in WAS patients, is defective migration of immune cells to inflammation sites. Enhancement of cellular migration improves the effectiveness of the immune response. Increased cellular function e.g. migration might compensate for reduced number of cells.

Granulocytes form the host's first line of defense against invading pathogens with neutrophils being among the first cells to respond. Impaired recruitment of neutrophils to inflammatory sites allows more time for pathogens to replicate and induce damage. Migration of neutrophils is impaired in WAS KO mice both in vitro and in vivo (Snapper S. B et al. *Journal of leukocyte biology* 2005). Thus, improving neutrophil migration is expected to improve clinical outcomes following infections. First, the effects of WASp-stabilizing SMC on neutrophil migration is examined, without prior chemo- or radiotherapy treatments.

Neutrophils are isolated from blood of healthy human donors using magnetic bead isolation kit (StemCell), and the cells are incubated with WASp-stabilizing SMC vs. control. Migration is examined using previously described protocols in response to complement component 5a (c5a), a known recruiter of phagocytes (Zhang, H et al. *Immunity* 2006).

Defects in adhesion and migration of neutrophils in WAS appear to be more apparent under conditions of physiologic shear flow, during which integrin attachment is critical. To further examine the effect of WASp upregulation on neutrophil recruitment, the effect of SMC treatment on the adhesion and migration of neutrophils under conditions of physiological shear flow is monitored. Briefly, neutrophils isolated from healthy donors, are treated with WASp-stabilizing SMC, and subjected to shear flow assay, as previously described (Zhang. H et al. *Immunity* 2006). Upregulated adhesion and migration of neutrophils is anticipated following treatment with WASp-stabilizing SMC.

Migration of B and T lymphocytes is crucial for their function. Defective migration of T cells causes reduced or delayed homing of effector T cells to the inflammatory site, hampering their ability to correctly regulate immune function at the infection site, as well as their ability to carry out direct effector functions. Defective B cell migration and chemotaxis disrupts the humoral immune response. T and B lymphocytes of WAS patients and WAS KO mice are impaired in their migratory capacity (Snapper S. B et al. *Journal of leukocyte biology* 2005). WASp-deficient B cells fail to migrate towards CXCL1359, a crucial chemokine for attracting B cells to the lymphoid follicles, and T cells do not respond to CCL19 and CCL2154, which mediate T cell homing to the secondary lymphoid tissue (Gunn, M. D., et al. *The Journal of experimental medicine* 1999). To monitor migration, splenic B and T lymphocytes are purified from WASp-stabilizing SMC or control pretreated mice that were subjected to chemotherapy or radiotherapy. Migration towards the chemokines SDFα and CXCL13 is induced, and measured using the Transwell system as previously described (Snapper S. B et al. *Journal of leukocyte biology* 2005). The effect of WASp-stabilizing SMC on T cell response to CCL19 and CCL21 is also measured. Although chemo- and radiotherapy destructive effects are mainly manifested by rapidly-dividing cells, increasing mature leukocyte migration and homing by WASp-stabilizing SMC is expected to improve clinical outcome of chemo- and radiotherapy related secondary immunodeficiencies.

Monocytes exit the circulation to enter inflamed tissues, where they can differentiate into macrophages or DCs. Impaired migration of DCs to lymphoid tissues delays priming and activation of antigen-specific T cells. Monocytes, macrophages and DCs from WAS patients are all defective in their ability to polarize and migrate in response to inflammatory chemokines (Altman, L. C., et al. The Journal of clinical investigation, 1974). The ability of isolated primary human monocytes, macrophages and DCs to polarize and migrate in response to inflammatory chemokines in vitro is examined using a standard migration assay following SMC treatment (Snapper S. B et al. *Journal of leukocyte biology* 2005). Treatment with WASp-stabilizing SMC should enhance the ability of these cells to efficiently migrate in response to external stimuli.

Next, the in vivo ability of murine DCs to migrate and to localize to the spleen or lymph node T cell areas is determined as previously described (Snapper S. B et al. *Journal of leukocyte biology* 2005). This is detected using the chemotherapy or radiotherapy treated mouse models, as described above. Spleen and lymph nodes are harvested, and the relative numbers of DCs are monitored using FACS analysis.

Contact of migrating myeloid cells with their substrate is mediated by podosomes, which are actin-rich structures that are surrounded by a ring of integrins and integrin-associated proteins. Podosomes play a crucial role in cellular motility and invasion. These structures are localized in close proximity with the leading edge of migrating cells, and their formation and function are dependent on WASp activity (Linder, S. & Kopp, P. *Journal of cell science* 2005). The ability of WASp-stabilizing SMC to increase podosome formation in macrophages and DCs is thus analyzed by isolating macrophages and DCs from human peripheral blood followed by their seeding over stimulating surfaces that promote migration. The formation of podosomes is quantified using cell staining with phalloidin, which probes F-actin within the podosomes, followed by confocal microscope analysis, as previously described (Linder, S, et al. *PNAS* 1999). Higher podosome formation are expected to be detected following treatment of the WASp-stabilizing SMCs vs. control.

Reverse Effector Cell Dysfunctions Using WASp-Stabilizing SMCs Upon Secondary Immunodeficiency Mediated by Chemo- or Radiotherapy.

The main consequence of secondary immunodeficiency caused by chemotherapy or radiotherapy in T cells is impaired cytokine production in response to TCR activation. WASp-deficient T cells also fail to produce cytokines upon TCR activation (Zhang, J., et al. *The Journal of experimental medicine,* 1999). The secretion of IL-2, IFN-γ, TNF-α, IL-4, and IL-10 by activated T cells obtained from immunocompromised mice (by chemo or radiotherapy) pretreated with IV injected WASp-stabilizing SMC or control is examined.

Several reports demonstrated that chemo- and radiotherapies decreases the cytotolytic activity of NK cells, exposing patients to life threatening infections. To evaluate whether upregulation of WASp expression rescues NK cell function in secondary immunodeficiency, NK cell cytotoxicity is analyzed in vitro in response to WASp-stabilizing SMC or control. Next, this activity is measured in vivo, in WASp-stabilizing SMC treated or control mice subjected to chemotherapy and/or radiotherapy. To examine the effect of WASp upregulation on NK cell cytotoxicity, the ability of NK cells to lyse susceptible target cells is tested using the standard 35S release assay Matalon, O., et al. *Science signaling* 2016). Due to the critical role of WASp in NK cell cytotoxicity, and the negative effects of chemo- and radiotherapies on NK cell effector function, treatment with WASp-stabilizing SMCs is expected to enhance NK cytolytic activity and to mitigate secondary immunodeficiencies.

Phagocytosis of pathogens and their presentation by DCs and macrophages is an essential step in the activation of T cells and in mediating adaptive immunity. WASp plays a key role in phagocytosis by DCs and macrophages. Phagocytic cups enclose extracellular particles and subsequently internalize them into phagosomes. To evaluate whether upregulation of WASp expression rescues macrophages or DC functions following chemotherapy or radiotherapy, phagocytic activity of bone marrow macrophages or DCs is examined. These cells are isolated form WASp-stabilizing SMC treated mice that have undergone chemotherapy or radiotherapy, and are exposed to fluorescent latex beads for 15 minutes. Following fixation, cells are labeled with cholera toxin and phalloidin to visualize the plasma membrane and cell area (by F-actin), respectively. Internalized beads are identified by single confocal planes and 3D reconstruction of z-stacks. For quantification of uptake, only those cells that contain a bead surrounded by plasma membrane are scored as positive.

To determine the role of WASp upregulation on phagocytic activity using a more physiological antigen, macrophages or DCs are incubated with GFP-expressing *Salmonella typhimurium*, and phagocytosis will be monitored by FACS analysis of CD11c+/GFP+ cells.

WASp is fundamental for B cell development and function in both humans and mice. Chemotherapy or radiotherapy damage the B-cell follicle, as well as the marginal zone (MZ) architecture. To understand whether WASp upregulation may reverse this damage, immunohistochemistry of mouse spleen sections is performed following IV injections of the WASp-stabilizing SMCs of the invention vs. control. Spleens are removed from the mice and fixed. Cryostat sections are prepared and immunostained with anti-WASp and anti-B220, which serves as a marker for MZ B-cells to monitor MZ integrity. A normal architecture of MZ is expected following the WASp-stabilizing SMCs of the invention. The number of regulatory T (Treg) cells, their suppressive function and their homing are known to be defective in WASp-deficient hosts, indicating the key role of WASp in regulating Treg activation (Zhang, J., et al. *The Journal of experimental medicine*, 1999). To investigate the effect of WASp-stabilizing SMC on the suppressive ability of Treg cells, in vitro suppression assays is performed. Briefly, CD4+CD25highCD127−/low Treg cells and CD4+ CD25− effector T cells are isolated by FACS sorting from PBMCs pretreated with either WASp-stabilizing SMC or control. CD4+CD25− effector T cells are stimulated by CD3-depleted APCs and 1 µg/ml of soluble anti-CD3 mAbs. Suppressive activity of naïve Treg (nTreg) cells is assessed by co-culture of effector T cells with nTreg cells at a 1 to 1 ratio. Proliferation of the CD4+CD25− effector T cells are evaluated by 3H-thymidine incorporation or XTT assay following stimulation. Furthermore, IFNγ and IL-2 secretion by the effector T cells is measured using ELISA. Less proliferation of effector T cells as well as reduced secretion of IFNγ and IL-2 by these cells upon restoration of Treg suppressive function is expected.

Example 8

Boosting Immune Protection Against Pathogens

By improving the ability of the immune system to deal with pathogenic challenges, WASp-stabilizing SMC offers a promising approach for improving health outcomes. In the following experiments, the ability of WASp-stabilizing SMC to improve key immune activities that are essential for eliminating infectious agents is determined.

The ability to phagocytose pathogens is a key property of the innate immune response. Phagocytosis not only serves as a direct mechanism for pathogen clearance, but also provides an essential step in presenting foreign antigens to the adaptive arm of the immune system. As described above, phagocytosis is mediated by the formation of actin-based membrane invaginations, called phagocytic cups. Since, WASp is essential for the formation of these structures, the effect of WASp-stabilizing SMC is analyzed on monocyte uptake of FITC-labelled *Escherichia coli*. Briefly, isolated primary monocytes are treated with WASp-stabilizing SMC vs. control treatment, incubated with fluorescently-labelled bacteria, and FACS analysis of CD11c+/FITC+ cell (active phagocytes) percentage is conducted to monitor phagocytosis.

Additionally, the ability of macrophages and DCs to phagocytose apoptotic cells and latex beads is examined. The phagocytic cells are incubated with fluorescent latex beads, fixed, and fluorescently labeled using cholera toxin and phalloidin. Quantification of internalized beads is performed using confocal microscopy, as described above.

Antibody production by B cells is a key component of the immune response to bacterial infections. WASp plays a pivotal role in the primary humoral immune response. To evaluate the antibody response to various antigens expressed on different types of pathogens, in vivo assays using antigens of different origins are performed including viral (e.g. CMV, EBV, influenza), or bacterial antigens (e.g. *Mycobacterium tuberculosis*, MTB; *Streptococcus pneumoniae*, pneumococcus or *S. pneumoniae*). To this end, C57BL/6 mice are inoculated with pathogenic antigens followed by treatment with WASp-stabilizing-SMC or control. Mice are challenged intraperitoneally (I.P) with 0.5 µg/mouse of a vaccine containing a mixture of highly purified capsular polysaccharides from the most 23 prevalent or invasive pneumococcal strains of *Streptococcus pneumoniae* (Pneumovax23; commercially available (Pneumovax23); Sanofi Pasteur MSD, Lyon, France. After 7 days, blood samples are collected from the facial vein of mice, and serum IgM antibodies specific for Pneumovax23 polysaccharidic components are measured by ELISA. Higher IgM levels in the serum of mice treated with the WASp-stabilizing SMC are expected due to enhanced B cell activation.

Example 9

Determine the Therapeutic Potential of WASp-Stabilizing SMC for Treating Thrombocytopenia and Specifically, Idiopathic Thrombocytopenic Purpura (ITP)

ITP is an autoimmune disease characterized by micro-thrombocytopenia caused by platelet clearance due to production of auto-antibodies targeting platelets. Since the expression of WASp is crucial for platelet production from megakaryocytes, the effect of WASp-stabilizing SMC on platelet activity and on the thrombocytopenic phenotype in ITP mouse models is examined.

First, the effect of WASp-stabilizing SMC on platelet function in vitro is determined. Platelets are isolated from the blood of healthy donors and incubated with WASp-stabilizing SMC in comparison to control treated cells. Adhesion of platelets to fibrinogen is a key process in platelet aggregation, mediated by integrins, such as αIIbβ3. WASp is important for αIIbβ3-mediated-cell adhesion of platelets and megakaryocytes. Several clinical observations indicate that WASp deficiency causes a substantial decrease in platelet number and aggregation. This leads to heavy bleeding in WAS/XLT patients. Thus, the binding of FITC-labelled soluble fibrinogen to platelet integrin αIIbβ3 following adenosine diphosphate (ADP) stimulation is determined via FACS analysis. The treatment with WASp-stabilizing SMC is expected to enhance platelet aggregation, relative to control cells in addition to the platelet activation demonstrated in FIG. 11. F-actin polymerization and rearrangement is pivotal for platelet activation and function. F-actin content per platelet is measured by quantitating FITC phalloidin staining using FACS analysis following ADP stimulation. Enhanced F-actin content per platelet is anticipated in response to treatment with the WASp-stabilizing SMCs of the invention, which is consistent with the data of FIG. 5 and FIG. 6 demonstrating upregulated WASp expression upon platelet treatment with the same SMC.

Platelet aggregation is mediated mainly by the activity of αIIbβ3 integrin, which undergoes a conformational change following platelet activation. The conformation of αIIbβ3 is converted from a low-affinity state to a high-affinity state following agonist stimulation. WASp levels, which are reduced in WAS/XLT patients, are not sufficient to associate the actin cytoskeleton to αIIbβ3 sites or to optimize the affinity of αIIbβ3 for its ligand. Thus, the 'affinity-maturation' of αIIbβ3 to its ligand following agonist stimulation is impaired in these patients. In order to determine the effect of WASp expression on αIIbβ3 activity, platelets are treated with WASp-stabilizing SMC, stimulated with thrombin (αIIbβ3 ligand), and stained with fluorescently labelled PAC-1 antibody. This monoclonal antibody recognizes only the activated form of αIIbβ3 extracellular domain. The activation of the αIIbβ3 integrin is measured by FACS analysis, assuming increased integrin activation following treatment with the WASp-stabilizing SMCs of the invention. Following their activation and F-actin polymerization, platelets must spread over intact blood vessels in the process of clot formation. Platelets are treated with WASp-stabilizing SMC followed by seeding over immobilized fibrinogen-coated slides. Spreading is analyzed as follows: platelets are stained with the fluorescent label calcein-AM, after their seeding over immobilized fibrinogen-coated 96 plates. Fluorescent signal is measured by fluorescence spectrophotometry after extensive washing of wells, to determine platelet adhesion as an indication of their spreading capacity.

Microthrombocytopenia is characterized by reduced expression of platelet surface markers, including GPIb, GPV, GPIX, CD9, GPVI, αIIbβ3. The expression of these surface proteins is determined in platelets isolated from the ITP mouse model, (NZW×BXSB) F1 mouse (also known as W/B F1 mice), following IV injection with WASp-stabilizing SMC vs. control. Cells are stained with specific antibodies for the indicated surface proteins followed by FACS analysis. The expression of these markers is expected to be increased following SMC treatment.

Platelets obtained from WAS/XLT patients are characterized by aberrant morphology and size resulting in reduced mean platelet volume. Since low mean platelet volume and short platelet lifespan are also hallmarks of ITP, these parameters are examined in W/B F1 mice treated with WASp-stabilizing SMC vs. control. Clearance of platelets from the blood circulation (reflecting platelet lifespan) is determined by the retro-orbital injection of fluorescently-labelled antibody against GPIX, a unique surface marker expressed over all platelets, into male W/B F1 mice. The percentage of labelled platelets is determined by daily blood withdrawal and subsequent FACS analysis. In addition, platelet volume is determined with an automated blood cell analyzer. Both platelet life span and volume are expected to increase following SMC-stabilizing WASp treatment.

The microthrombocytopenia in XLT patients is caused by both accelerated platelet clearance by macrophages and the premature release of platelets from their precursors into the BM due to altered cytoskeletal dynamics. Thus, platelet release from megakaryocytes is measured by immunofluorescence staining of BM-cross sections. Staining with anti-GPIb (for platelet and megakaryocyte detection) and anti-CD105 (for endothelium detection) is performed, and analyzed by confocal microscopy. To this end, W/B F1 mice are utilized following WASp-stabilizing SMC vs. control treatment to determine whether increased WASp expression enhances platelet count.

To confirm that WASp-stabilizing SMC present potential therapeutic approach for ITP by improving platelet count and size, the aforementioned experimental procedures are also conducted on blood samples from human ITP patients.

Example 10

Supportive Treatment for the Rapid Reconstitution of Leukocyte and Megakaryocyte Populations Following HSCT, Gene Therapy or Adoptive Cell Transfer Successful human stem cell transplantation (HSCT) is a challenging procedure that is highly dependent on the ability of the donor/autologous stem cells to accommodate the recipient microenvironment. Enhancement of WASp expression restores hematopoietic cell growth and survival, which is a key factor for successful reconstitution of the host system. Thus the ability of WASp-stabilizing SMC to improve BM engraftment and hematopoietic reconstitution is determined. To this end, recipient mice are subjected to either WASp-stabilizing SMC or control treatment. Syngeneic B6D2F1 male mice serve as donors for matched female bone marrow recipients. Bone marrow transplantation is performed as follows: briefly, following whole body irradiation with 1,200 cGy, the female recipients are injected via the tail vein with 20,000 male whole BM cells.

The reconstitution of the hematopoietic system is examined by blood collection from mice, followed by FACS analysis with gating on the following population: T (CD3+), NK (CD3−CD56+) and B (CD19+) cells using FACS. The relative distribution of cell subsets is analyzed to confirm normal reconstitution of lymphoid cells following WASp-stabilizing SMC treatment.

To further examine hematopoietic system reconstitution, tissue sections of liver and spleen is formalin-fixed and paraffin embedded. To detect donor-derived cells in these tissues, fluorescence in situ hybridization (FISH) for the Y-chromosome is performed. Male BM engraftment as well as BM-derived cells are quantified by FISH. Intense Y-chromosome probe staining in sections obtained from the mice treated with WASp-stabilizing agents is expected.

Example 11

Upregulation of Anti-Cancer Immune Response by Boosting Cytotoxic Lymphocyte Activity NK cells and CTLs constitute the two major cytotoxic effector immune populations, able to directly mediate lysis of viral infected and cancerous cells. WASp deficiency, either in mice or in WAS patients, results in compromised activation and function of cytotoxic lymphocytes, impairing tumor surveillance. In accordance with this defective cytotoxicity, WAS patients demonstrate increased frequency of malignancies, with 13% of WAS patients developing malignancy at an average age of 9.5 years. Thus, the role of WASp-stabilizing SMC in enhancing NK and CTL activation and cytotoxicity is determined. Following formation of a stable effector-cancer cell conjugates, cytotoxic effector cells must first elevate their intracellular $Ca^{2+}$ flux to achieve activation. Intracellular calcium concentration is measured upon NK cell interaction with 721.221 B lymphoma target cells following NK cell incubation with WASp-stabilizing SMC. For this purpose, the human NK YTS line, or primary isolated cells is used. As shown in FIG. 11, WASp-stabilizing SMCs increase calcium flux in platelets upon activation. Similar effects in NK cells are expected.

Next, the role of WASp-stabilizing SMC in enhancing NK cell effector functions i.e. cytotoxicity and/or cytokine production is examined. To address this goal, the effects of WASp-stabilizing SMC are studied on primary or YTS NK cells interacting with the 721.221 cancer cell line. The ability of NK cells to mediate target cell cytotoxicity is measured using 35S-release (Lee, S. H., et al. *J Immunol* 2009) and degranulation analyses (Anfossi, N., et al. *Immunity* 2006). IFNγ secretion by the NK cells following WASp-stabilizing SMC and target cell incubation is measured as well by ELISA. Increases in all NK cell functions are expected following WASp upregulation.

NK cells play a major role in the elimination of metastatic cells and small tumor grafts, and exhibit an antitumor response in patients after leukemia relapse. Therefore, the effect of WASp-stabilizing-SMC on NK cell killing efficiencies of different cancerous cell targets is determined. For this purpose, the following human cancer cell lines are used as target cells: 1106mel melanoma cells, HeLa cervical carcinoma, and A549 and H1975 Lung Carcinoma cell lines. The killing efficiency of these cancer cells is measured using the 35S-release assay (Lee, S. H., et al. *J Immunol* 2009) following NK cell pretreatment with WASp-stabilizing SMC vs. control.

To extend these experiments, NK cell killing efficiency of various primary patient-derived tumor cells is determined, using the above described experimental system. In addition, the anti-tumor effect of human NK cells is examined in vivo using humanized SCID mice carrying human tumor xenografts.

Example 12

The SMCs of the Invention in Combined Supportive Treatment with G-CSF

It is important to emphasize that few agents exist that are able to boost the immune response, and those that are under development are at very early stages. Almost no suitable agents are available, with the exception of granulocyte colony stimulating factor (G-CSF). Currently, modalities for boosting the immune response are limited to lifestyle changes e.g. physical activity and diet.

G-CSF is a growth factor that stimulates the production, maturation, and activation of neutrophils. GCSF stimulates the release of neutrophils from the bone marrow. It is being used for patients receiving chemotherapy to accelerate the recovery of neutrophils, reducing the neutropenic phase. Today, hundreds of thousands of patients are treated with G-CSF to boost their immune systems after chemotherapy or BM transplants. G-CSF may also be used after a stem cell transplant to help accelerate recovery of the new stem cells in the bone marrow.

While G-CSF exclusively induces differentiation of granulocytes from hematopoietic progenitor cells, WASp is known to enhance the activity of all immune cells and platelets. Furthermore, WASp was widely demonstrated to increase the growth rate and survival of mature lymphocytes including T, B, NK and Treg. Given the multiple immunological tasks coordinated by WASp through its regulation of the actin cytoskeleton, and specifically, actin-dependent processes, pharmacological intervention in WASp-mediated signaling pathways is expected to have greater effects on the immune system than GCSF, which affects a single proliferative process. Therefore, WASp-stabilizing SMCs could eventually evolve as a rational strategy for the treatment of secondary immunodeficiencies. In contrast to G-CSF, the major activity of WASp is on differentiated or mature hematopoietic cells. By acting on different processes necessary for an appropriate and robust immune response, administration of G-CSF and the WASp-stabilizing SMCs might be complimentary approaches with additive value. However, administration of WASp-stabilizing SMCs may be relevant in cases in which G-CSF will not have an effect e.g. immune dysfunction of the lymphatic system.

To assess whether the WASp-stabilizing-SMCs of the invention could be used in a combined treatment regimen with other supportive agents, in restoring normal lymphoid cell counts, mice are subjected to chemotherapy or radiotherapy and hematopoietic recovery is monitored. To determine the effect of the combined SMC and G-CSF treatment on the immune response following chemotherapy, C57BL/6 mice are treated with the chemotherapeutic agents oxaliplatin (5 mg/kg), or doxorubicin (2 mM in 100 ml PBS) injected intraperitoneally (IP).

For radiotherapy experiments, C57BL/6 mice are briefly anesthetized using isoflurane, and subjected to total body X-irradiation at a dose of 7.5 Gray (Gy). Mice are used at 6 to 20 weeks of age. The mice are injected intravenously (IV) with the WASp-stabilizing SMCs of the invention vs. control and monitored by complete blood cell counts to determine the absolute numbers of T, B, and NK cells. Blood sample are withdrawn from the tail vein and the cells are counted primarily using a blood analyzer (KX21N, Sysmex, Kobe, Japan) followed by Giemsa-staining of blood smears.

Additionally, total cell counts in bone marrow, thymus, and spleen are evaluated after preparation of single-cell suspensions and elimination of red blood cells.

---

The invention claimed is:

1. A method for modulating degradation and/or stabilizing of Wiskott-Aldrich Syndrome protein (WASp) in a cell, comprising the step of contacting said cell with an effective amount of at least one small molecule compound (SMC) modulator of WASp degradation, or any vehicle, matrix, nano- or micro-particle or any composition comprising the same, said modulator having the general formula (XI):

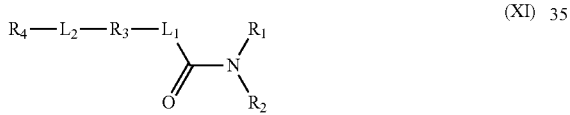

(XI)

or a pharmaceutically acceptable salt, solvate, hydrate, or stereoisomer thereof,
wherein
$R_1$ and $R_2$ are each, independently from each other, selected from the group consisting of H, straight $C_1$-$C_{12}$ alkyl and a ring system containing five to seven atoms, each optionally substituted by at least one ring system containing five to seven atoms optionally substituted by at least one halide or straight $C_1$-$C_5$ alkyl,
or
$R_1$ and $R_2$, together with the nitrogen atom they are connected to, form a five to seven membered saturated or unsaturated ring optionally including at least one N or O and optionally substituted with at least one straight $C_1$-$C_5$ alkyl,
$L_1$ is absent or is selected from the group consisting of —CH$_2$—S—, —CH$_2$—CH$_2$—C(O)—NH—CH$_2$—C(O)—NH—CH$_2$, and —CH$_2$—, each optionally substituted with ethyl, methyl, or an aryl optionally substituted with a methyl or ethyl,
$L_2$ is absent or —CH$_2$—O— or —CH$_2$—;
$R_3$ and $R_4$ are each, independently from each other, absent or selected from the group consisting of a ring system containing five to 12 atoms, each optionally substituted with at least one of straight or branched $C_1$-$C_5$ alkyl, (=O), (=S), —C(O)—O—CH$_3$ or $R_5$,
$R_5$ being a ring system containing five to seven atoms optionally substituted by at least one halide or straight $C_1$-$C_5$ alkyl.

2. The method according to claim 1, wherein $R_1$ and $R_2$ are each, independently from each other, selected from the group consisting of H, cyclopentane and thiazole, or
$R_1$ and $R_2$, together with the nitrogen atom they are connected to, form a six membered unsaturated ring substituted with at least one methyl,
$L_1$ is absent or is selected from the group consisting of —CH$_2$—S— and —CH$_2$—CH$_2$—C(O)—N—CH$_2$—C(O)—NH—CH$_2$—, substituted with an aryl optionally substituted with a methyl,
$L_2$ is absent, —CH$_2$— or —CH$_2$—O—, and
$R_3$ and $R_4$ are each, independently from each other, absent or selected from the group consisting of piperidine, piperazine, quinoline, isoquinoline, phthalazine, tetrahydro-quinoline, pyridine, tetrahydro-quinazoline 1, 2, 4-triazole, oxadiazole quinoline, pyridine, phenyl, and naphthalene substituted with —C(O)—O—CH$_3$, or methyl.

3. The method according to claim 1, wherein said SMC has the general formula (XIII):

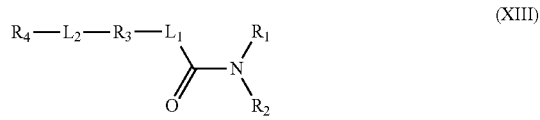

(XIII)

or a pharmaceutically acceptable salt, solvate, hydrate, or stereoisomer thereof,
wherein
$R_1$ and $R_2$ are each, independently from each other, selected from the group consisting of H and a ring system containing five to seven atoms, each optionally substituted by at least one of halide;
$L_1$ is absent or is selected from the group consisting of —CH$_2$—S—, —CH$_2$—CH$_2$—C(O)—NH—CH$_2$—C(O)—NH—CH$_2$, and —CH$_2$—, each optionally substituted with ethyl, methyl, or an aryl optionally substituted with a methyl or ethyl, L₂ is absent or —CH₂—O— or —CH₂—; and R₃ and R₄ are each, independently from each other, absent or a ring system containing five to 12 atoms, each optionally substituted with at least one of straight C₁-C₅ alkyl, (=O), (=S), —C(O)—O—CH₃, or R₅, R₅ being a ring system containing five to seven atoms optionally substituted by at least one halide or straight C₁-C₅ alkyl.

4. The method according to claim 3, wherein at least one of:

(a) at least one of R₁ and R₂ is C₅-C₇ saturated cycloalkyl, C₅-C₇ saturated cycloalkylene, C₅-C₇ aryl or C₅-C₇ arylene, L₁ is absent or selected from the group consisting of —CH₂—CH₂—C(O)—NH—CH₂—C(O)—NH—CH₂—, and —CH₂—, each optionally substituted with ethyl, methyl, or an aryl optionally substituted with a methyl or ethyl, L₂ is absent or —CH₂—, at least one of R₃ and R₄ is a C₅-C₁₂ heterocycloalkyl ring, C₅-C₁₂ heteroaryl or C₅-C₁₂ heteroarylene, wherein the heteroatom is N, O or S; and (b) at least one of R₁ and R₂ is selected from the group consisting of cyclopentane or thiazole, L₁ is absent or —CH₂—CH₂—C(O)—NH—CH₂—C(O)—NH—CH₂—, substituted with an aryl optionally substituted with a methyl, L₂ is absent or CH₂, at least one of R₃ and R₄ is selected from the group consisting of piperidine, piperazine, quinoline, isoquinoline, phthalazine, tetrahydro-quinoline, pyridine, and tetrahydro-quinazoline substituted with —C(O)—O—CH₃.

5. The method according to claim 3, wherein said SMC is (a)

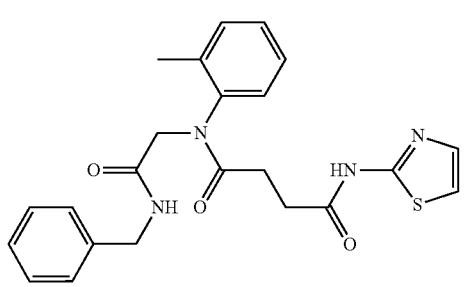

N'-[2-(benzylamino)-2-oxoethyl]-N'-(2-methylphenyl)-N-(1,3-thiazol-2-yl) butanediamide
(Designated herein as SMC #33); or (b)

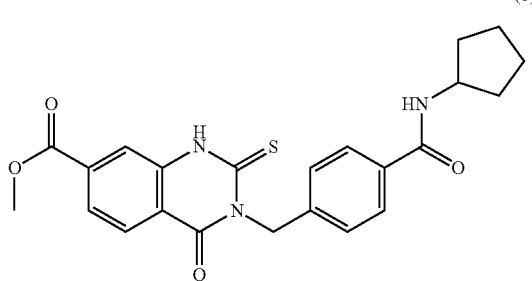

3-(4-Cyclopentylcarbamoyl-benzyl)-4-oxo-2-thioxo-1,2,3,4-tetrahydro-quinazoline-7-carboxylic acid methyl ester
(Designated herein as SMC #30).

6. The method according to claim 1, wherein said SMC is

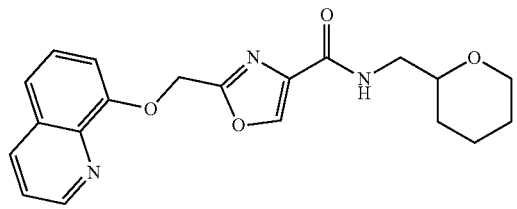 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10).

7. The method according to claim 1, wherein said modulation results in reduced WASp degradation in a cell, optionally, said reduced degradation restores, enhances or extends at least one of WASp levels and function in said cell.

8. The method according to claim 1, wherein said cell is a non-erythroid hematopoietic cell.

9. The method according to claim 1, wherein said cell is of a subject suffering from an innate or acquired immune-related disorder or condition, and wherein said contacting step comprises administering to said subject a therapeutically effective amount of at least one of said SMC modulator of WASp.

10. A method for inhibiting, reducing, or delaying the onset of a an innate or acquired immune-related disorder or condition in a subject in need thereof, said method comprises administering to said subject a therapeutically effective amount of at least one SMC modulator of WASp having the general formula (XI):

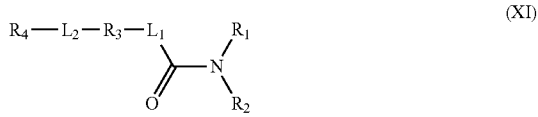

(XI)

or a pharmaceutically acceptable salt, solvate, hydrate, or stereoisomer thereof,
wherein
R₁ and R₂ are each independently from each other, selected from the group consisting of H, straight C₁-C₁₂ alkyl and a ring system containing five to seven atoms, each optionally substituted by at least one ring system containing five to seven atoms optionally substituted by at least one halide or straight C₁-C₅ alkyl,
or
R₁ and R₂ together with the nitrogen atom they are connected to form a five to seven membered saturated or unsaturated ring optionally including at least one N or O and optionally substituted with at least one straight C₁-C₅ alkyl,
L₁ is absent or is selected from the group consisting of —CH₂—S—, —CH₂—CH₂—C(O)—NH—CH₂—C(O)—NH—CH₂, and —CH₂—, each optionally substituted with ethyl, methyl, or an aryl optionally substituted with a methyl or ethyl,
L₂ is absent or —CH₂—O— or —CH₂—;
R₃ and R4 are each, independently from each other, absent or selected from the group consisting of a ring system containing five to 12 atoms, each optionally substituted with at least one of straight or branched C$_1$-C$_5$ alkyl, (=O), (=S), —C(O)—O—CH$_3$ or R$_5$, R$_5$ being a ring system containing five to seven atoms optionally substituted by at least one halide or straight C$_1$-C$_5$ alkyl.

11. The method according to claim 10, wherein R$_1$ and R$_2$ are each, independently from each other, selected from the group consisting of H, cyclopentane and thiazole, or R$_1$ and R$_2$, together with the nitrogen atom they are connected to, form a six membered unsaturated ring substituted with at least one methyl, L$_1$ is absent or is selected from the group consisting of —CH$_2$—S— and —CH$_2$—CH$_2$—C(O)—N—CH$_2$—C(O)—NH—CH$_2$—, substituted with an aryl optionally substituted with a methyl, L$_2$ is absent, —CH$_2$— or —CH$_2$—O—, and R$_3$ and R$_4$ are each, independently from each other, absent or selected from the group consisting of piperidine, piperazine, quinoline, isoquinoline, phthalazine, tetrahydro-quinoline, pyridine, tetrahydro-quinazoline 1, 2, 4-triazole, oxadiazole quinoline, pyridine, phenyl, and naphthalene substituted with —C(O)—O—CH$_3$ or methyl.

12. The method according to claim 10, wherein said SMC has the general formula (XIII):

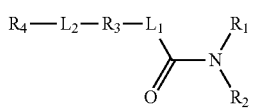

(XIII)

or a pharmaceutically acceptable salt, solvate, hydrate, or stereoisomer thereof, wherein R$_1$ and R$_2$ are each, independently from each other, selected from the group consisting of H and a ring system containing five to seven atoms, each optionally substituted by at least one of halide;

L$_1$ is absent or is selected from the group consisting of —CH$_2$—S—, —CH$_2$—CH$_2$—C(O)—NH—CH$_2$—C(O)—NH—CH$_2$, and —CH$_2$—, each optionally substituted with ethyl, methyl, or an aryl optionally substituted with a methyl or ethyl, L$_2$ is absent or —CH$_2$—O— or —CH$_2$—; and R$_3$ and R$_4$ are each, independently from each other, absent or a ring system containing five to 12 atoms, each optionally substituted with at least one of straight C$_1$-C$_5$ alkyl, (=O), (=S), —C(O)—O—CH$_3$, or R$_5$, R$_5$ being a ring system containing five to seven atoms optionally substituted by at least one halide or straight C$_1$-C$_5$ alkyl.

13. The method according to claim 12, wherein at least one of:

(a) at least one of R$_1$ and R$_2$ is C$_5$-C$_7$ saturated cycloalkyl, C$_5$-C$_7$ saturated cycloalkylene, C$_5$-C$_7$ aryl or C$_5$-C$_7$ arylene, L$_1$ is absent or selected from the group consisting of —CH$_2$—CH$_2$—C(O)—NH—CH$_2$—C(O)—NH—CH$_2$— and —CH$_2$—, each optionally substituted with ethyl, methyl, or an aryl optionally substituted with a methyl or ethyl, L$_2$ is absent or —CH$_2$—, and at least one of R$_3$ and R$_4$ is a C$_5$-C$_{12}$ heterocycloalkyl ring, C$_5$-C$_{12}$ heteroaryl or C$_5$-C$_{12}$ heteroarylene, wherein the heteroatom is N, O or S; and (b) at least one of R$_1$ and R$_2$ is selected from the group consisting of cyclopentane or thiazole, L$_1$ is absent or —CH$_2$—CH$_2$—C(O)—NH—CH$_2$—C(O)—NH—CH$_2$—, substituted with an aryl optionally substituted with a methyl, L$_2$ is absent or —CH$_2$—, and at least one of R$_3$ and R$_4$ is selected from the group consisting of piperidine, piperazine, quinoline, isoquinoline, phthalazine, tetrahydro-quinoline, pyridine, and tetrahydro-quinazoline substituted with —C(O)—O—CH$_3$.

14. The method according to claim 12, wherein said SMC is

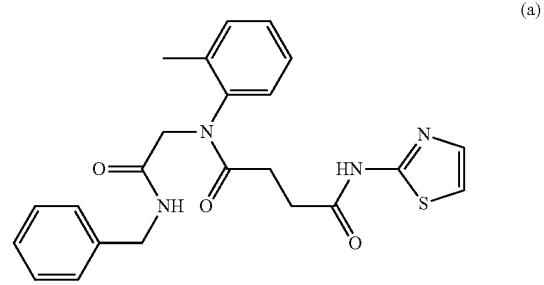 [SMILES: Cc1ccccc1N(CC(=O)NCc1ccccc1)C(=O)CCC(=O)Nc1nccs1]

(a)

N'-[2-(benzylamino)-2-oxoethyl]-N'-(2-methylphenyl)-N-(1,3-thiazol-2-yl) butanediamide (Designated herein as SMC #33); or

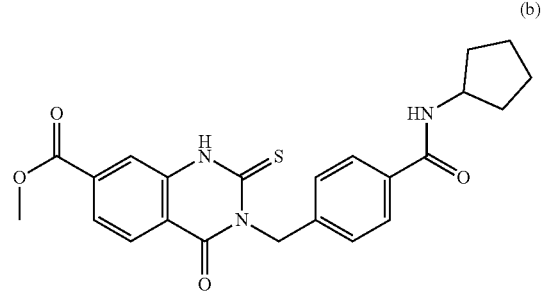 [SMILES: COC(=O)c1ccc2c(=O)n(Cc3ccc(C(=O)NC4CCCC4)cc3)c(=S)[nH]c2c1]

(b)

3-(4-Cyclopentylcarbamoyl-benzyl)-4-oxo-2-thioxo-1,2,3,4-tetrahydro-quinazoline-7-carboxylic acid methyl ester (Designated herein as SMC #30).

15. The method according to claim 10, wherein said SMC is selected from the group consisting of:

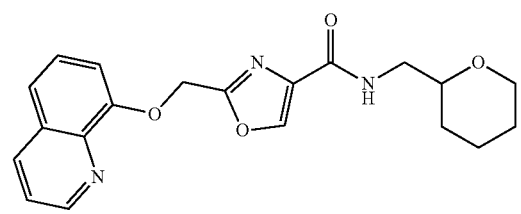 [SMILES: O=C(NCC1CCCCO1)c1coc(COc2cccc3cccnc23)n1]

2-(Quinolin-8-yloxymethyl)-oxazole-4-carboxylic acid (tetrahydro-pyran-2-ylmethyl)-amide (SMC 34.10);

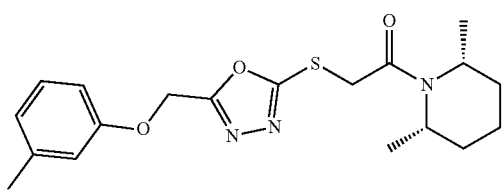 [SMILES: Cc1cccc(OCc2nnc(SCC(=O)N3[C@H](C)CCC[C@@H]3C)o2)c1]

1-(2,6-dimethyl-piperidin-1-yl)-2-(5-m-tolyloxymethyl-[1,3,4]oxadiazol-2-ylsulfanyl)-ethanone (SMC 34.1);

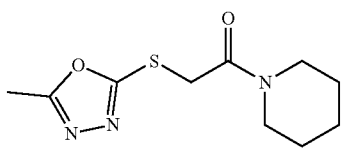

2-(5-methyl-[1,3,4]oxadiazol-2-ylsulfanyl)-1-piperidin-1-yl-ethanone (SMC 34.3);

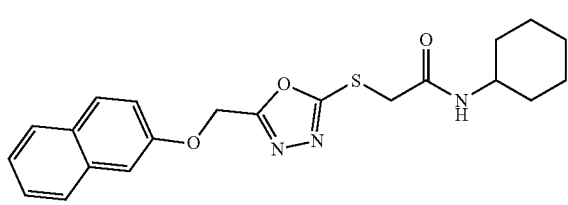 [SMILES: O=C(CSc1nnc(COc2ccc3ccccc3c2)o1)NC1CCCCC1]

N-cyclohexyl-2-[5-(naphthalen-2-yloxymethyl)-[1,3,4]oxadiazol-2-ylsulfanyl]-acetamide (SMC 34.4);

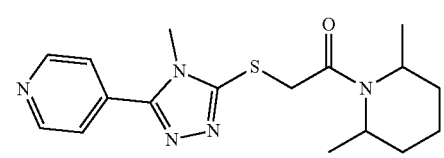 [SMILES: CC1CCCC(C)N1C(=O)CSc1nnc(-c2ccncc2)n1C]

1-(2,6-dimethyl-piperidin-1-yl)-2-(4-methyl-5-pyridin-4-yl-4H-[1,2,4]triazol-3-ylsulfanyl)-ethanone (SMC 34.5);

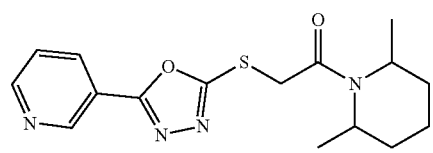

1-(2,6-dimethyl-piperidin-1-yl)-2-(5-pyridin-3-yl-[1,3,4]oxadiazol-2-ylsulfanyl)-ethanone (SMC 34.6);

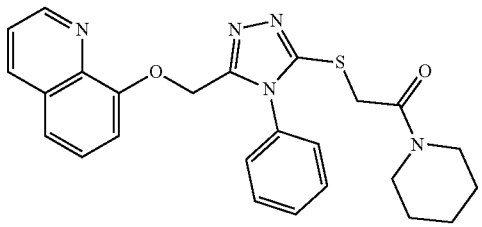 [SMILES: O=C(CSc1nnc(COc2cccc3cccnc23)n1-c1ccccc1)N1CCCCC1]

2-(5-phenoxymethyl-[1,3,4]oxadiazol-2-ylsulfanyl)-1-pyrrolidin-1-yl-ethanone (SMC 34.8);

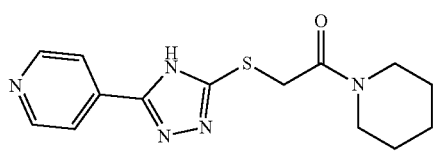 [SMILES: O=C(CSc1nnc(-c2ccncc2)[nH]1)N1CCCCC1]

2-[4-phenyl-5-(quinolin-8-yloxymethyl)-4H-[1,2,4]triazol-3-ylsulfanyl]-1-piperidin-1-yl-ethanone (SMC 34.11);

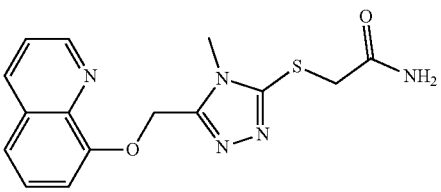 [SMILES: Cn1c(COc2cccc3cccnc23)nnc1SCC(N)=O]

1-piperidin-1-yl-2-(5-pyridin-4-yl-4H-[1,2,4]triazol-3-ylsulfanyl)-ethanone (SMC 34.12); and 2-[4-methyl-5-(quinolin-8-yloxymethyl)-4H-[1,2,4]triazol-3-ylsulfanyl]-acetamide (SMC 34.13).

16. The method according to claim 9, wherein said immune-related disorder or condition is a primary or a secondary immunodeficiency.

17. The method according to claim 9, wherein at least one of:
   (a) said primary immunodeficiency is a hereditary or acquired disorder associated with WASp dysfunction, optionally, said hereditary disorder associated with WASp dysfunction is at least one of WAS and XLT, or any condition or disorder associated therewith; and
   (b) said secondary immunodeficiency is caused by at least one of chemotherapy, radiotherapy, biological therapy, bone marrow transplantation, gene therapy, adoptive cell transfer or any combinations thereof.

18. The method according to claim 9, wherein:
   (a) said immune-related disorder or condition is a pathologic condition caused by at least one pathogen; or (b) said immune-related disorder or condition is thrombocytopenia.

19. The method according to claim 9, wherein said immune-related disorder or condition is cancer, optionally, said subject undergoes at least one of chemotherapy, radiotherapy, biological therapy, or any combinations thereof, and wherein said method further comprises the step of administering to said subject before, simultaneously with, after or any combination thereof, the administration of said SMC modulator, at least one agent that induces differentiation of hematopoietic progenitor cells.

\* \* \* \* \*

SEQUENCE LISTING

<160> NUMBER OF SEQ ID NOS: 18

<210> SEQ ID NO 1
<211> LENGTH: 502
<212> TYPE: PRT
<213> ORGANISM: Homo sapiens

<400> SEQUENCE: 1

Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Gln Leu Phe Glu Met Leu Gly Arg Lys Cys Leu Thr Leu Ala Thr
        35                  40                  45

```
Ala Val Val Gln Leu Tyr Leu Ala Leu Pro Pro Gly Ala Glu His Trp
    50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Tyr Ser Thr Pro Thr Pro
            100                 105                 110

Phe Phe His Thr Phe Ala Gly Asp Asp Cys Gln Ala Gly Leu Asn Phe
        115                 120                 125

Ala Asp Glu Asp Glu Ala Gln Ala Phe Arg Ala Leu Val Gln Glu Lys
    130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
    195                 200                 205

Ser Ser Arg Tyr Arg Gly Leu Pro Ala Pro Gly Pro Ser Pro Ala Asp
    210                 215                 220

Lys Lys Arg Ser Gly Arg Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
        275                 280                 285

Leu Ile Tyr Asp Phe Ile Glu Asp Gln Gly Gly Leu Glu Ala Val Arg
    290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
            340                 345                 350

Pro Pro Thr Pro Arg Gly Pro Pro Pro Gly Arg Gly Gly Pro Pro
        355                 360                 365

Pro Pro Pro Pro Pro Ala Thr Gly Arg Ser Gly Pro Leu Pro Pro Pro
    370                 375                 380

Pro Pro Gly Ala Gly Gly Pro Pro Met Pro Pro Pro Pro Pro Pro
385                 390                 395                 400

Pro Pro Pro Pro Ser Ser Gly Asn Gly Pro Ala Pro Pro Leu Pro
                405                 410                 415

Pro Ala Leu Val Pro Ala Gly Gly Leu Ala Pro Gly Gly Arg Gly
                420                 425                 430

Ala Leu Leu Asp Gln Ile Arg Gln Gly Ile Gln Leu Asn Lys Thr Pro
        435                 440                 445

Gly Ala Pro Glu Ser Ser Ala Leu Gln Pro Pro Gln Ser Ser Glu
    450                 455                 460

Gly Leu Val Gly Ala Leu Met His Val Met Gln Lys Arg Ser Arg Ala
```

```
                465                 470                 475                 480
            Ile His Ser Ser Asp Glu Gly Glu Asp Gln Ala Gly Asp Glu Asp Glu
                                485                 490                 495
            Asp Asp Glu Trp Asp Asp
                        500

<210> SEQ ID NO 2
<211> LENGTH: 1509
<212> TYPE: DNA
<213> ORGANISM: Homo sapiens

<400> SEQUENCE: 2
atgagtgggg gcccaatggg aggaaggccc gggggccgag gagcaccagc ggttcagcag         60
aacatacccc tcaccctcct ccaggaccac gagaaccagc aactctttga gatgcttgga        120
cgaaaatgct tgacgctggc cactgcagtt gttcagctgt acctggcgct gccccctgga        180
gctgagcact ggaccaagga gcattgtggg gctgtgtgct tcgtgaagga taacccccag        240
aagtcctact tcatccgcct ttacggcctt caggctggtc ggctgctctg ggaacaggag        300
ctgtactcac agcttgtcta ctccaccccc acccccttct tccacacctt cgctggagat        360
gactgccaag cggggctgaa cttttgcagac gaggacgagg cccaggcctt ccgggccctc        420
gtgcaggaga agatacaaaa aaggaatcag aggcaaagtg gagacagacg ccagctaccc        480
ccaccaccaa caccagccaa tgaagagaga agggagggc tcccacccct gccctgcat         540 ccaggtggag accaaggagg ccctccagtg ggtccgctct ccctggggct ggcgacagtg        600
gacatccaga accctgacat cacgagttca cgataccgtg ggctcccagc acctggacct        660
agcccagctg ataagaaacg ctcagggagg aagaagatca gcaaagctga tattggtgca        720
cccagtggat tcaagcatgt cagccacgtg gggtgggacc cccagaatgg atttgacgtg        780
aacaacctcg acccagatct gcggagtctg ttctccaggg caggaatcag cgaggcccag        840
ctcaccgacg ccgagacctc taaacttatc tacgacttca ttgaggacca gggtgggctg        900
gaggctgtgc ggcaggagat gaggcgccag gagccacttc cgccgccccc accgccatct        960
cgaggaggga accagctccc ccggcccccct attgtggggg gtaacaaggg tcgttctggt       1020
ccactgcccc ctgtaccttt ggggattgcc ccaccccac caacacccg ggaccccca         1080 ccccaggcc gaggggccc tccaccacca cccctccag ctactggacg ttctggacca         1140
ctgccccctc cacccctgg agctggtggg ccacccatgc caccaccacc gccaccaccg        1200
ccaccgccgc ccagctccgg gaatggacca gcccctcccc cactccctcc tgctctggtg        1260
cctgccgggg gcctggcccc tggtgggggt cggggagcgc ttttggatca aatccggcag        1320
ggaattcagc tgaacaagac ccctgggggcc ccagagagct cagcgctgca gccaccacct        1380
cagagctcag agggactggt ggggggccctg atgcacgtga tgcagaagag aagcagagcc        1440
atccactcct ccgacgaagg ggaggaccag gctggcgatg aagatgaaga tgatgaatgg        1500
gatgactag                                                                1509

<210> SEQ ID NO 3
<211> LENGTH: 25
<212> TYPE: RNA
<213> ORGANISM: Artificial Sequence
<220> FEATURE:
<223> OTHER INFORMATION: HUMAN PKC theta RNA SEQUENCE

<400> SEQUENCE: 3
gagucuccgu uggaugaggu ggaua                                               25
```

```
<210> SEQ ID NO 4
<211> LENGTH: 25
<212> TYPE: RNA
<213> ORGANISM: Artificial Sequence
<220> FEATURE:
<223> OTHER INFORMATION: HUMAN PKC theta RNA SEQUENCE
<220> FEATURE:
<221> NAME/KEY: misc_feature
<223> OTHER INFORMATION: Synthetic

<400> SEQUENCE: 4
gcauccguuu cugacgcaca uguuu                                            25

<210> SEQ ID NO 5
<211> LENGTH: 25
<212> TYPE: RNA
<213> ORGANISM: Artificial Sequence
<220> FEATURE:
<223> OTHER INFORMATION: HUMAN PKC theta RNA SEQUENCE
<220> FEATURE:
<221> NAME/KEY: misc_feature
<223> OTHER INFORMATION: Synthetic

<400> SEQUENCE: 5
ccggccgaaa gugaaaucac cauuu                                            25

<210> SEQ ID NO 6
<211> LENGTH: 19
<212> TYPE: RNA
<213> ORGANISM: Artificial Sequence
<220> FEATURE:
<223> OTHER INFORMATION: NONSPECIFIC siRNA
<220> FEATURE:
<221> NAME/KEY: misc_feature
<223> OTHER INFORMATION: Synthetic

<400> SEQUENCE: 6
uagcgacuaa acacaucaa                                                   19

<210> SEQ ID NO 7
<211> LENGTH: 19
<212> TYPE: RNA
<213> ORGANISM: Artificial Sequence
<220> FEATURE:
<223> OTHER INFORMATION: NONSPECIFIC siRNA
<220> FEATURE:
<221> NAME/KEY: misc_feature
<223> OTHER INFORMATION: Synthetic

<400> SEQUENCE: 7
uaaggcuaug aagagauac                                                   19

<210> SEQ ID NO 8
<211> LENGTH: 19
<212> TYPE: RNA
<213> ORGANISM: Artificial Sequence
<220> FEATURE:
<223> OTHER INFORMATION: NONSPECIFIC siRNA
<220> FEATURE:
<221> NAME/KEY: misc_feature
<223> OTHER INFORMATION: Synthetic

<400> SEQUENCE: 8
auguauuggc cuguauuag                                                   19

<210> SEQ ID NO 9
<211> LENGTH: 19
```

```
<212> TYPE: RNA
<213> ORGANISM: Artificial Sequence
<220> FEATURE:
<223> OTHER INFORMATION: NONSPECIFIC siRNA
<220> FEATURE:
<221> NAME/KEY: misc_feature
<223> OTHER INFORMATION: Synthetic

<400> SEQUENCE: 9
augaacguga auugcucaa                                                      19

<210> SEQ ID NO 10
<211> LENGTH: 19
<212> TYPE: RNA
<213> ORGANISM: Artificial Sequence
<220> FEATURE:
<223> OTHER INFORMATION: NONSPECIFIC siRNA
<220> FEATURE:
<221> NAME/KEY: misc_feature
<223> OTHER INFORMATION: Synthetic

<400> SEQUENCE: 10
ugguuuacau gucgacuaa                                                      19

<210> SEQ ID NO 11
<211> LENGTH: 26
<212> TYPE: DNA
<213> ORGANISM: Artificial Sequence
<220> FEATURE:
<223> OTHER INFORMATION: RNA guide
<220> FEATURE:
<221> NAME/KEY: misc_feature
<223> OTHER INFORMATION: Synthetic

<400> SEQUENCE: 11
aaactcgctg gagatgtaag tggatc                                              26

<210> SEQ ID NO 12
<211> LENGTH: 25
<212> TYPE: DNA
<213> ORGANISM: Artificial Sequence
<220> FEATURE:
<223> OTHER INFORMATION: RNA guide
<220> FEATURE:
<221> NAME/KEY: misc_feature
<223> OTHER INFORMATION: Synthetic

<400> SEQUENCE: 12
caccgatcac ttacatctcc agcga                                               25

<210> SEQ ID NO 13
<211> LENGTH: 502
<212> TYPE: PRT
<213> ORGANISM: Artificial Sequence
<220> FEATURE:
<223> OTHER INFORMATION: Human WASp mutant R86C
<220> FEATURE:
<221> NAME/KEY: misc_feature
<223> OTHER INFORMATION: Synthetic

<400> SEQUENCE: 13

Met Ser Gly Gly Pro Met Gly Gly Arg Pro Gly Gly Arg Gly Ala Pro
 1               5                  10                  15

Ala Val Gln Gln Asn Ile Pro Ser Thr Leu Leu Gln Asp His Glu Asn
                20                  25                  30

Gln Gln Leu Phe Glu Met Leu Gly Arg Lys Cys Leu Thr Leu Ala Thr
            35                  40                  45
```

```
Ala Val Val Gln Leu Tyr Leu Ala Leu Pro Pro Gly Ala Glu His Trp
     50                  55                  60

Thr Lys Glu His Cys Gly Ala Val Cys Phe Val Lys Asp Asn Pro Gln
 65                  70                  75                  80

Lys Ser Tyr Phe Ile Cys Leu Tyr Gly Leu Gln Ala Gly Arg Leu Leu
                 85                  90                  95

Trp Glu Gln Glu Leu Tyr Ser Gln Leu Val Tyr Ser Thr Pro Thr Pro
                100                 105                 110

Phe Phe His Thr Phe Ala Gly Asp Asp Cys Gln Ala Gly Leu Asn Phe
            115                 120                 125

Ala Asp Glu Asp Glu Ala Gln Ala Phe Arg Ala Leu Val Gln Glu Lys
    130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
    195                 200                 205

Ser Ser Arg Tyr Arg Gly Leu Pro Ala Pro Gly Pro Ser Pro Ala Asp
210                 215                 220

Lys Lys Arg Ser Gly Arg Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
    275                 280                 285

Leu Ile Tyr Asp Phe Ile Glu Asp Gln Gly Gly Leu Glu Ala Val Arg
290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
            340                 345                 350

Pro Pro Thr Pro Arg Gly Pro Pro Pro Gly Arg Gly Gly Pro Pro
    355                 360                 365

Pro Pro Pro Pro Pro Ala Thr Gly Arg Ser Gly Pro Leu Pro Pro Pro
370                 375                 380

Pro Pro Gly Ala Gly Gly Pro Pro Met Pro Pro Pro Pro Pro Pro Pro
385                 390                 395                 400

Pro Pro Pro Pro Ser Ser Gly Asn Gly Pro Ala Pro Pro Leu Pro
                405                 410                 415

Pro Ala Leu Val Pro Ala Gly Gly Leu Ala Pro Gly Gly Gly Arg Gly
            420                 425                 430

Ala Leu Leu Asp Gln Ile Arg Gln Gly Ile Gln Leu Asn Lys Thr Pro
                435                 440                 445

Gly Ala Pro Glu Ser Ser Ala Leu Gln Pro Pro Gln Ser Ser Glu
450                 455                 460

Gly Leu Val Gly Ala Leu Met His Val Met Gln Lys Arg Ser Arg Ala
```

```
                    465                 470                 475                 480
Ile His Ser Ser Asp Glu Gly Glu Asp Gln Ala Gly Asp Glu Asp Glu
                        485                 490                 495
Asp Asp Glu Trp Asp Asp
            500
```

<210> SEQ ID NO 14
<211> LENGTH: 1509
<212> TYPE: DNA
<213> ORGANISM: Artificial Sequence
<220> FEATURE:
<223> OTHER INFORMATION: Human WASp mutant R86C
<220> FEATURE:
<221> NAME/KEY: misc_feature
<223> OTHER INFORMATION: Synthetic

<400> SEQUENCE: 14

```
atgagtgggg gcccaatggg aggaaggccc gggggccgag gagcaccagc ggttcagcag      60
aacataccct ccaccctcct ccaggaccac gagaaccagc aactctttga gatgcttgga     120
cgaaaatgct tgacgctggc cactgcagtt gttcagctgt acctggcgct gccccctgga     180
gctgagcact ggaccaagga gcattgtggg gctgtgtgct cgtgaaggga taaccccag     240
aagtcctact tcatctgcct ttacggcctt caggctggtc ggctgctctg ggaacaggag     300
ctgtactcac agcttgtcta ctccacccc accccttct tccacacctt cgctggagat      360
gactgccaag cggggctgaa cttttgcagac gaggacgagg cccaggcctt ccgggccctc     420
gtgcaggaga agatacaaaa aaggaatcag aggcaaagtg gagacagacg ccagctaccc     480
ccaccaccaa caccagccaa tgaagagaga gaggagggc tcccacccct gcccctgcat     540
ccaggtggag accaaggagg ccctccagtg ggtccgctct ccctggggct ggcgacagtg     600
gacatccaga accctgacat cacgagttca cgataccgtg ggctcccagc acctggacct     660
agcccagctg ataagaaacg ctcagggagg aagaagatca gcaaagctga tattggtgca     720
cccagtggat tcaagcatgt cagccacgtg gggtgggacc ccagaatgg atttgacgtg     780
aacaacctcg acccagatct gcggagtctg ttctccaggg caggaatcag cgaggcccag     840
ctcaccgacg ccgagacctc taaacttatc tacgacttca ttgaggacca gggtgggctg     900
gaggctgtgc ggcaggagat gaggcgccag gagccacttc cgccgccccc accgccatct     960
cgaggaggga accagctccc ccggcccct attgtggggg gtaacaaggg tcgttctggt    1020
ccactgcccc ctgtaccttt ggggattgcc ccacccccac caacacccg ggaccccca    1080
cccccaggcc gagggggccc tccaccacca cccctccag ctactggacg ttctggacca    1140
ctgcccctc cacccctgg agctggtggg ccaccatgc caccaccacc gccaccaccg    1200
ccaccgccgc cagctccgg gaatggacca gccctccc cactccctcc tgctctggtg    1260
cctgccgggg gcctggcccc tggtgggggt cggggagcgc ttttggatca aatccggcag    1320
ggaattcagc tgaacaagac ccctgggcc cagagagct cagcgctgca gccaccacct    1380
cagagctcag agggactggt gggggccctg atgcacgtga tgcagaagag aagcagagcc    1440
atccactcct ccgacgaagg ggaggaccag gctggcgatg aagatgaaga tgatgaatgg    1500
gatgactag                                                            1509
```

<210> SEQ ID NO 15
<211> LENGTH: 502
<212> TYPE: PRT
<213> ORGANISM: Artificial Sequence
<220> FEATURE:

<223> OTHER INFORMATION: Human WASp mutant Y107C
<220> FEATURE:
<221> NAME/KEY: misc_feature
<223> OTHER INFORMATION: Synthetic

<400> SEQUENCE: 15

```
Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Gln Leu Phe Glu Met Leu Gly Arg Lys Cys Leu Thr Leu Ala Thr
        35                  40                  45

Ala Val Val Gln Leu Tyr Leu Ala Leu Pro Pro Gly Ala Glu His Trp
    50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Cys Ser Thr Pro Thr Pro
            100                 105                 110

Phe Phe His Thr Phe Ala Gly Asp Asp Cys Gln Ala Gly Leu Asn Phe
        115                 120                 125

Ala Asp Glu Asp Glu Ala Gln Ala Phe Arg Ala Leu Val Gln Glu Lys
    130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
        195                 200                 205

Ser Ser Arg Tyr Arg Gly Leu Pro Ala Pro Gly Pro Ser Pro Ala Asp
    210                 215                 220

Lys Lys Arg Ser Gly Arg Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
        275                 280                 285

Leu Ile Tyr Asp Phe Ile Glu Asp Gln Gly Gly Leu Glu Ala Val Arg
    290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
            340                 345                 350

Pro Pro Thr Pro Arg Gly Pro Pro Pro Gly Arg Gly Gly Pro Pro Pro
        355                 360                 365

Pro Pro Pro Pro Pro Ala Thr Gly Arg Ser Gly Pro Leu Pro Pro Pro
    370                 375                 380
```

```
Pro Pro Gly Ala Gly Gly Pro Pro Met Pro Pro Pro Pro Pro Pro
385                 390                 395                 400

Pro Pro Pro Pro Ser Ser Gly Asn Gly Pro Ala Pro Pro Leu Pro
            405                 410                 415

Pro Ala Leu Val Pro Ala Gly Gly Leu Ala Pro Gly Gly Arg Gly
        420                 425                 430

Ala Leu Leu Asp Gln Ile Arg Gln Gly Ile Gln Leu Asn Lys Thr Pro
            435                 440                 445

Gly Ala Pro Glu Ser Ser Ala Leu Gln Pro Pro Gln Ser Ser Glu
        450                 455                 460

Gly Leu Val Gly Ala Leu Met His Val Met Gln Lys Arg Ser Arg Ala
465                 470                 475                 480

Ile His Ser Ser Asp Glu Gly Glu Asp Gln Ala Gly Asp Glu Asp
                485                 490                 495

Asp Asp Glu Trp Asp Asp
            500
```

```
<210> SEQ ID NO 16
<211> LENGTH: 1509
<212> TYPE: DNA
<213> ORGANISM: Artificial Sequence
<220> FEATURE:
<223> OTHER INFORMATION: Human WASp mutant Y107C
<220> FEATURE:
<221> NAME/KEY: misc_feature
<223> OTHER INFORMATION: Synthetic

<400> SEQUENCE: 16
```

| | | |
|---|---|---|
| atgagtgggg gcccaatggg aggaaggccc ggggccgag gagcaccagc ggttcagcag | 60 |
| aacataccct ccaccctcct ccaggaccac gagaaccagc aactctttga gatgcttgga | 120 |
| cgaaaatgct tgacgctggc cactgcagtt gttcagctgt acctggcgct gccccctgga | 180 |
| gctgagcact ggaccaagga gcattgtggg gctgtgtgct tcgtgaagga taaccccag | 240 |
| aagtcctact tcatccgcct ttacggcctt caggctggtc ggctgctctg ggaacaggag | 300 |
| ctgtactcac agcttgtctg ctccaccccc acccccttct tccacacctt cgctggagat | 360 |
| gactgccaag cggggctgaa ctttgcagac gaggacgagg cccaggcctt ccgggccctc | 420 |
| gtgcaggaga agatacaaaa aaggaatcag aggcaaagtg agacagacg ccagctaccc | 480 |
| ccaccaccaa caccagccaa tgaagagaga agaggagggc tcccacccct gcccctgcat | 540 |
| ccaggtggag accaaggagg ccctccagtg ggtccgctct ccctggggct ggcgacagtg | 600 |
| gacatccaga accctgacat cacgagttca cgataccgtg gctcccagc acctggacct | 660 |
| agcccagctg ataagaaacg ctcagggagg aagaagatca gcaaagctga tattggtgca | 720 |
| cccagtggat tcaagcatgt cagccacgtg gggtgggacc cccagaatgg atttgacgtg | 780 |
| aacaacctcg acccagatct gcggagtctg ttctccaggg caggaatcag cgaggcccag | 840 |
| ctcaccgacg ccgagacctc taaacttatc tacgacttca ttgaggacca gggtgggctg | 900 |
| gaggctgtgc ggcaggagat gaggcgccag gagccacttc gccgccccc accgccatct | 960 |
| cgaggaggga accagctccc ccggccccct attgtgggg gtaacaaggg tcgttctggt | 1020 |
| ccactgcccc ctgtaccttt ggggattgcc ccaccccac caaacccg ggaccccca | 1080 |
| cccccaggcc gagggggccc tccaccacca cccctccag ctactggacg ttctggacca | 1140 |
| ctgcccctc cacccctgg agctggtggg ccaccatgc caccaccacc gccaccaccg | 1200 |
| ccaccgccgc ccagctccgg gaatggacca gcccctcccc cactccctcc tgctctggtg | 1260 |

```
cctgccgggg gcctggcccc tgtggggggt cggggagcgc ttttggatca aatccggcag   1320
ggaattcagc tgaacaagac ccctgggggcc ccagagagct cagcgctgca gccaccacct   1380
cagagctcag agggactggt ggggggccctg atgcacgtga tgcagaagag aagcagagcc   1440
atccactcct ccgacgaagg ggaggaccag gctggcgatg aagatgaaga tgatgaatgg   1500
gatgactag                                                           1509
```

<210> SEQ ID NO 17
<211> LENGTH: 499
<212> TYPE: PRT
<213> ORGANISM: Artificial Sequence
<220> FEATURE:
<223> OTHER INFORMATION: Human WASp mutant A134T
<220> FEATURE:
<221> NAME/KEY: misc_feature
<223> OTHER INFORMATION: Synthetic

<400> SEQUENCE: 17

```
Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Gln Leu Phe Glu Met Leu Gly Arg Lys Cys Leu Thr Leu Ala Thr
        35                  40                  45

Ala Val Val Gln Leu Tyr Leu Ala Leu Pro Pro Gly Ala Glu His Trp
    50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Tyr Ser Thr Pro Thr Pro
            100                 105                 110

Phe Phe His Thr Phe Ala Gly Asp Asp Cys Gln Ala Gly Leu Asn Phe
        115                 120                 125

Ala Asp Glu Asp Glu Thr Gln Arg Ala Leu Val Gln Glu Lys Ile Gln
    130                 135                 140

Lys Arg Asn Gln Arg Gln Ser Gly Asp Arg Arg Gln Leu Pro Pro Pro
145                 150                 155                 160

Pro Thr Pro Ala Asn Glu Glu Arg Arg Gly Gly Leu Pro Pro Leu Pro
                165                 170                 175

Leu His Pro Gly Gly Asp Gln Gly Gly Pro Pro Val Gly Pro Leu Ser
            180                 185                 190

Leu Gly Leu Ala Thr Val Asp Ile Gln Asn Pro Asp Ile Thr Ser Ser
        195                 200                 205

Arg Tyr Arg Gly Leu Pro Ala Pro Gly Pro Ser Pro Ala Asp Lys Lys
    210                 215                 220

Arg Ser Gly Arg Lys Lys Ile Ser Lys Ala Asp Ile Gly Ala Pro Ser
225                 230                 235                 240

Gly Phe Lys His Val Ser His Val Gly Trp Asp Pro Gln Asn Gly Phe
                245                 250                 255

Asp Val Asn Asn Leu Asp Pro Asp Leu Arg Ser Leu Phe Ser Arg Ala
            260                 265                 270

Gly Ile Ser Glu Ala Gln Leu Thr Asp Ala Glu Thr Ser Lys Leu Ile
        275                 280                 285

Tyr Asp Phe Ile Glu Asp Gln Gly Gly Leu Glu Ala Val Arg Gln Glu
    290                 295                 300
```

```
Met Arg Arg Gln Glu Pro Leu Pro Pro Pro Pro Ser Arg Gly
305                 310                 315                 320

Gly Asn Gln Leu Pro Arg Pro Pro Ile Val Gly Gly Asn Lys Gly Arg
                325                 330                 335

Ser Gly Pro Leu Pro Pro Val Pro Gly Ile Ala Pro Pro Pro Thr
            340                 345                 350

Pro Arg Gly Pro Pro Pro Gly Arg Gly Pro Pro Pro Pro
        355                 360                 365

Pro Pro Ala Thr Gly Arg Ser Gly Pro Leu Pro Pro Pro Pro Gly
    370                 375                 380

Ala Gly Gly Pro Pro Met Pro Pro Pro Pro Pro Pro Pro Pro
385                 390                 395                 400

Pro Ser Ser Gly Asn Gly Pro Ala Pro Pro Leu Pro Pro Ala Leu
                405                 410                 415

Val Pro Ala Gly Gly Leu Ala Pro Gly Gly Gly Arg Gly Ala Leu Leu
            420                 425                 430

Asp Gln Ile Arg Gln Gly Ile Gln Leu Asn Lys Thr Pro Gly Ala Pro
                435                 440                 445

Glu Ser Ser Ala Leu Gln Pro Pro Pro Gln Ser Ser Glu Gly Leu Val
450                 455                 460

Gly Ala Leu Met His Val Met Gln Lys Arg Ser Arg Ala Ile His Ser
465                 470                 475                 480

Ser Asp Glu Gly Glu Asp Gln Ala Gly Asp Glu Asp Glu Asp Asp Glu
                485                 490                 495

Trp Asp Asp
```

<210> SEQ ID NO 18
<211> LENGTH: 1509
<212> TYPE: DNA
<213> ORGANISM: Artificial Sequence
<220> FEATURE:
<223> OTHER INFORMATION: Human WASp mutant A134T
<220> FEATURE:
<221> NAME/KEY: misc_feature
<223> OTHER INFORMATION: Synthetic

<400> SEQUENCE: 18

```
atgagtgggg gcccaatggg aggaaggccc gggggccgag gagcaccagc ggttcagcag    60 aacatacccct ccaccctcct ccaggaccac gagaaccagc aactctttga gatgcttgga   120
cgaaaatgct tgacgctggc cactgcagtt gttcagctgt acctggcgct ccccctgga    180 gctgagcact ggaccaagga gcattgtggg gctgtgtgct tcgtgaagga taaccccag    240 aagtcctact tcatccgcct ttacggcctt caggctggtc ggctgctctg gaacaggag    300 ctgtactcac agcttgtcta ctccaccccc acccccttct tccacacctt cgctggagat   360
gactgccaag cggggctgaa ctttgcagac gaggacgaga cccaggcctt ccgggccctc   420
gtgcaggaga agatacaaaa aaggaatcag aggcaaagtg agacagacg ccagctaccc    480 ccaccaccaa caccagccaa tgaagagaga agaggagggc tcccacccct gccctgcat    540 ccaggtggag accaaggagg ccctccagtg ggtccgctct ccctggggct ggcgacagtg   600
gacatccaga accctgacat cacgagttca cgataccgtg ggctcccagc acctggacct   660
agcccagctg ataagaaacg ctcagggagg aagaagatca gcaaagctga tattggtgca   720
cccagtggat tcaagcatgt cagccacgtg gggtgggacc cccagaatgg atttgacgtg   780 aacaaccctcg acccagatct gcggagtctg ttctccaggg caggaatcag cgaggcccag   840
```

```
ctcaccgacg ccgagacctc taaacttatc tacgacttca ttgaggacca gggtgggctg      900
gaggctgtgc ggcaggagat gaggcgccag gagccacttc cgccgccccc accgccatct      960
cgaggaggga accagctccc ccggccccct attgtggggg gtaacaaggg tcgttctggt     1020
ccactgcccc ctgtaccttt ggggattgcc ccaccccac caacaccccg ggaccccca      1080 ccccaggcc gagggggccc tccaccacca ccccctccag ctactggacg ttctggacca     1140
ctgccccctc cacccctgg agctggtggg ccacccatgc caccaccacc gccaccaccg     1200
ccaccgccgc ccagctccgg gaatggacca gcccctcccc cactccctcc tgctctggtg     1260
cctgccgggg gcctggcccc tggtggggt cggggagcgc ttttggatca aatccggcag     1320
ggaattcagc tgaacaagac ccctggggcc ccagagagct cagcgctgca gccaccacct     1380
cagagctcag agggactggt gggggccctg atgcacgtga tgcagaagag aagcagagcc     1440
atccactcct ccgacgaagg ggaggaccag gctggcgatg aagatgaaga tgatgaatgg     1500
gatgactag                                                             1509
```